(12) United States Patent
Kim et al.

(10) Patent No.: US 10,276,808 B2
(45) Date of Patent: Apr. 30, 2019

(54) ORGANIC ELECTROLUMINESCENT COMPOUND AND ORGANIC ELECTROLUMINESCENT DEVICE COMPRISING THE SAME

(71) Applicant: Rohm and Haas Electronic Materials Korea Ltd., Cheonan (KR)

(72) Inventors: Hyun Kim, Suwon (KR); Ga-Won Lee, Hwaseong (KR); Sung-Woo Jang, Suwon (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 0 days.

(21) Appl. No.: 15/779,607

(22) PCT Filed: Dec. 9, 2016

(86) PCT No.: PCT/KR2016/014435
§ 371 (c)(1),
(2) Date: May 29, 2018

(87) PCT Pub. No.: WO2017/099516
PCT Pub. Date: Jun. 15, 2017

(65) Prior Publication Data
US 2018/0351114 A1    Dec. 6, 2018

(30) Foreign Application Priority Data

Dec. 10, 2015 (KR) .................. 10-2015-0176262
Dec. 7, 2016 (KR) .................. 10-2016-0165699

(51) Int. Cl.
*C07F 15/00* (2006.01)
*H01L 51/00* (2006.01)
*C09K 11/06* (2006.01)
*H01L 51/50* (2006.01)
*H01L 51/56* (2006.01)

(52) U.S. Cl.
CPC ...... *H01L 51/0085* (2013.01); *C07F 15/0033* (2013.01); *C09K 11/06* (2013.01); *C09K 2211/1029* (2013.01); *C09K 2211/185* (2013.01); *H01L 51/001* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/56* (2013.01)

(58) Field of Classification Search
CPC ........................... C07F 15/0033; H01L 51/50
USPC .......................................... 546/10; 313/504
See application file for complete search history.

(56) References Cited

U.S. PATENT DOCUMENTS 7,951,472 B2    5/2011   Igarashi et al.

FOREIGN PATENT DOCUMENTS

WO    2015/056993 A1    4/2015

*Primary Examiner* — Charanjit Aulakh
(74) *Attorney, Agent, or Firm* — S. Matthew Cairns

(57) ABSTRACT

The present disclosure relates to an organic electroluminescent compound and an organic electroluminescent device comprising the same. The organic electroluminescent compound according to the present disclosure is capable of producing an organic electroluminescent device with reasonably improved color purity and efficiency.

8 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to organic electroluminescent compounds and an organic electroluminescent device comprising the same.

BACKGROUND FIELD

Among display devices, an electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules and aluminum complexes as materials for forming a light-emitting layer [Appl. Phys. Lett. 51, 913, 1987].

An organic electroluminescent device (OLED) has a structure comprising an anode, a cathode, and an organic layer between the anode and the cathode, wherein the organic layer may comprise a hole injection layer, a hole transport layer, an electron blocking layer, a light-emitting layer, a hole blocking layer, an electron transport layer, an electron injection layer, etc. In the organic electroluminescent device, when a voltage is applied, holes and electrons are injected from the anode and the cathode, respectively, to the light-emitting layer, in which excitons having high energies are formed by a recombination of the holes and the electrons. The excition's energy puts the organic luminescent compound in an excited state, and light is emitted by energy released while returning from the excited state to a ground state. Accordingly, the most important factor determining luminous efficiency in an organic electroluminescent device is a light-emitting material.

The EL material can be categorized into a host material and a dopant material according to their functions. Generally, a device having the most excellent EL characteristic has a structure comprising a light-emitting layer formed by doping a dopant to a host. A host/dopant system is for increasing light-emitting efficiency by energy transfer from a host to a dopant. The host and dopant materials greatly influence the efficiency and lifespan of the EL device when using a dopant/host material system.

Until now, iridium(III) complexes have been widely known as a dopant of phosphorescent materials, and bis(2-(2'-benzothienyl)-pyridinato-N,C3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red, green, and blue light-emitting material, respectively.

However, considering EL characteristic requirements for a middle or large-sized panel of OLED, a development of a dopant compound of iridium complexes providing more excellent EL performance, such as long lifespan, high efficiency and high color purity, is still needed.

In particular, in order to realize full color display, to which an organic EL device is applied, a pixel configured to emit a particular color called "saturated" color is required. In particular, saturated red, green, and blue pixels are required. These saturated colors can be measured by using a CIE coordinate publicly known in the art.

In order to express more various colors, a color purity of each of red, green, and blue should be high. In case of red color, the closer to the red color coordinate near 0.680 (CIE X-coordinate standard), the higher the color purity is. Accordingly, a requirement for a suitable dopant compound is increased.

U.S. Pat. No. 7,951,472 discloses iridium complexes having 2-phenylquinoline-based ligand as a dopant compound of OLED, but iridium complexes having fused azabenzofluorene is not disclosed.

DISCLOSURE OF THE INVENTION

Problems to be Solved

The object of the present disclosure is first, to provide compounds capable of producing an organic electroluminescent device with excellent color purity and efficiency, and second, to provide an organic electroluminescent device comprising the compounds.

Solution to Problems

As a result of intensive studies to achieve the technical objects above, the present inventors found that the object can be achieved by an organic electroluminescent compound represented by the following formula 1:

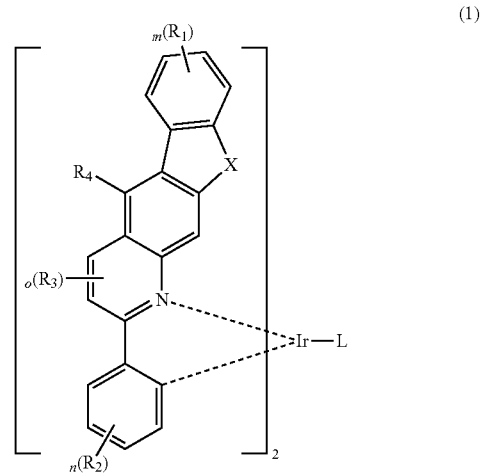

(1)

wherein

X represents $CR_{11}R_{12}$, O or S;

$R_1$ to $R_3$, each independently, represent hydrogen, deuterium, a substituted or unsubstituted (C1-C10)alkyl, or a substituted or unsubstituted (C6-C30)aryl;

$R_4$ represents hydrogen, or a substituted or unsubstituted (C1-C10)alkyl;

$R_{11}$ and $R_{12}$, each independently, represent a substituted or unsubstituted (C1-C10)alkyl, or a substituted or unsubstituted (C6-C30)aryl;

m and n, each independently, represent an integer of 0 to 4;

o represents an integer of 0 to 2;

where m, n or o is an integer of 2 or more, each of $R_1$, each of $R_2$, or each of $R_3$ may be the same or different;

L represents

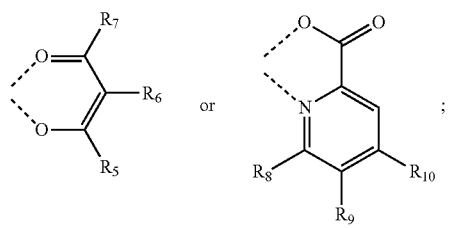

where L is

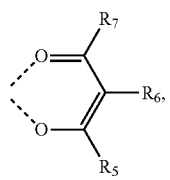

$R_5$ to $R_7$, each independently, represent hydrogen, deuterium, a substituted or unsubstituted (C1-C10)alkyl, or a substituted or unsubstituted (C6-C30)aryl;

where L is

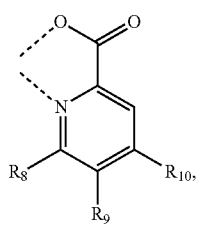

$R_5$ to $R_{10}$, each independently, represent hydrogen, deuterium, a substituted or unsubstituted (C1-C10)alkyl, or a substituted or unsubstituted (C6-C30)aryl; or may be linked to an adjacent substituent to form a substituted or unsubstituted 9- to 20-membered heteroaryl including the pyridine ring linked to $R_5$ to $R_{10}$; and the heteroaryl may comprise one or more hetero atoms selected from a nitrogen, an oxygen, and a sulfur, in addition to the nitrogen atom of the pyridine ring.

Effects of the Invention

By using a compound according to the present disclosure, an organic electroluminescent device showing significant improvement in color purity and efficiency can be prepared.

EMBODIMENTS OF THE INVENTION

Hereinafter, the present disclosure will be described in detail. However, the following description is intended to explain the invention, and is not meant in any way to restrict the scope of the invention.

The present disclosure relates to a compound represented by formula 1 above, an organic electroluminescent material comprising said compound, and an organic electroluminescent device comprising said compound.

Hereinafter, the compound represented by formula 1 of the present disclosure will be specifically described in detail.

Herein, "(C1-C10)alkyl" indicates a linear or branched alkyl having 1 to 10 carbon atoms, in which the number of carbon atoms is preferably 1 to 5, and more preferably 1 to 4, and includes, as a specific example, methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, and 1-ethylpropyl. Herein, "(C6-C30)aryl" indicates a monocyclic or fused ring radical derived from an aromatic hydrocarbon having 6 to 30 ring backbone carbon atoms, in which the number of ring backbone carbon atoms is preferably 6 to 20, more preferably 6 to 15, and includes, as a specific example, phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc.

Herein, "3- to 30-membered heteroaryl" indicates an aryl group having 3 to 30 ring backbone atoms, including at least one hetero atom selected from the group consisting of B, N, O, S, Si, and P, in which, the number of ring backbone atoms is preferably 9 to 20, and more preferably 9 to 16, and the number of hetero atoms is preferably 1 to 4. Herein, heteroaryl may be a monocyclic ring, or a fused ring condensed with at least one benzene ring; may be partially saturated; and the heteroaryl may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc.

Herein, "substituted" in the expression "substituted or unsubstituted" means that hydrogen atom in a certain functional group is replaced with another atom or another functional group, i.e. a substituent. In $R_1$ to $R_{12}$ of formula 1 of the present disclosure, the substituents of the substituted alkyl, the substituted aryl, or the substituted heteroaryl each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a 3- to 7-membered heterocycloalkyl; a (C6-C30)aryloxy; a (C6-C30)arylthio; a 3- to 30-membered heteroaryl unsubstituted or substituted with a (C6-C30)aryl; a (C6-C30)aryl unsubstituted or substituted with a (C1-C30)alkyl, a cyano, a 3- to 30-membered heteroaryl or a tri(C6-C30)arylsilyl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl; preferably, are each independently, deuterium or a (C1-C6)alkyl.

In formula 1, X represents $CR_{11}R_{12}$, O or S.

In formula 1, $R_1$ to $R_3$ are each independently hydrogen, deuterium, a substituted or unsubstituted (C1-C10)alkyl, or a substituted or unsubstituted (C6-C30)aryl; preferably, hydrogen, a substituted or unsubstituted (C1-C5)alkyl, or a substituted or unsubstituted (C6-C20)aryl; more preferably, hydrogen, an unsubstituted (C1-C4)alkyl, or a (C6-C15)aryl unsubstituted or substituted with a (C1-C4)alkyl. For example, $R_1$ to $R_3$ may be each independently hydrogen, methyl, isobutyl, tert-butyl, or phenyl unsubstituted or substituted with methyl, isobutyl, or tert-butyl.

In formula 1, $R_4$ represents hydrogen, or a substituted or unsubstituted (C1-C10)alkyl; and preferably, hydrogen.

In formula 1, L represents

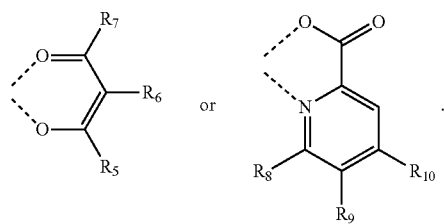

In formula 1, if L is

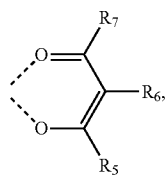

$R_5$ to $R_7$ are each independently hydrogen, deuterium, a substituted or unsubstituted (C1-C10)alkyl, or a substituted or unsubstituted (C6-C30)aryl; preferably, hydrogen, a substituted or unsubstituted (C1-C5)alkyl, or a substituted or unsubstituted (C6-C15)aryl; more preferably, hydrogen, an unsubstituted (C1-C15)alkyl, or an unsubstituted (C6-C15)aryl. For example, L may be hydrogen, methyl, isobutyl, tert-butyl, pentyl, or phenyl.

In formula 1, if L is

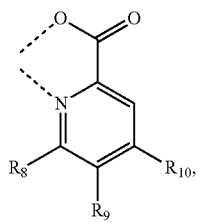

$R_8$ to $R_{10}$ may be each independently hydrogen, deuterium, a substituted or unsubstituted (C1-C10)alkyl, or a substituted or unsubstituted (C6-C30)aryl or at least two of $R_8$ to $R_{10}$ may be linked to each other as an adjacent substituent to form a substituted or unsubstituted 9- to 20-membered heteroaryl including the pyridine ring linked to $R_8$ to $R_{10}$, and the heteroaryl may comprise one or more hetero atoms selected from a nitrogen, an oxygen, and a sulfur in addition to the nitrogen atom of the pyridine ring; preferably, hydrogen, a substituted or unsubstituted (C1-C5)alkyl, or a substituted or unsubstituted (C6-C20)aryl or at least two of $R_8$ to $R_{10}$ may be linked to an adjacent substituent to form a 9- to 16-membered heteroaryl which includes the pyridine ring linked to $R_8$ to $R_{10}$ and is unsubstituted or substituted with a (C1-C15)alkyl, and the heteroaryl may comprise one or more hetero atoms selected from a nitrogen, an oxygen, and a sulfur in addition to the nitrogen atom of the pyridine ring; and for example, hydrogen, methyl, or phenyl substituted with methyl or at least two of $R_8$ to $R_{10}$ may be linked to each other as an adjacent substituent to form a quinoline which includes the pyridine ring linked to $R_8$ to $R_{10}$ and is unsubstituted or substituted with a (C1-C6)alkyl.

In formula 1, $R_{11}$ and $R_{12}$ are each independently, a substituted or unsubstituted (C1-C10)alkyl, or a substituted or unsubstituted (C6-C30)aryl. $R_{11}$ and $R_{12}$ each independently may be preferably a substituted or unsubstituted (C1-C5)alkyl, or a substituted or unsubstituted (C6-C20) aryl; more preferably, a (C1-C4)alkyl unsubstituted or substituted with deuterium, or an unsubstituted (C6-C15)aryl; and for example, methyl unsubstituted or substituted with deuterium, ethyl unsubstituted or substituted with deuterium, or phenyl.

In formula 1, m and n, each independently, represent an integer of 0 to 4; o represents an integer of 0 to 2; and where m, n or o is an integer of 2 or more, each of $R_1$, each of $R_2$, or each of $R_3$ may be the same or different.

According to one embodiment of the present disclosure, in formula 1, X may represent $CR_{11}R_{12}$, O or S; $R_1$ to $R_3$ may be each independently hydrogen, a substituted or unsubstituted (C1-C5)alkyl, or a substituted or unsubstituted (C6-C20)aryl; $R_4$ may represent hydrogen; L may represent

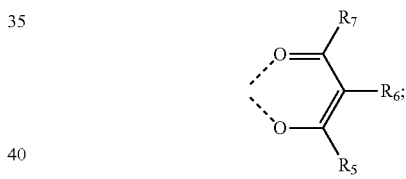

$R_5$ to $R_7$ may be each independently hydrogen, a substituted or unsubstituted (C1-C5)alkyl, or a substituted or unsubstituted (C6-C15)aryl; $R_{11}$ and $R_{12}$ may be each independently, a substituted or unsubstituted (C1-C5)alkyl, or a substituted or unsubstituted (C6-C20)aryl; m and n, each independently, represent an integer of 0 to 4; o represents an integer of 0 to 2; and where m, n or o is an integer of 2 or more, each of $R_1$, each of $R_2$, or each of $R_3$ may be the same or different.

According to another embodiment of the present disclosure, in formula 1, X may represent $CR_{11}R_{12}$, O or S; $R_1$ to $R_3$ may be each independently hydrogen, a substituted or unsubstituted (C1-C5)alkyl, or a substituted or unsubstituted (C6-C20)aryl; $R_4$ may represent hydrogen; L may represent

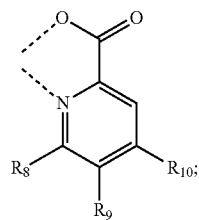

$R_8$ to $R_{10}$ may be each independently hydrogen, a substituted or unsubstituted (C1-C5)alkyl, or a substituted or unsubstituted (C6-C20)aryl, or at least two of $R_8$ to $R_{10}$ may be linked to each other as an adjacent substituent to form a 9- to 16-membered heteroaryl which includes the pyridine ring linked to $R_5$ to $R_{10}$ and is unsubstituted or substituted with a (C1-C15)alkyl, and the heteroaryl may comprise one or more hetero atoms selected from a nitrogen, an oxygen, and a sulfur in addition to a nitrogen atom of the pyridine ring; $R_{11}$ and $R_{12}$ may be each independently, a substituted or unsubstituted (C1-C5)alkyl, or a substituted or unsubstituted (C6-C20)aryl; m and n, each independently, may represent an integer of 0 to 4; o may represent an integer of 0 to 2; and where m, n or o is an integer of 2 or more, each of $R_1$, each of $R_2$, or each of $R_3$ may be the same or different.

According to another embodiment of the present disclosure, in formula 1, X may represent $CR_{11}R_{12}$, O or S; $R_1$ to $R_3$ may be each independently hydrogen, an unsubstituted (C1-C4)alkyl, or a (C6-C15)aryl unsubstituted or substituted with a (C1-C4)alkyl; $R_4$ may represent hydrogen; L may represent

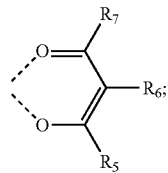

$R_5$ to $R_7$ may be each independently hydrogen, an unsubstituted (C1-C15)alkyl, or an unsubstituted (C6-C15)aryl; $R_{11}$ and $R_{12}$ may be each independently a (C1-C4)alkyl unsubstituted or substituted with deuterium, or an unsubstituted (C6-C15)aryl; m and n, each independently, may represent an integer of 0 to 4; o may represent an integer of 0 to 2; and where m, n or o is an integer of 2 or more, each of $R_1$, each of $R_2$, or each of $R_3$ may be the same or different.

According to another embodiment of the present disclosure, in formula 1, X may represent $CR_{11}R_{12}$, O or S; $R_1$ to $R_3$ may be each independently hydrogen, an unsubstituted (C1-C4)alkyl, or a (C6-C15)aryl unsubstituted or substituted with a (C1-C4)alkyl; $R_4$ may represent hydrogen; L may represent

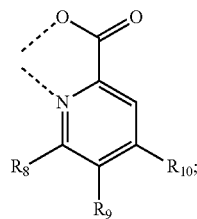

$R_8$ to $R_{10}$ may be each independently hydrogen, methyl, or phenyl substituted with methyl; or at least two of $R_8$ to $R_{10}$ may be linked to each other as an adjacent substituent to form a quinoline which includes the pyridine ring linked to $R_8$ to $R_{10}$ and is unsubstituted or substituted with a (C1-C6) alkyl; $R_{11}$ and $R_{12}$ may be each independently, a (C1-C4) alkyl unsubstituted or substituted with deuterium, or an unsubstituted (C6-C15)aryl; m and n, each independently, may represent an integer of 0 to 4; o may represent an integer of 0 to 2; and where m, n or o is an integer of 2 or more, each of $R_1$, each of $R_2$, or each of $R_3$ may be the same or different.

According to another embodiment of the present disclosure, in formula 1, X may represent $CR_{11}R_{12}$, O or S; $R_1$ to $R_3$ may be each independently hydrogen, methyl, isobutyl, tert-butyl, or phenyl unsubstituted or substituted with methyl, isobutyl, or tert-butyl; $R_4$ may represent hydrogen; L may represent

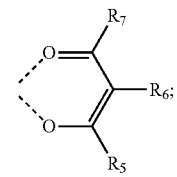

$R_5$ to $R_7$ may be each independently hydrogen, methyl, isobutyl, tert-butyl, pentyl, or phenyl; $R_{11}$ and $R_{12}$ may be each independently methyl unsubstituted or substituted with deuterium, ethyl unsubstituted or substituted with deuterium, or phenyl; m and n, each independently, may represent an integer of 0 to 4; o may represent an integer of 0 to 2; and where m, n or o is an integer of 2 or more, each of $R_1$, each of $R_2$, or each of $R_3$ may be the same or different.

According to another embodiment of the present disclosure, in formula 1, X may represent $CR_{11}R_{12}$, O or S; $R_1$ to $R_3$ may be each independently hydrogen, methyl, isobutyl, tert-butyl, or phenyl unsubstituted or substituted with methyl, isobutyl, or tert-butyl; $R_4$ may represent hydrogen; L may represent

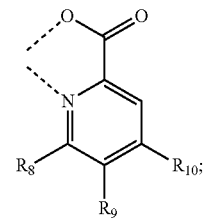

$R_8$ to $R_{10}$ may be each independently hydrogen, methyl, or phenyl substituted with methyl; or at least two of $R_8$ to $R_{10}$ may be linked to each other as an adjacent substituent to form a quinoline which includes the pyridine ring linked to $R_8$ to $R_{10}$ and is unsubstituted or substituted with a (C1-C6) alkyl; $R_{11}$ and $R_{12}$ may be each independently methyl unsubstituted or substituted with deuterium, ethyl unsubstituted or substituted with deuterium, or phenyl; m and n, each independently, may represent an integer of 0 to 4; o may represent an integer of 0 to 2; and where m, n or o is an integer of 2 or more, each of $R_1$, each of $R_2$, or each of $R_3$ may be the same or different.

The compound represented by formula 1 includes the following compounds, but is not limited thereto:

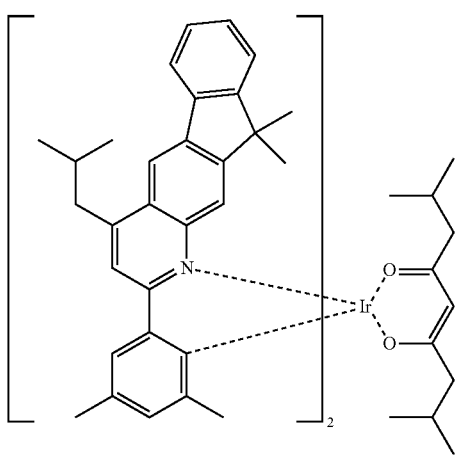
D-1
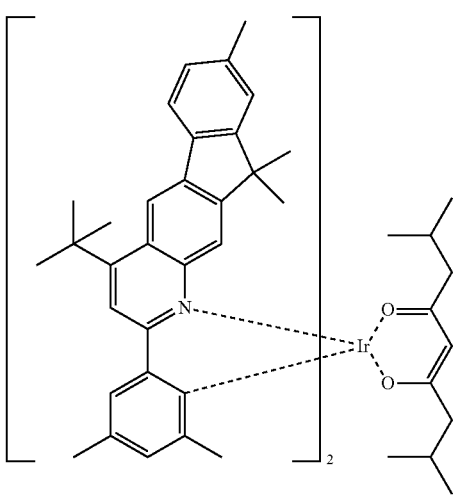
D-4
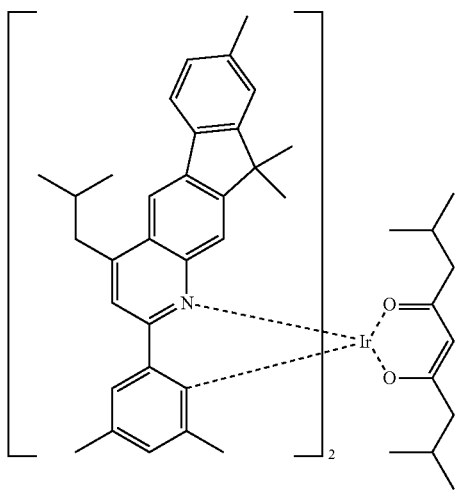
D-2
D-5
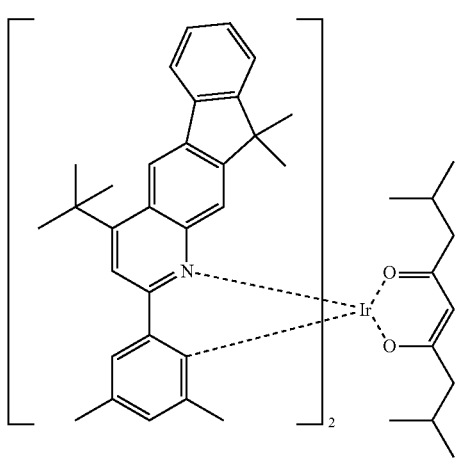
D-3
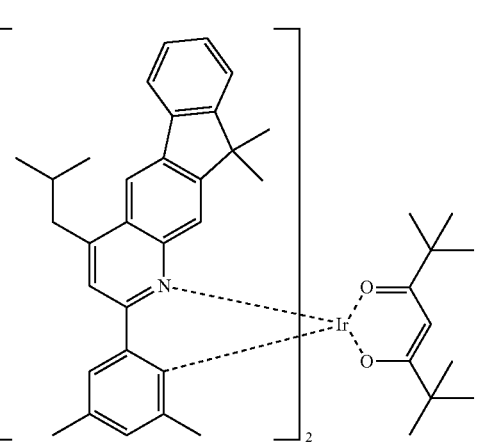
D-6

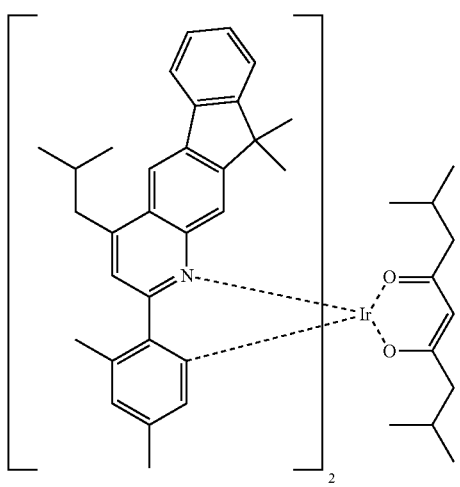
D-7
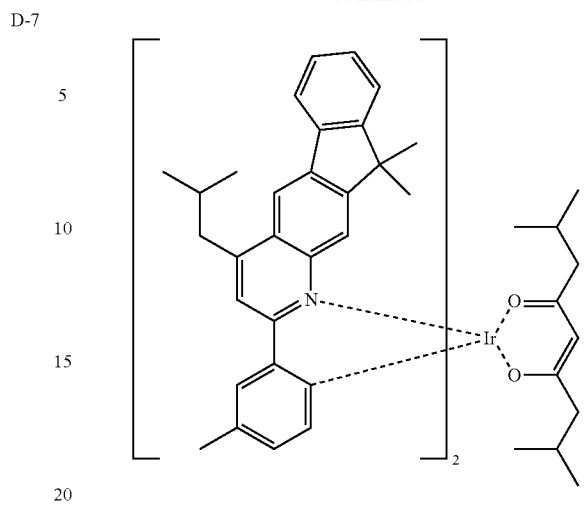
D-10
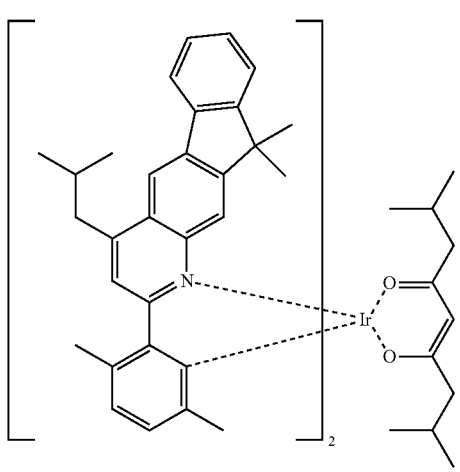
D-8
D-11
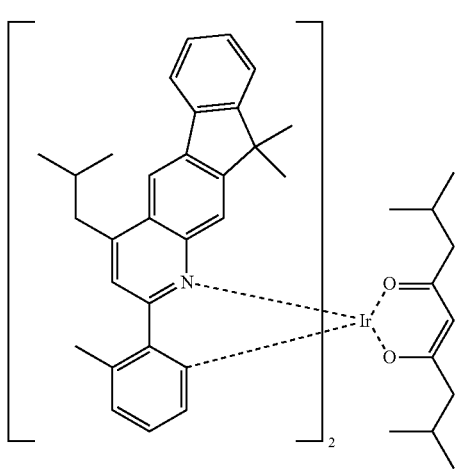
D-9
D-12

D-13
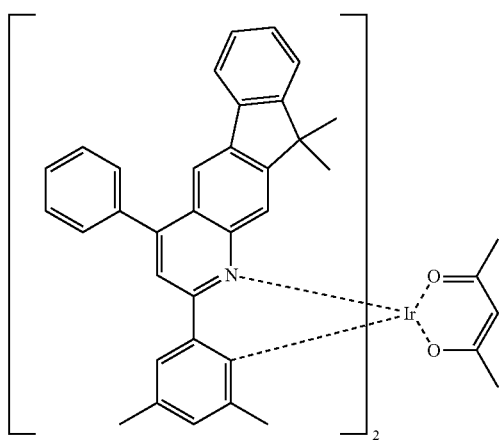
D-14
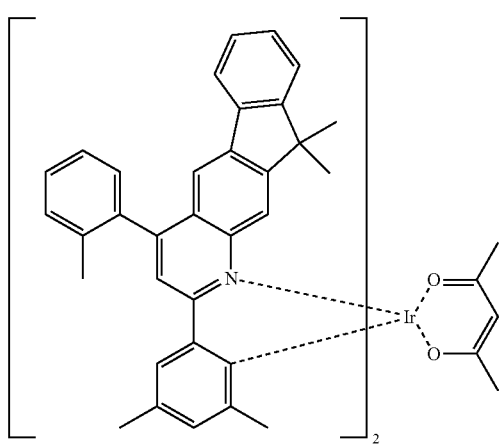
D-15
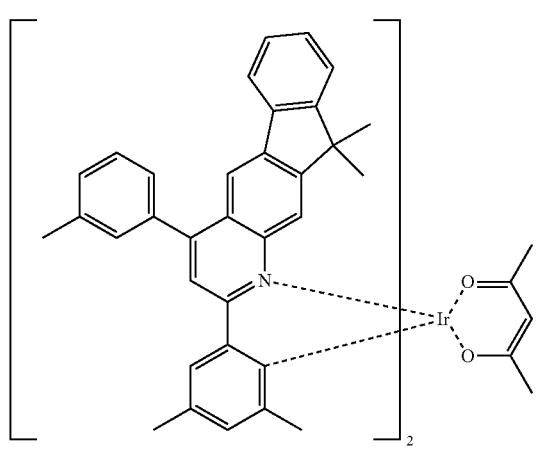
D-16
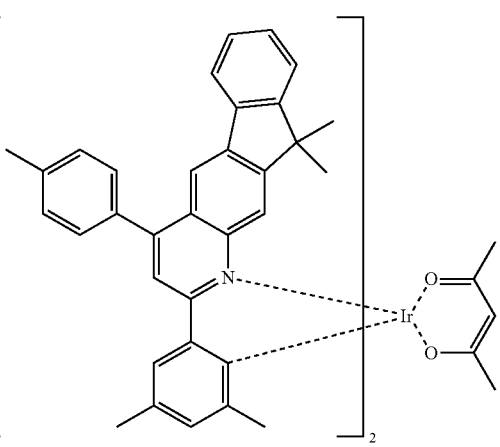
D-17
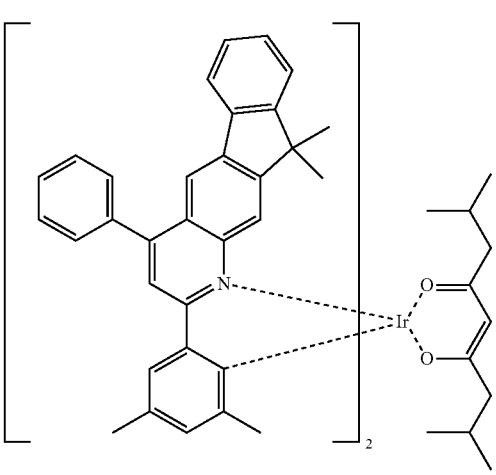
D-18
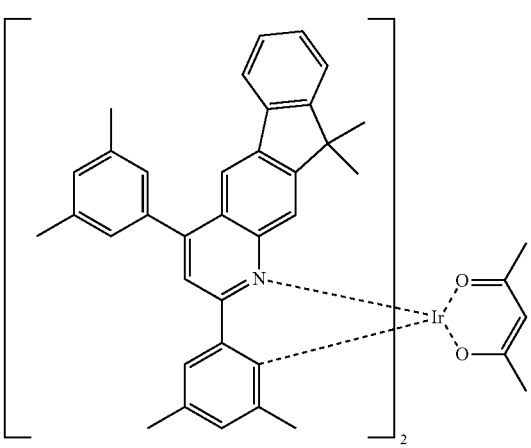

D-19
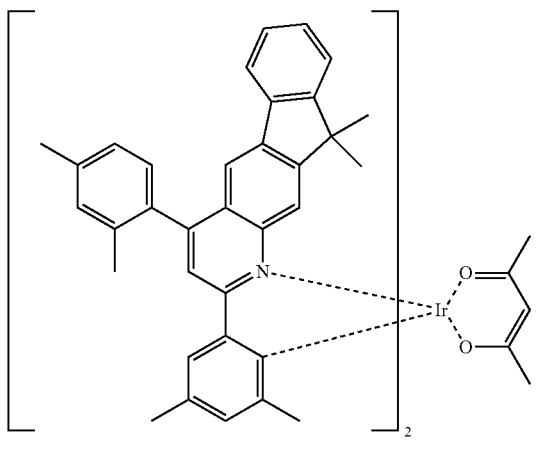
D-20
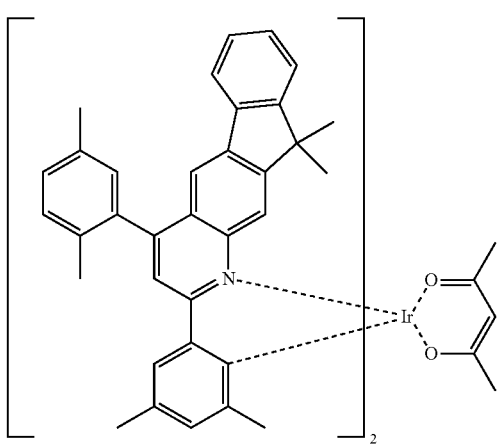
D-21
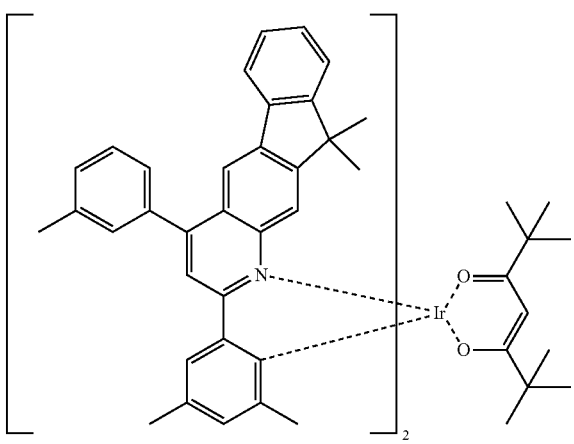
D-22
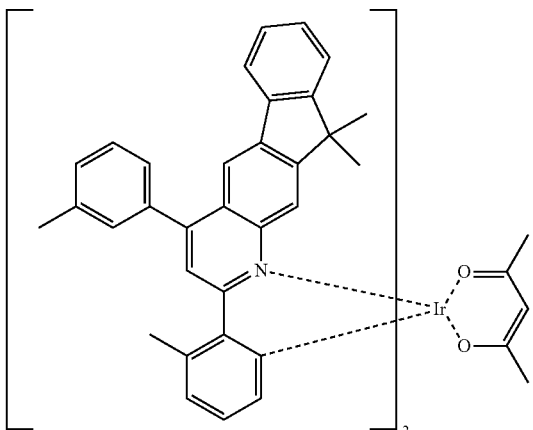
D-23
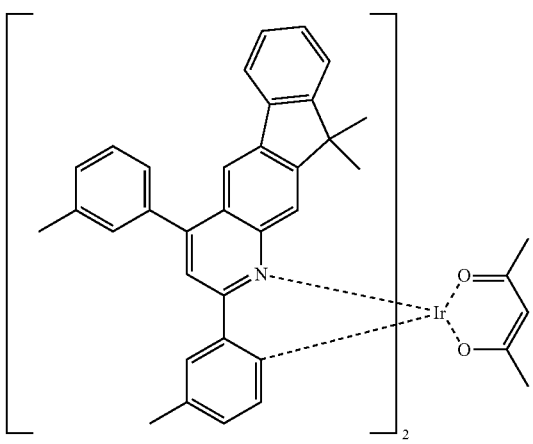
D-24
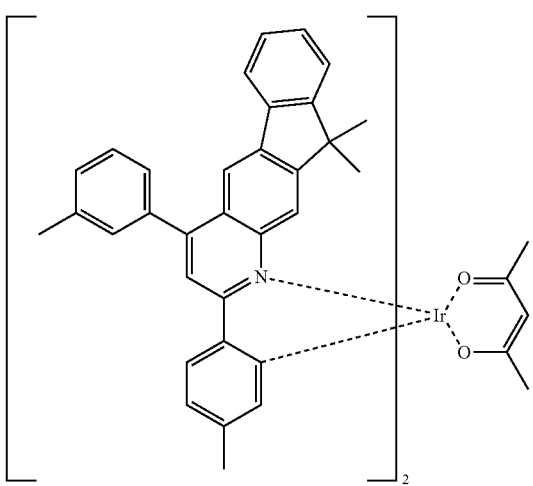

D-25
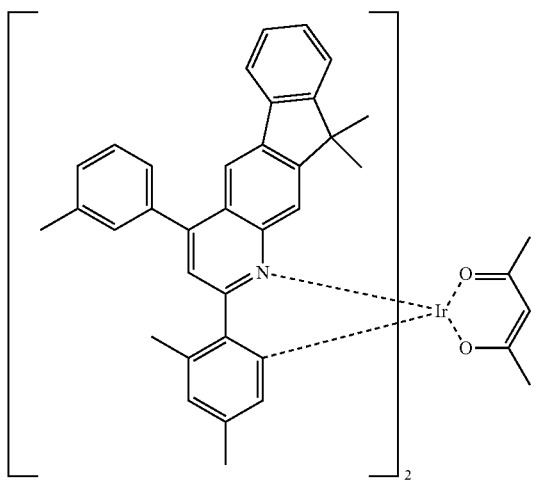
D-26
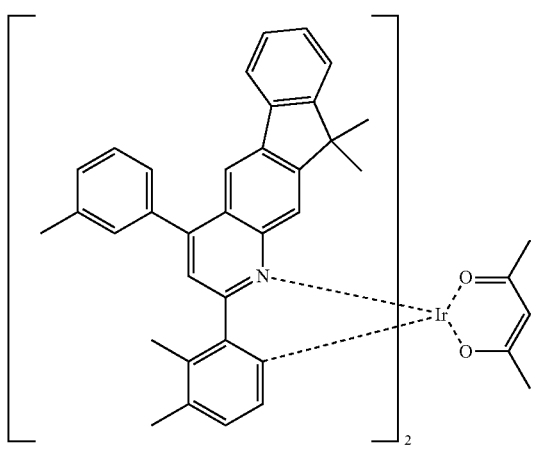
D-27
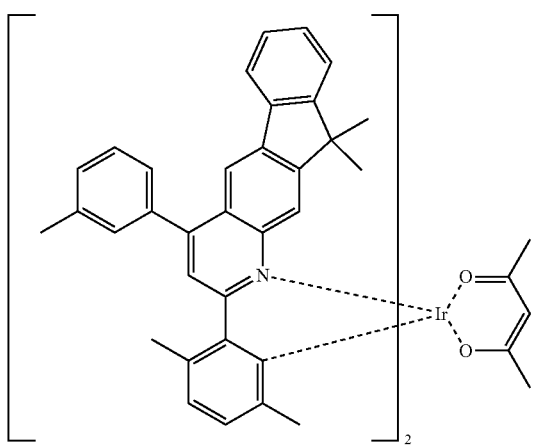
D-28
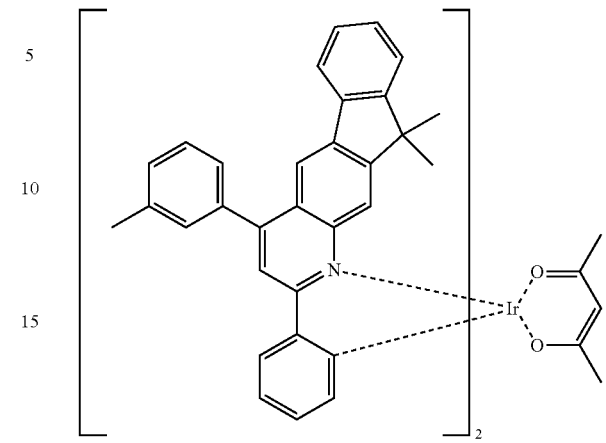
D-29
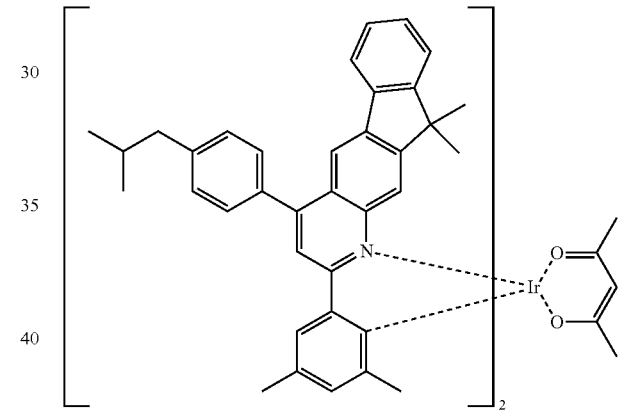
D-30
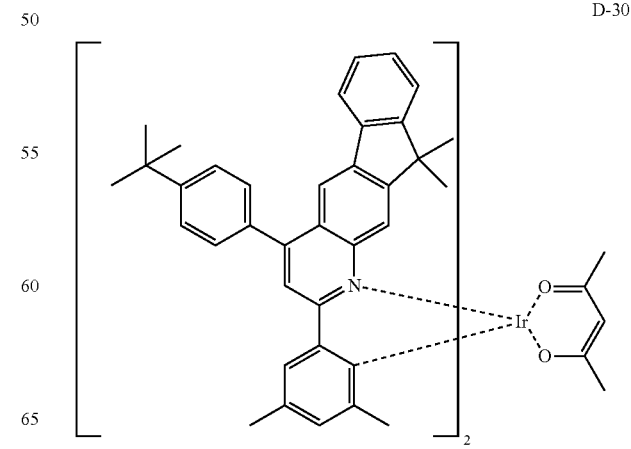

-continued
D-31
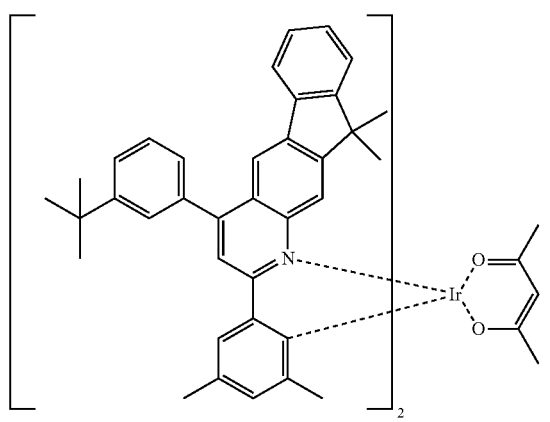
D-32
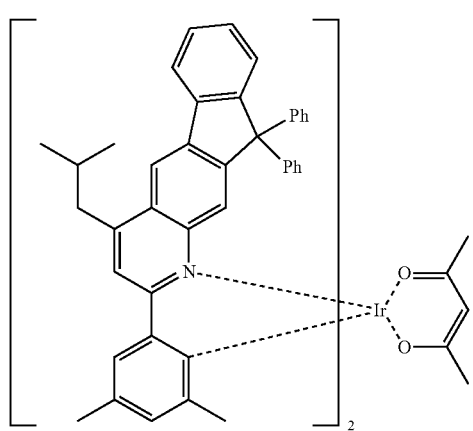
D-33
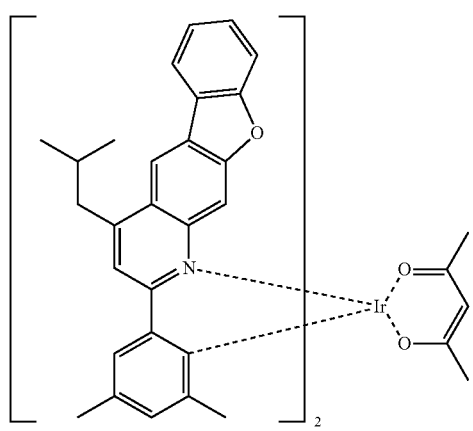
-continued
D-34
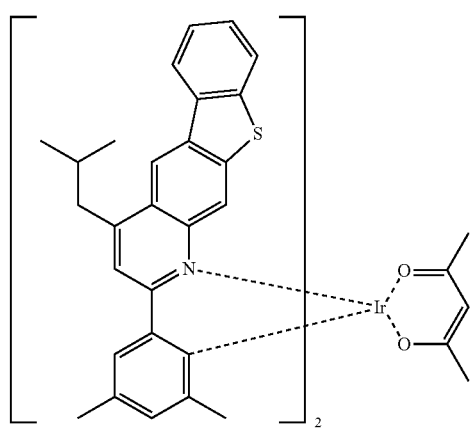
D-35
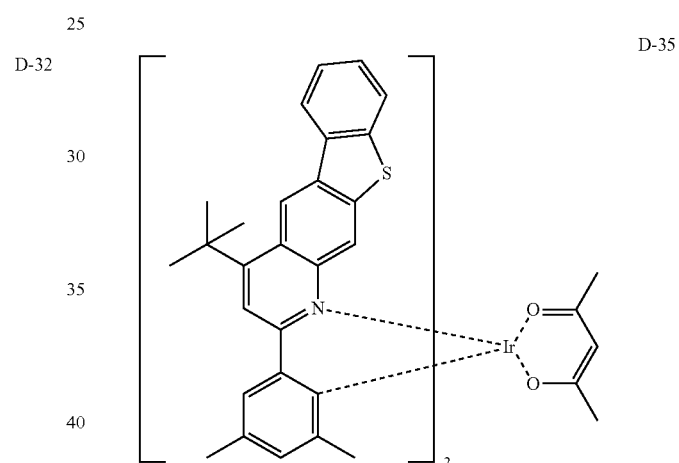
D-36
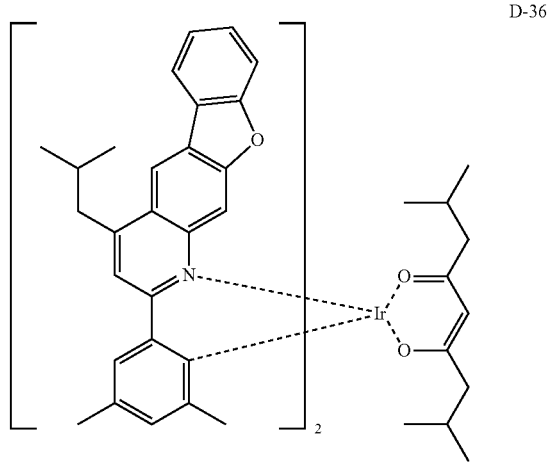

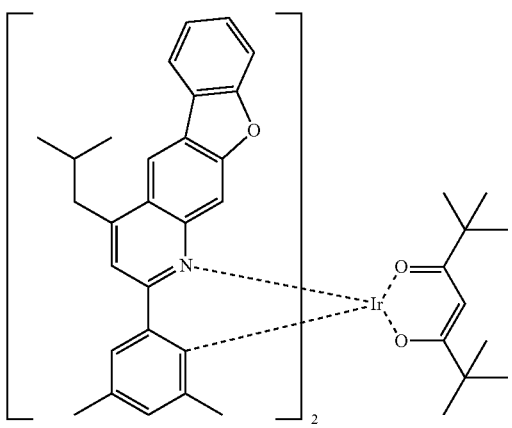
D-37
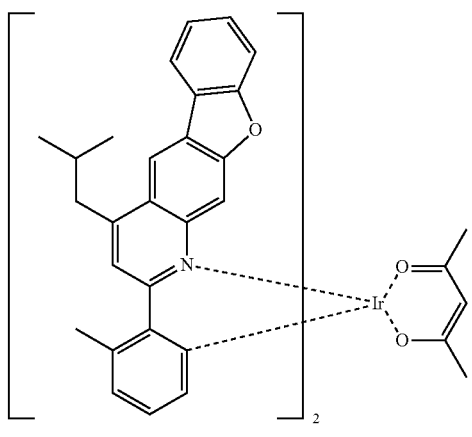
D-40
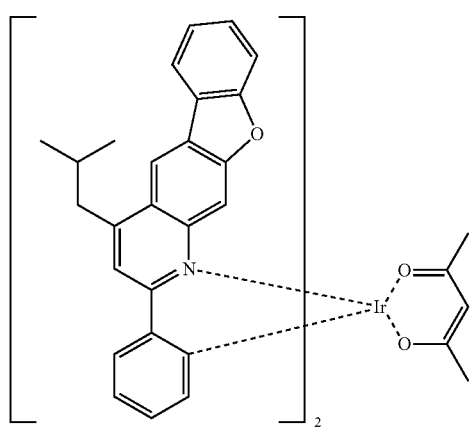
D-38
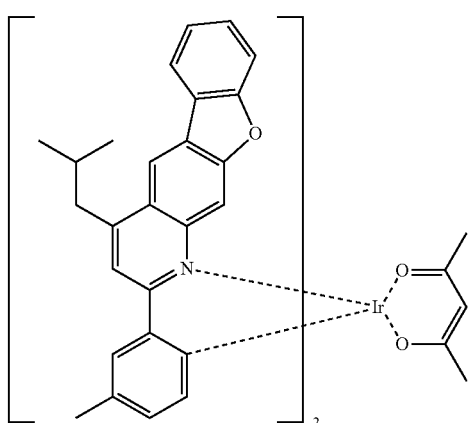
D-41
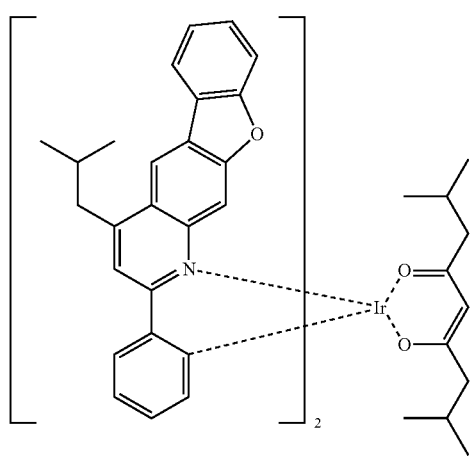
D-39
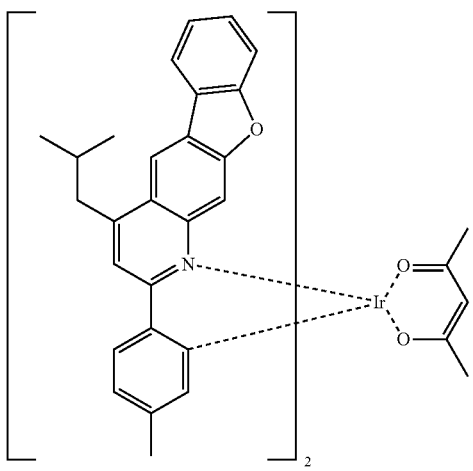
D-42

-continued
D-43
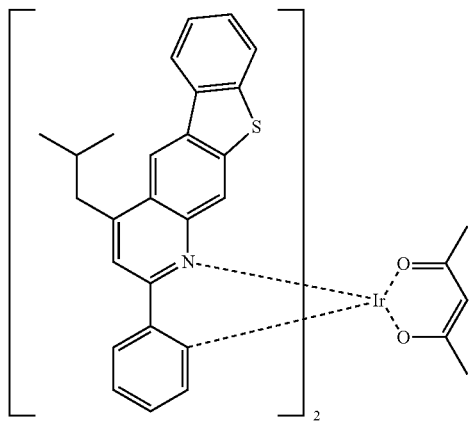
D-44
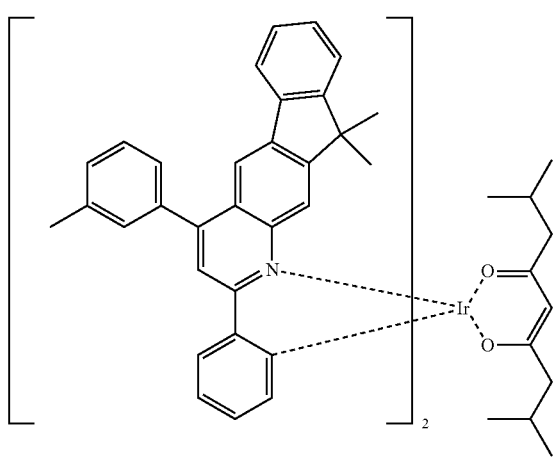
D-45
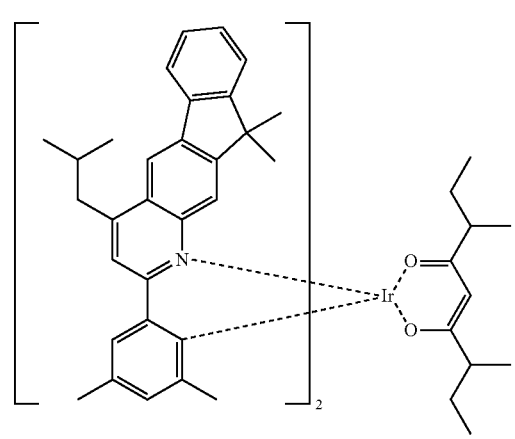
-continued
D-46
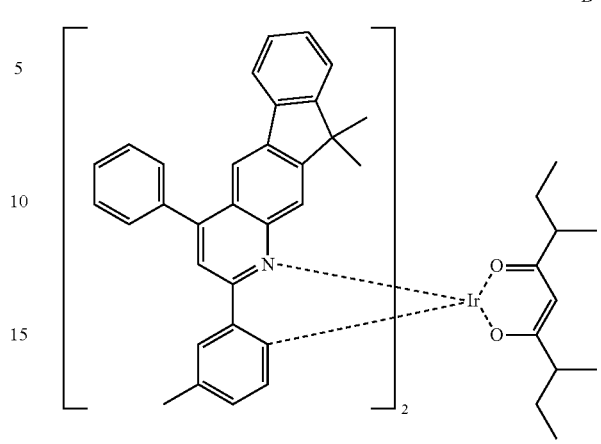
D-47
D-48
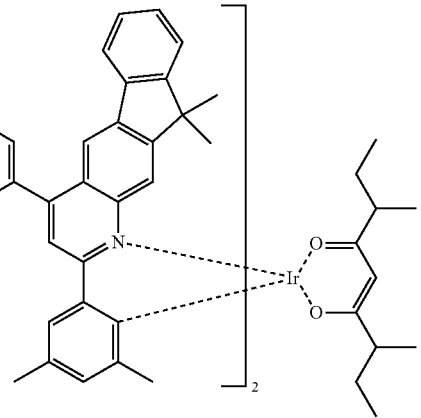

D-49
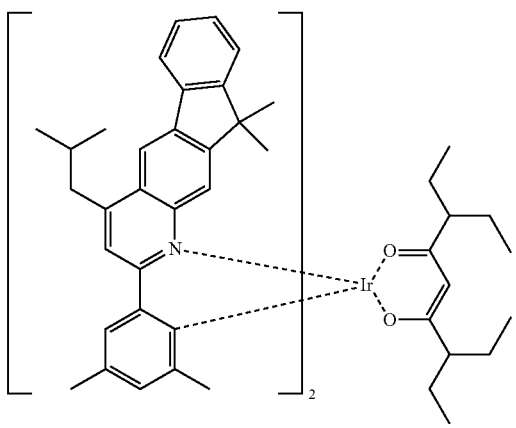
D-52
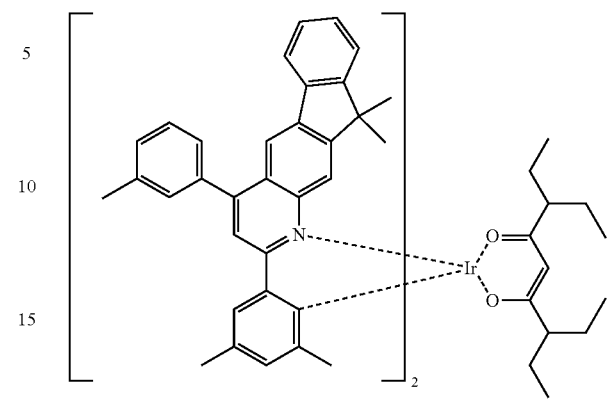
D-50
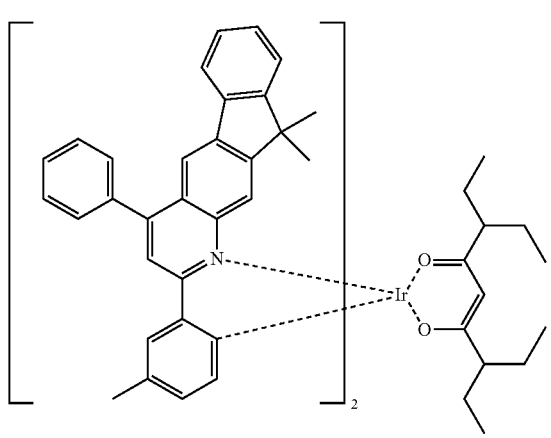
D-53
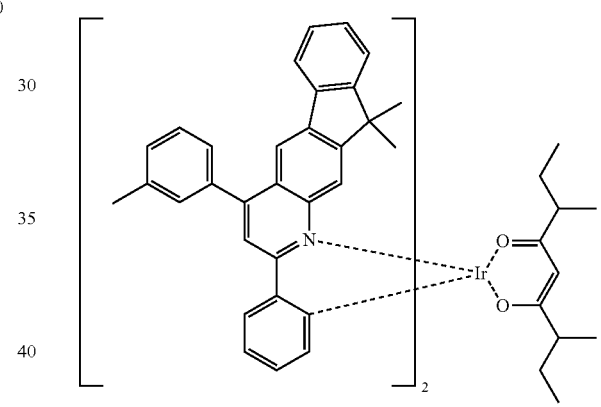
D-51
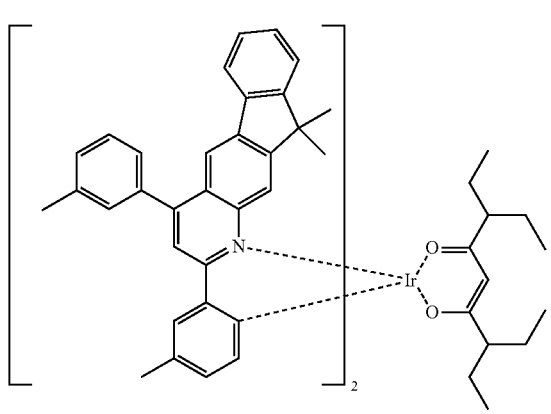
D-54
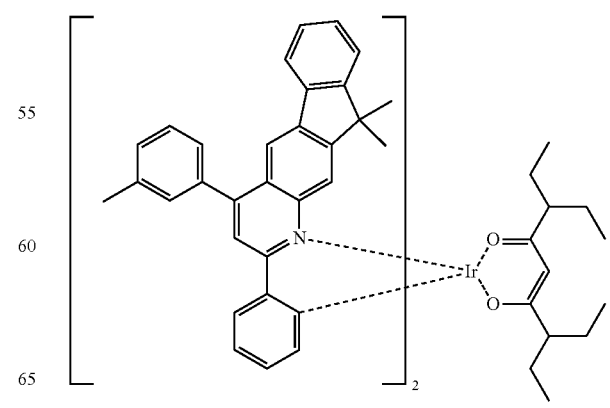

D-55
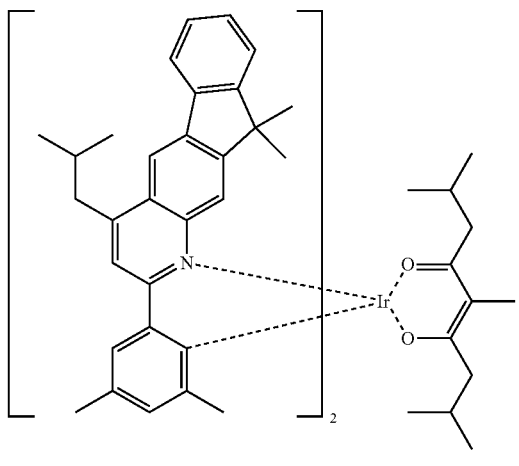
D-56
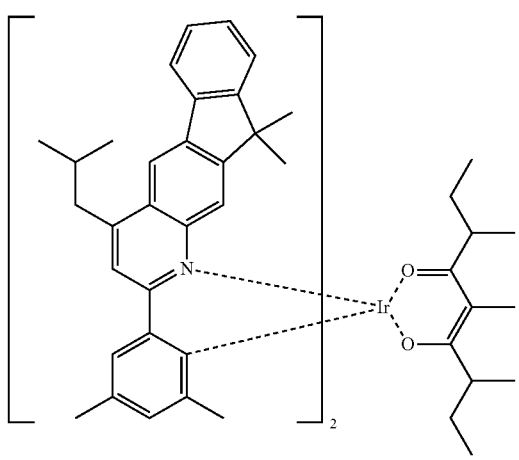
D-57
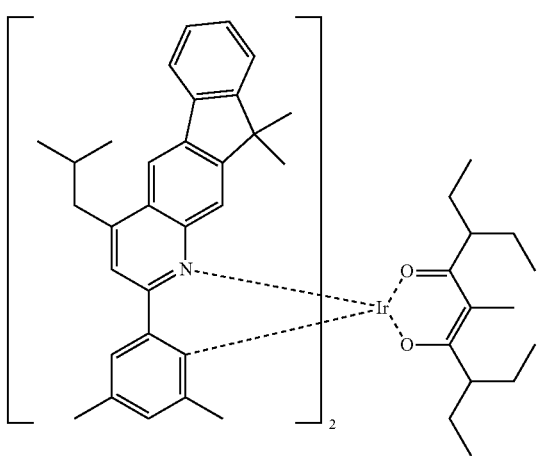
D-58
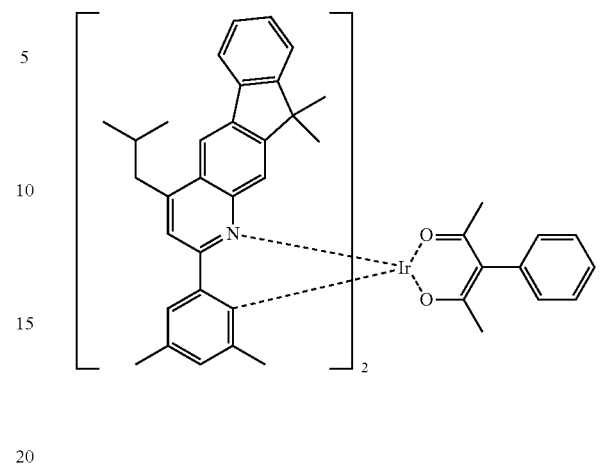
D-59
D-60
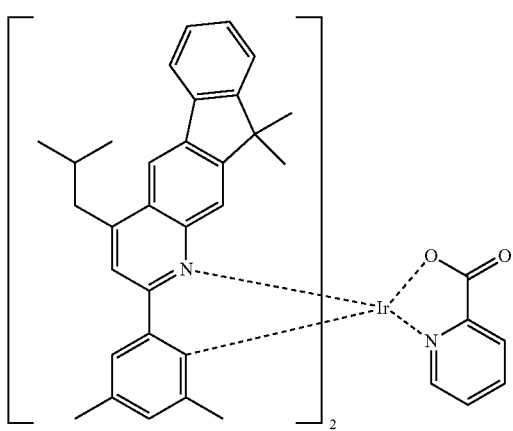

D-61
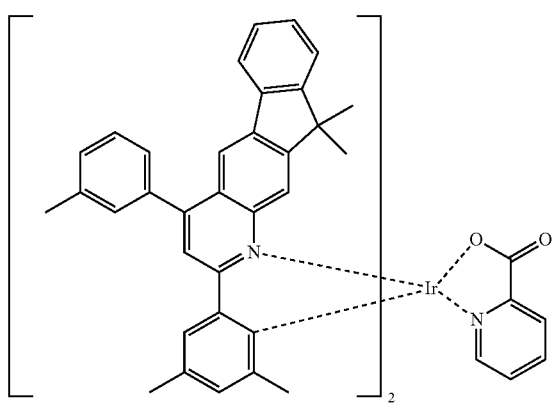
D-64
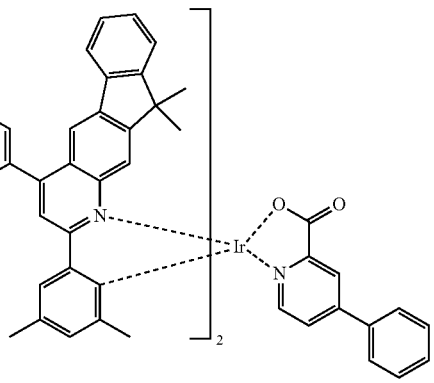
D-62
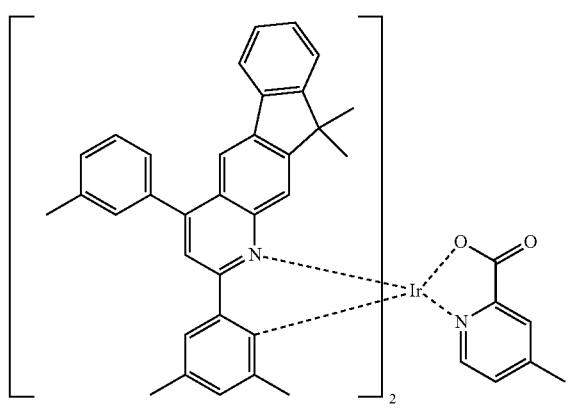
D-65
D-63
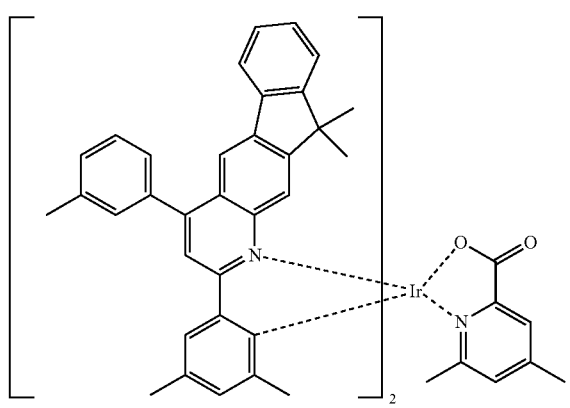
D-66
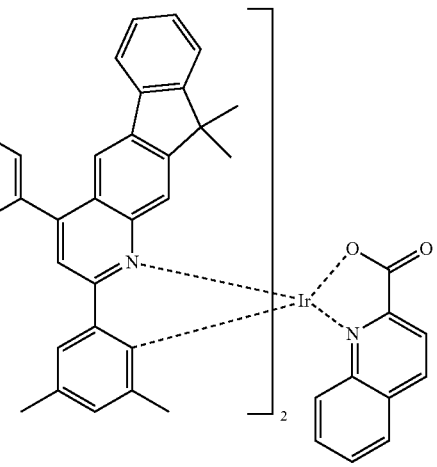

D-67
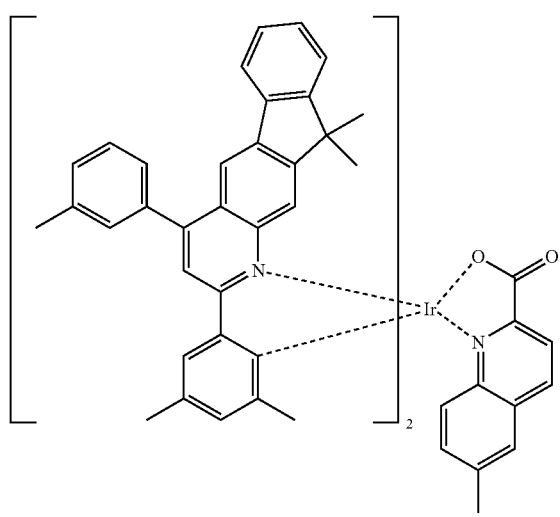
D-68
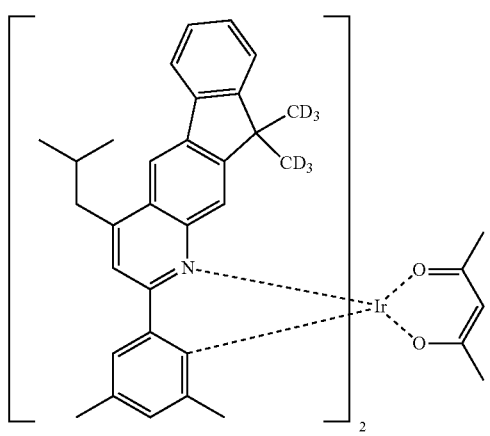
D-69
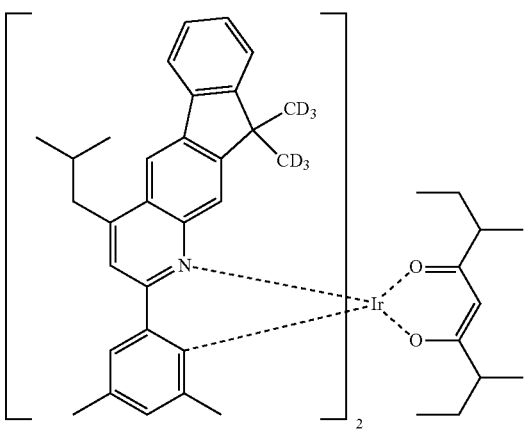
D-70
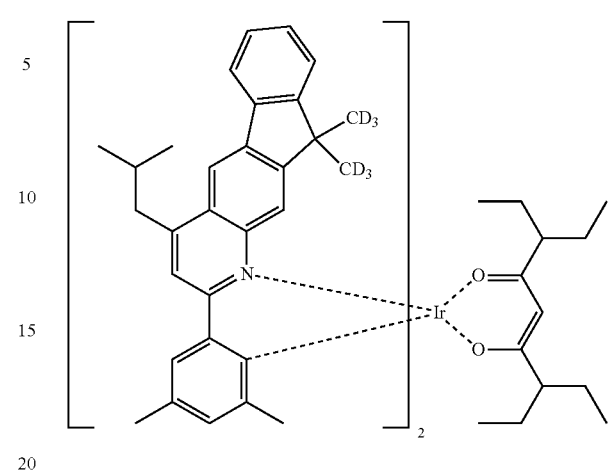
D-71
D-72
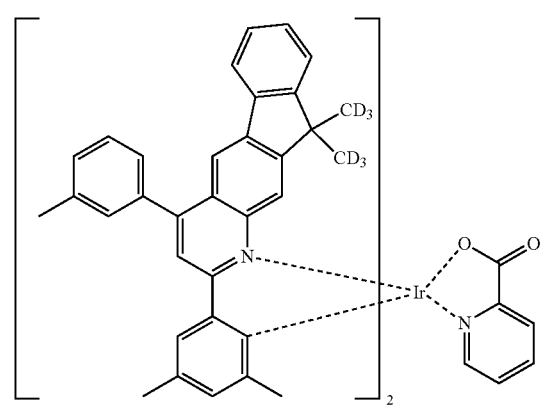

D-73
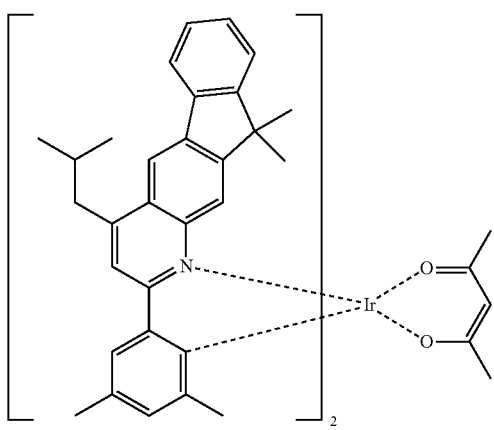
D-74
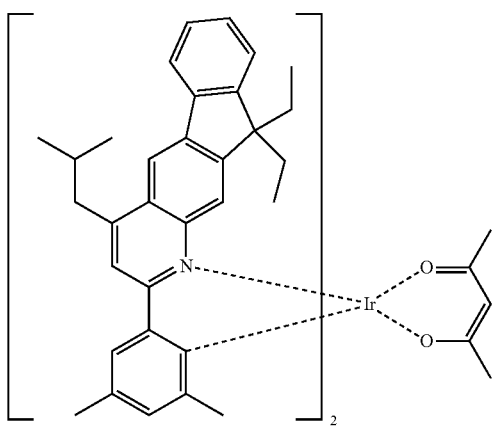
D-75
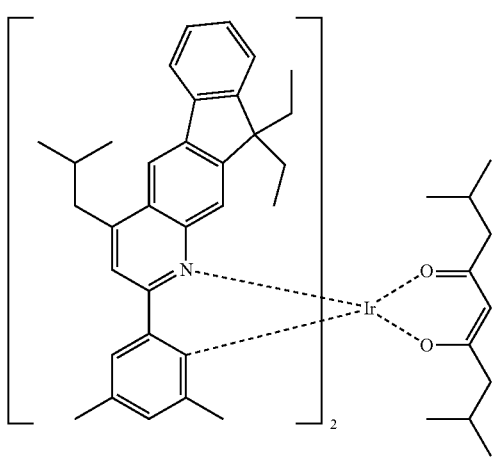
D-76
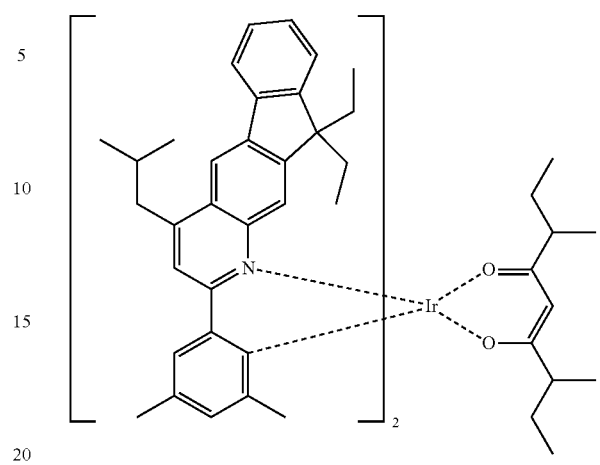
D-77
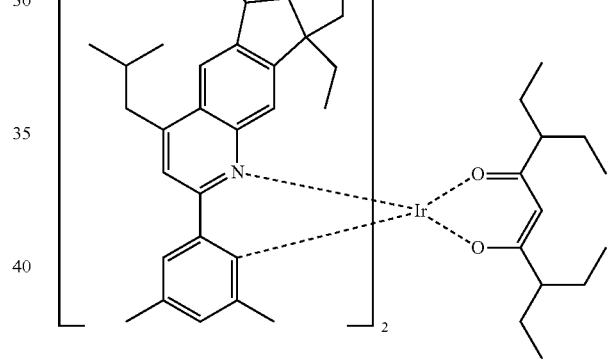
D-78
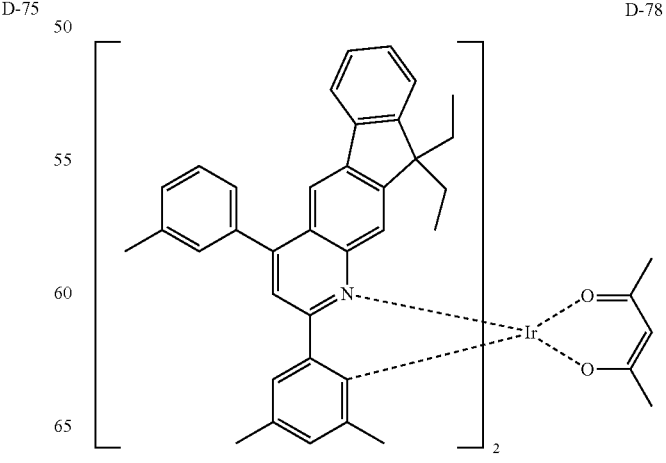

D-79
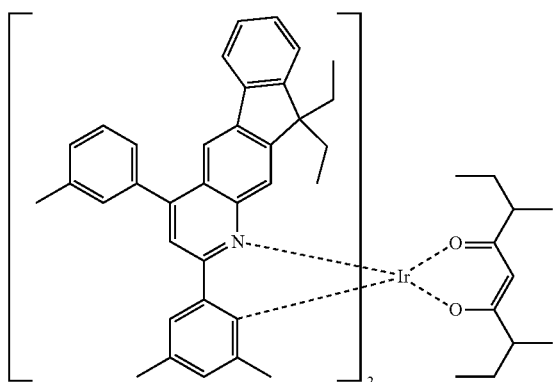
D-80
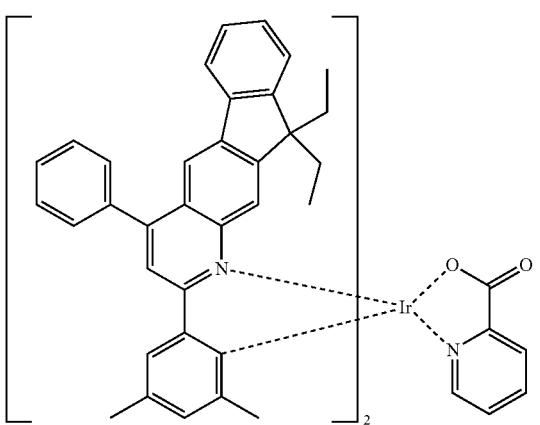
D-81
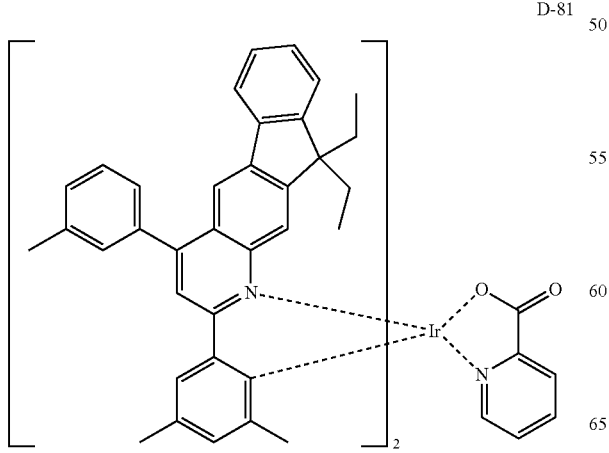
D-82
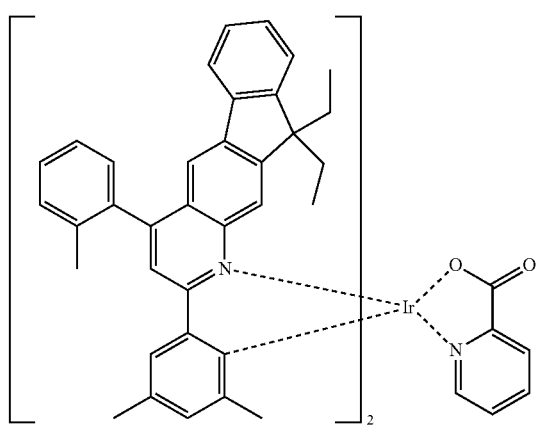
D-83
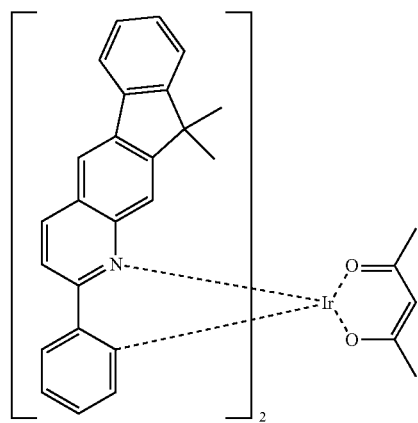
D-84
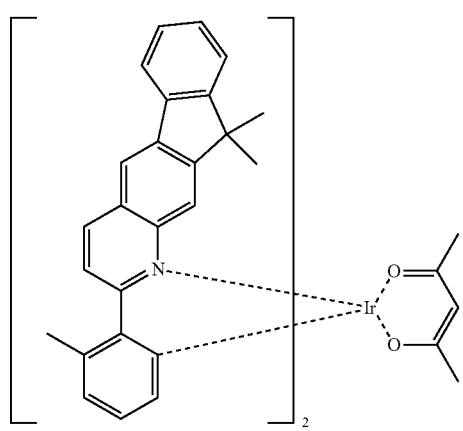

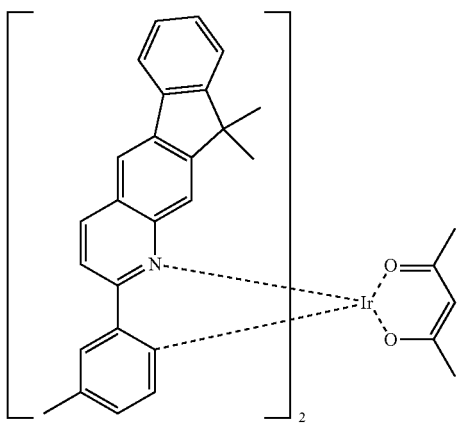
D-85
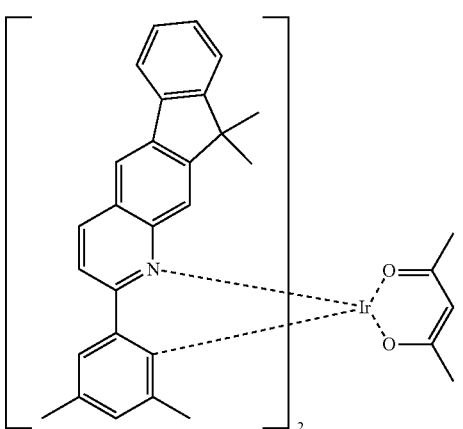
D-88
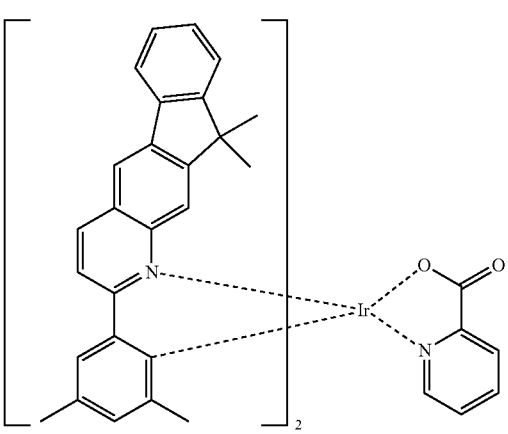
D-89
D-86
D-87
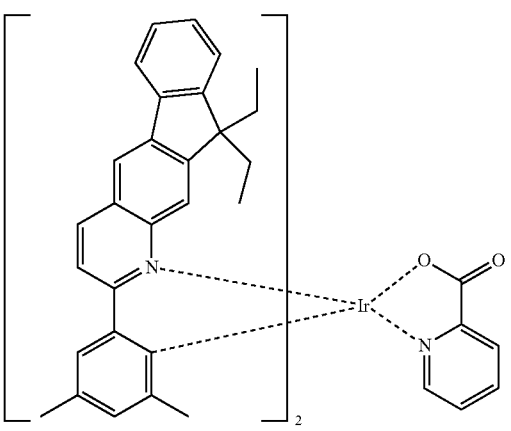
D-90

-continued
D-91
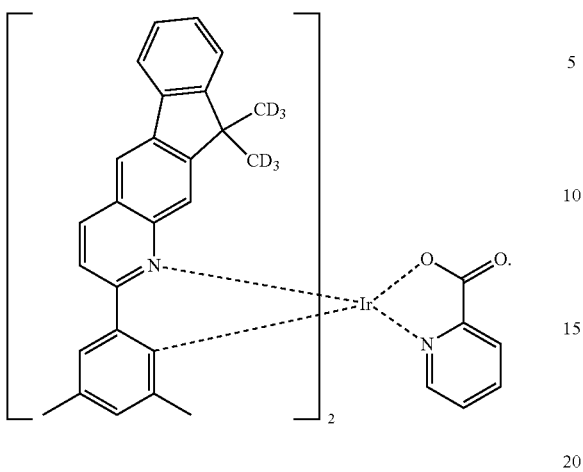
The compound according to the present disclosure may be produced by a synthetic method known to a person skilled in the art. For example, it may be produced by the following reaction scheme 1:
[Reaction Scheme 1]
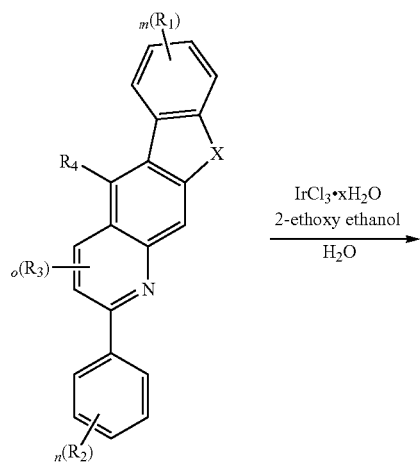
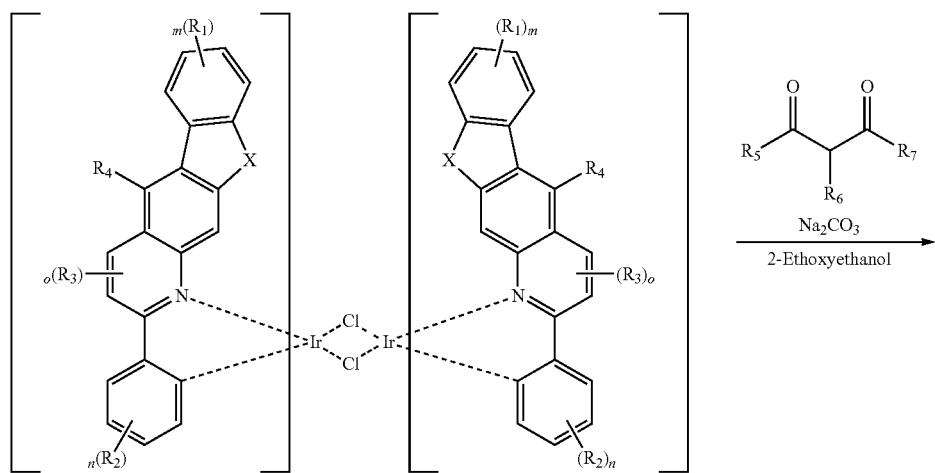

-continued

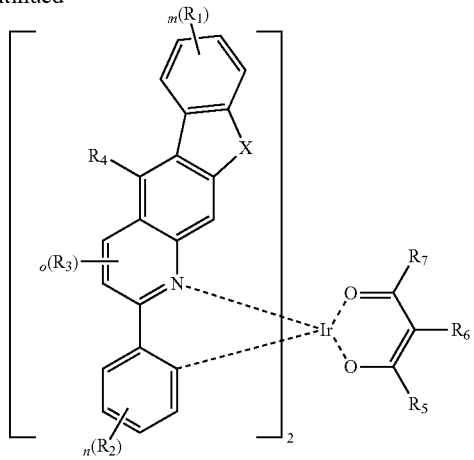

wherein, $R_1$ to $R_7$, X, m, n, and o are as defined in formula 1.

The present disclosure also discloses an organic electroluminescent material comprising the compound of formula 1, and an organic electroluminescent device comprising the material.

The organic electroluminescent material may consist of the organic electroluminescent compound of the present disclosure as a sole compound, or may further comprise conventional materials generally used in organic electroluminescent materials.

The organic electroluminescent device of the present disclosure may comprise a first electrode, a second electrode, and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron buffer layer, and an electron blocking layer.

Herein, the light-emitting auxiliary layer may be placed between the anode and the light-emitting layer, or the cathode and the light-emitting layer, which may be used for facilitating the injection and/or transport of the hole or for blocking the overflow of the electron when placed between the anode and the light-emitting layer, or which may be used for facilitating the injection and/or transport of the electron or for blocking the overflow of the hole when placed between the cathode and the light-emitting layer. In addition, the hole auxiliary layer is placed between the hole transport layer (or the hole injection layer) and the light-emitting layer, which may exhibit facilitating a transport rate (or injection rate) of a hole or blocking a hole, thereby controlling a charge balance. In addition, the electron blocking layer is placed between the hole transport layer (or the hole injection layer) and the light-emitting layer, which prevents light leakage by blocking the overflow of the electron from the light-emitting layer and confining excitons in the light-emitting layer. If two or more hole transport layers are included, the additional hole transport layer(s), which is (are) included in addition to the hole transport layer, may be used as the hole auxiliary layer or electron blocking layer.

The hole auxiliary layer or the electron blocking layer provides excellent efficiencies and improved lifespan of an organic electroluminescent device.

The compound represented by formula 1 of the present disclosure is a dopant material, which may be included in the light-emitting layer. In addition, the light-emitting layer may further include one or more host materials.

The host compounds which are capable of being used with the compound of the present disclosure may be the following compounds represented by formula 2.

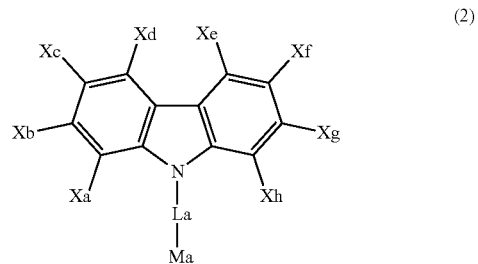

wherein

Ma represents a substituted or unsubstituted, nitrogen-containing 5- to 11-membered heteroaryl; La represents a single bond, or a substituted or unsubstituted (C6-C30) arylene;

Xa to Xh, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted (C1-C30)alkyl(C6-C30)arylamino, or a substituted or unsubstituted mono- or di-(C6-C30)arylamino; or may be linked to an adjacent substituent(s) to form a substituted or unsubstituted (C3-C30) mono- or polycyclic, alicyclic or aromatic ring, whose carbon atom(s) may be replaced with at least one hetero atom selected from the group consisting of nitrogen, oxygen, and sulfur; and the heteroaryl contains at least one hetero atom selected from B, N, O, S, Si, and P.

In formula 2, the substituents of a substituted alkyl, a substituted alkenyl, a substituted alkynyl, a substituted cycloalkyl, a substituted aryl, a substituted heteroaryl, a substituted trialkylsilyl, a substituted triarylsilyl, a substituted dialkylarylsilyl, a substituted alkyldiarylsilyl, a substituted alkylarylamino, a substituted monoarylamino, a substituted diarylamino, or a substituted mono- or polycyclic, alicyclic or aromatic ring may be each independently, at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a 3- to 7-membered heterocycloalkyl; a (C6-C30)aryloxy; a (C6-C30)arylthio; a 3- to 30-membered heteroaryl unsubstituted or substituted with a tri(C6-C30)arylsilyl, a (C6-C30)aryl, a (C1-C30)alkyl(C6-C30)aryl, or a tri(C6-C30)arylsilyl(C6-C30)aryl; a (C6-C30)aryl unsubstituted or substituted with a (C1-C30)alkyl, a halogen, a (C6-C30)aryl or a 3- to 30-membered heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

In formula 2, La may represent preferably, a single bond, or a substituted or unsubstituted (C6-C12)arylene; and more preferably, a single bond, or a (C6-C12)arylene unsubstituted or substituted with a tri(C6-C10)arylsilyl. Specifically, La may represent a single bond, a substituted or unsubstituted phenylene, a substituted or unsubstituted naphthylene, or a substituted or unsubstituted biphenylene.

In formula 2, Ma may represent preferably, a substituted or unsubstituted, nitrogen-containing 5- to 11-membered heteroaryl; and more preferably, a nitrogen-containing 6- to 11-membered heteroaryl unsubstituted or substituted with a cyano, a (C1-C6)alkyl, a tri(C6-C12)arylsilyl, a (C6-C18) aryl, or a 5- to 15-membered heteroaryl.

Specifically, Ma may represent a substituted or unsubstituted pyrrolyl, a substituted or unsubstituted imidazolyl, a substituted or unsubstituted pyrazolyl, a substituted or unsubstituted triazinyl, a substituted or unsubstituted tetrazinyl, a substituted or unsubstituted triazolyl, a substituted or unsubstituted tetrazolyl, a substituted or unsubstituted pyridyl, a substituted or unsubstituted pyrazinyl, a substituted or unsubstituted pyrimidinyl, a substituted or unsubstituted pyridazinyl, a substituted or unsubstituted benzimidazolyl, a substituted or unsubstituted isoindolyl, a substituted or unsubstituted indolyl, a substituted or unsubstituted indazolyl, a substituted or unsubstituted benzothiadiazolyl, a substituted or unsubstituted quinolyl, a substituted or unsubstituted isoquinolyl, a substituted or unsubstituted cinnolinyl, a substituted or unsubstituted quinazolinyl, a substituted or unsubstituted naphthyridinyl, or a substituted or unsubstituted quinoxalinyl. More specifically, Ma may represent a substituted or unsubstituted triazinyl, a substituted or unsubstituted pyrimidinyl, a substituted or unsubstituted pyridyl, a substituted or unsubstituted quinolyl, a substituted or unsubstituted isoquinolyl, a substituted or unsubstituted quinazolinyl, a substituted or unsubstituted naphthyridinyl, or a substituted or unsubstituted quinoxalinyl.

Preferably, Xa to Xh, each independently, may represent hydrogen, a cyano, a substituted or unsubstituted (C6-C15) aryl, a substituted or unsubstituted 6- to 20-membered heteroaryl, or a substituted or unsubstituted tri(C6-C15) arylsilyl; or may be linked to an adjacent substituent(s) to form a substituted or unsubstituted 6- to 20-membered, mono- or polycyclic aromatic ring, whose carbon atom(s) may be replaced with at least one hetero atom selected from the group consisting of nitrogen, oxygen, and sulfur. More preferably, Xa to Xh, each independently, may represent hydrogen, a cyano, a (C6-C15)aryl unsubstituted or substituted with a tri(C6-C12)arylsilyl, or a 10- to 20-membered heteroaryl unsubstituted or substituted with a (C6-C12)aryl; or may be linked to an adjacent substituent(s) to form a substituted or unsubstituted benzene, a substituted or unsubstituted indole, a substituted or unsubstituted benzoindole, a substituted or unsubstituted indene, a substituted or unsubstituted benzofuran, or a substituted or unsubstituted benzothiophene. Specifically, at least one of Xa to Xh, for example, Xb, Xc, Xf, or Xg, each independently, may represent a substituted or unsubstituted dibenzothiophene, a substituted or unsubstituted dibenzofuran, a substituted or unsubstituted carbazole, or a substituted or unsubstituted benzocarbazole; or may be linked to an adjacent substituent(s) to form a substituted or unsubstituted benzene, a substituted or unsubstituted indole, a substituted or unsubstituted benzindole, a substituted or unsubstituted indene, a substituted or unsubstituted benzofuran, or a substituted or unsubstituted benzothiophene.

More specifically, the compound of formula 2 includes the following, but is not limited thereto.

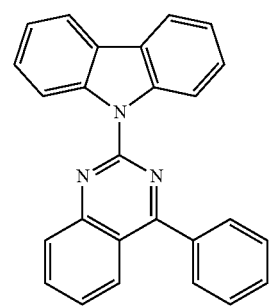

H2-1

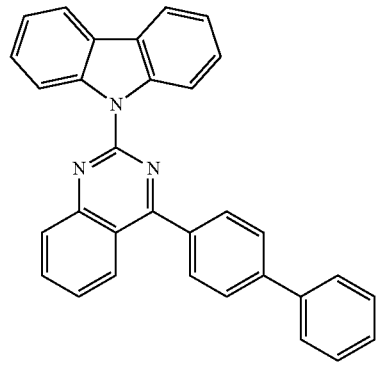

H2-2

-continued
H2-3
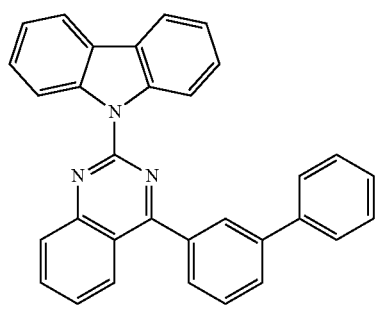
H2-4
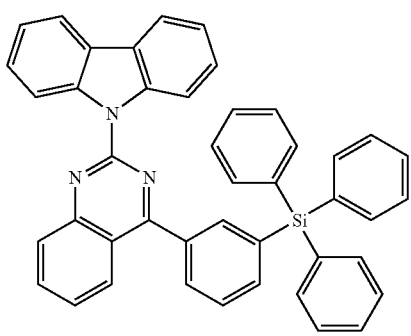
H2-5
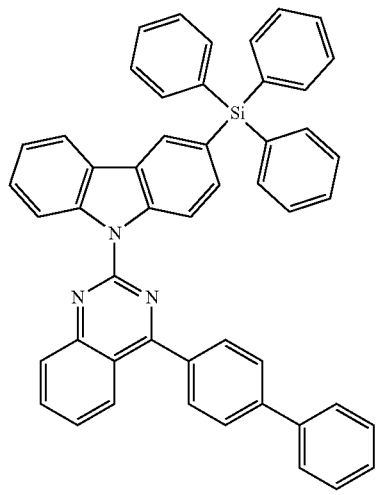
H2-6
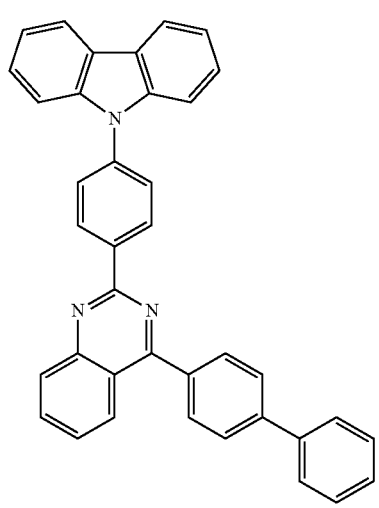
-continued
H2-7
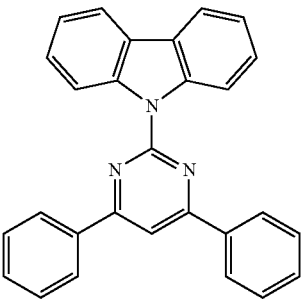
H2-8
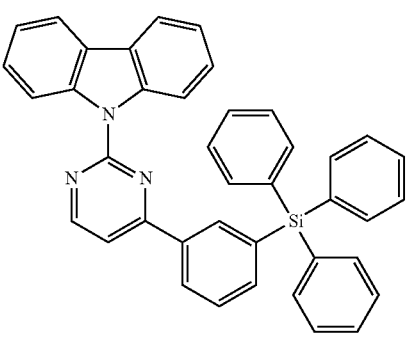
H2-9
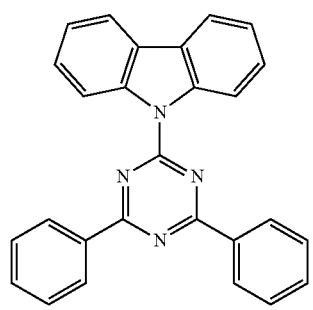
H2-10
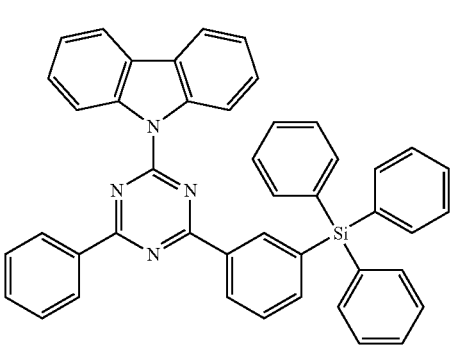

H2-11
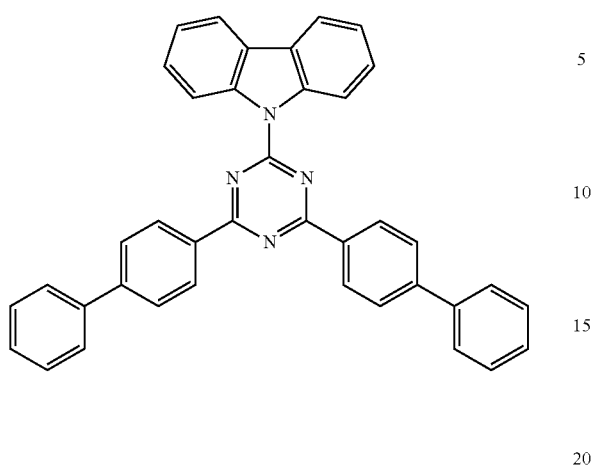
H2-14
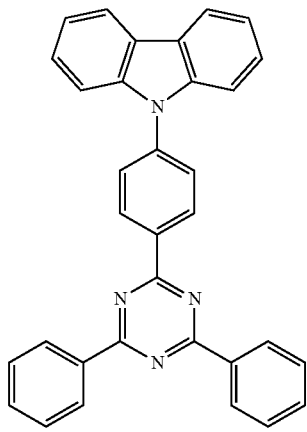
H2-12
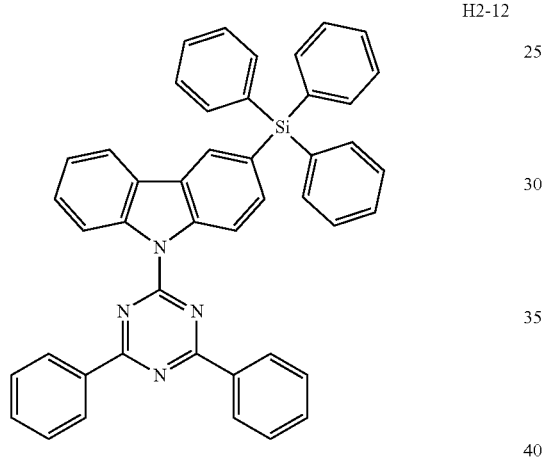
H2-15
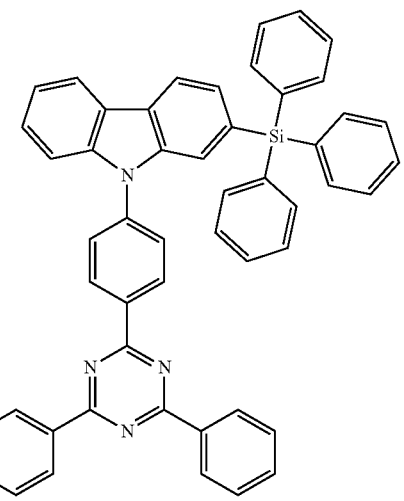
H2-13
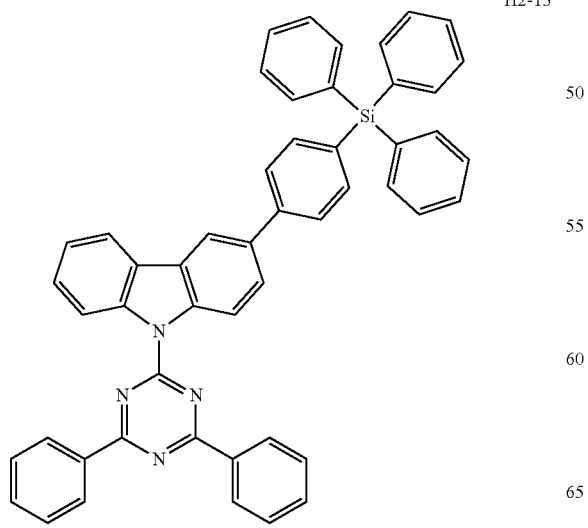
H2-16
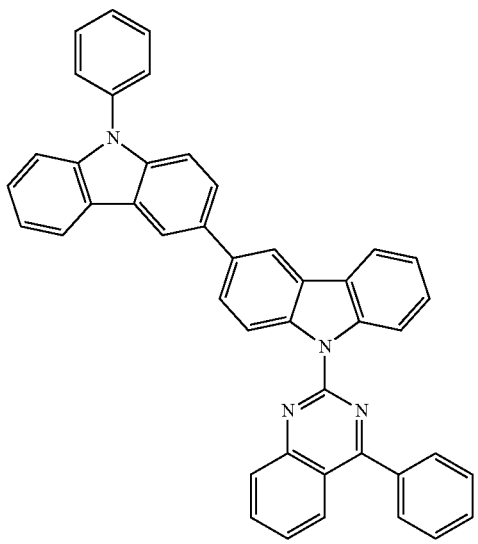

H2-17
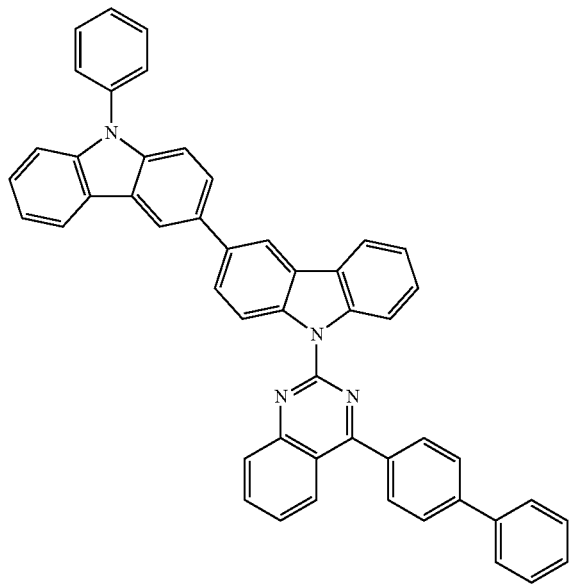
H2-18
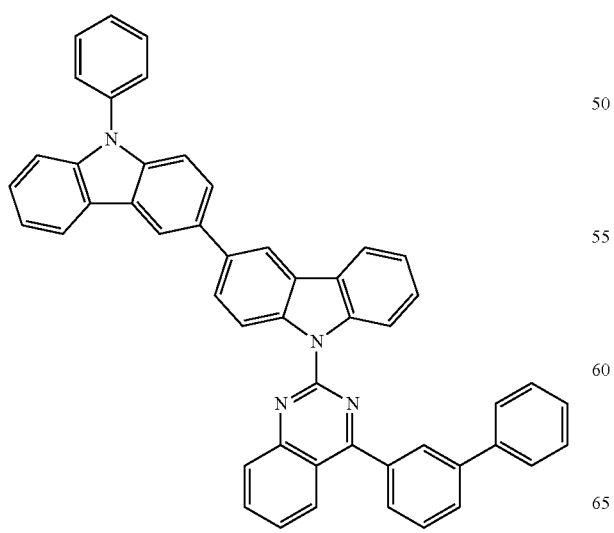
H2-19
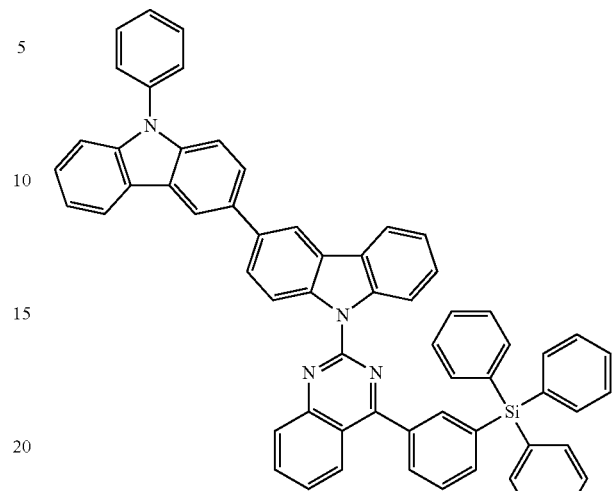
H2-20
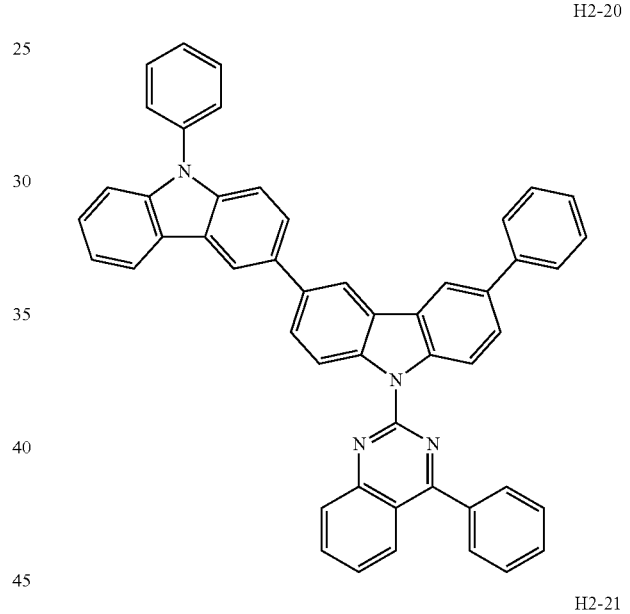
H2-21
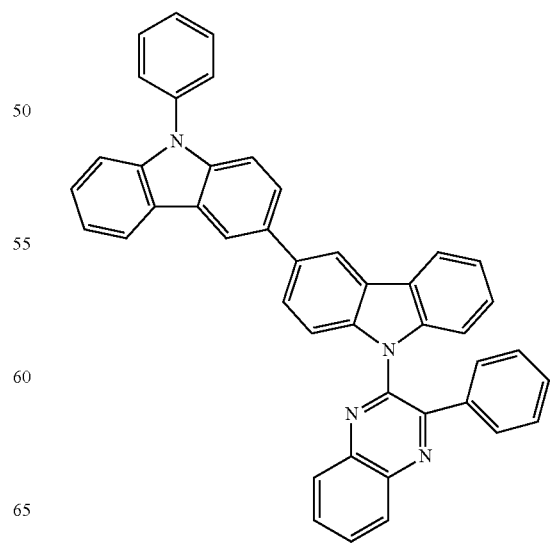

H2-22
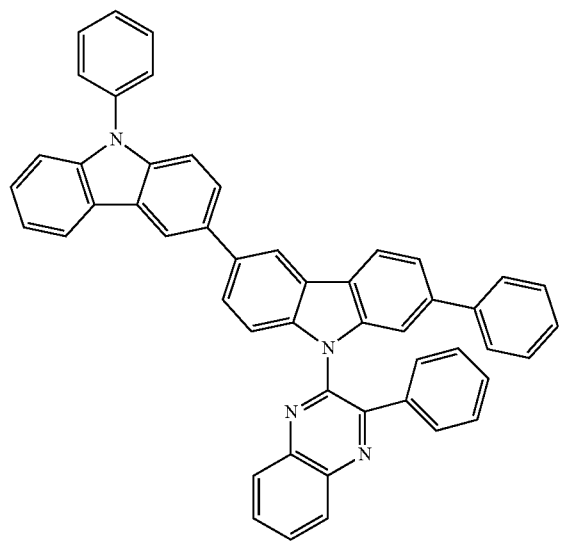
H2-23
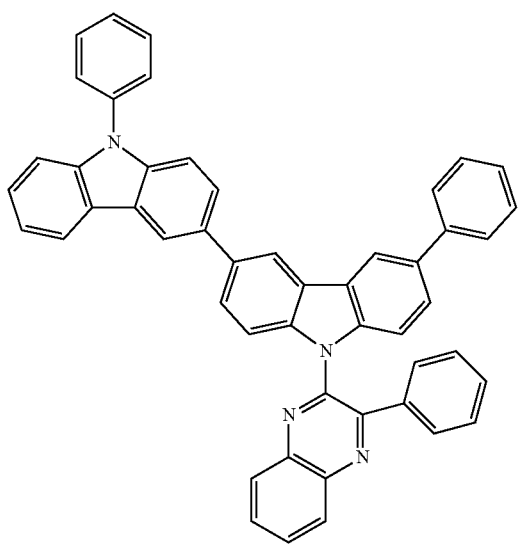
H2-24
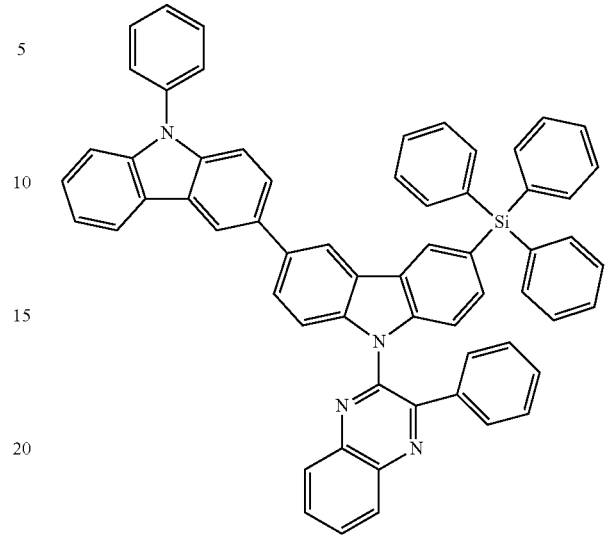
H2-25
H2-26
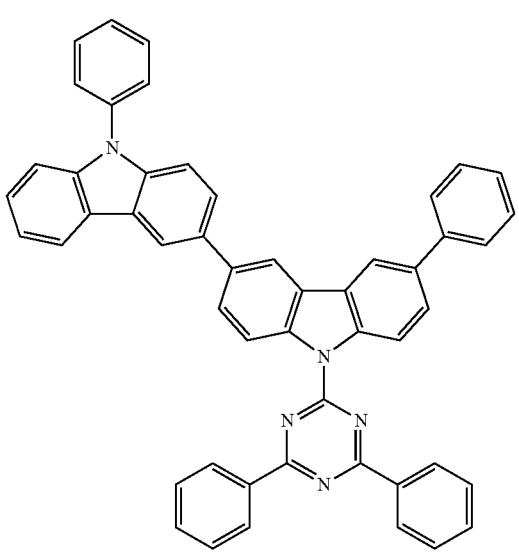

H2-27
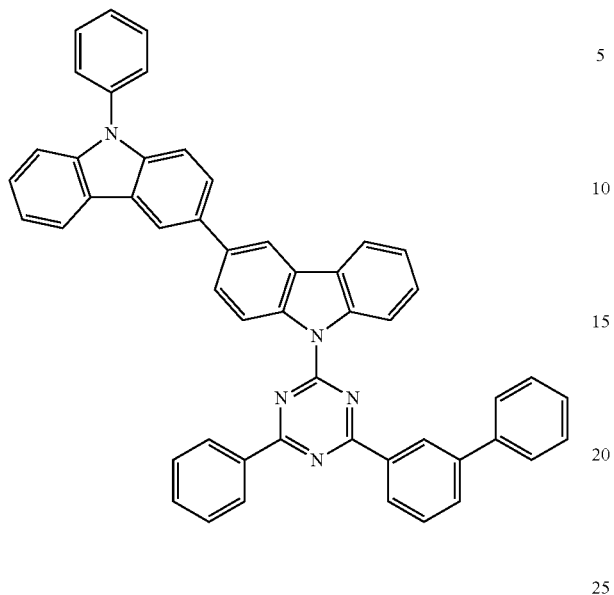
H2-29
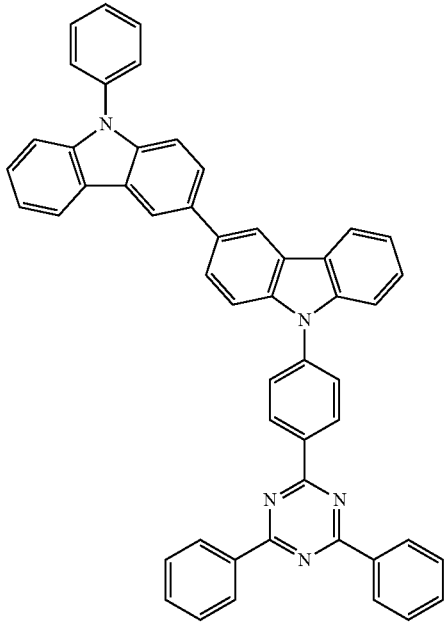
H2-28
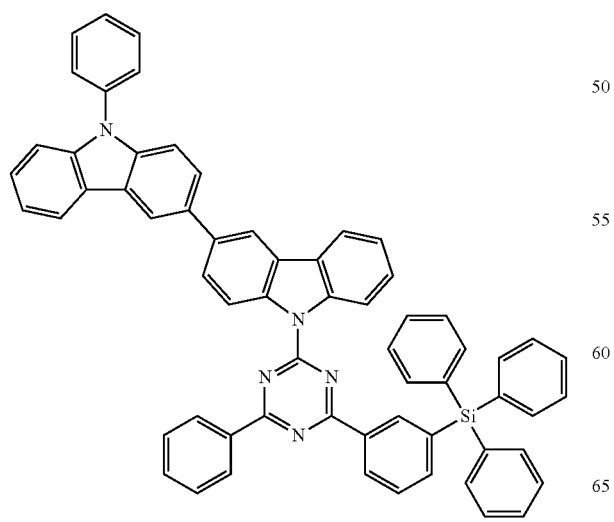
H2-30
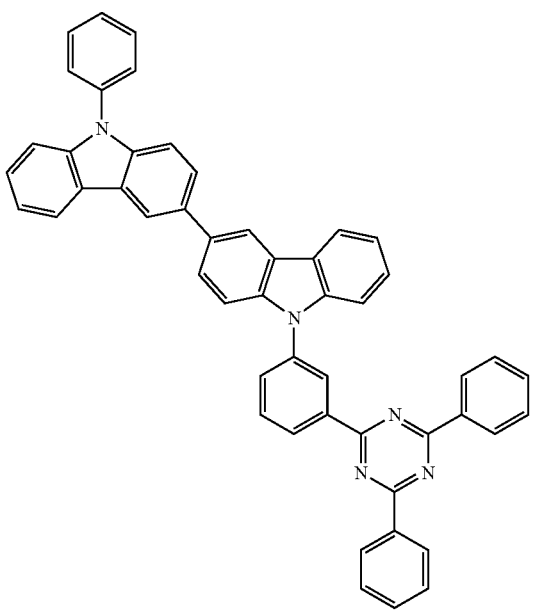

-continued
H2-31
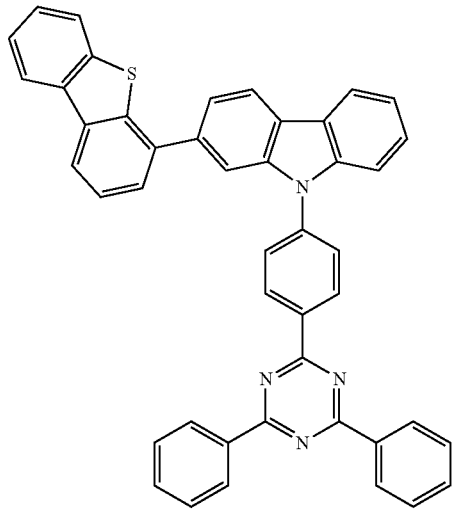
H2-32
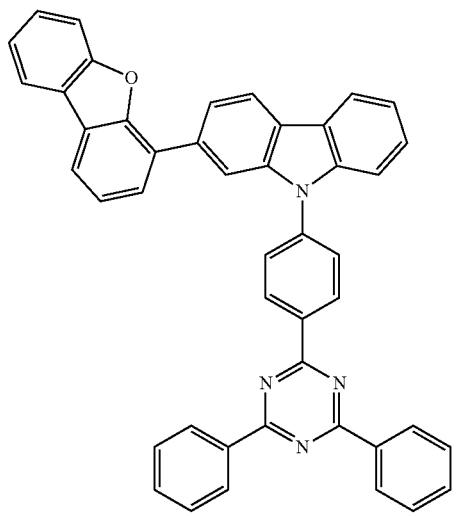
H2-33
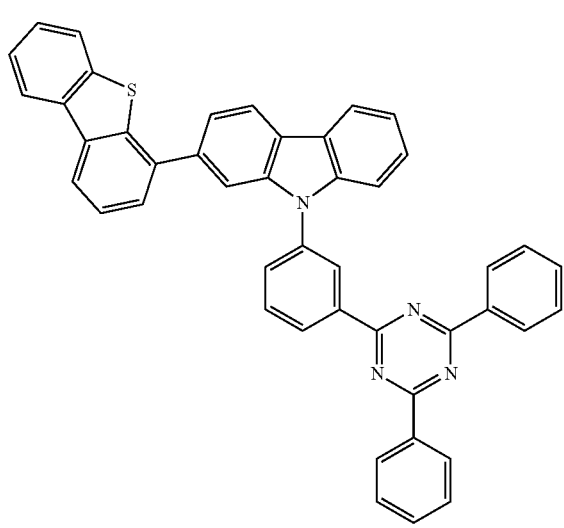
-continued
H2-34
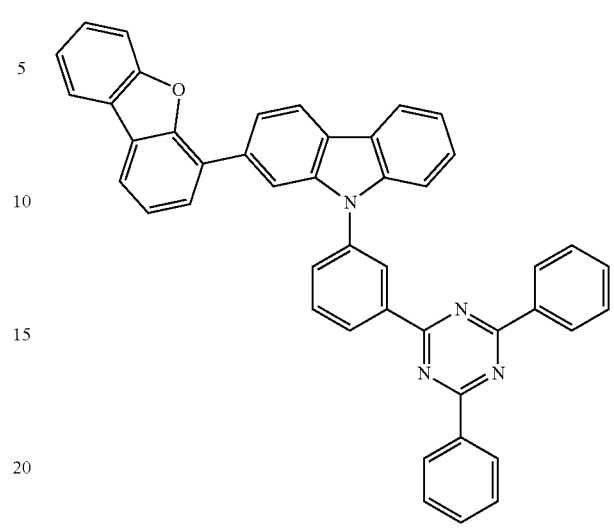
H2-35
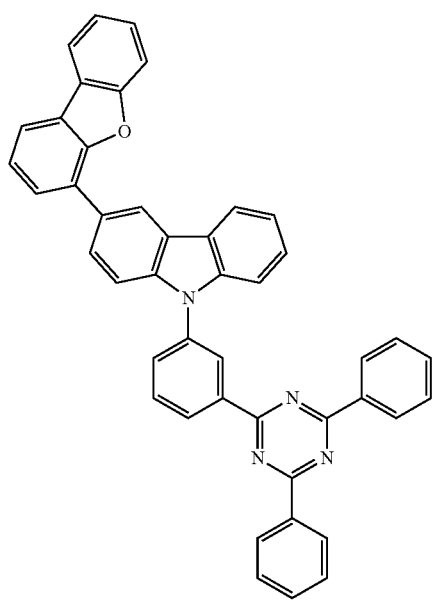
H2-36
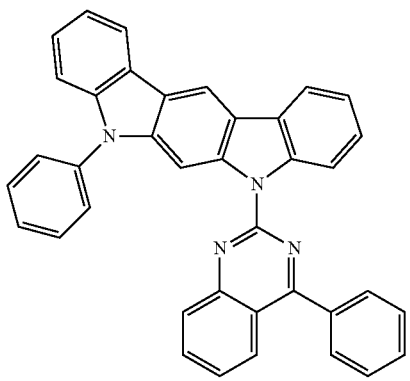

-continued
H2-37
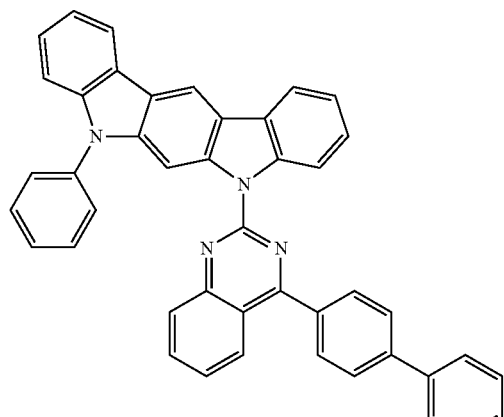
H2-38
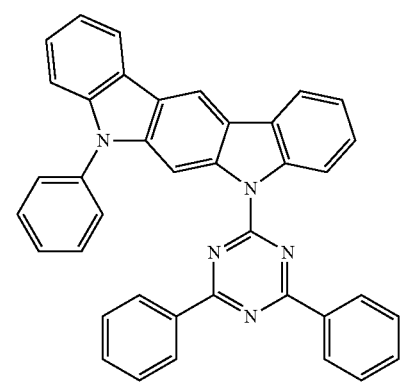
H2-39
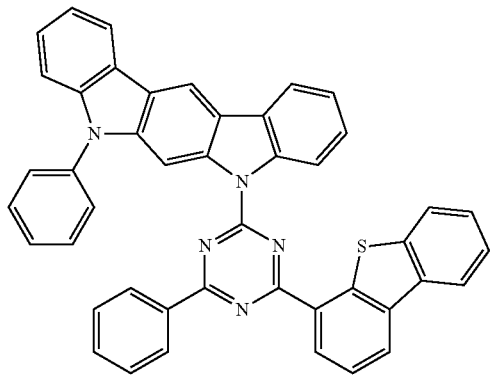
H2-40
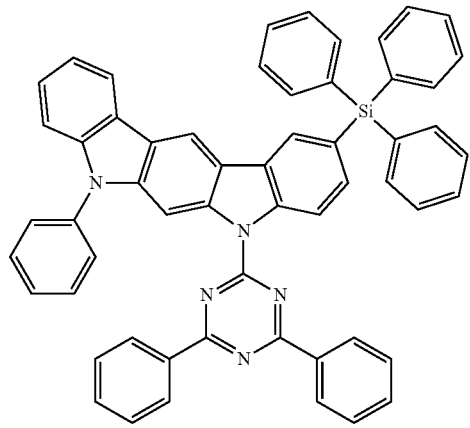
-continued
H2-41
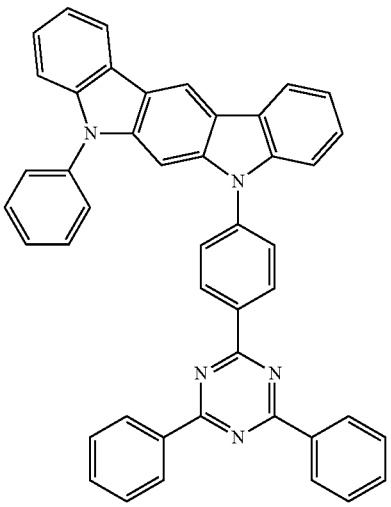
H2-42
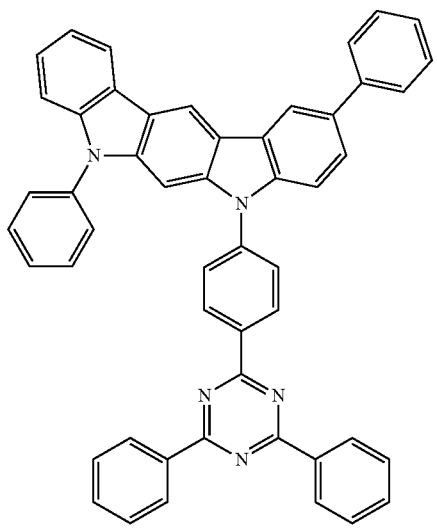
H2-43
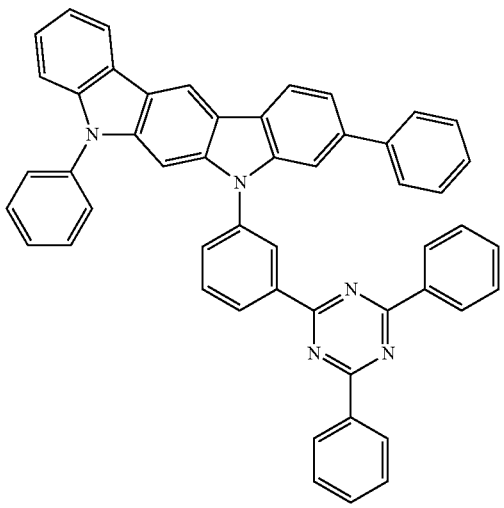

H2-44
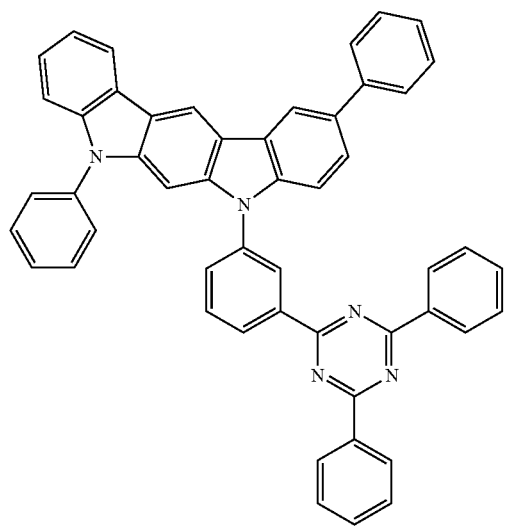
H2-45
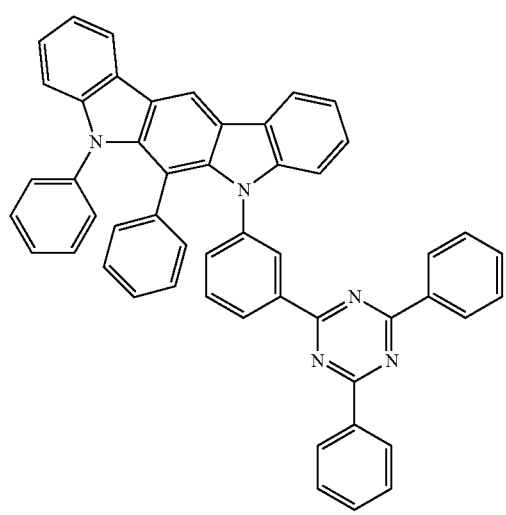
H2-46
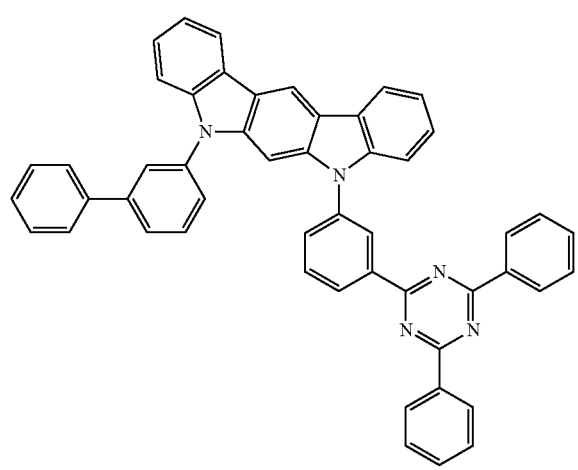
H2-47
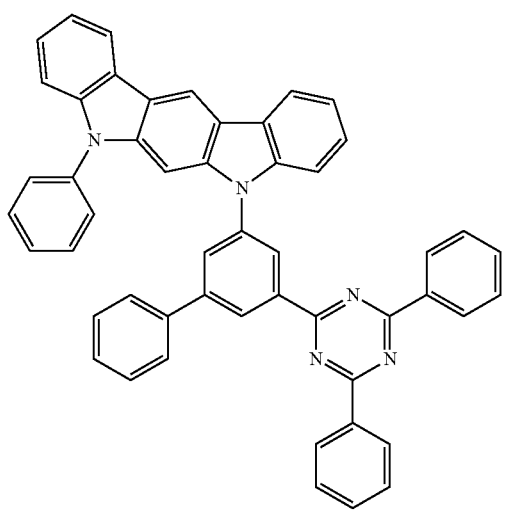
H2-48
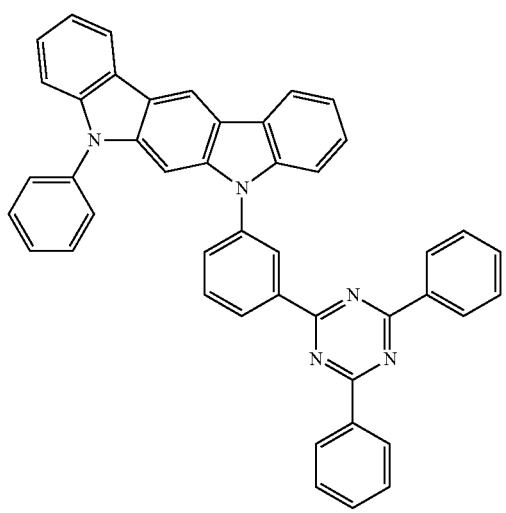
H2-49
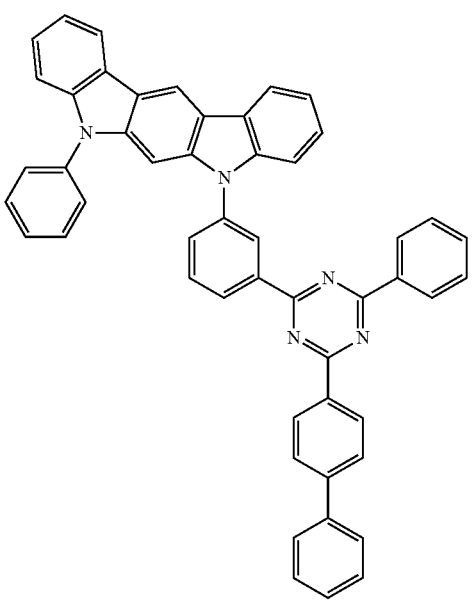

-continued
H2-50
H2-53
H2-51
H2-52
H2-54
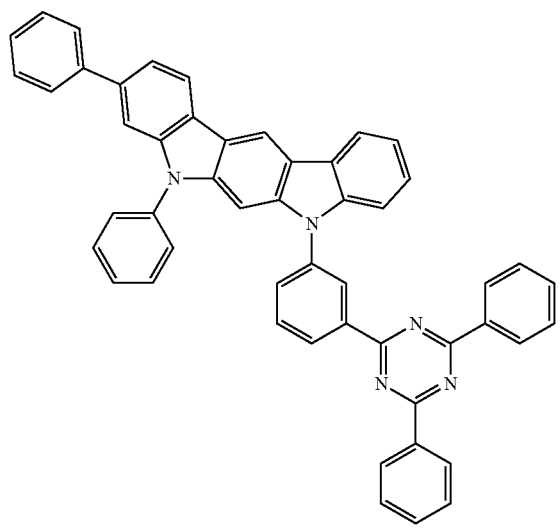
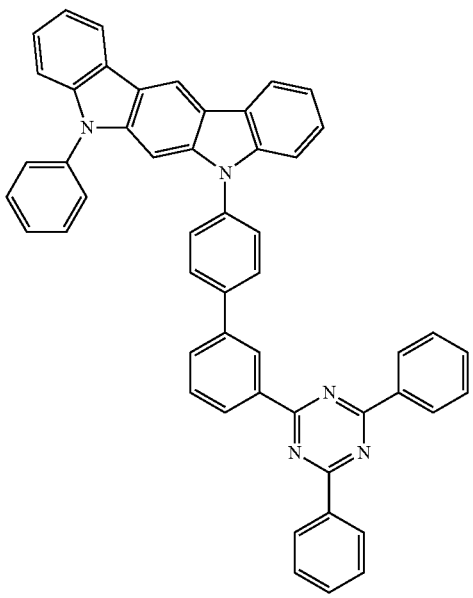

H2-55
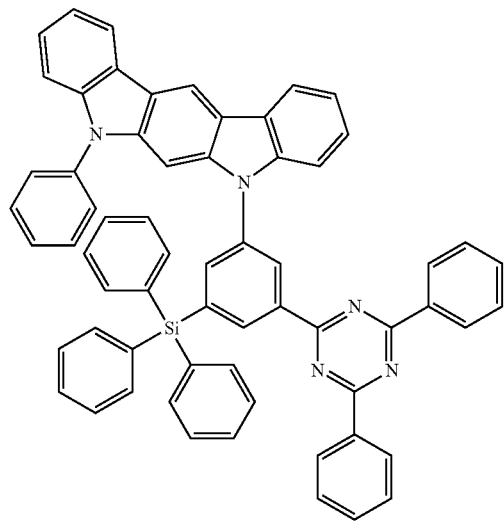
H2-56
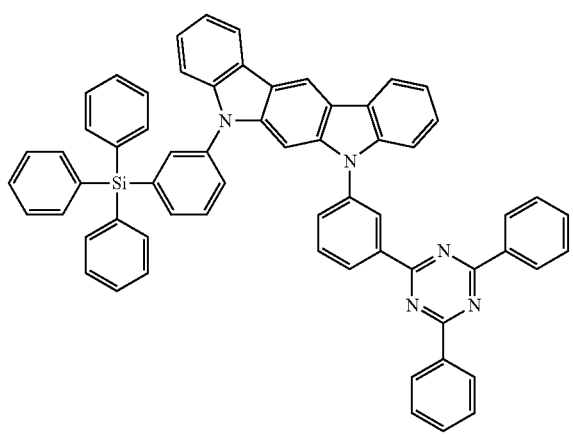
H2-57
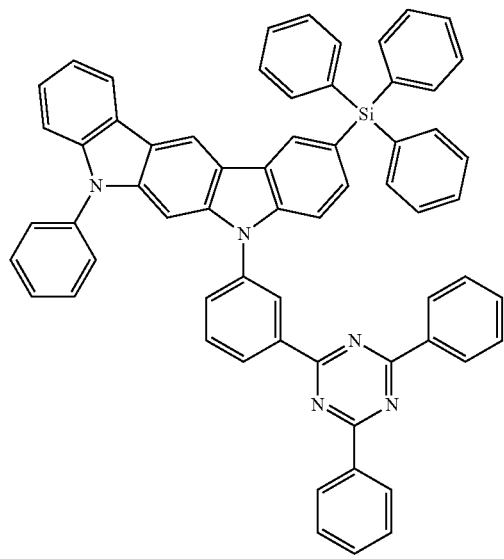
H2-58
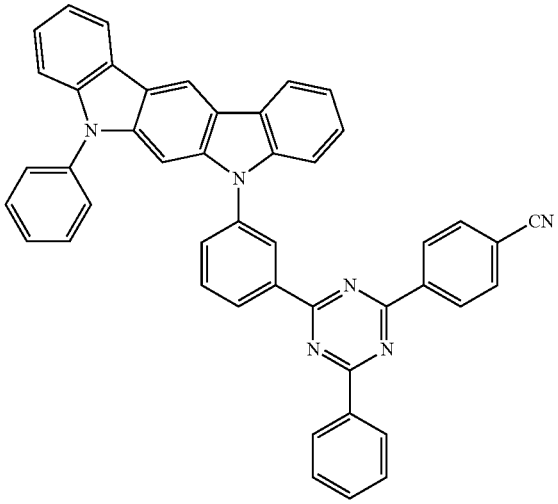
H2-59
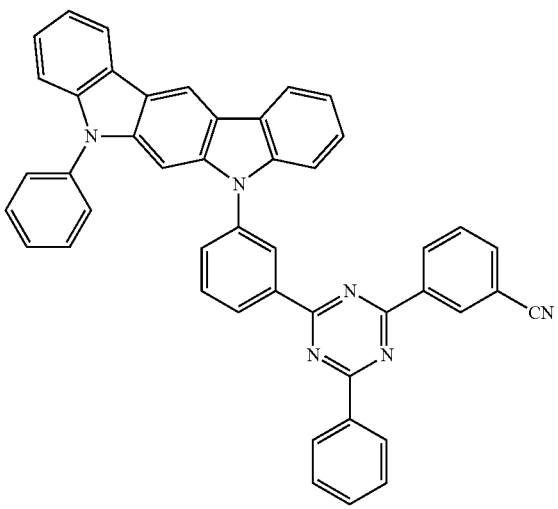
H2-60
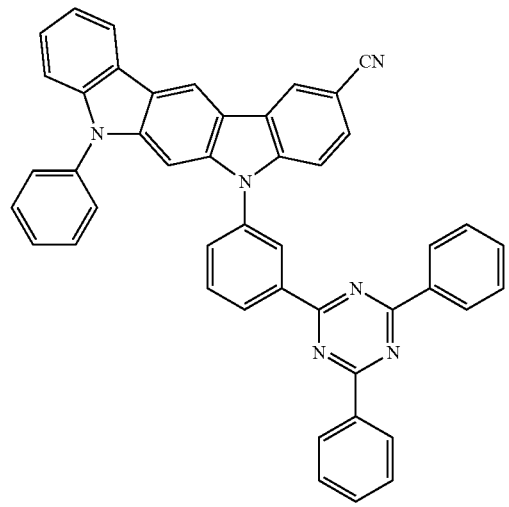

H2-61
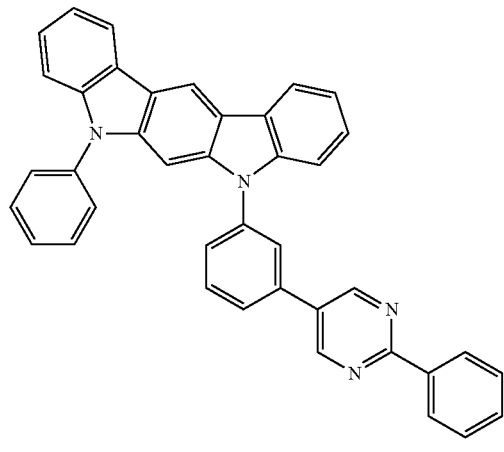
H2-64
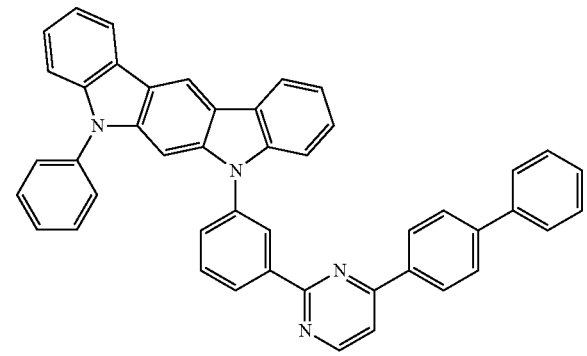
H2-62
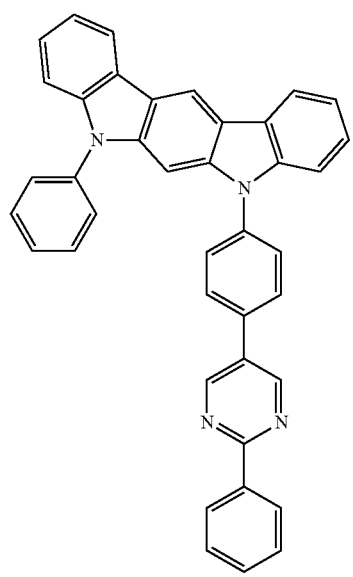
H2-65
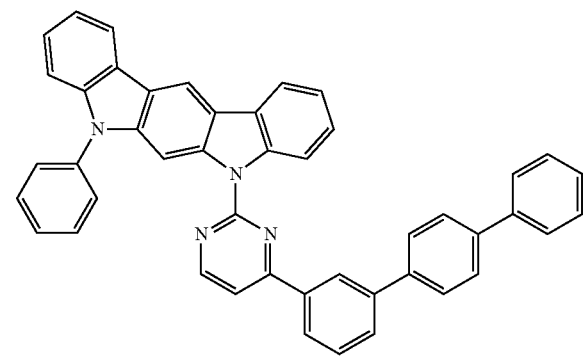
H2-63
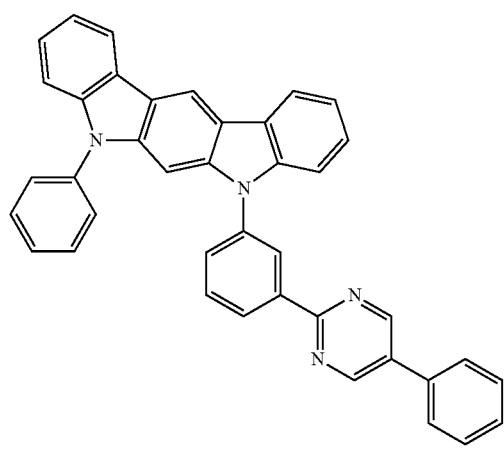
H2-66
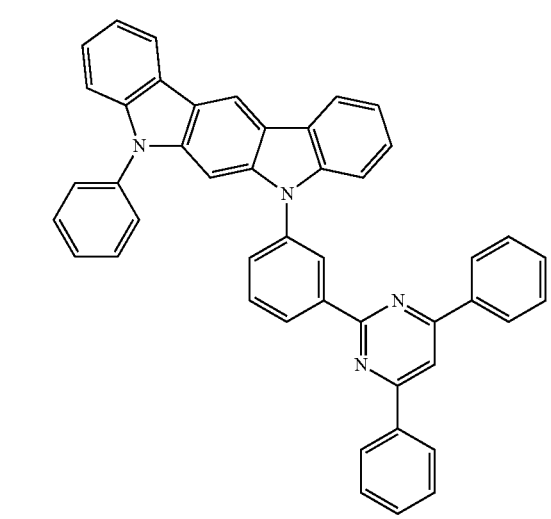

H2-67
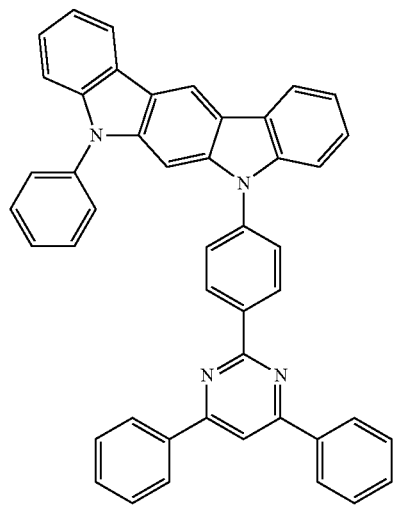
H2-68
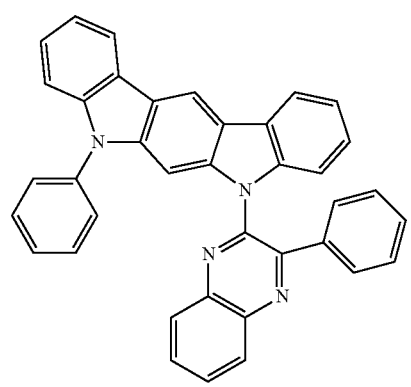
H2-69
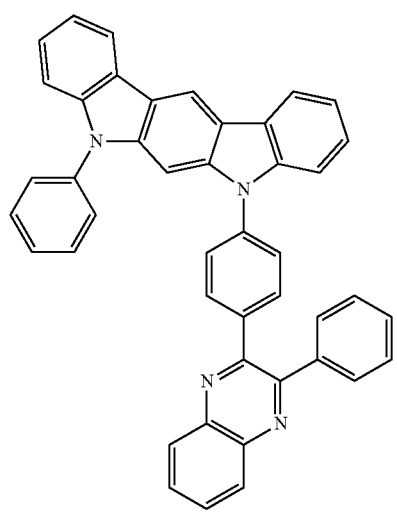
H2-70
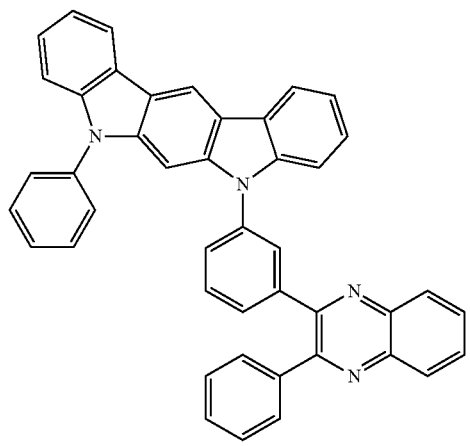
H2-71
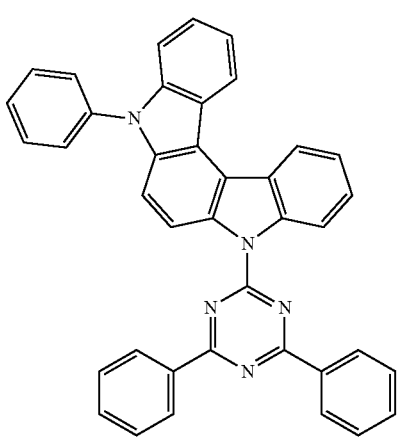
H2-72
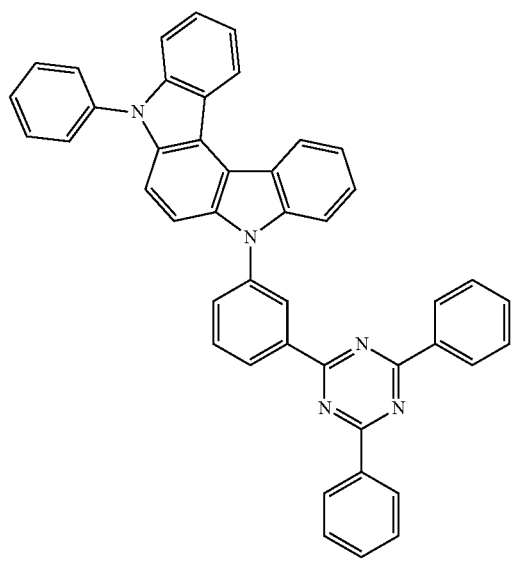

-continued
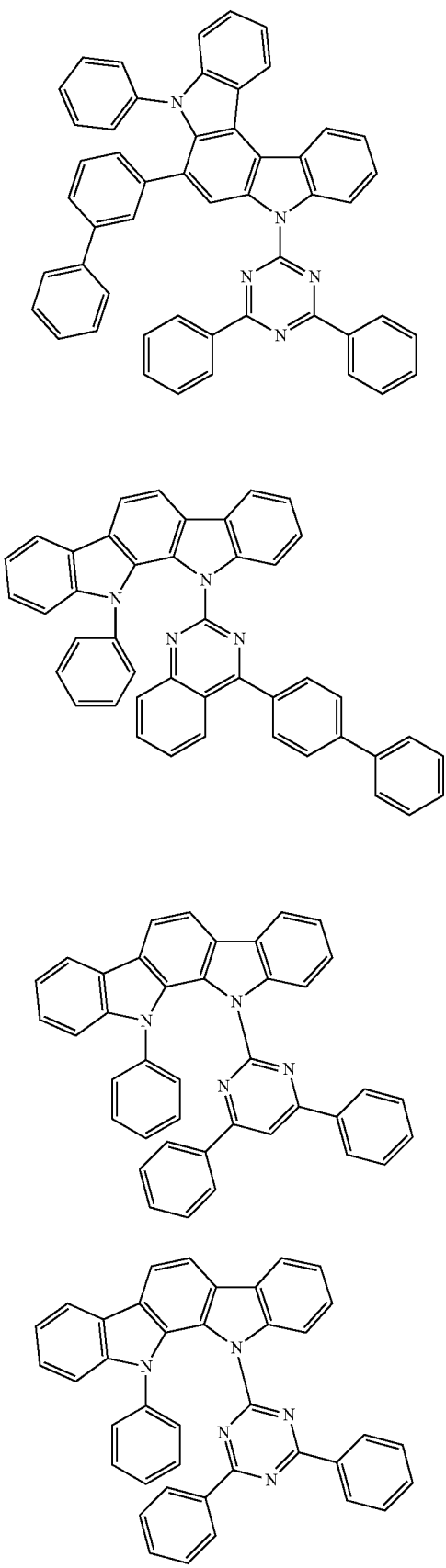
H2-73
H2-74
H2-75
H2-76
-continued
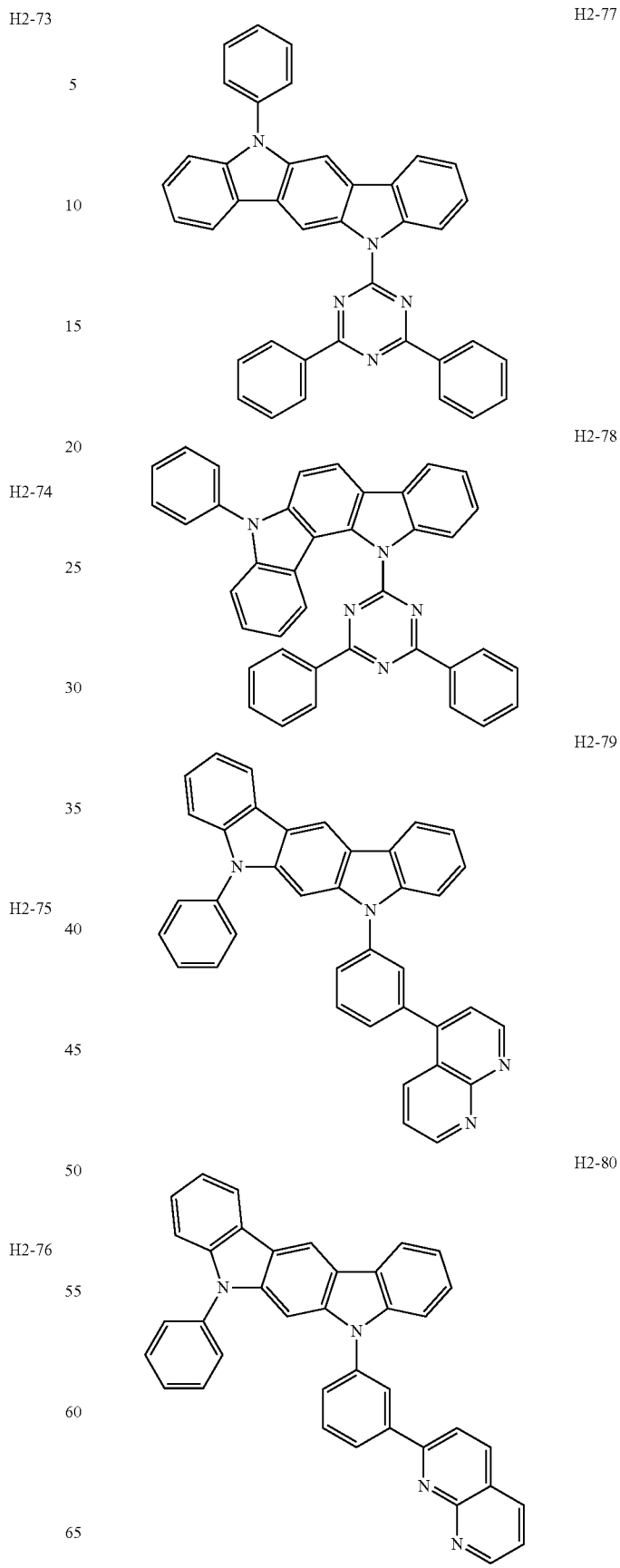
H2-77
H2-78
H2-79
H2-80

-continued
H2-81
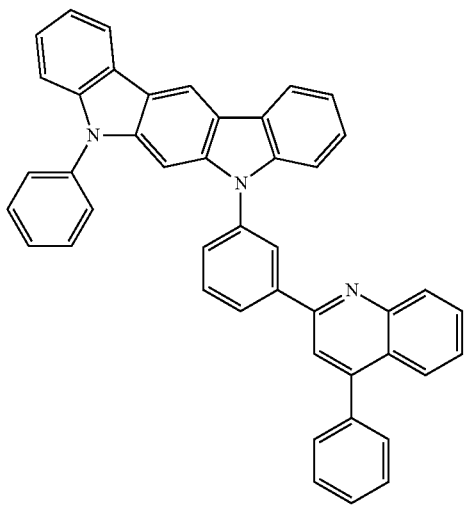
H2-84
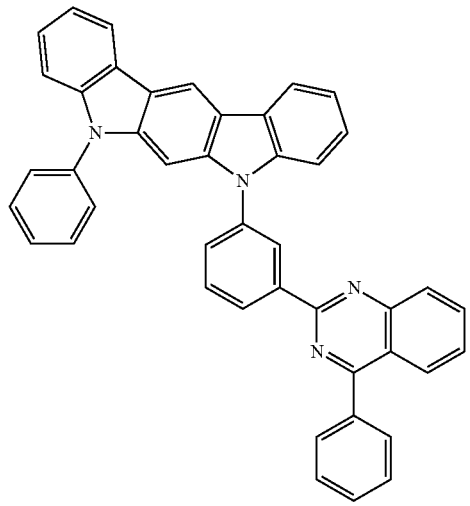
H2-82
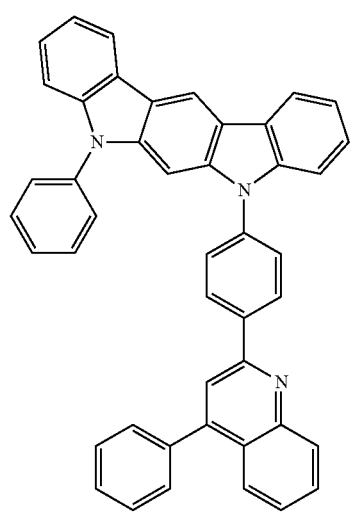
H2-85
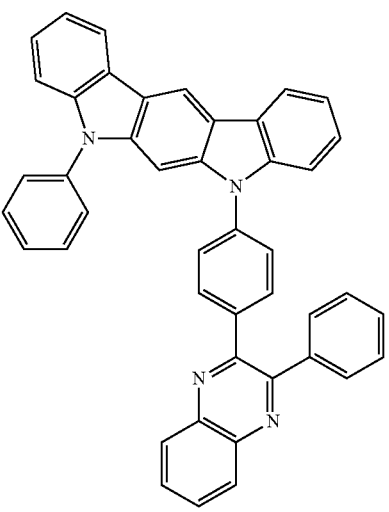
H2-83
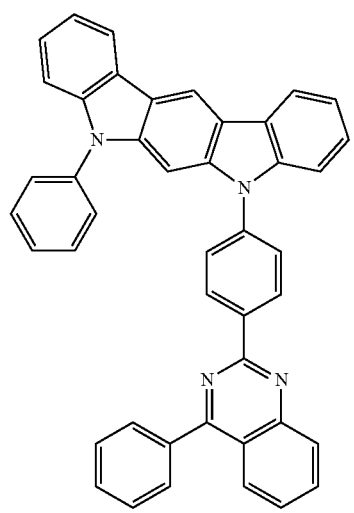
H2-86
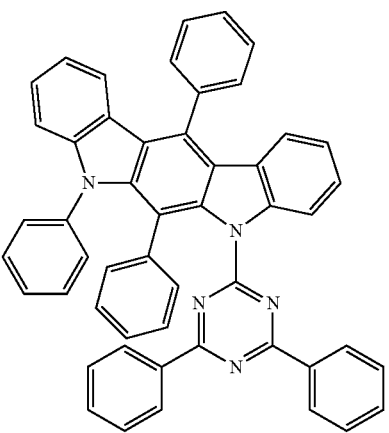

H2-87
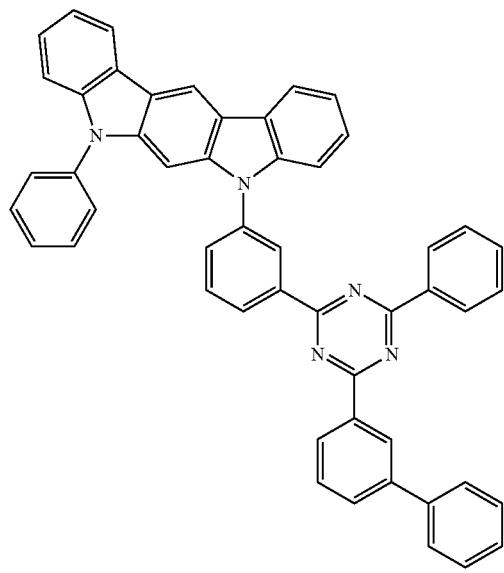
H2-89
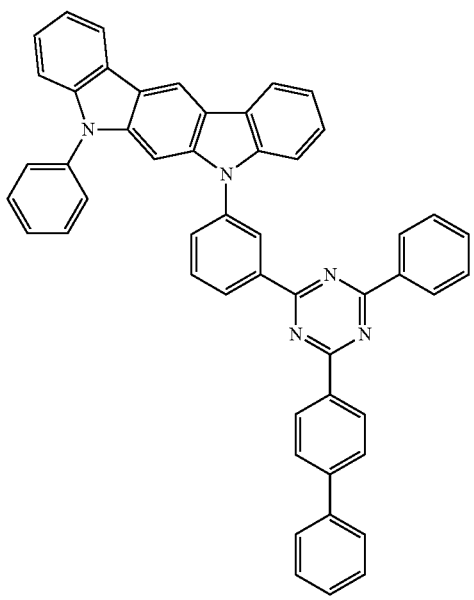
H2-90
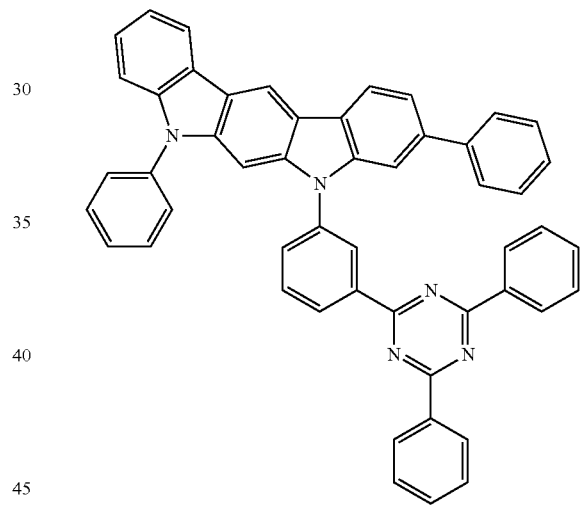
H2-88
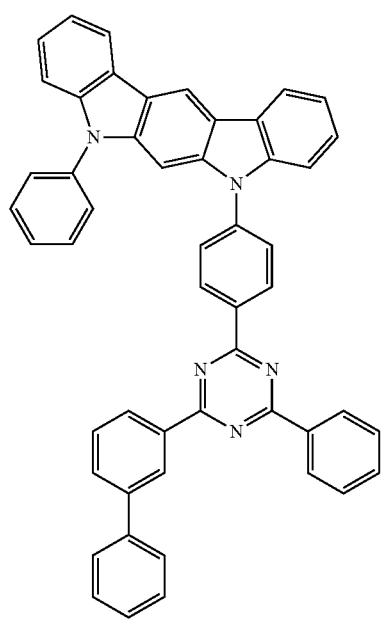
H2-91
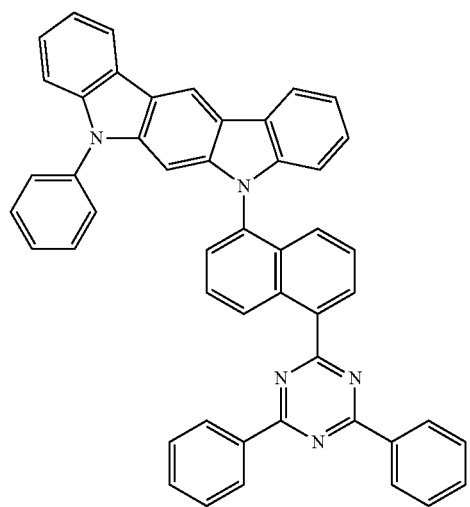

H2-92
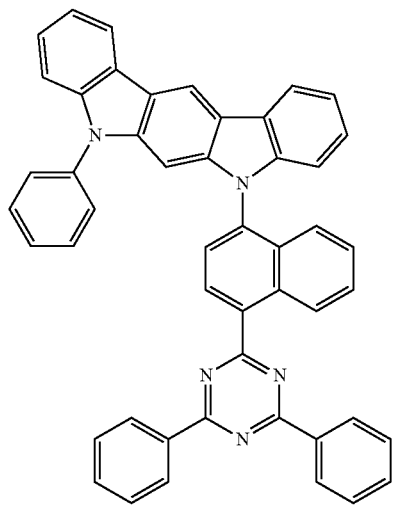
H2-93
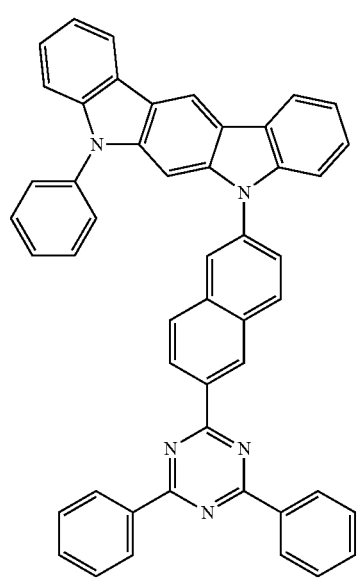
H2-94
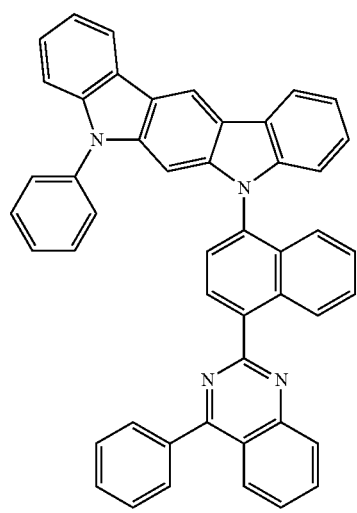
H2-95
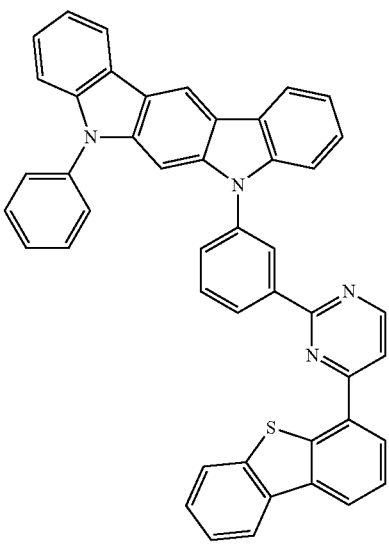
H2-96
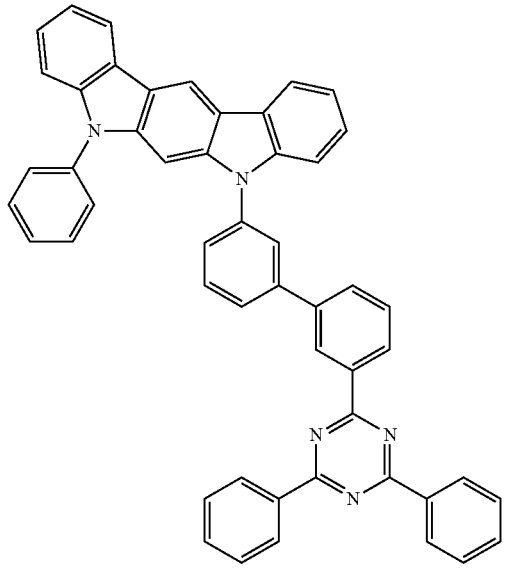

H2-97
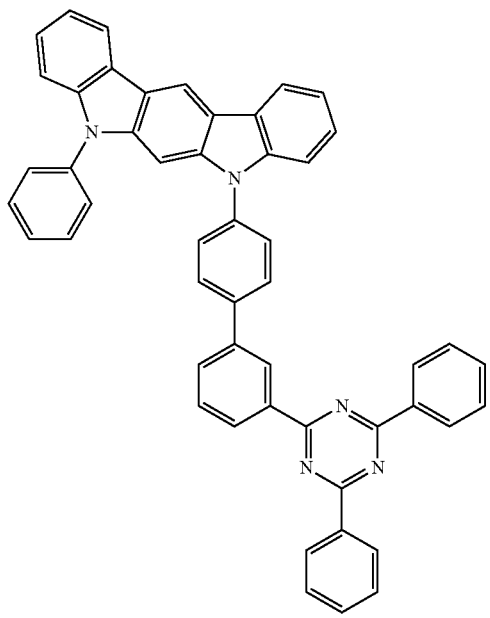
H2-99
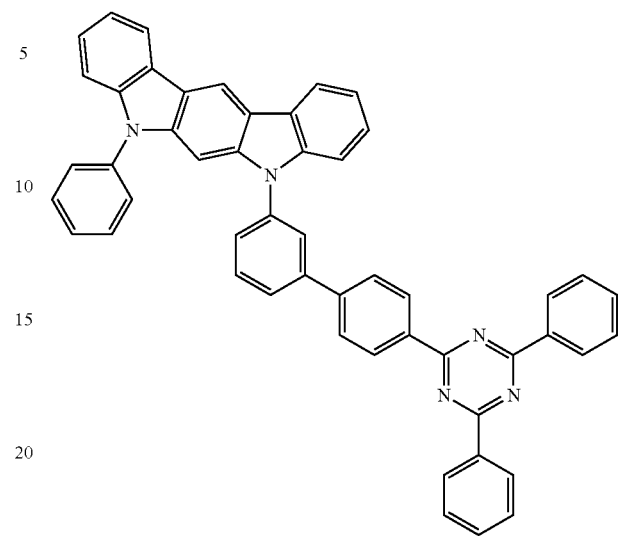
H2-100
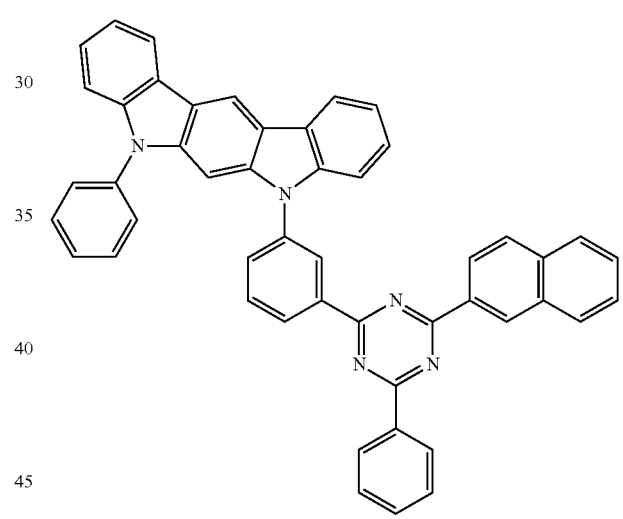
H2-98
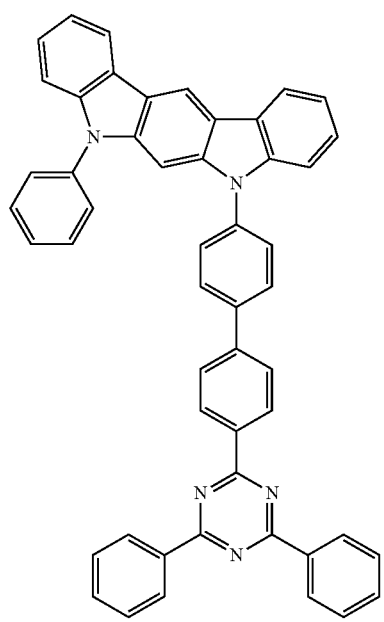
H2-101
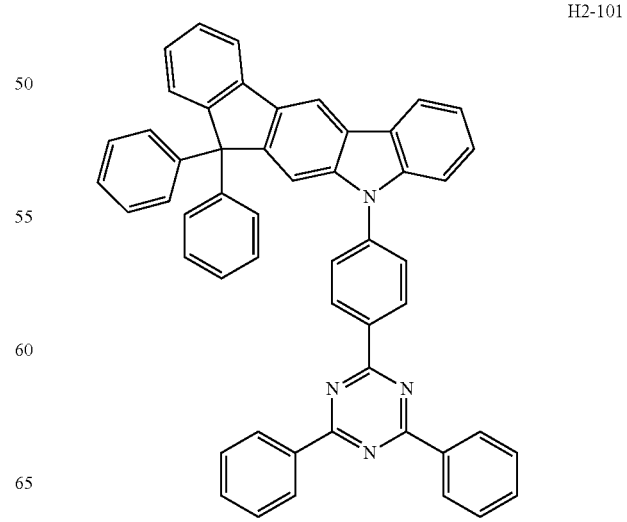

H2-102
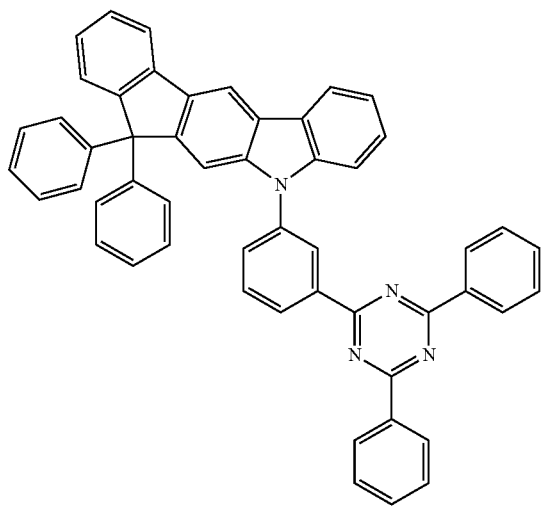
H2-105
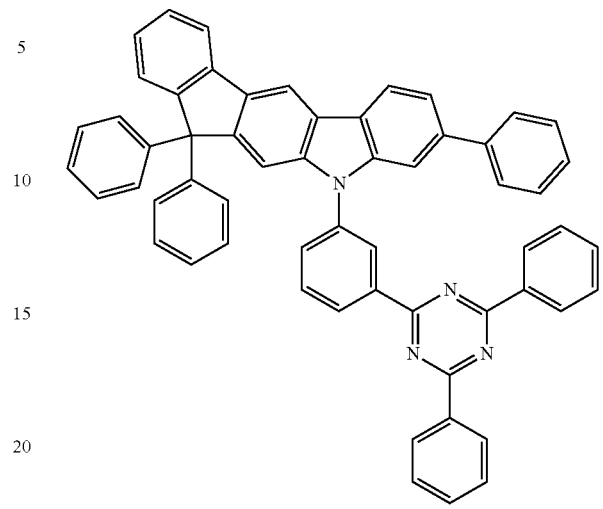
H2-103
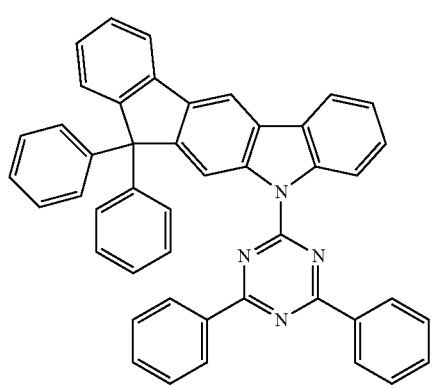
H2-106
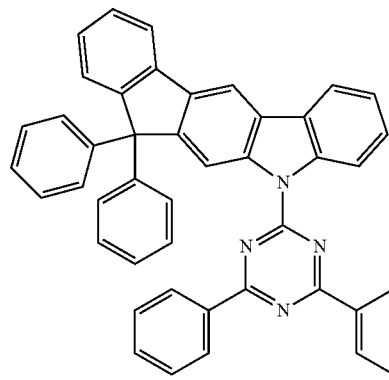
H2-104
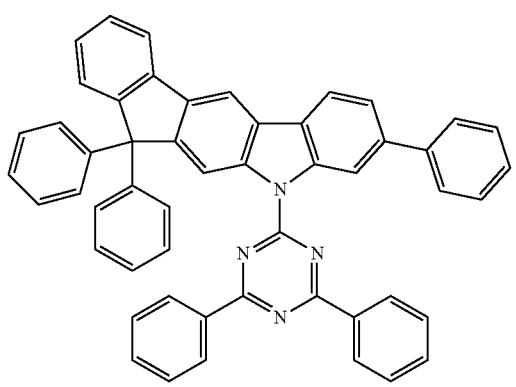
H2-107
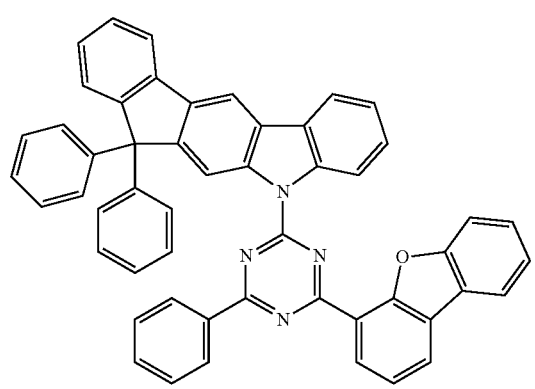

H2-108
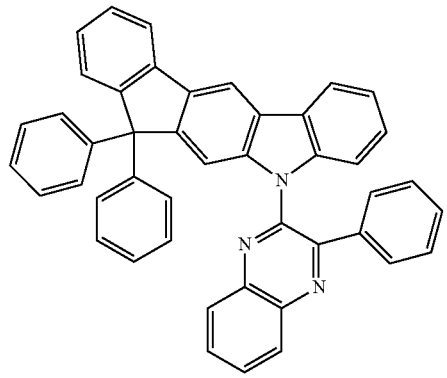
H2-109
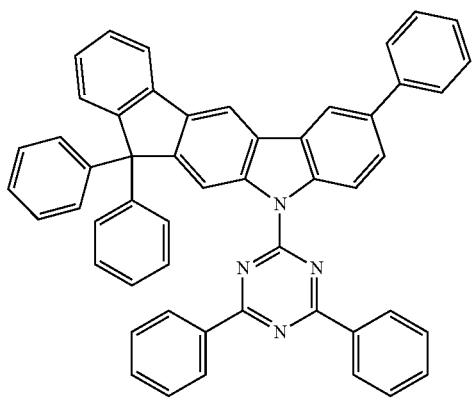
H2-110
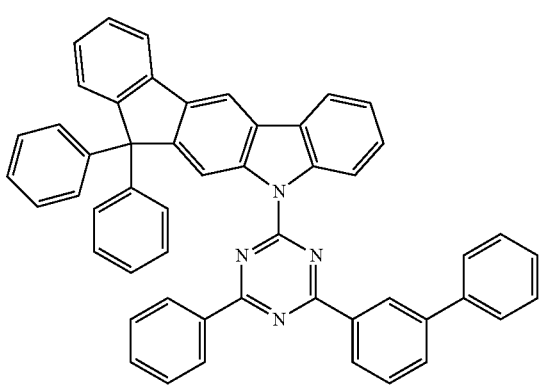
H2-111
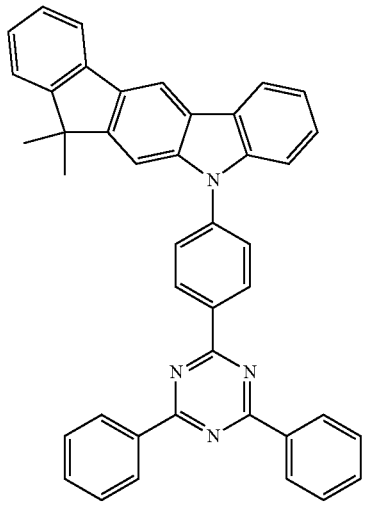
H2-112
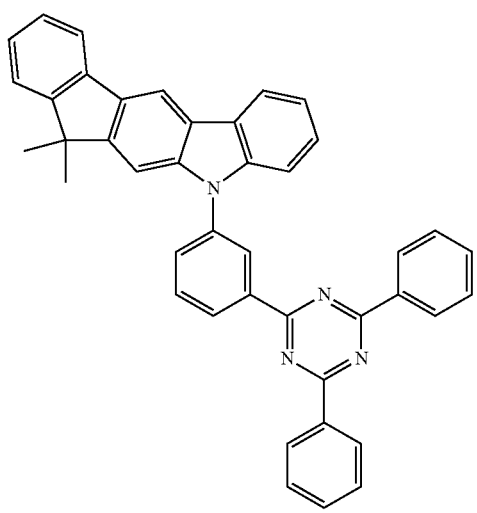
H2-113
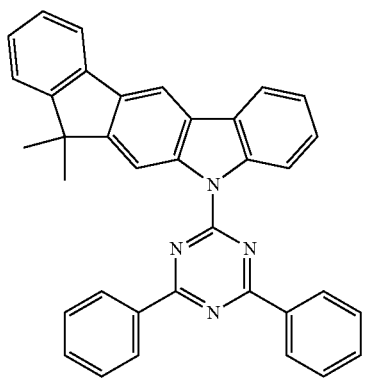

H2-114
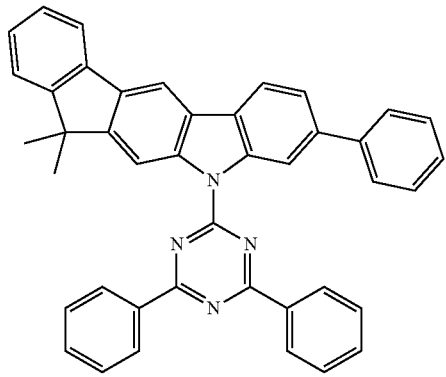
H2-115
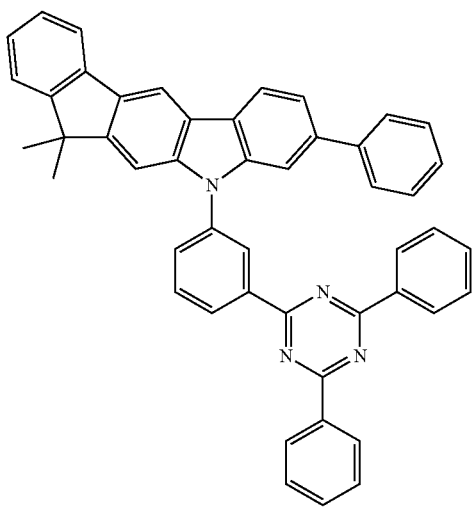
H2-116
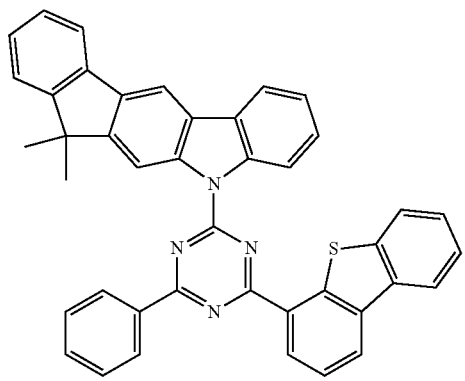
H2-117
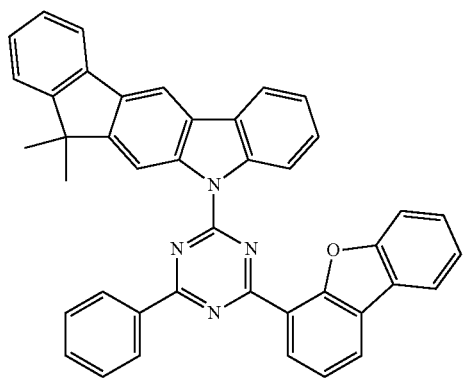
H2-118
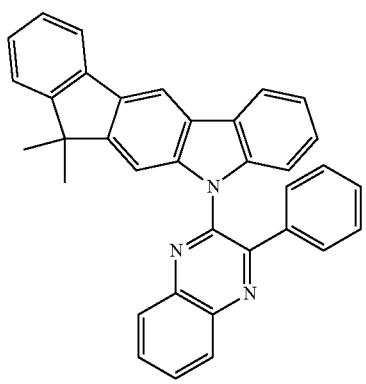
H2-119
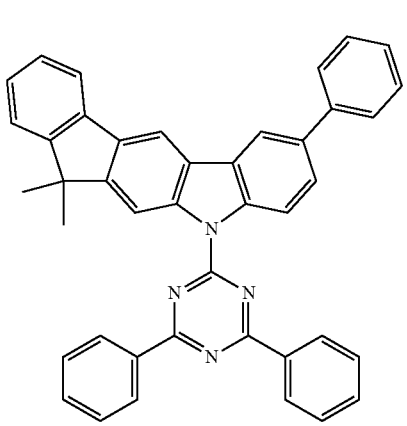
H2-120
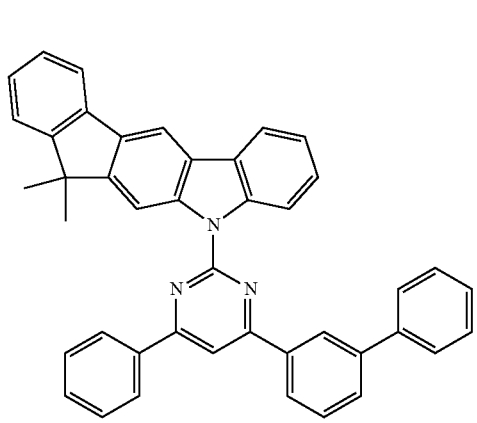
H2-121
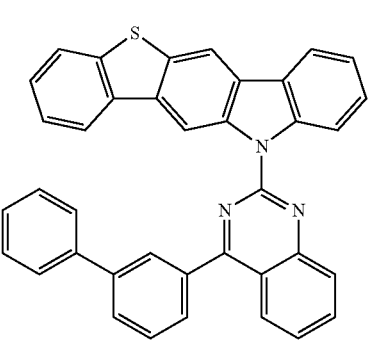

H2-122 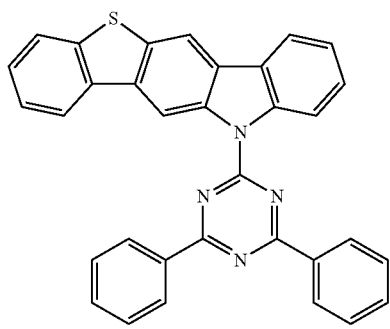
H2-123 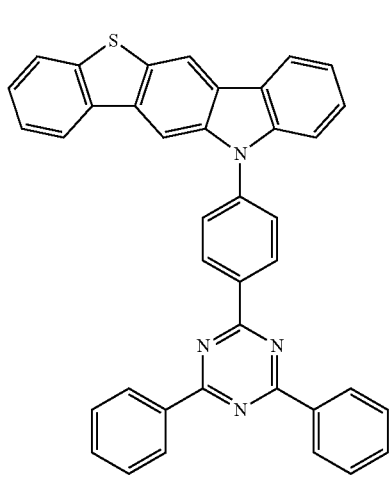
H2-124 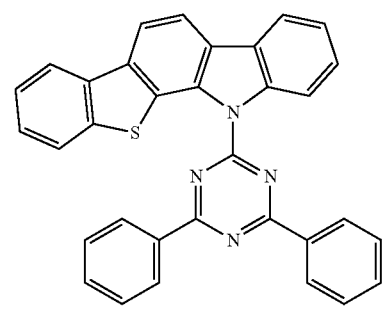
H2-125 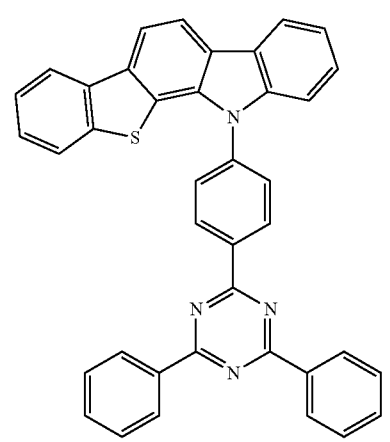
H2-126 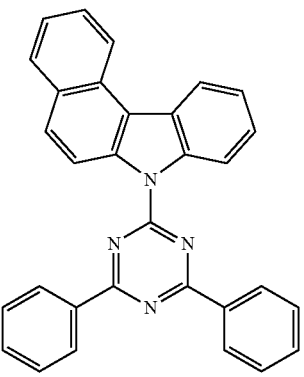
H2-127 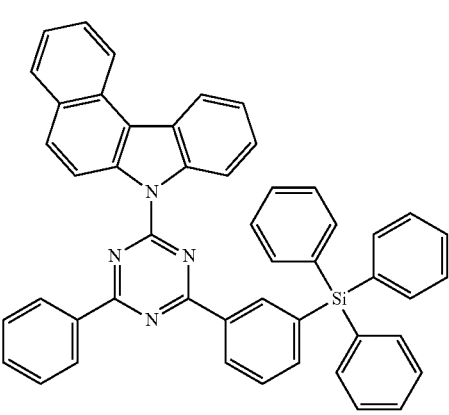
H2-128 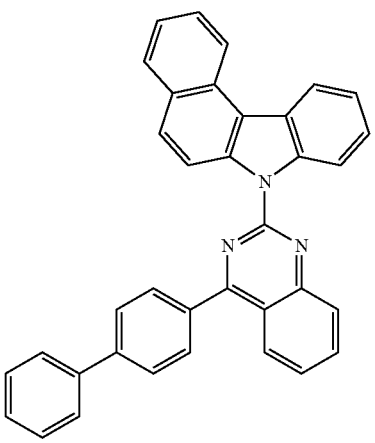

H2-129
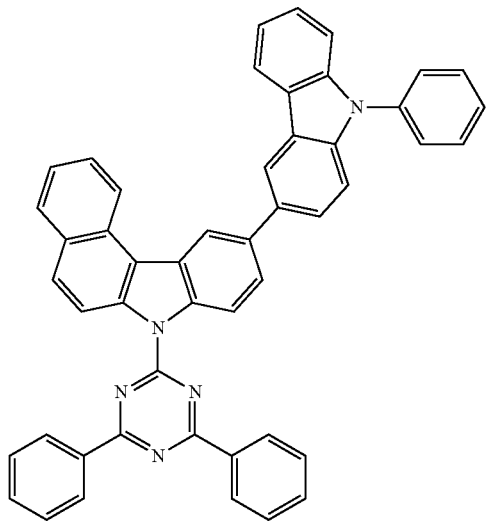
H2-130
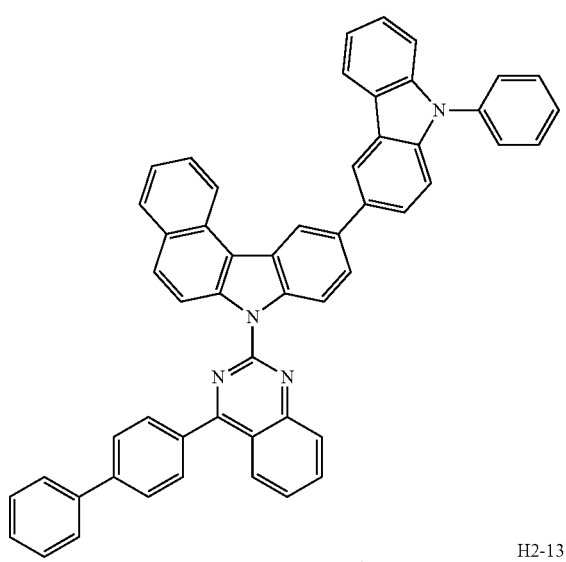
H2-131
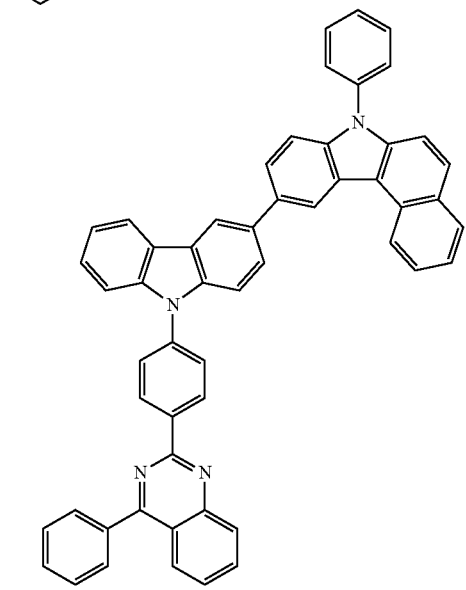
H2-132
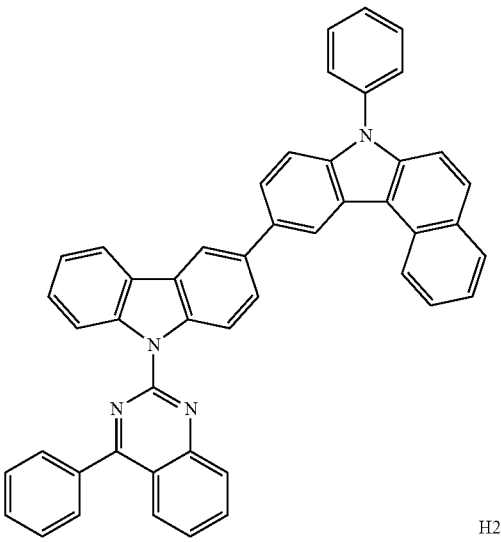
H2-133
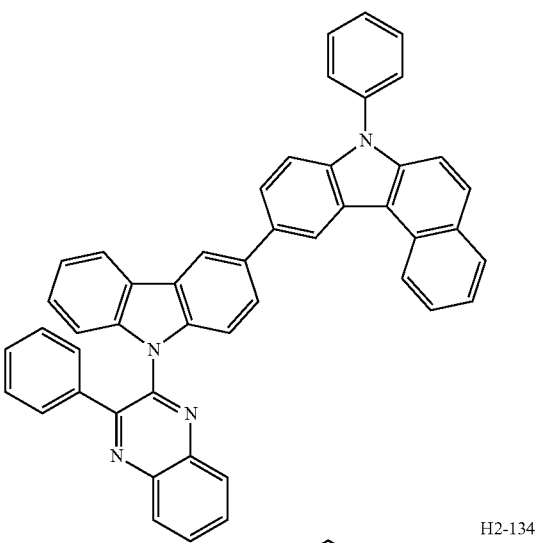
H2-134
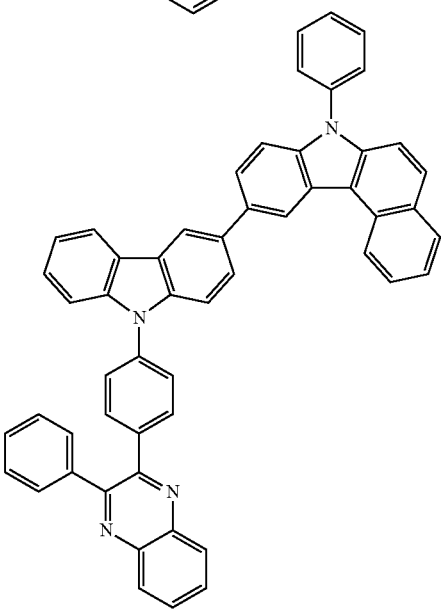

H2-135
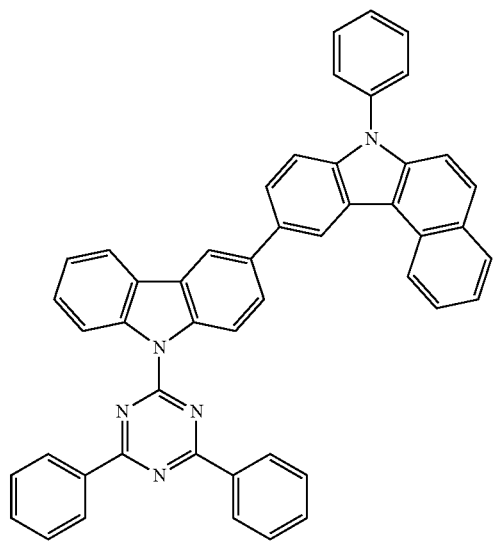
H2-136
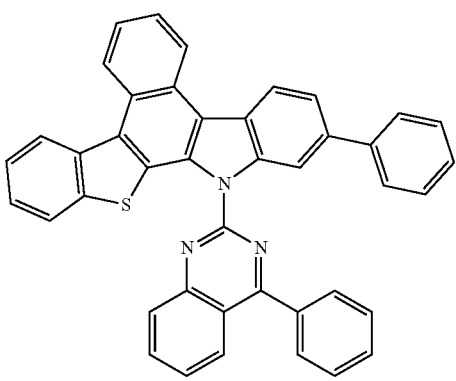
H2-137
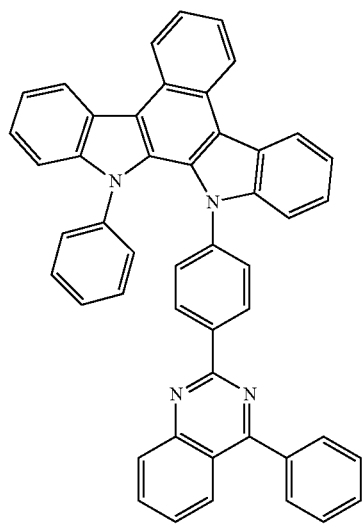
H2-138
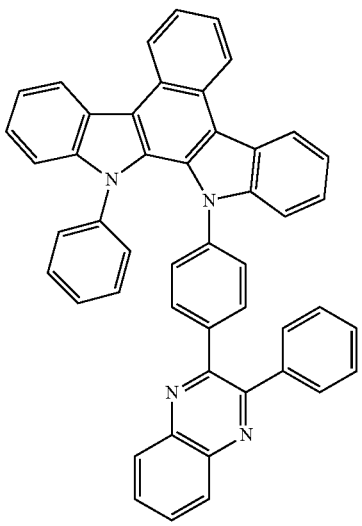
H2-139
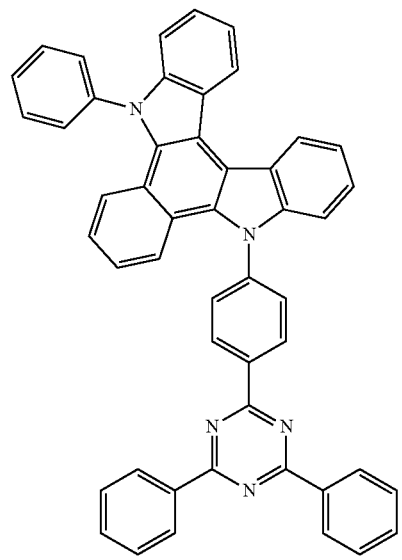
H2-140
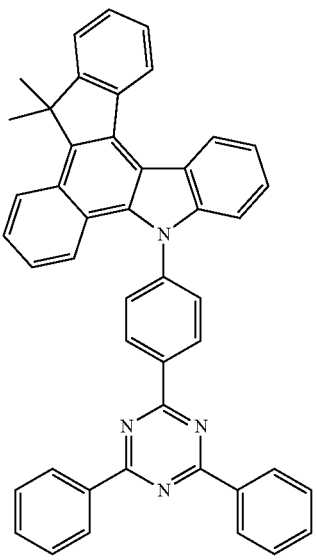

H2-141
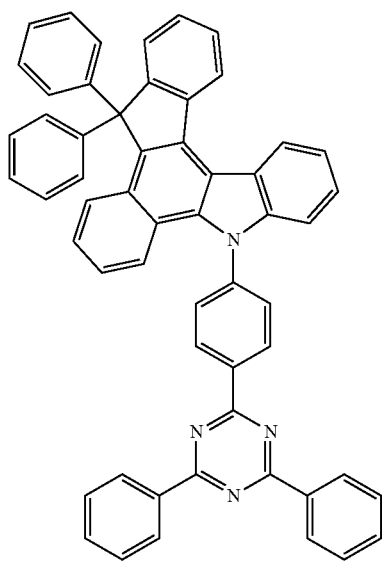
H2-142
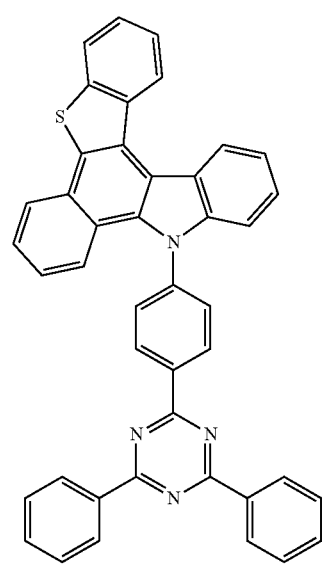
H2-143
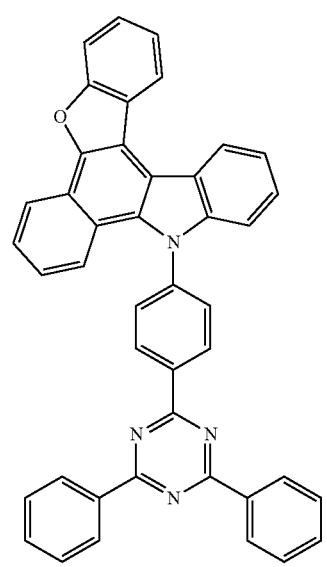
H2-144
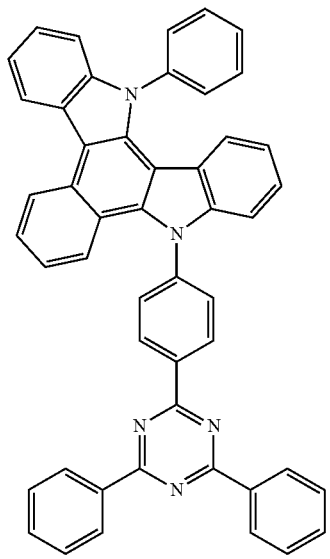
H2-145
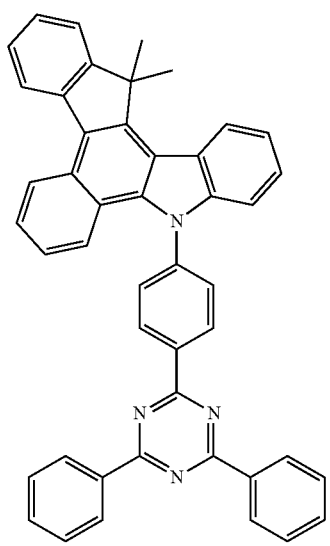

H2-146
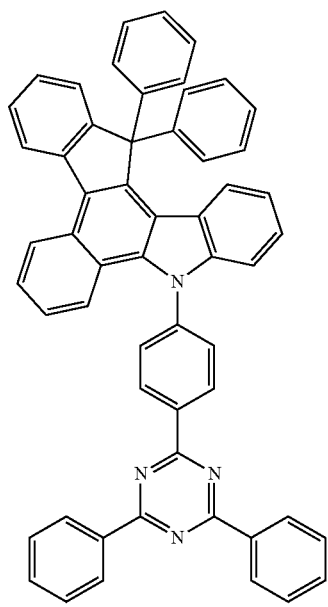
H2-147
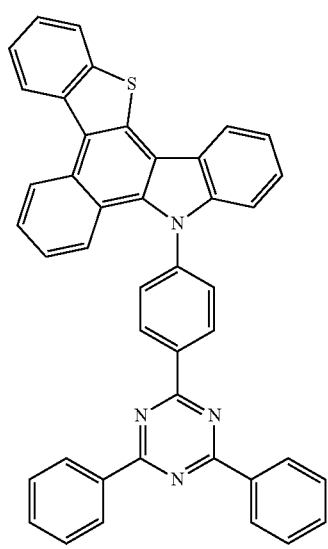
H2-148
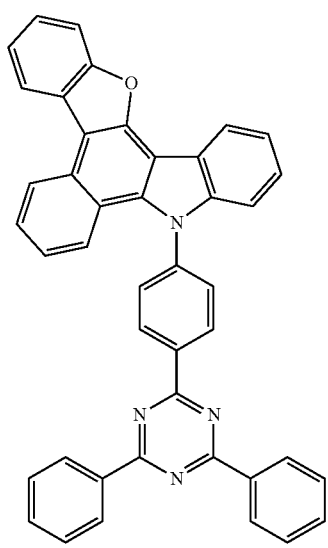
H2-149
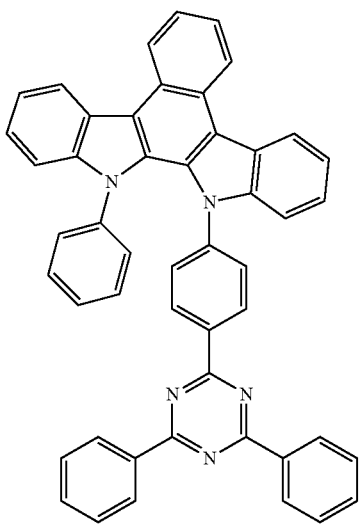
H2-150
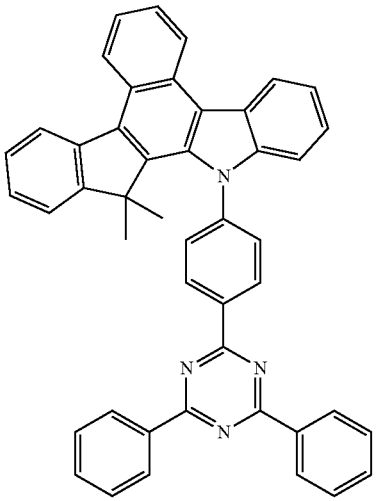

H2-151
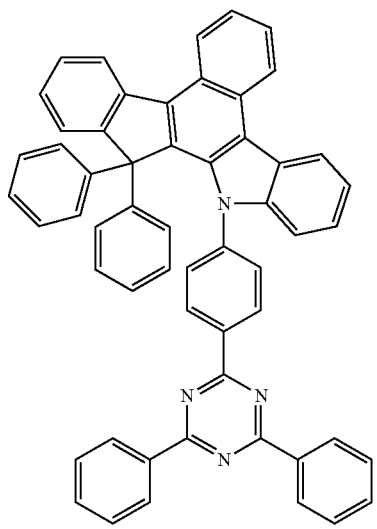
H2-152
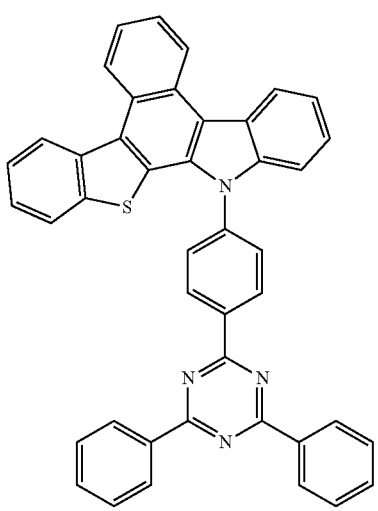
H2-153
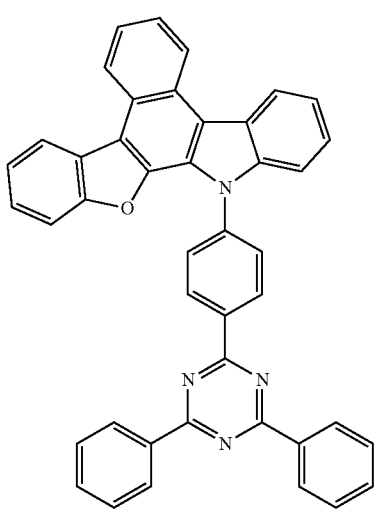
H2-154
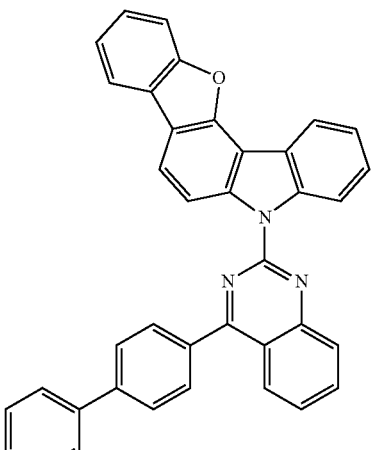
H2-155
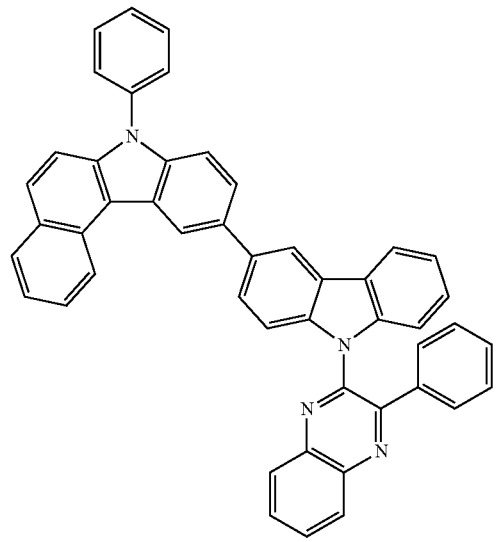
H2-156
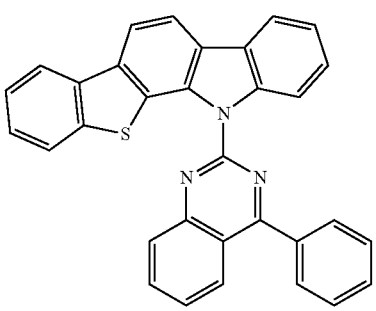

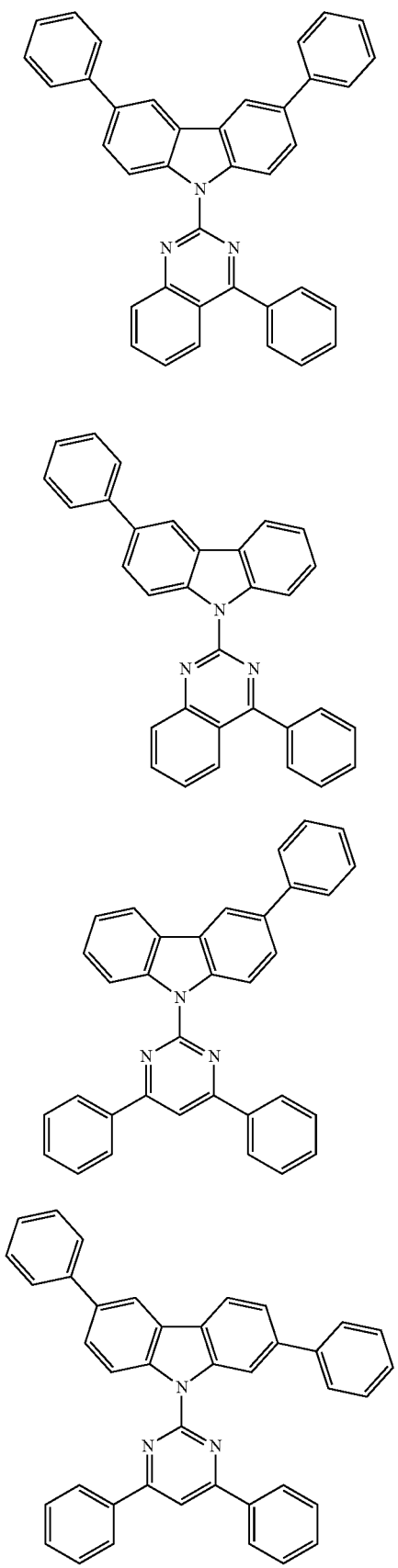
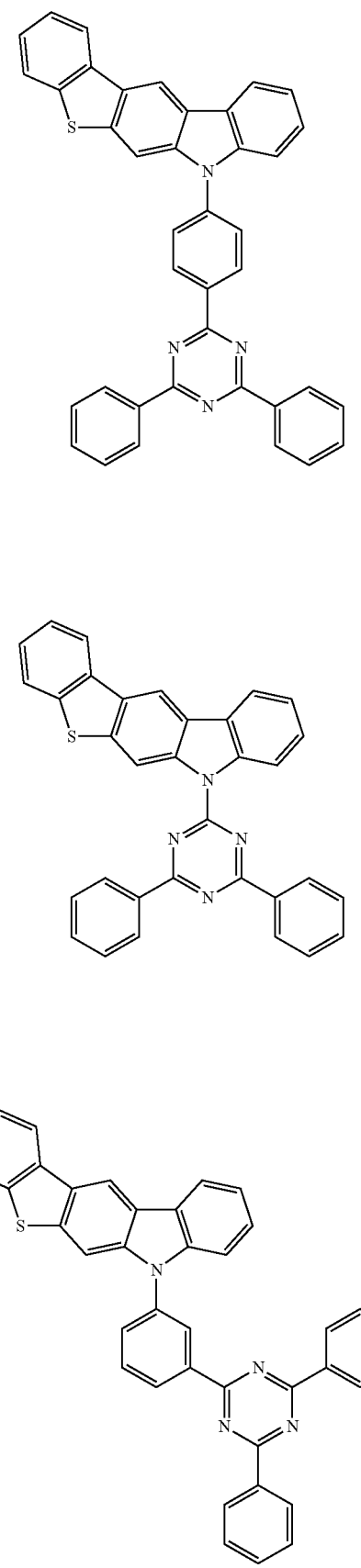

H2-164
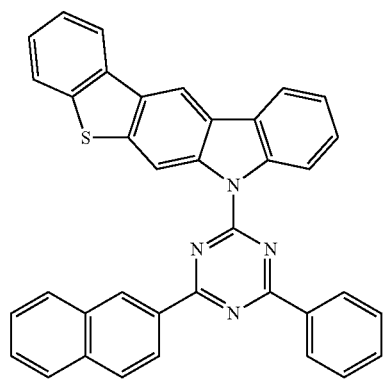
H2-165
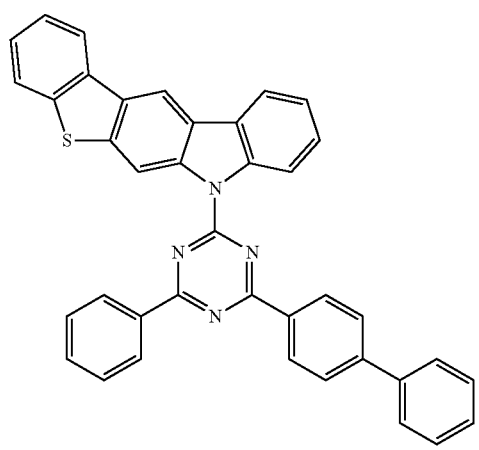
H2-166
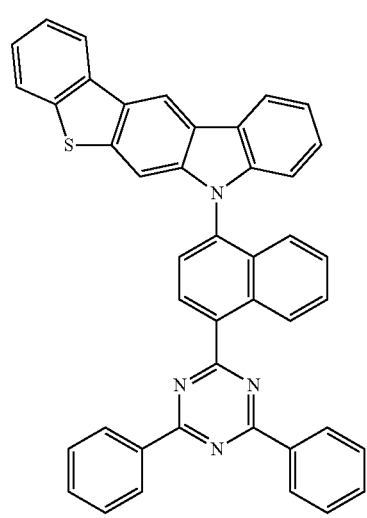
H2-167
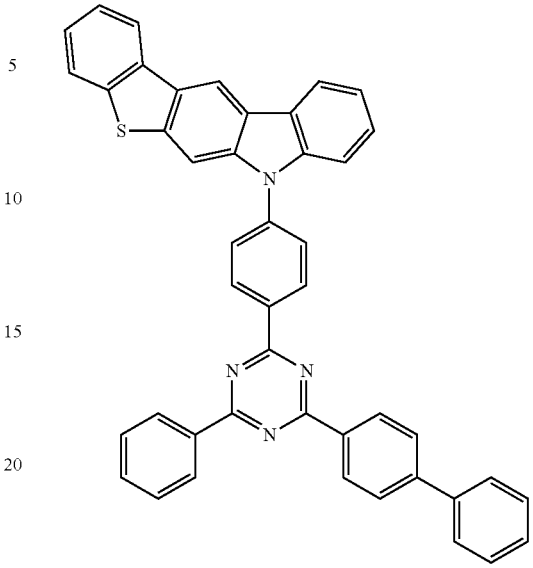
H2-168
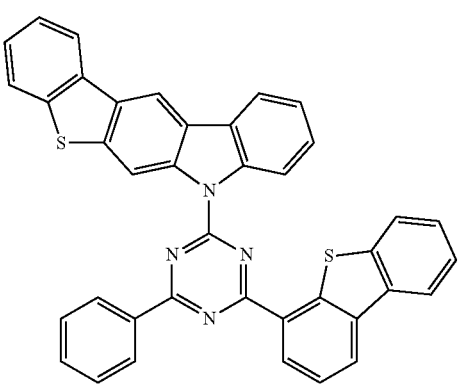
H2-169
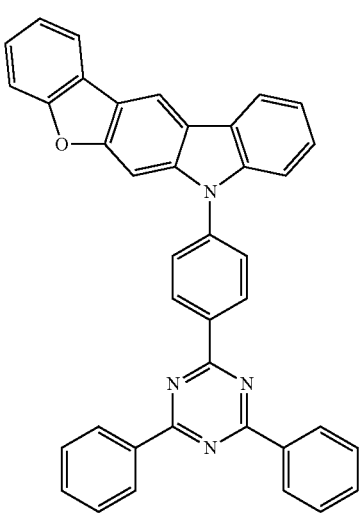

-continued
H2-170
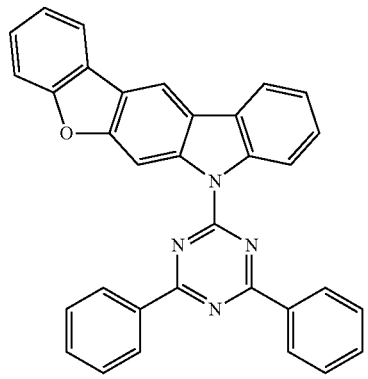
H2-171
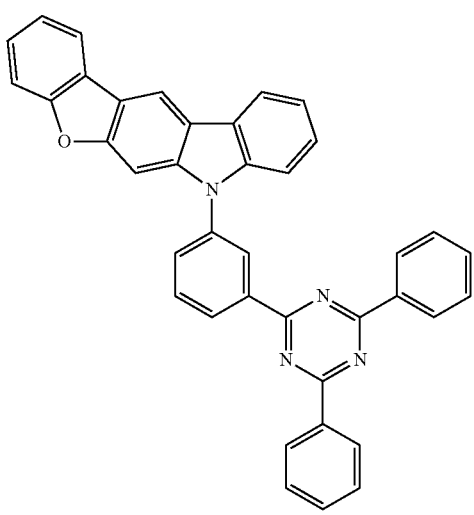
H2-172
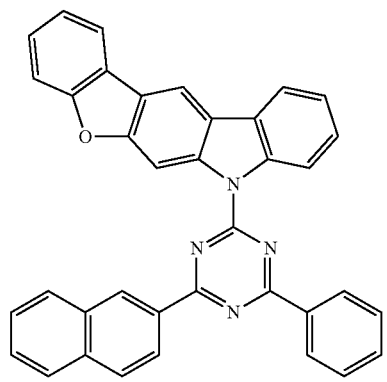
-continued
H2-173
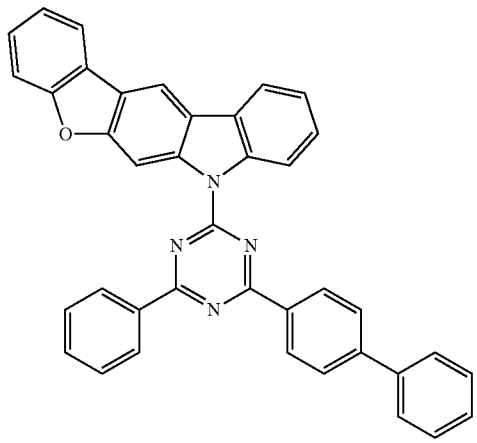
H2-174
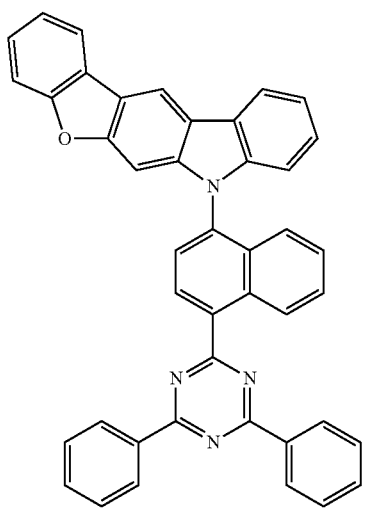
H2-175
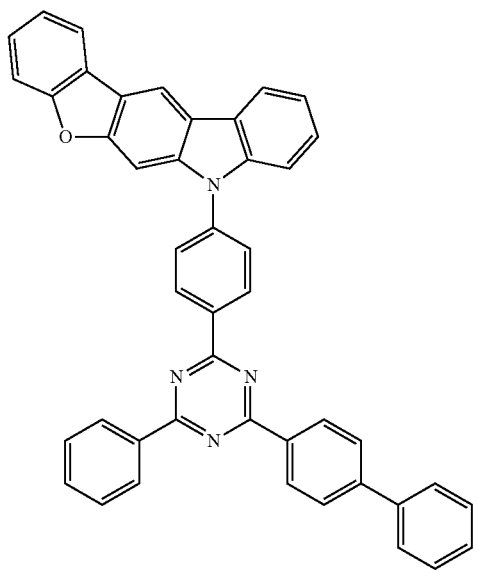

H2-176
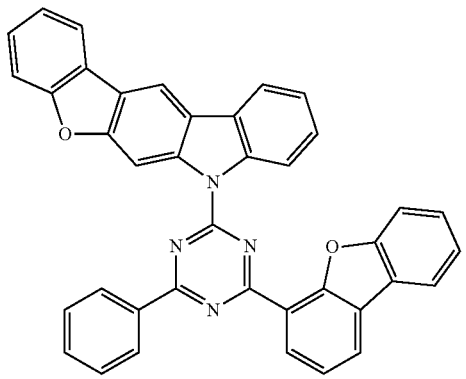
H2-177
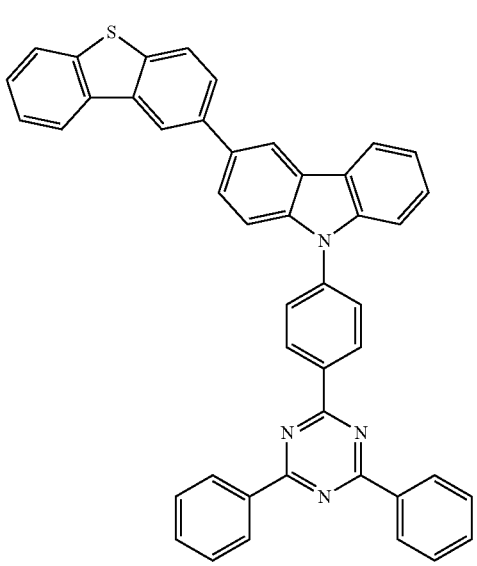
H2-178
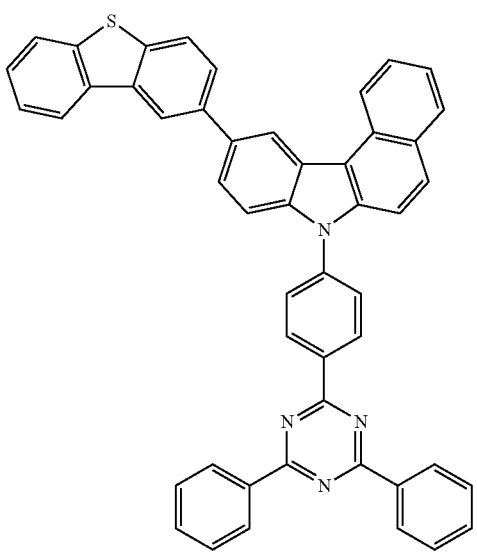
H2-179
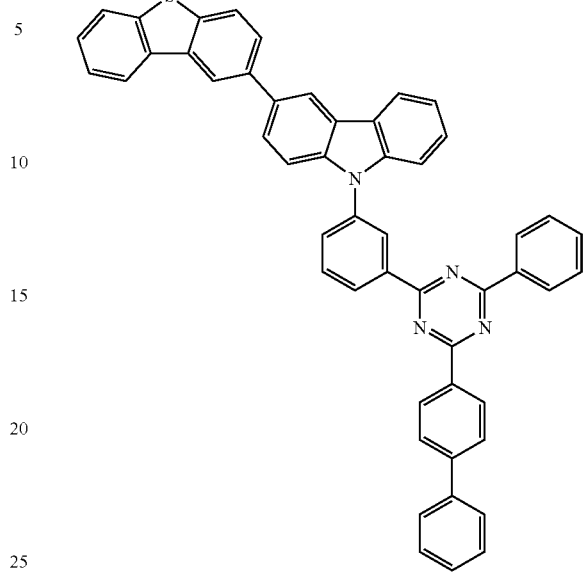
H2-180
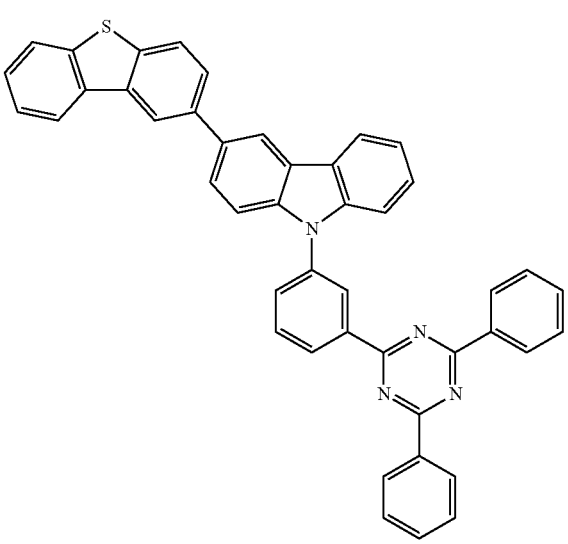

H2-181
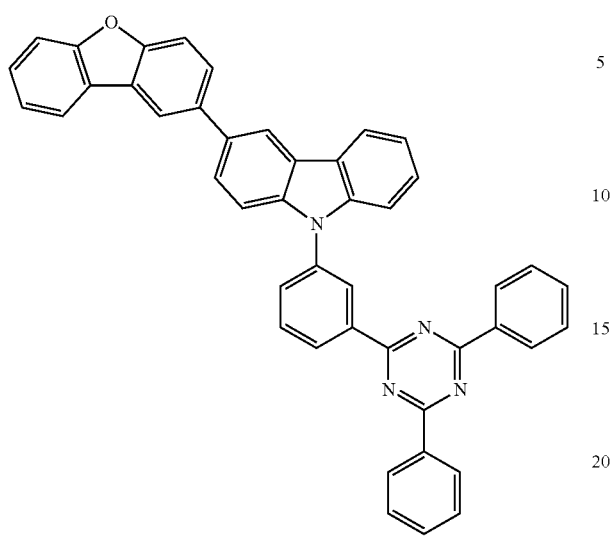
H2-184
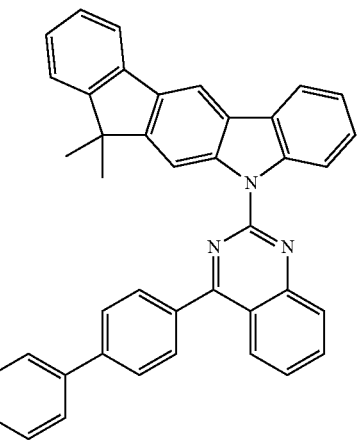
H2-182
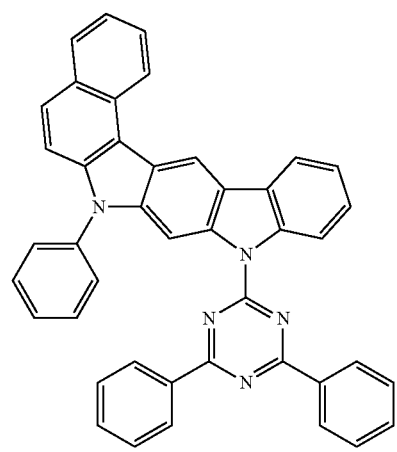
H2-185
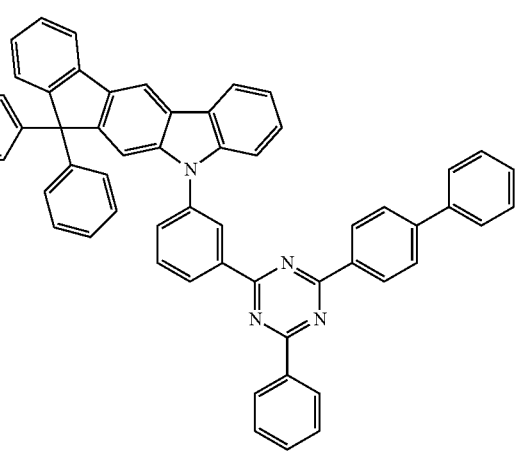
H2-183
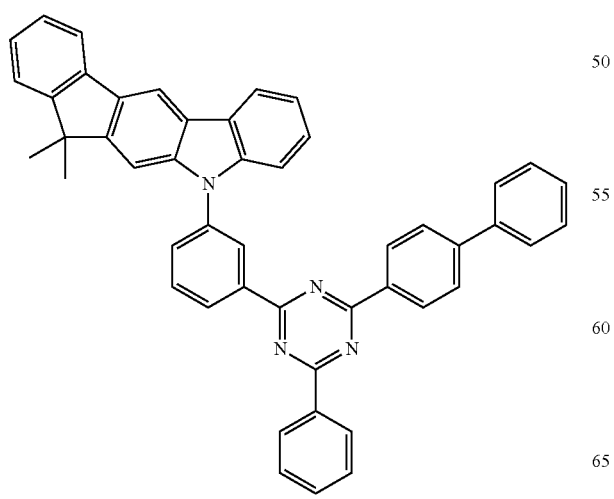
H2-186
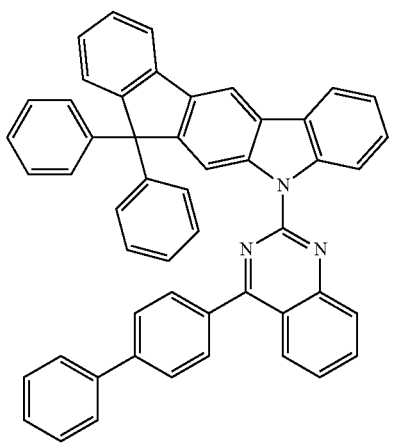

H2-187
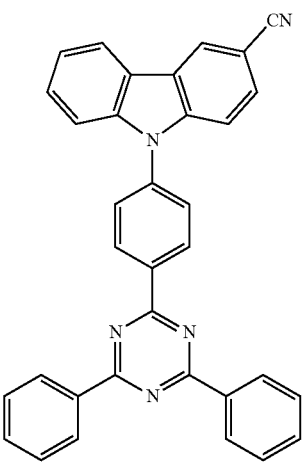
H2-188
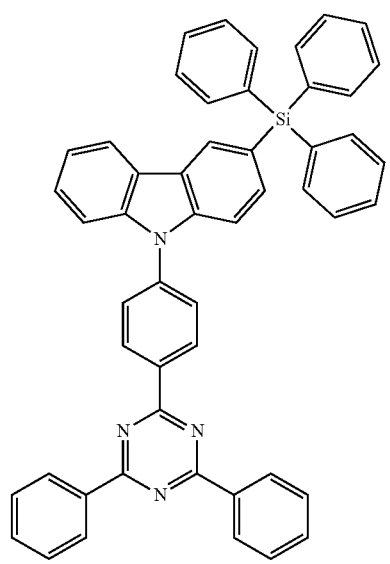
H2-189
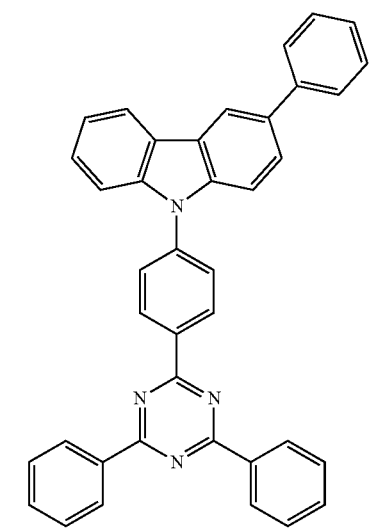
H2-190
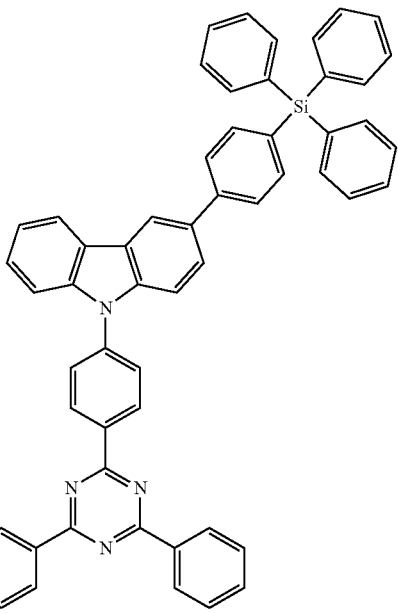
H2-191
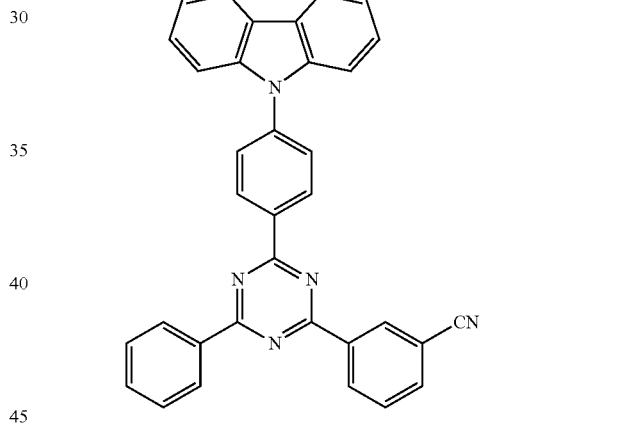
H2-192
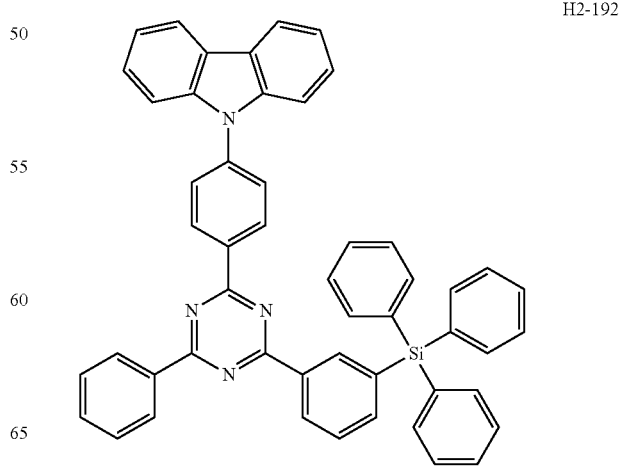

H2-193
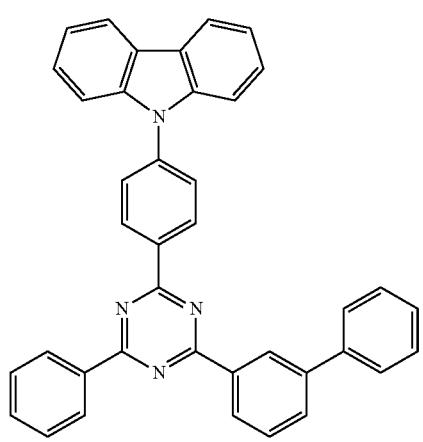
H2-194
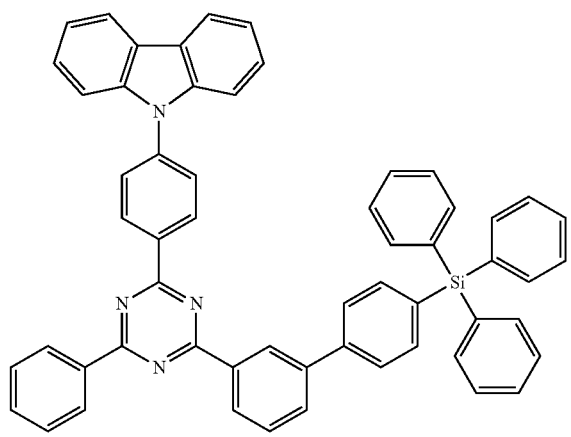
H2-195
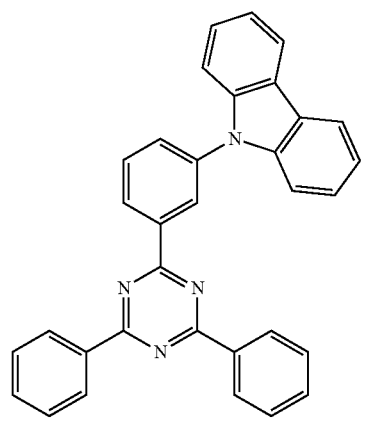
H2-196
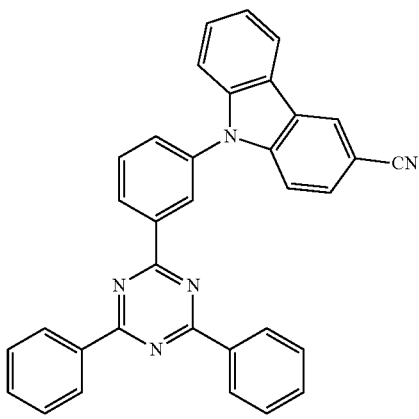
H2-197
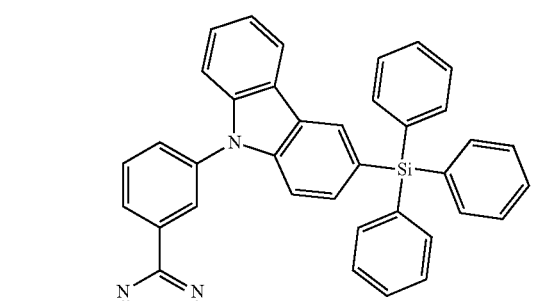
H2-198
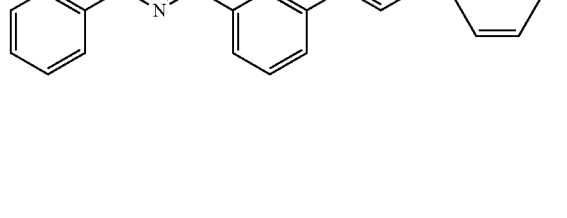
H2-199
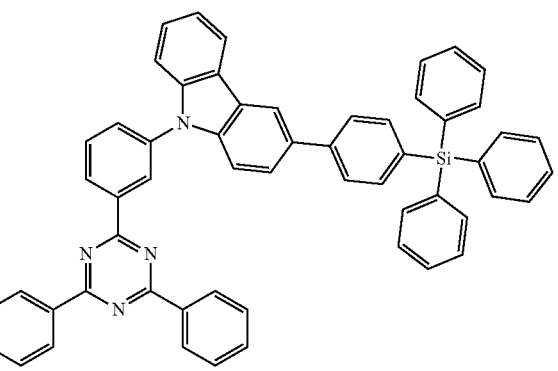

H2-200
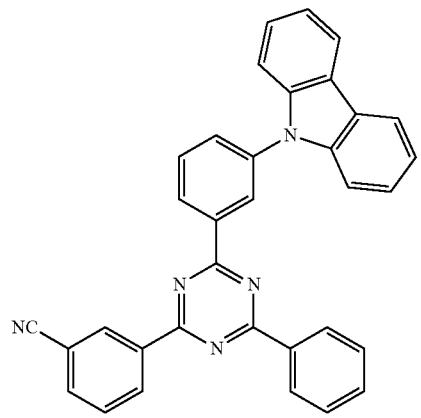
H2-201
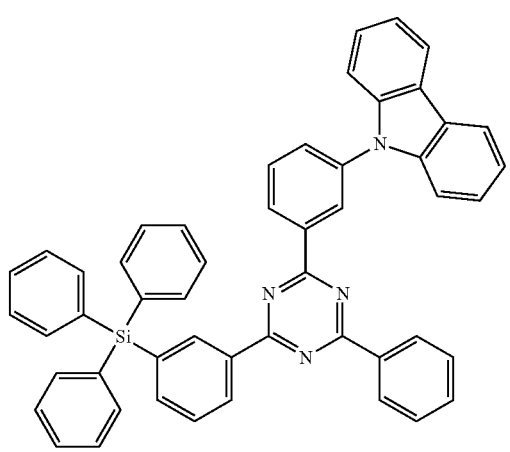
H2-202
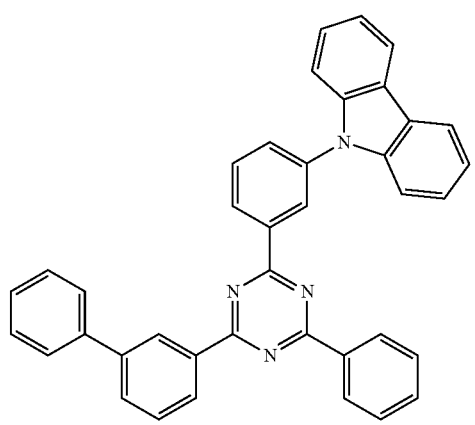
H2-203
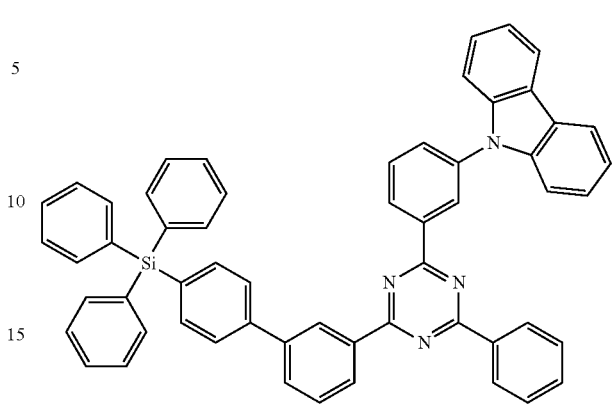
H2-204
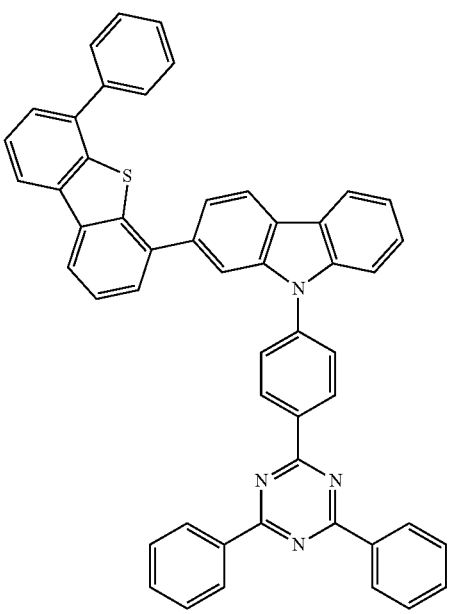
H2-205
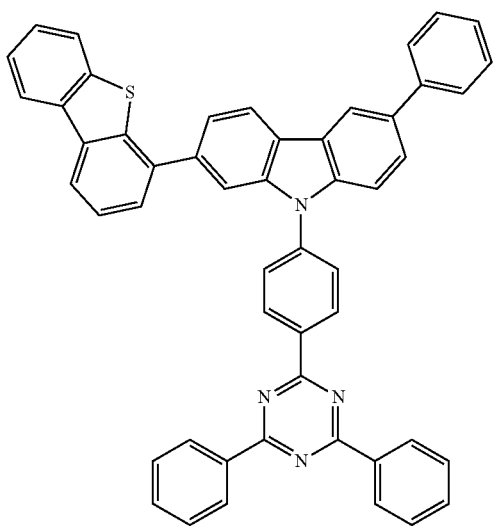

H2-206
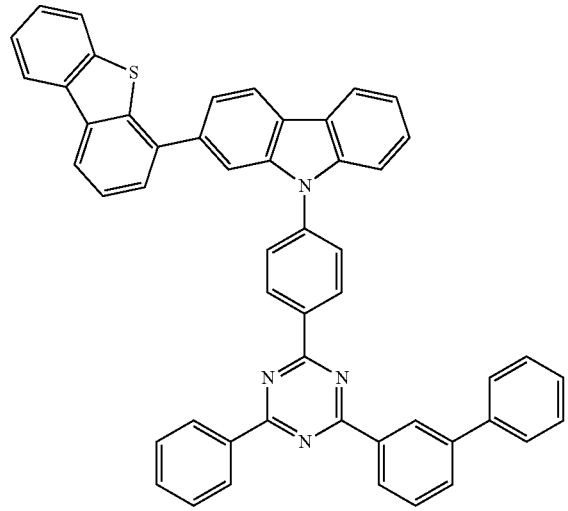
H2-207
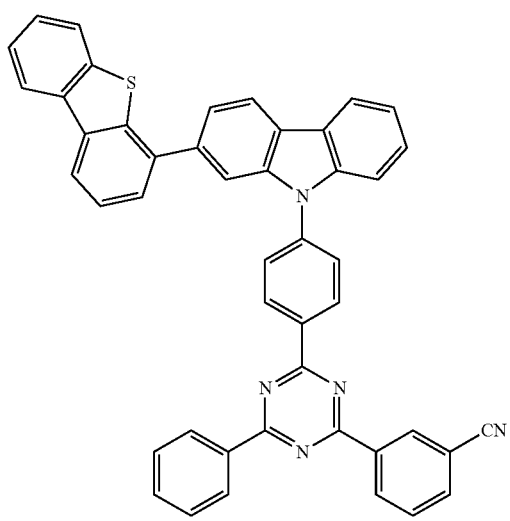
H2-208
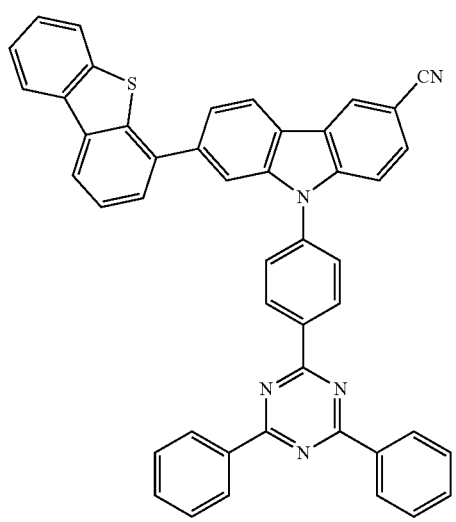
H2-209
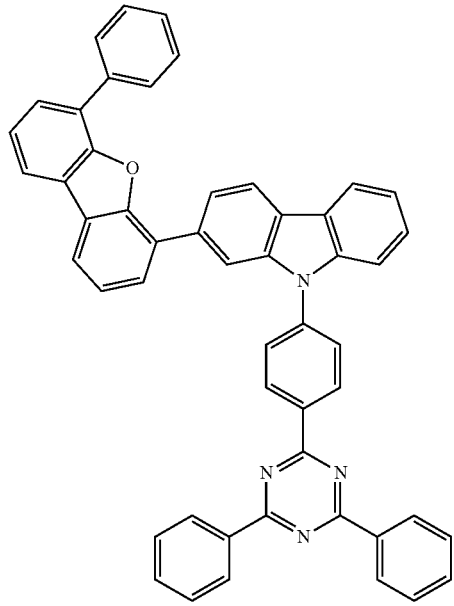
H2-210
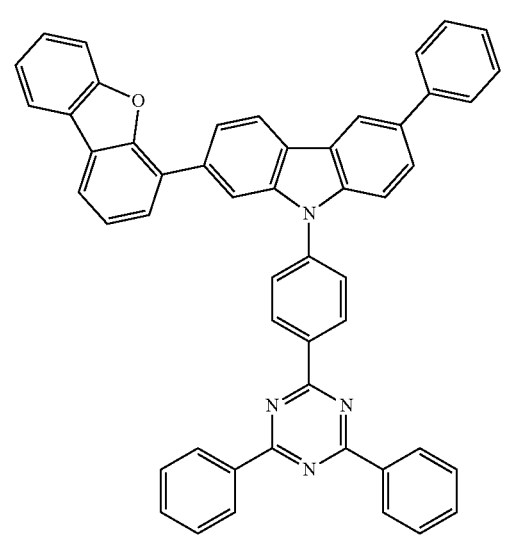

H2-211
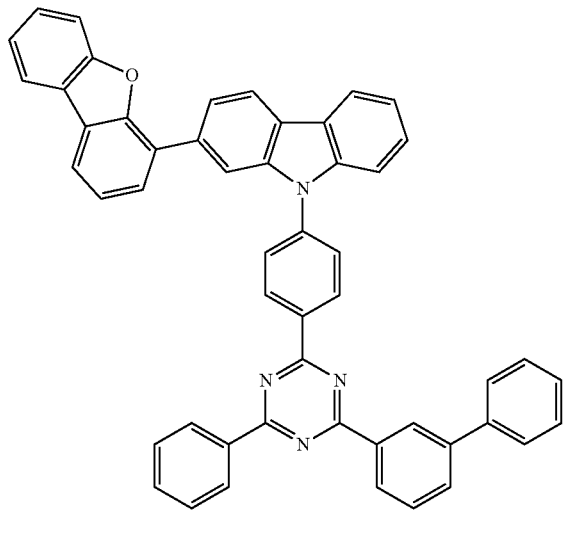
H2-212
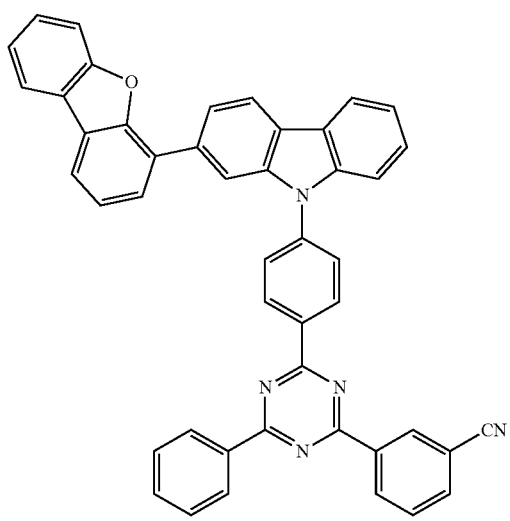
H2-213
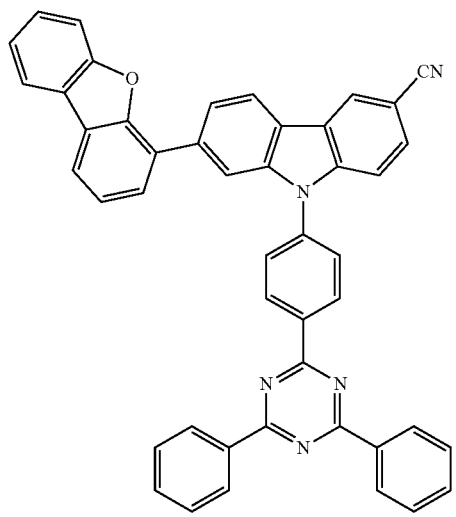
H2-214
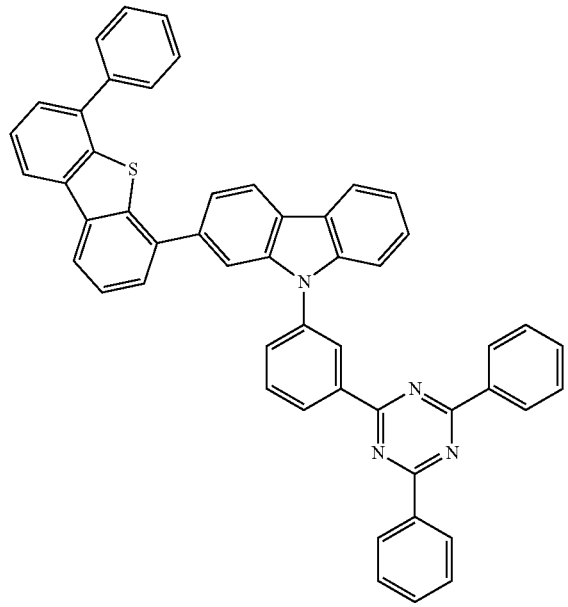
H2-215
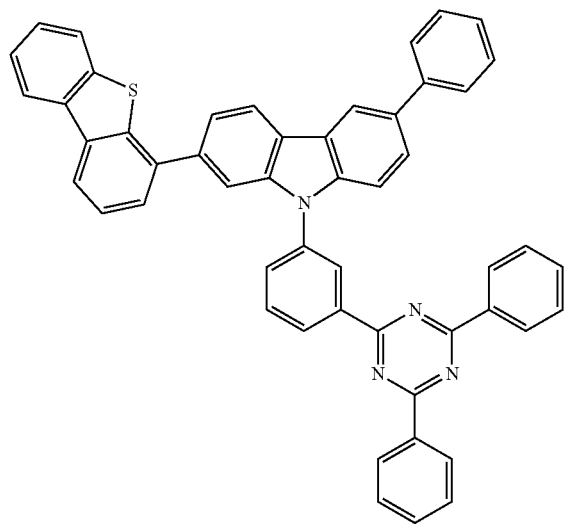
H2-216
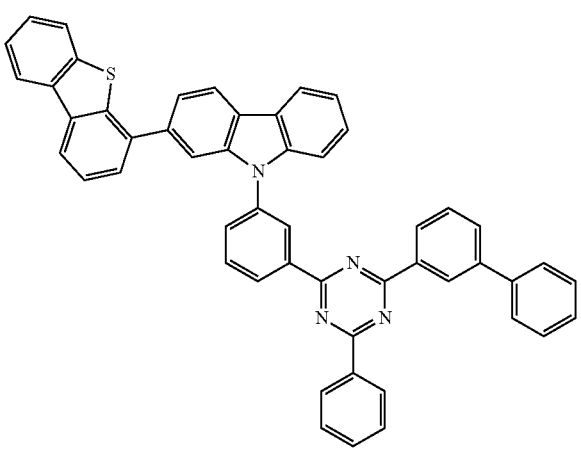

-continued
H2-217
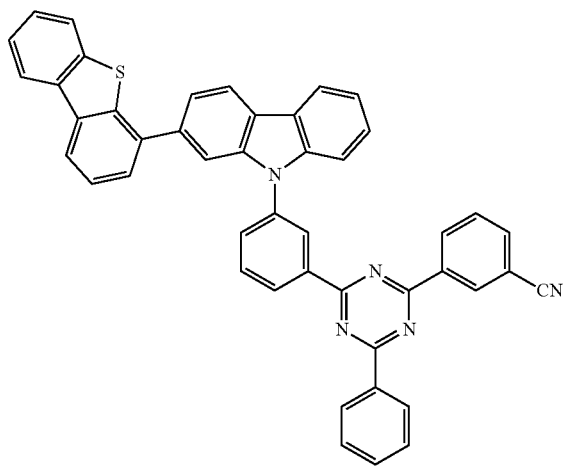
H2-218
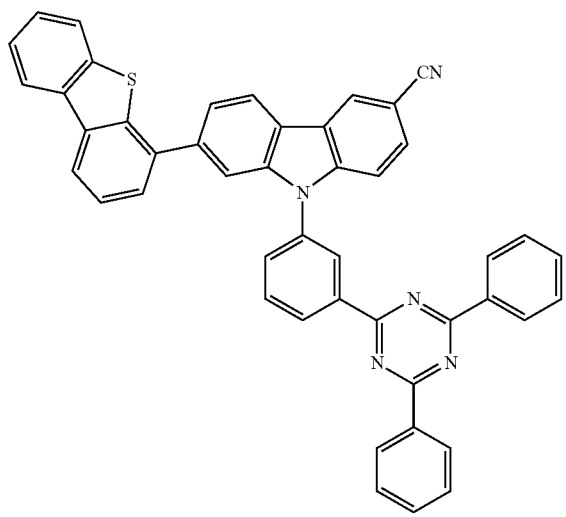
H2-219
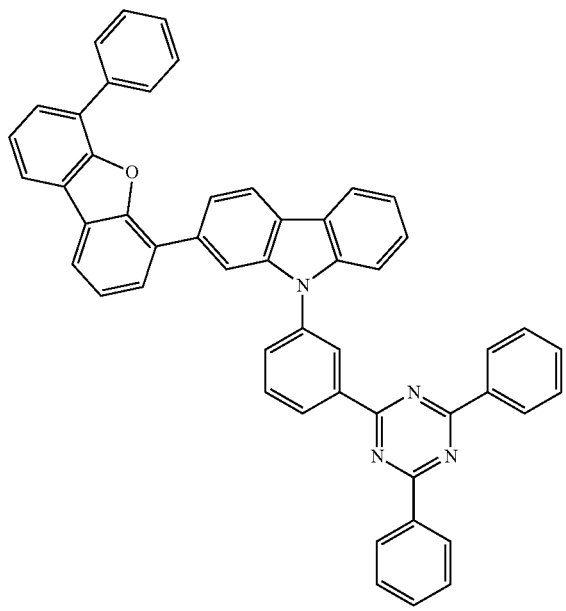
-continued
H2-220
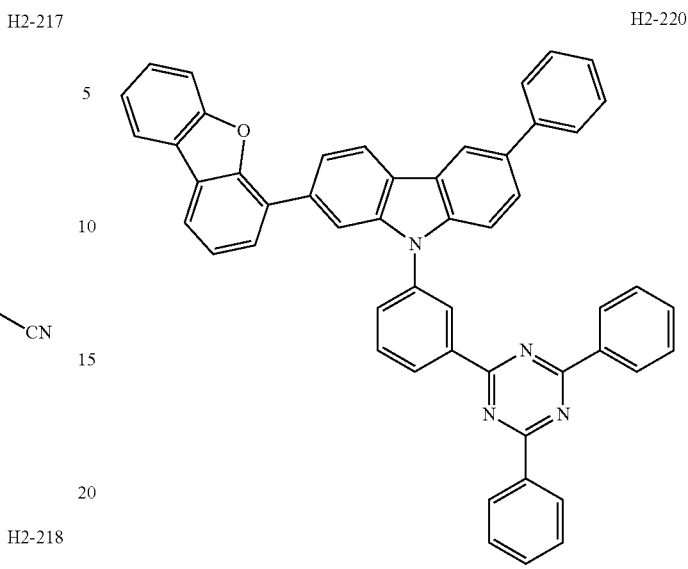
H2-221
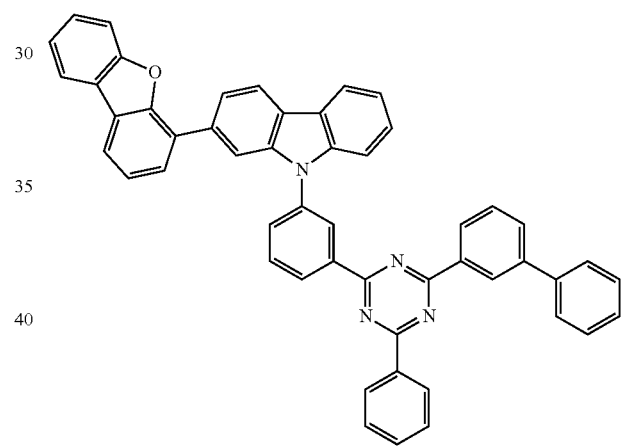
H2-222
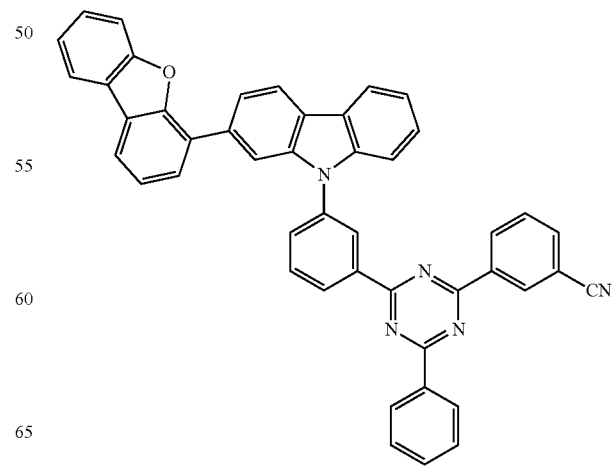

H2-223
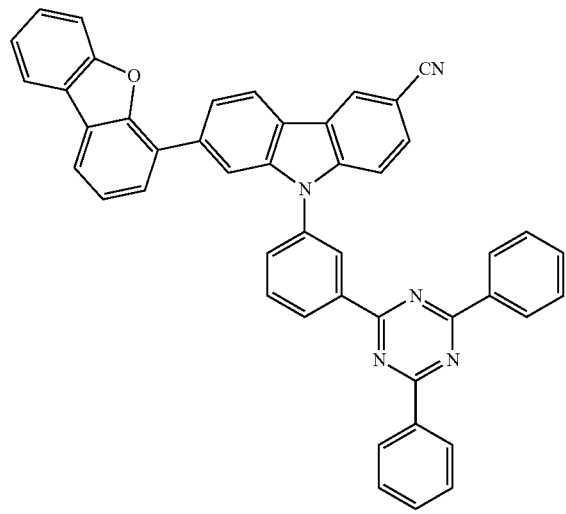
H2-225
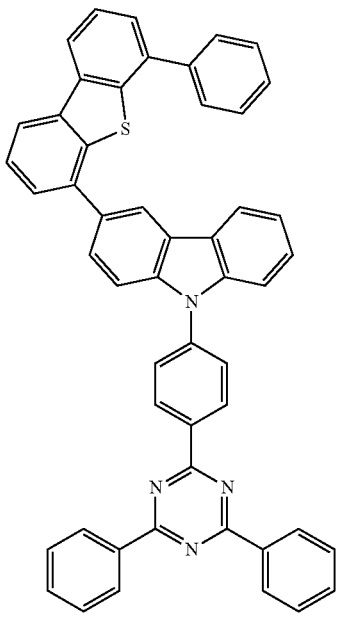
H2-224
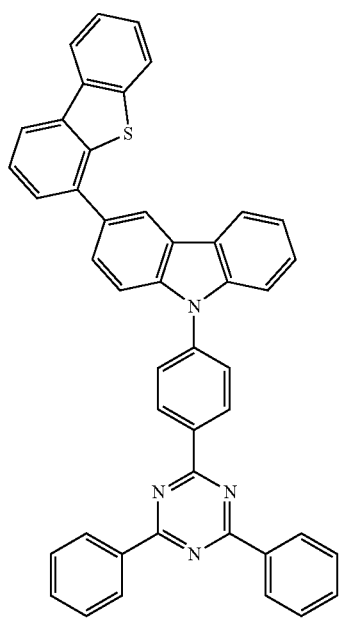
H2-226
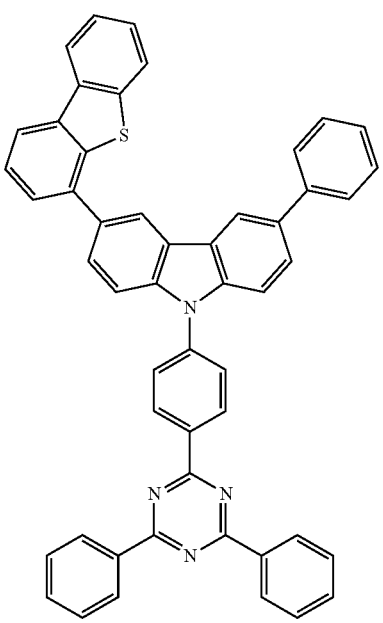

H2-227
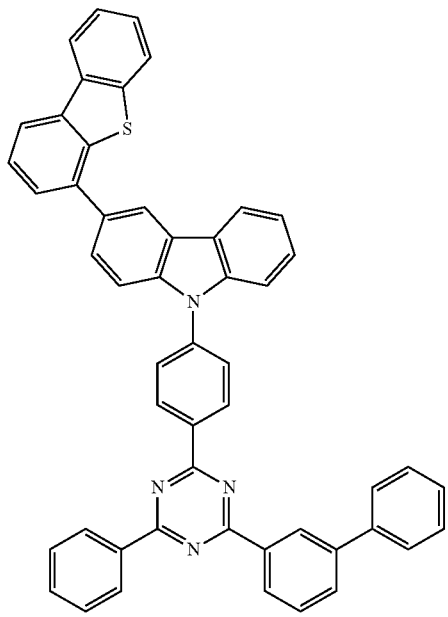
H2-229
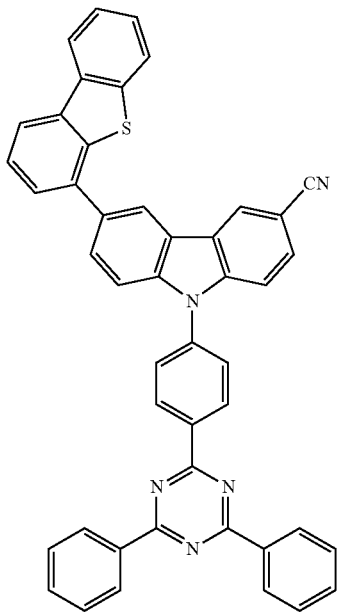
H2-228
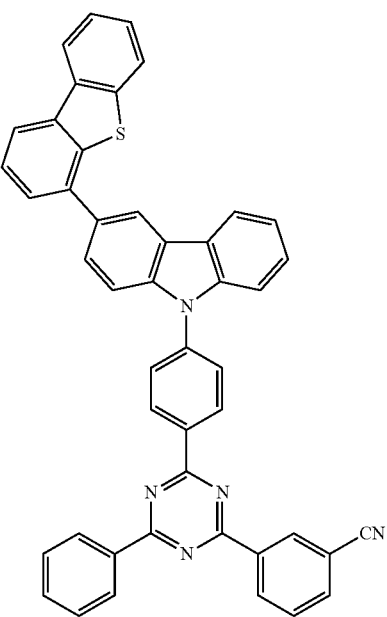
H2-230
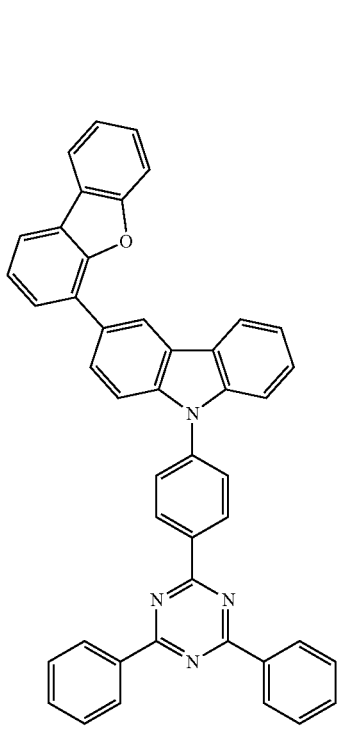

H2-231
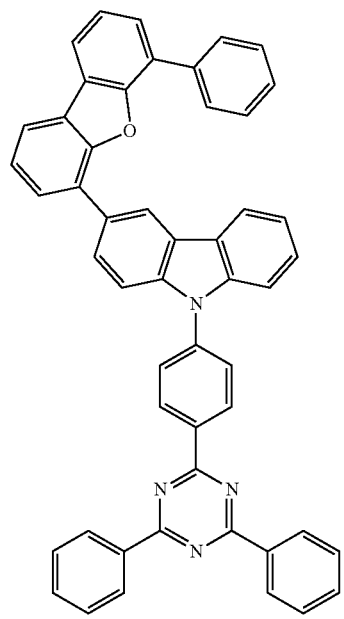
H2-233
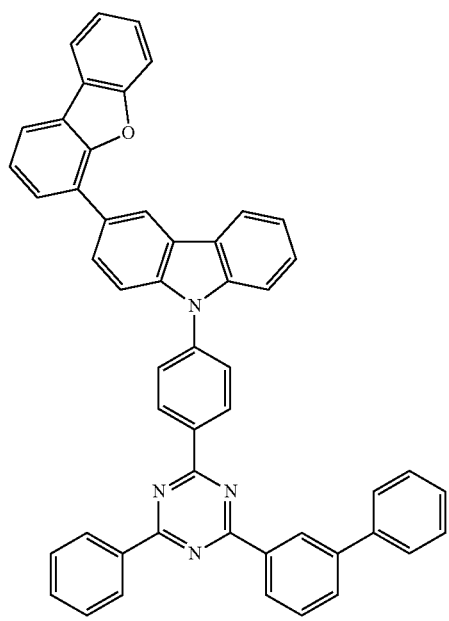
H2-232
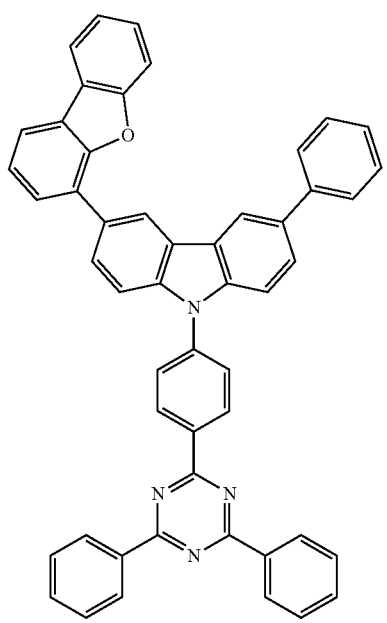
H2-234
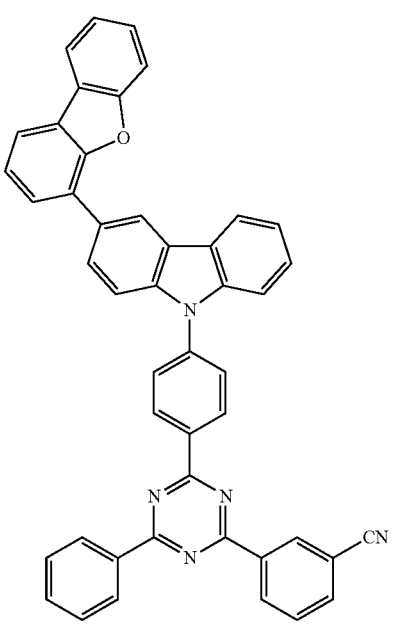

H2-235
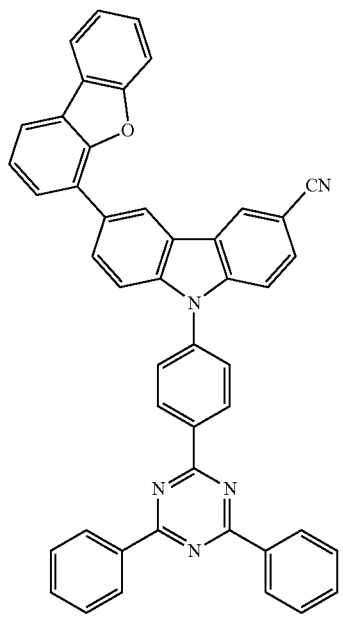
H2-236
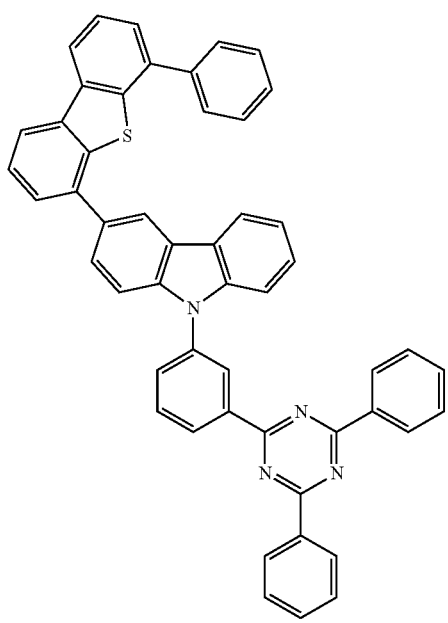
H2-237
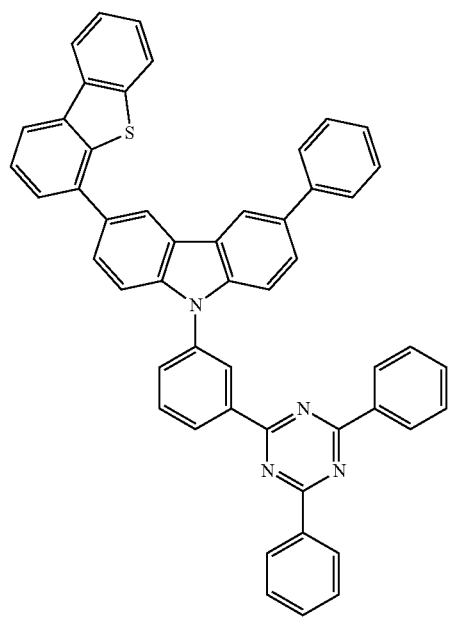
H2-238
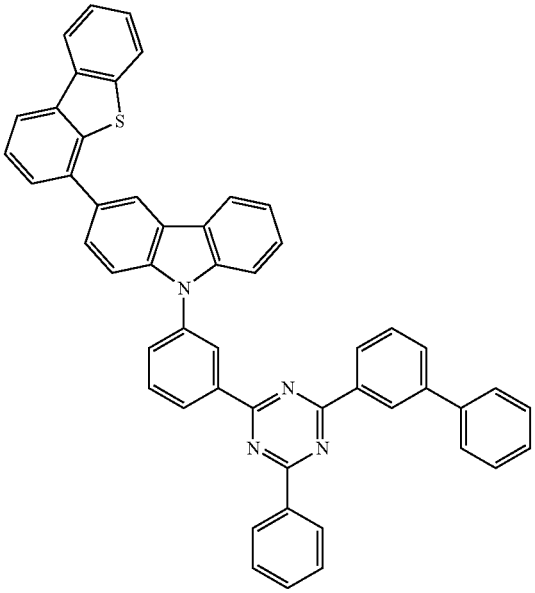

H2-239
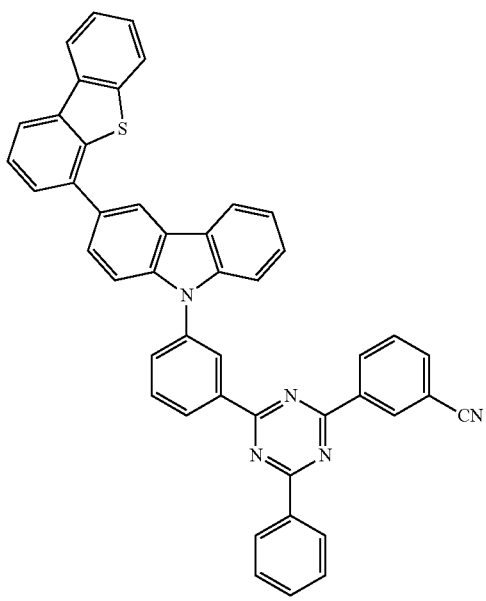
H2-240
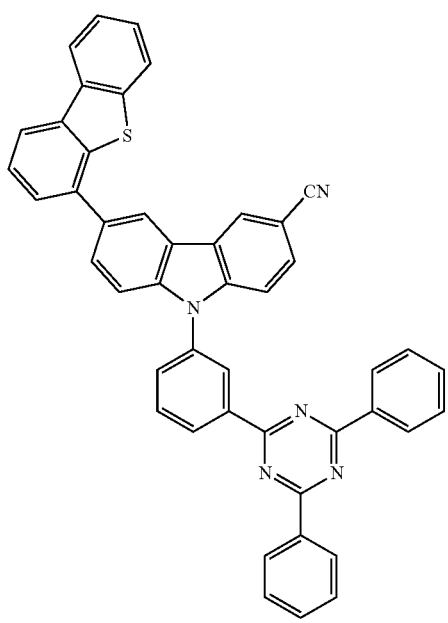
H2-241
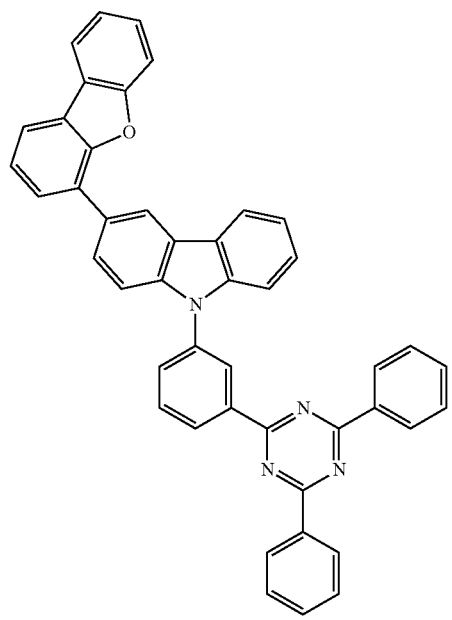
H2-242
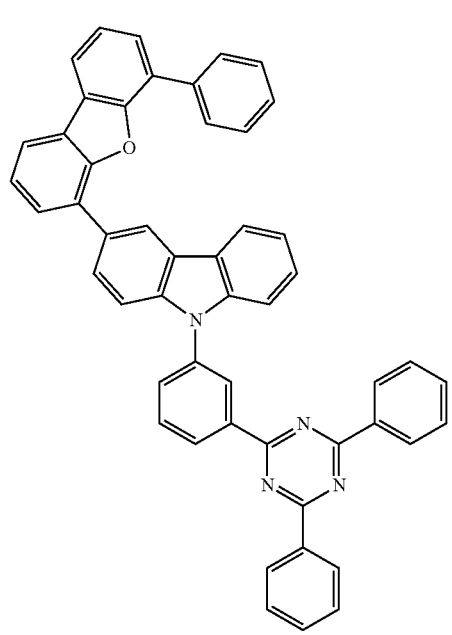

H2-243
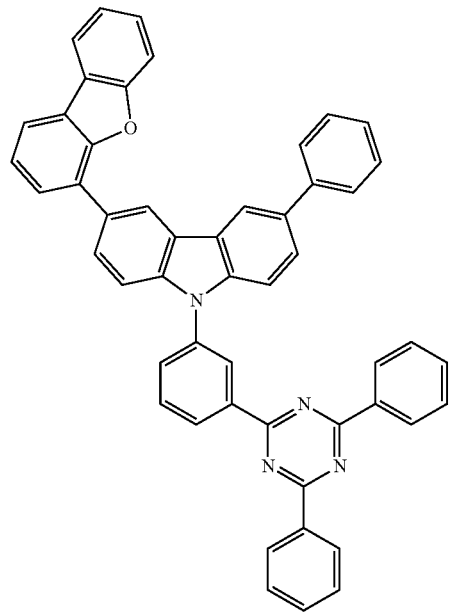
H2-244
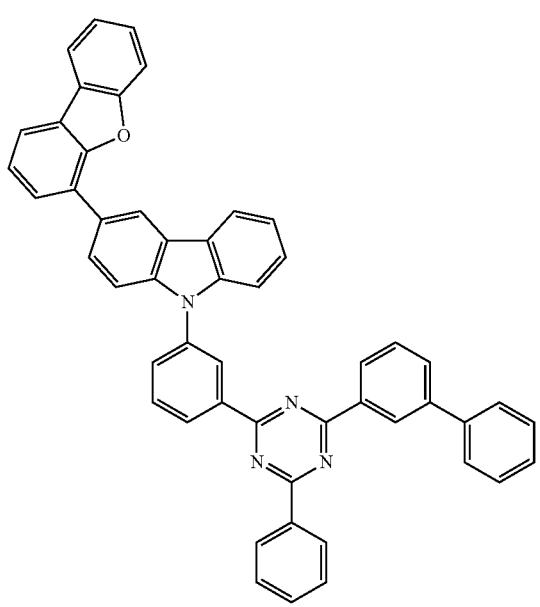
H2-245
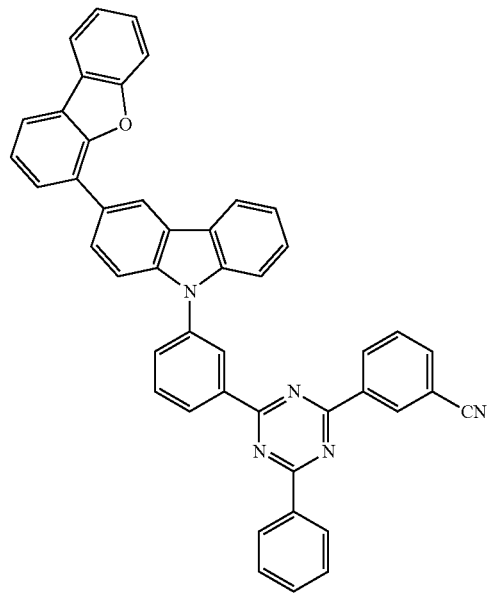
H2-246
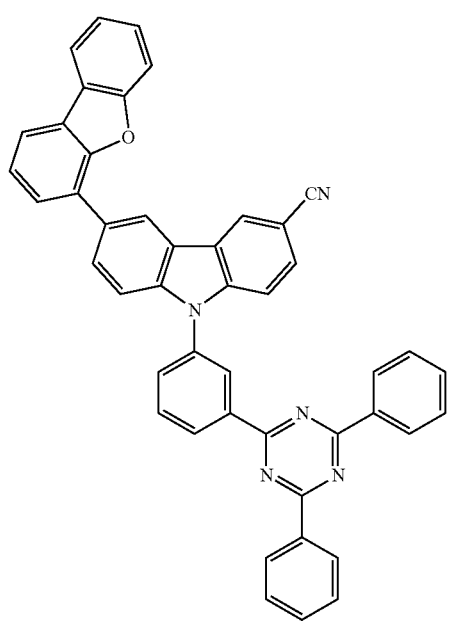
H2-247
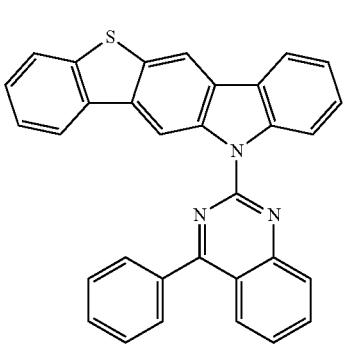

H2-248
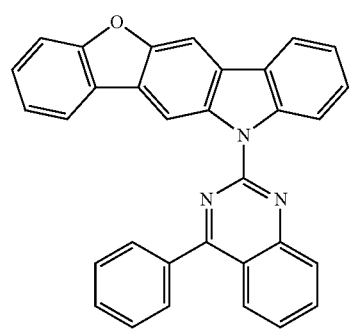
H2-249
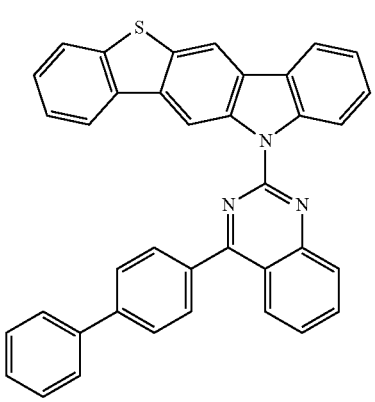
H2-250
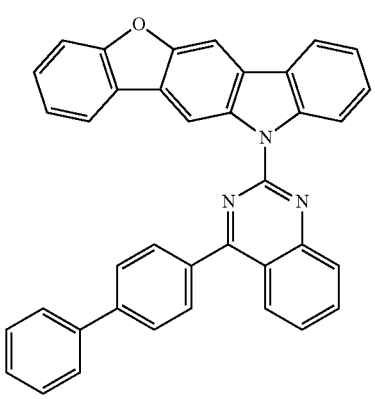
H2-251
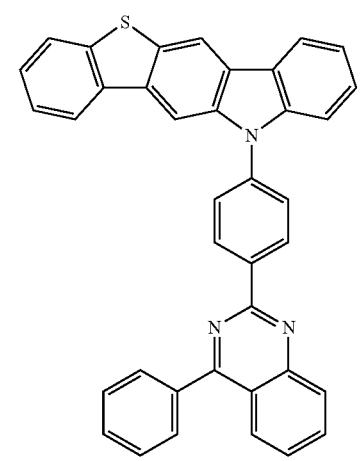
H2-252
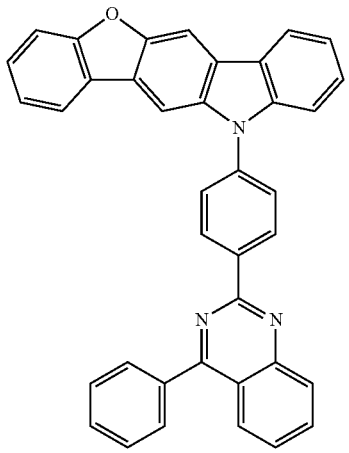
H2-253
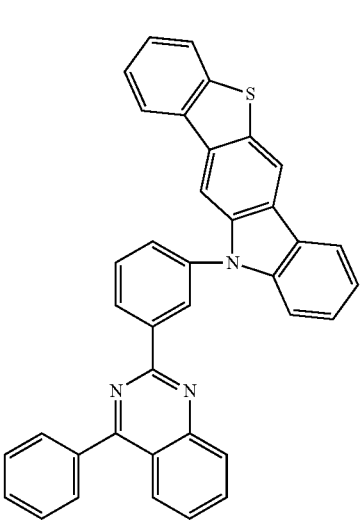
H2-254
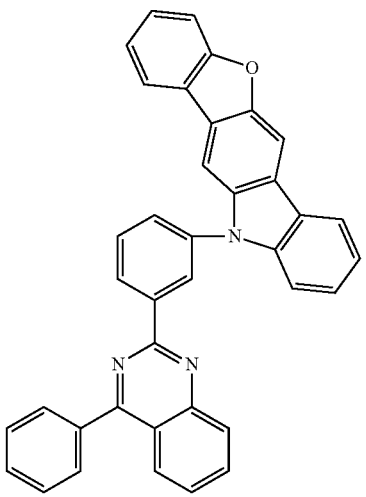

-continued
H2-255
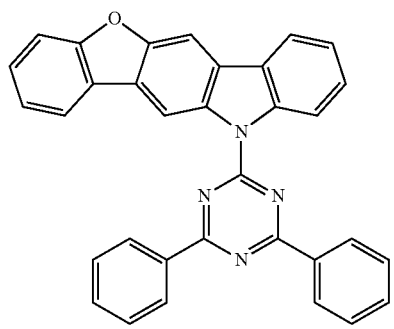
H2-256
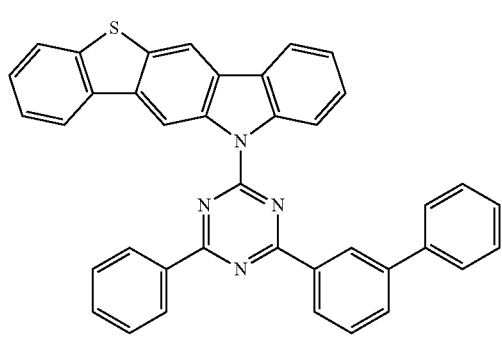
H2-257
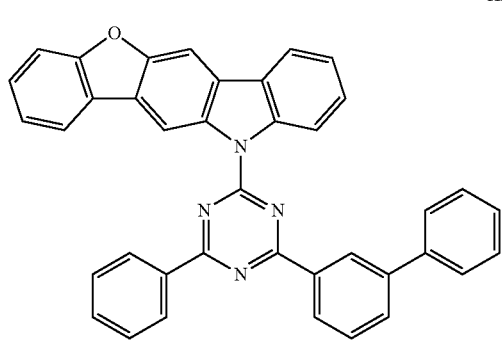
H2-258
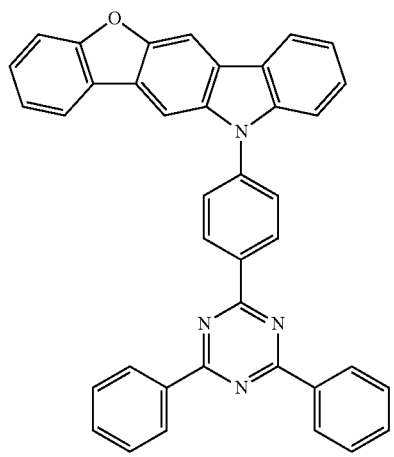
-continued
H2-259
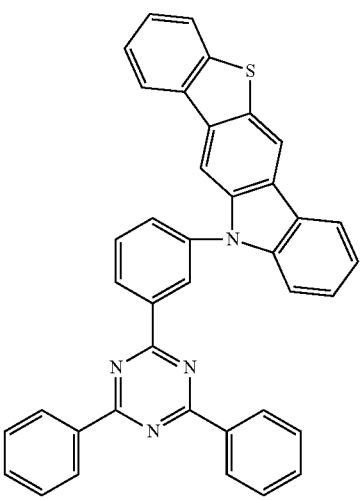
H2-260
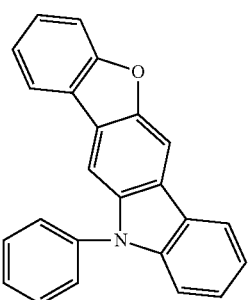
H2-261
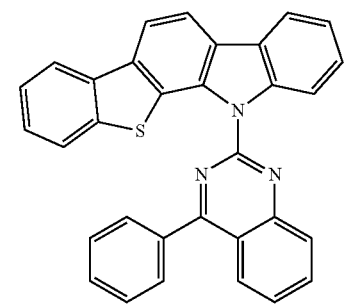
H2-262
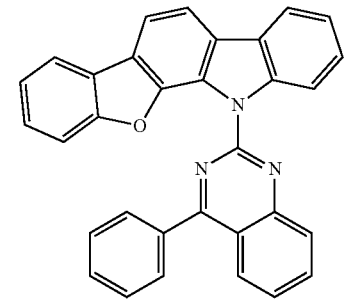

-continued
H2-263
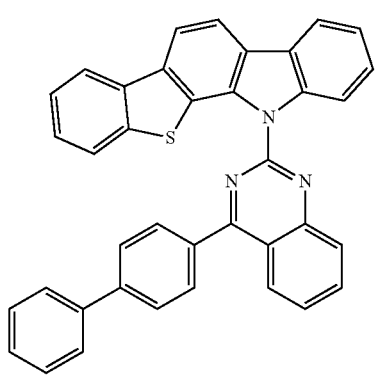
H2-264
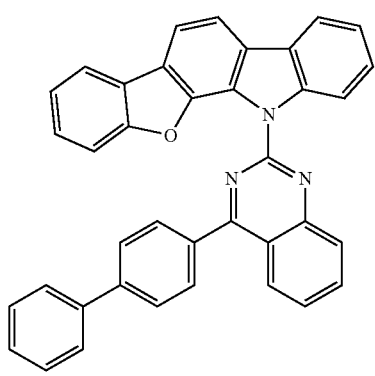
H2-265
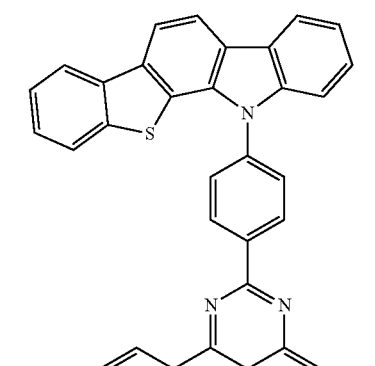
H2-266
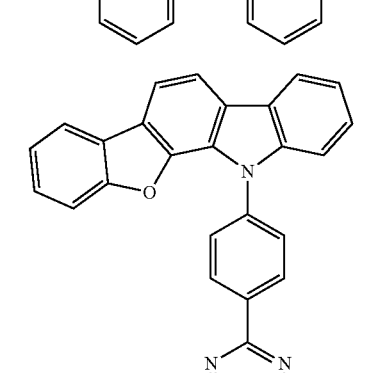
-continued
H2-267
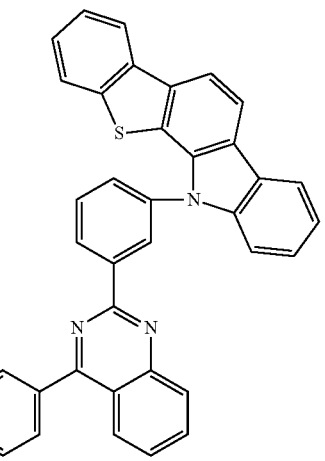
H2-268
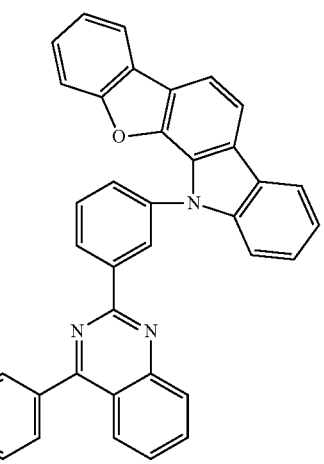
H2-269
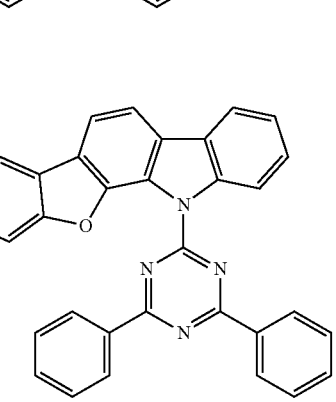
H2-270
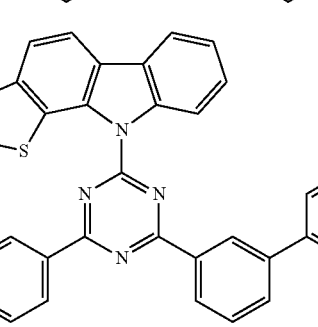

H2-271
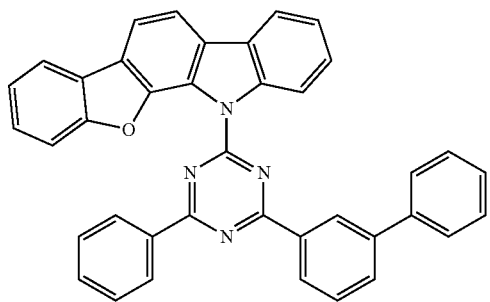
H2-272
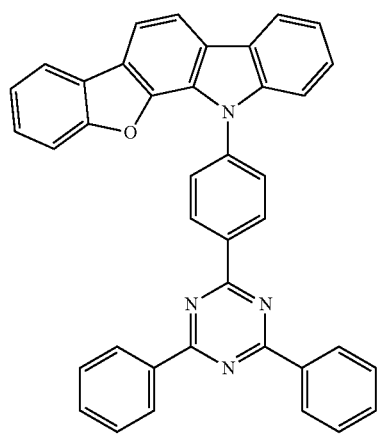
H2-273
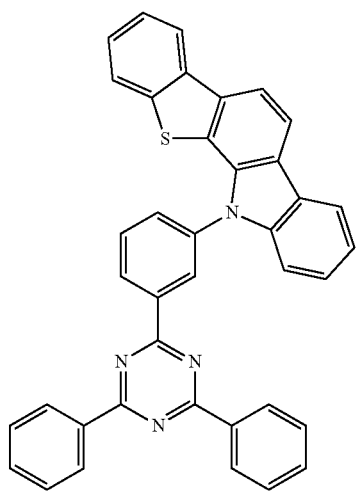
H2-274
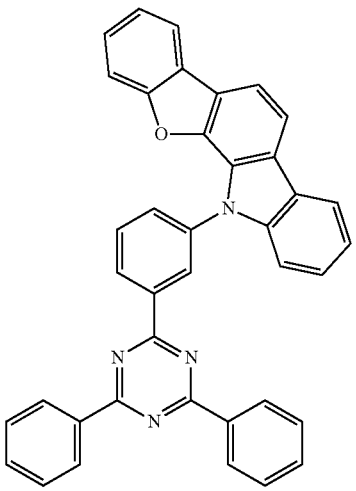
H2-275
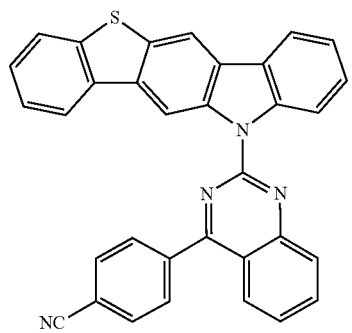
H2-276
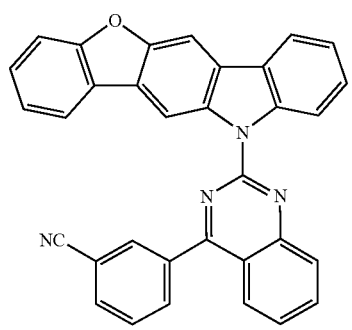
H2-277
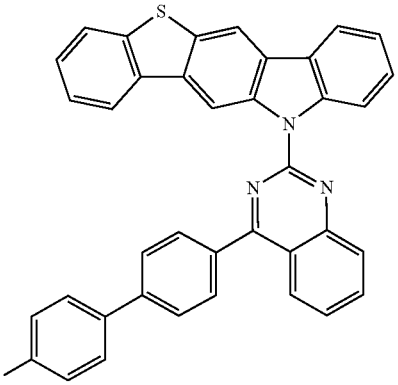

-continued
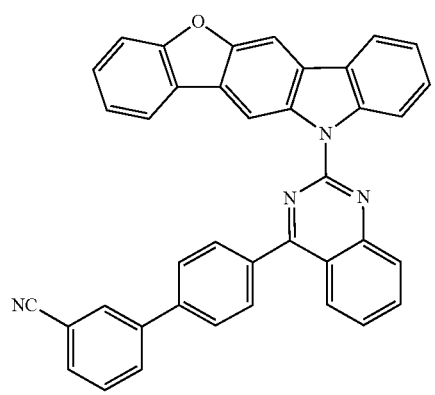
H2-278
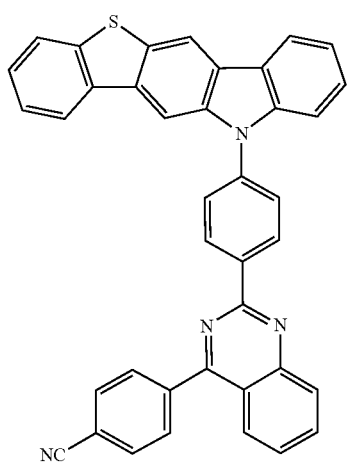
H2-279
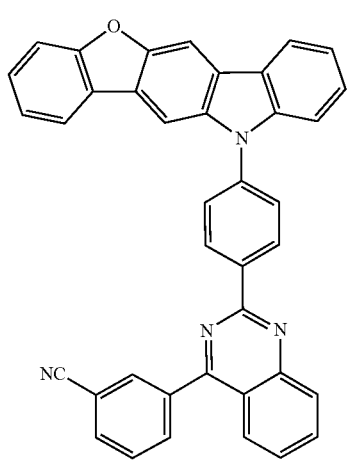
H2-280
-continued
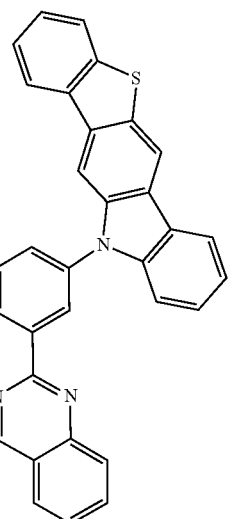
H2-281
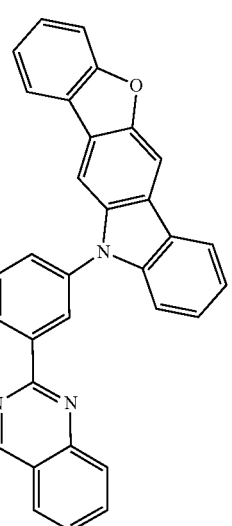
H2-282
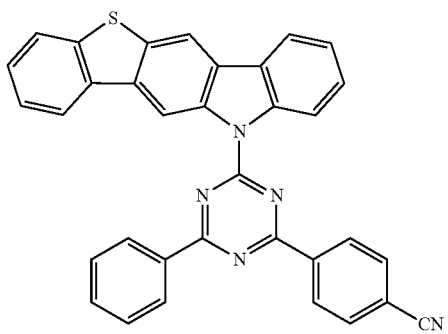
H2-283

H2-284
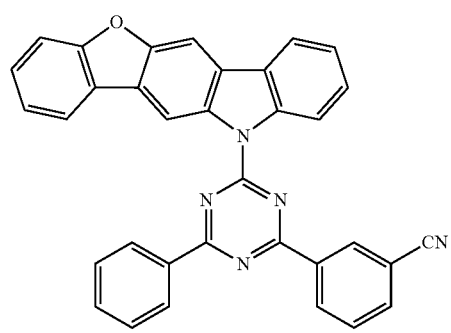
H2-285
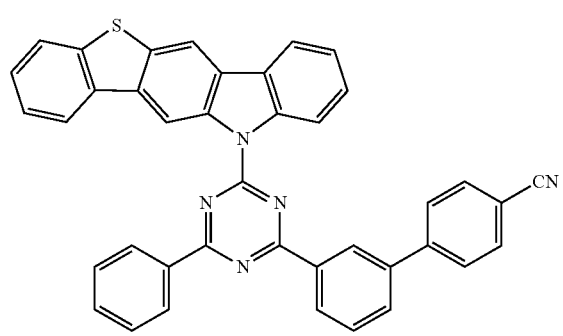
H2-286
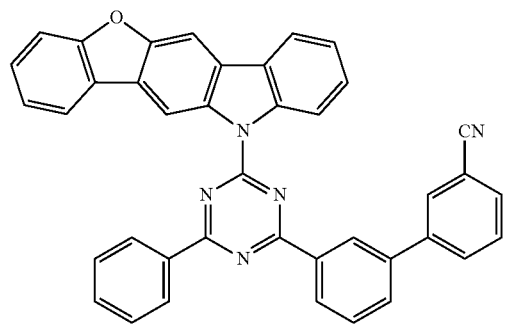
H2-287
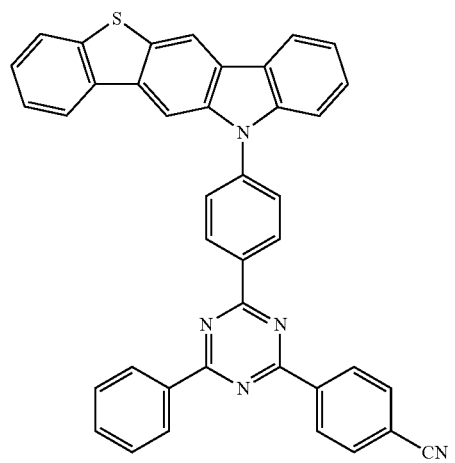
H2-288
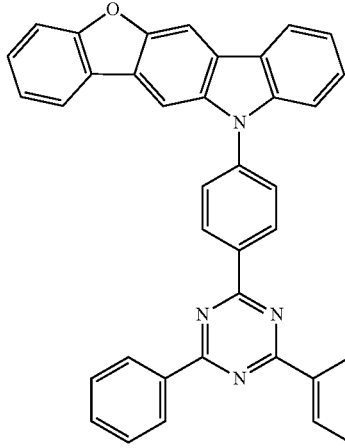
H2-289
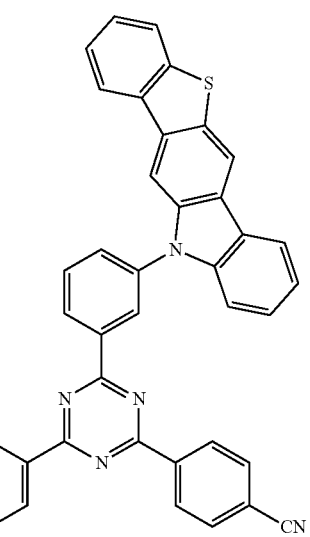
H2-290
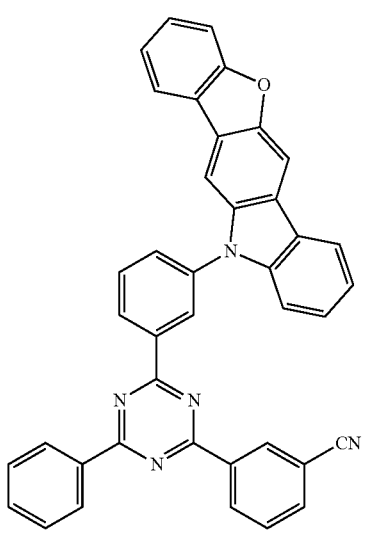

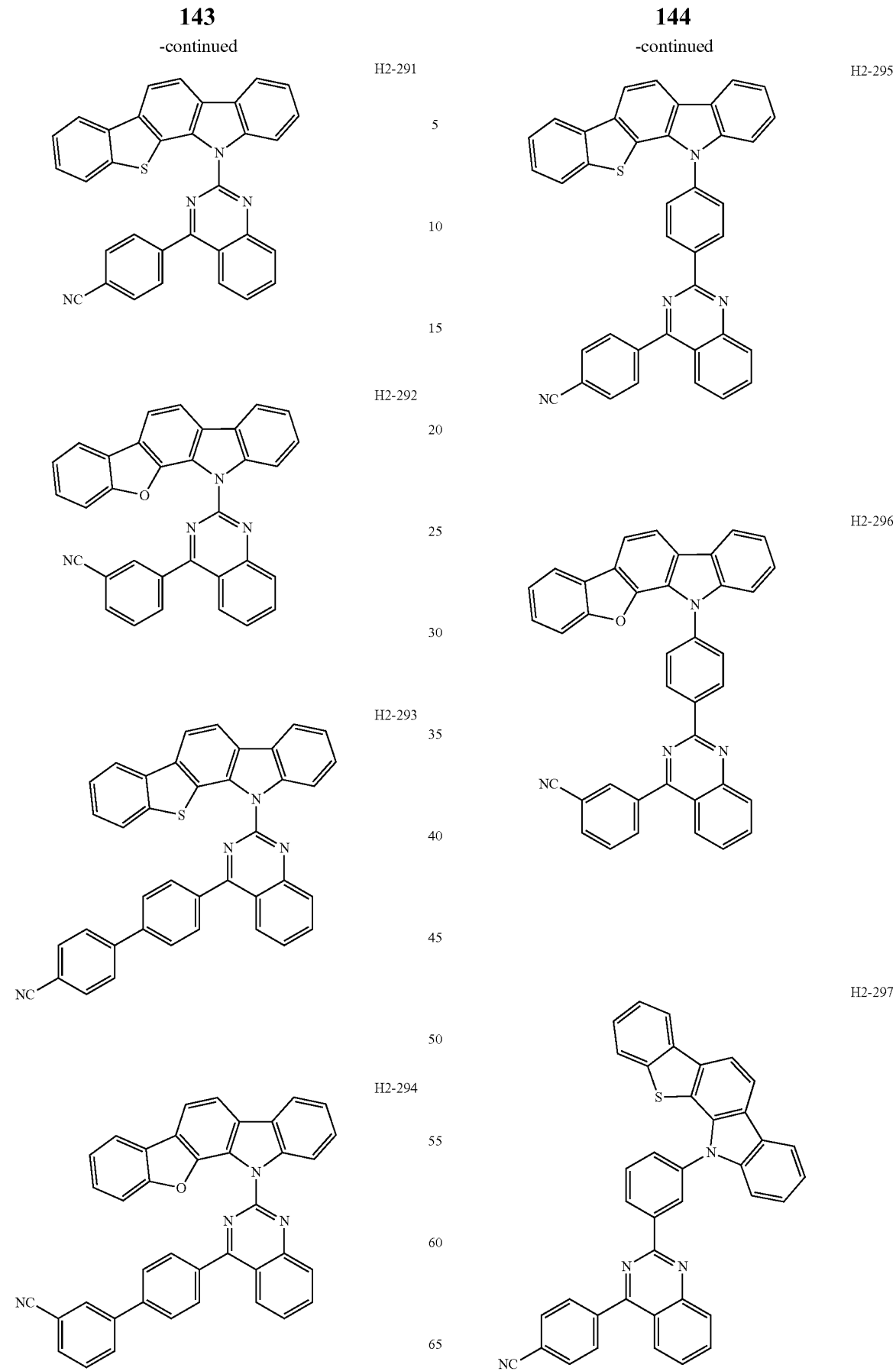

145
-continued

H2-298

H2-299

H2-300

H2-301

146
-continued

H2-302

H2-303

H2-304

-continued
H2-305
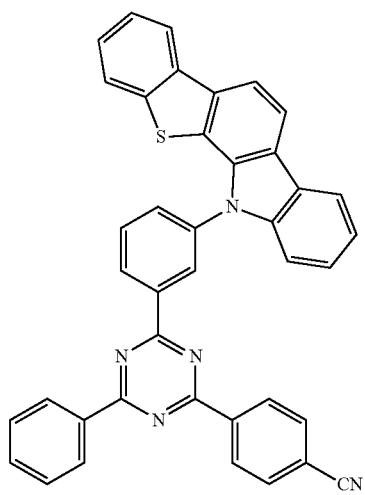
H2-306
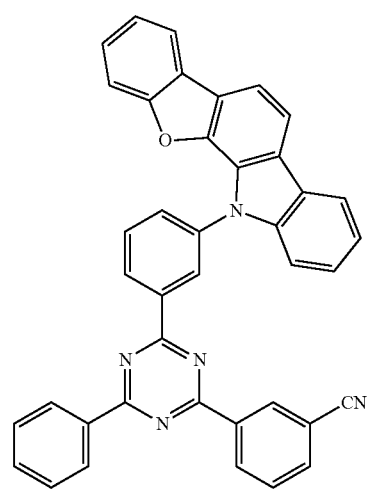
H2-307
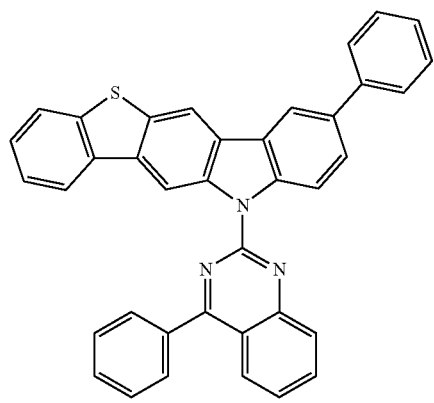
-continued
H2-308
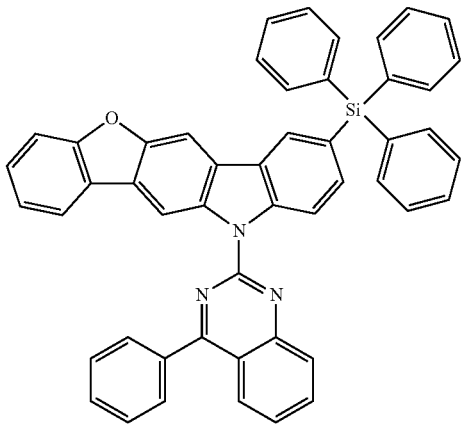
H2-309
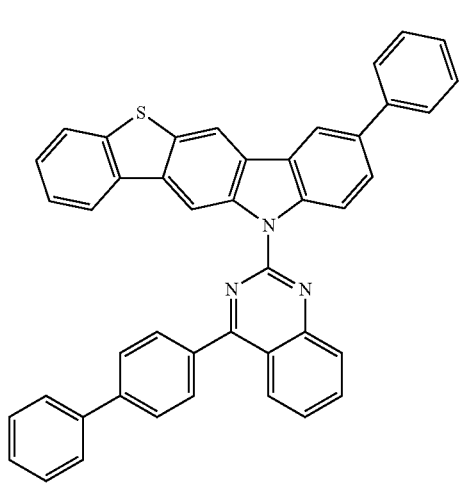
H2-310
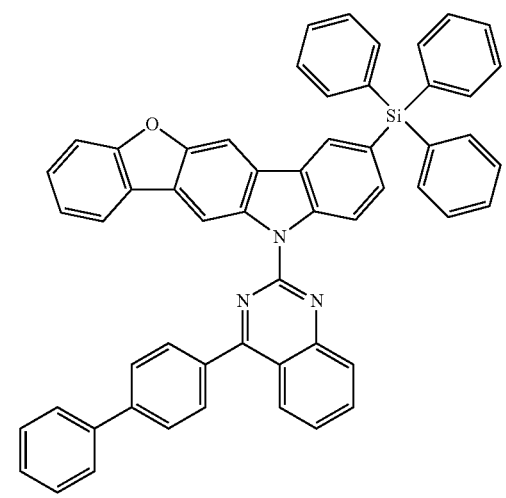

H2-311
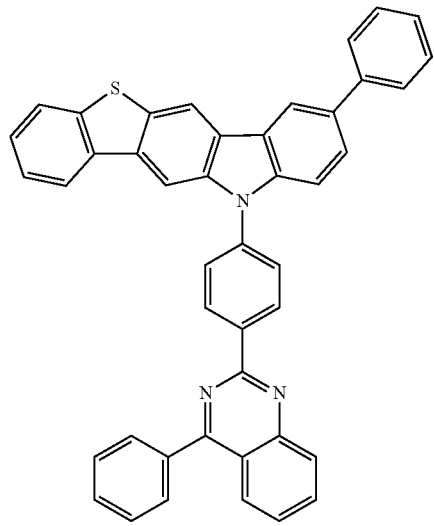
H2-312
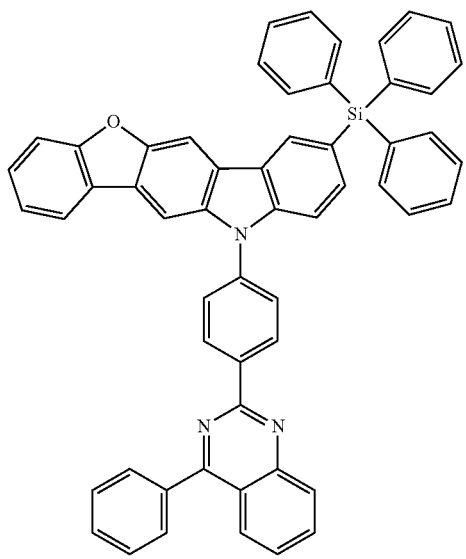
H2-313
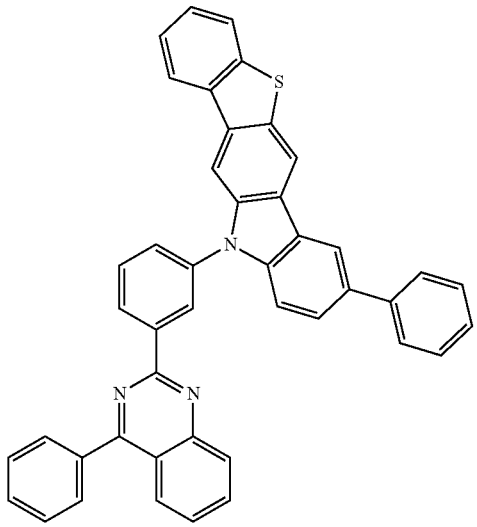
H2-314
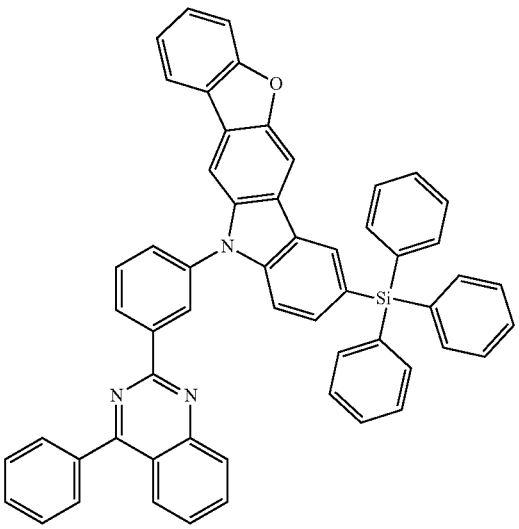
H2-315
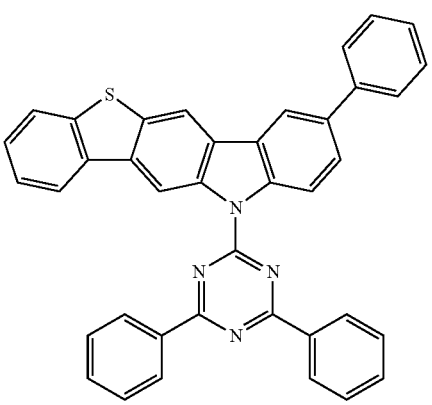
H2-316
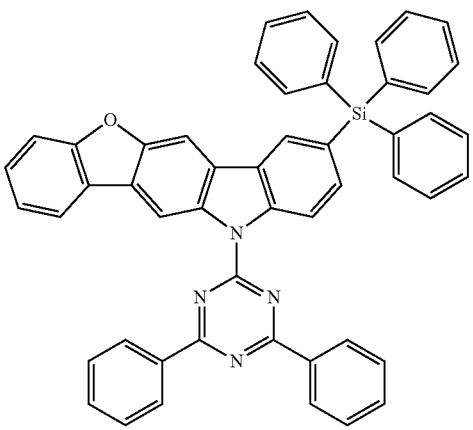

H2-317
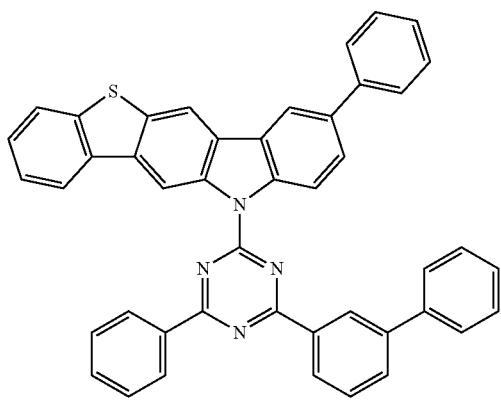
H2-318
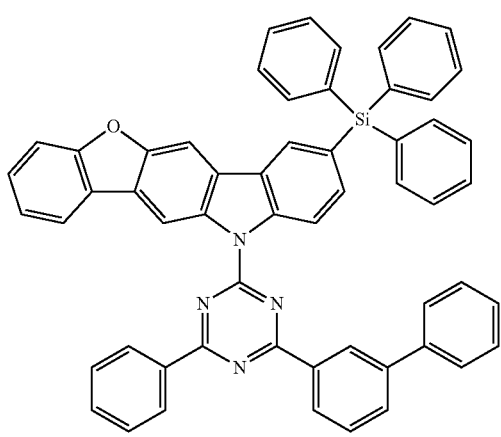
H2-319
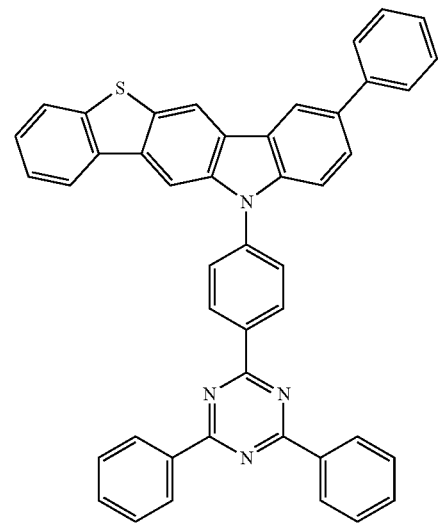
H2-320
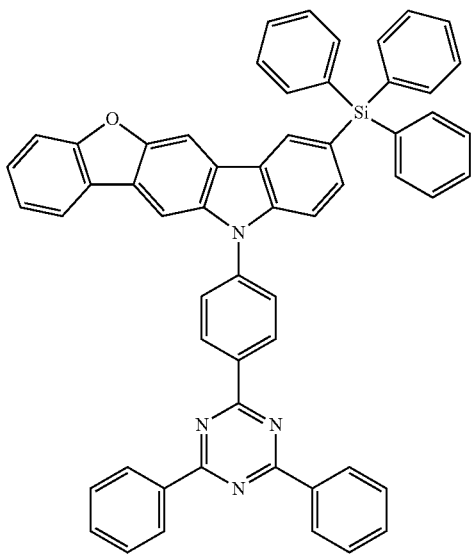
H2-321
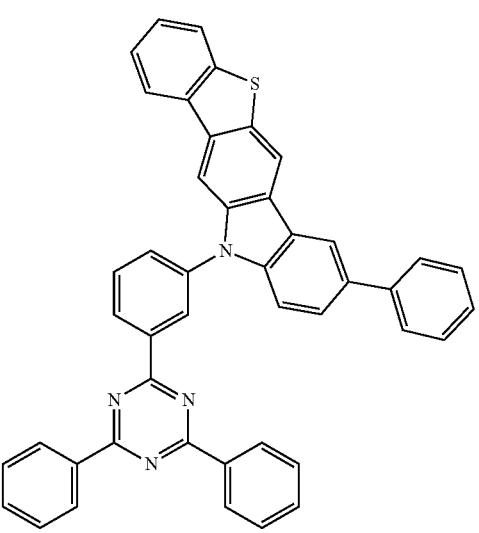
H2-322
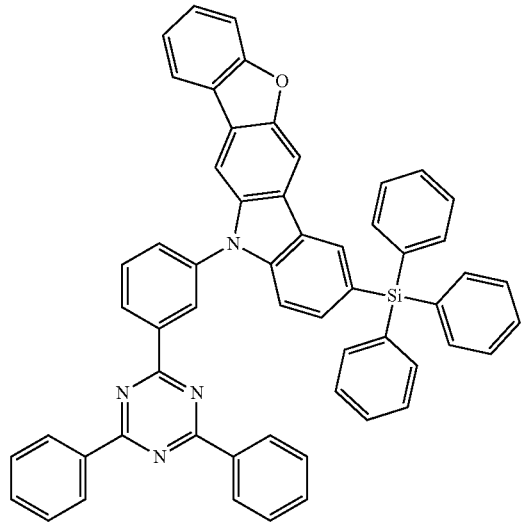

H2-323
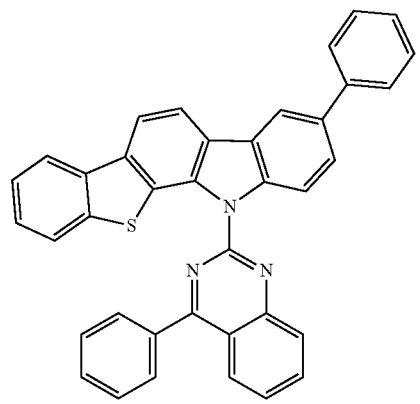
H2-324
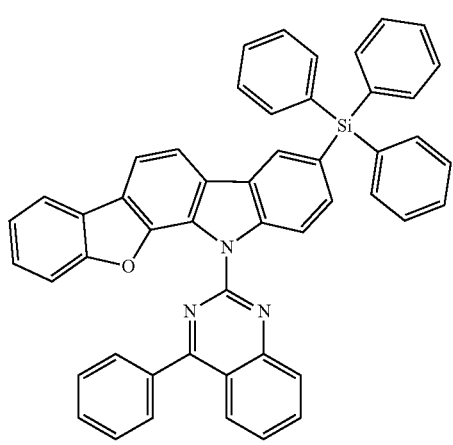
H2-325
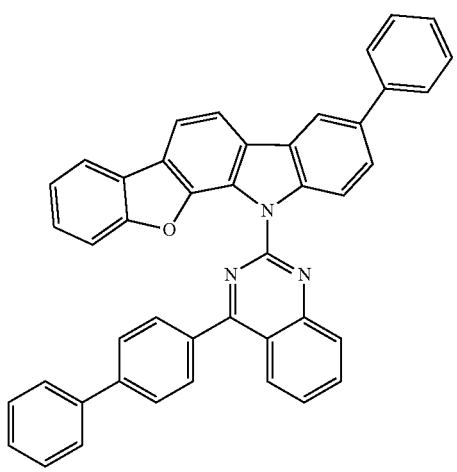
H2-326
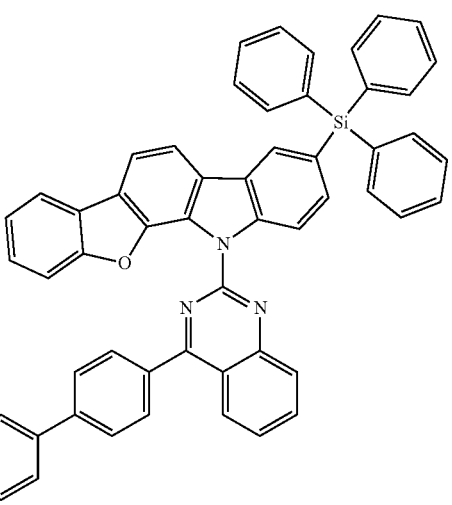
H2-327
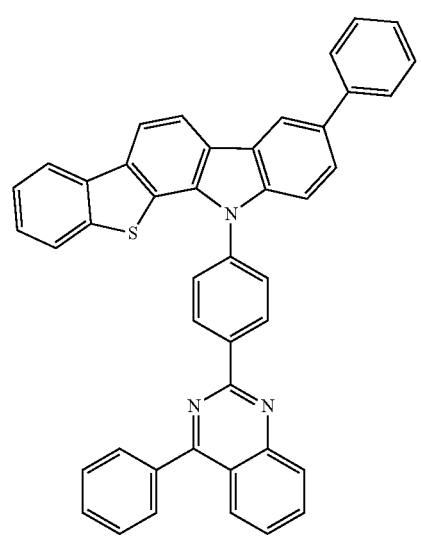
H2-328
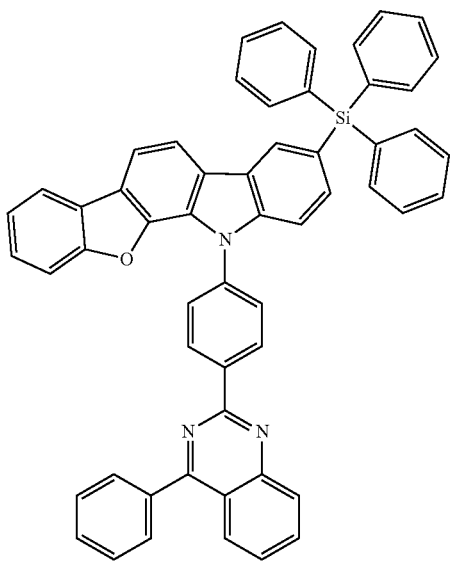

H2-329
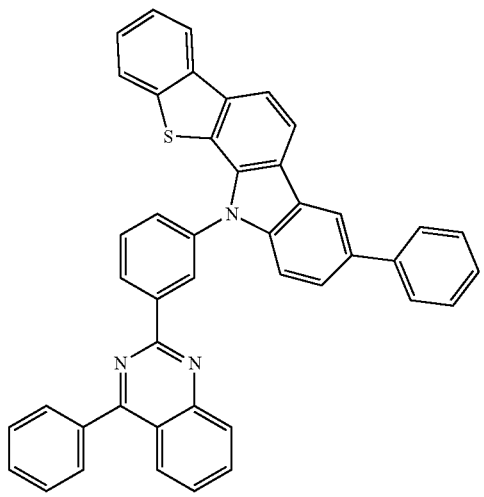
H2-330
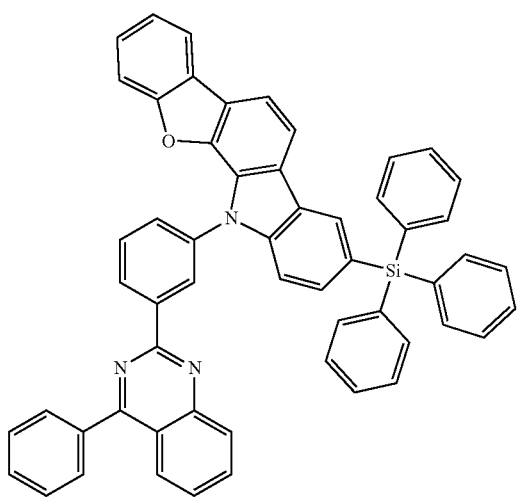
H2-332
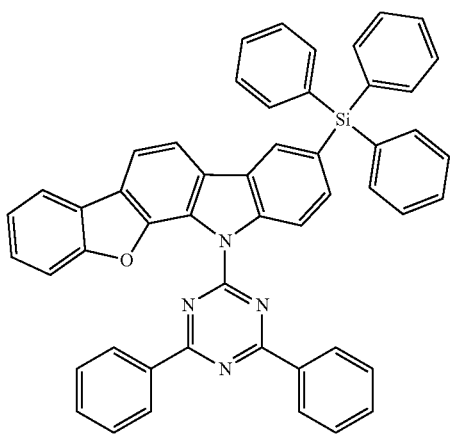
H2-333
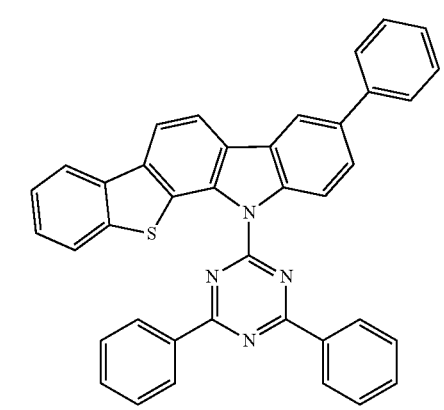
H2-331
H2-334
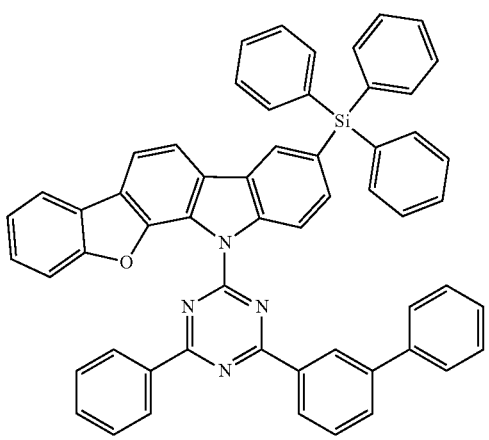

H2-335
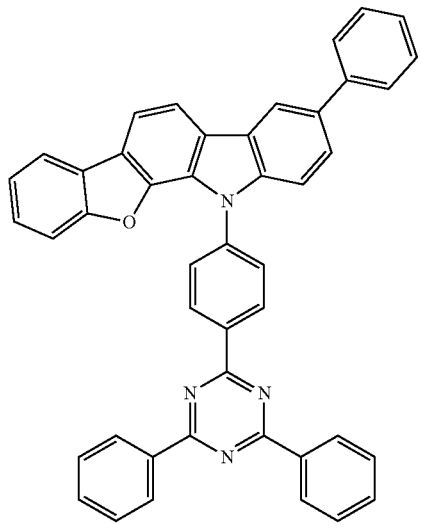
H2-336
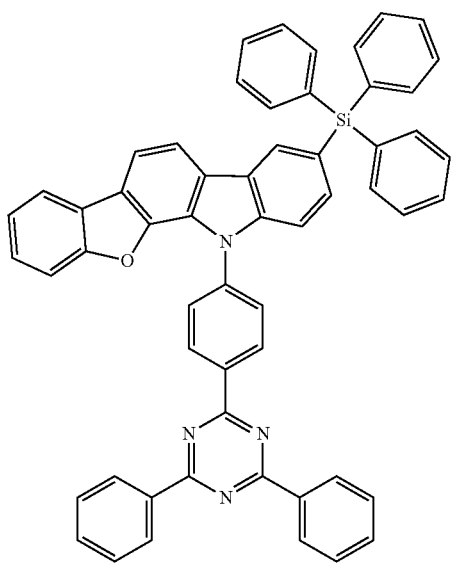
H2-337
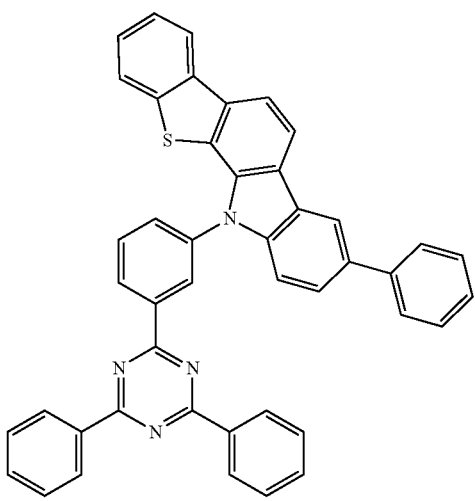
H2-338
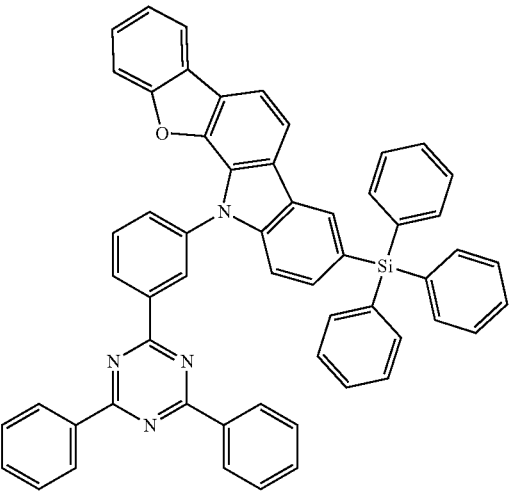
H2-339
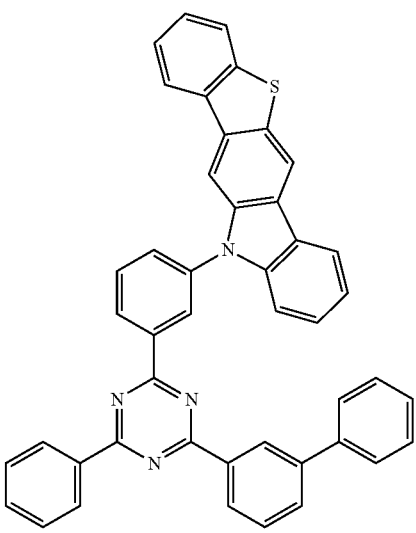
H2-340
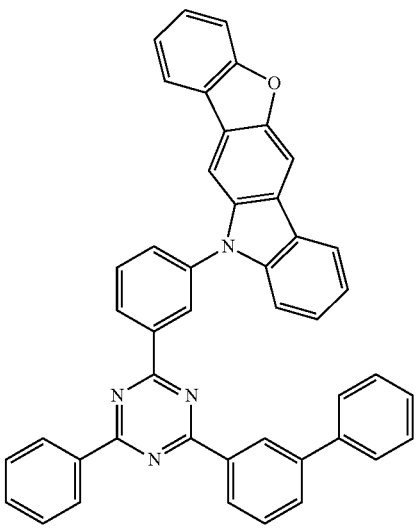

H2-341
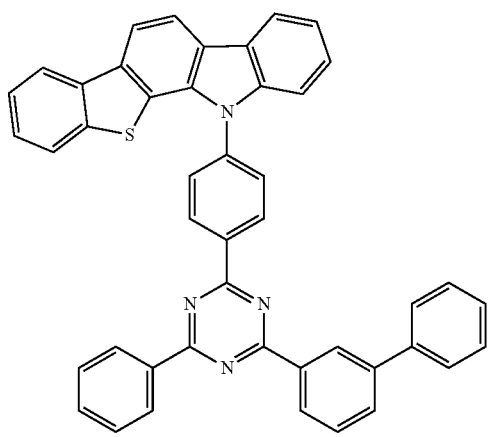
H2-342
H2-343
H2-344
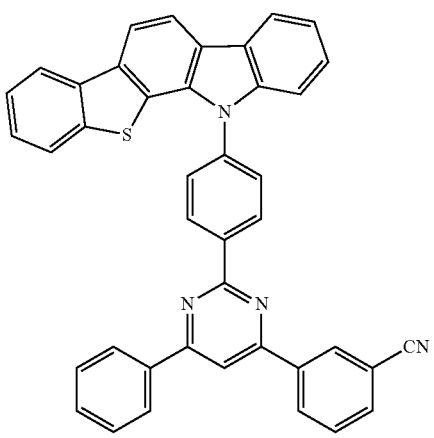
H2-345
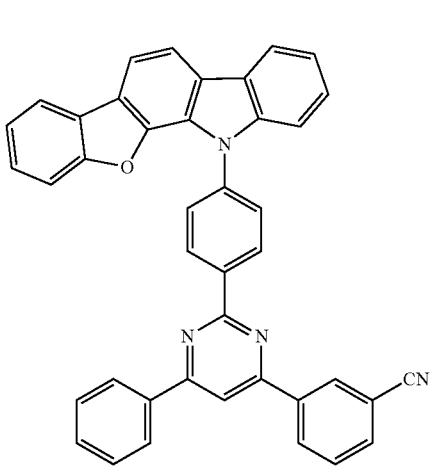
H2-346
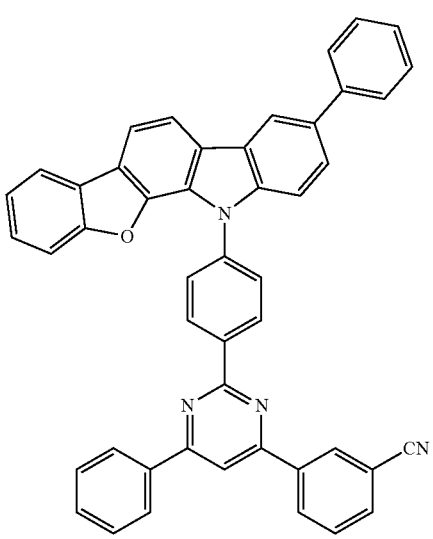

-continued
H2-347
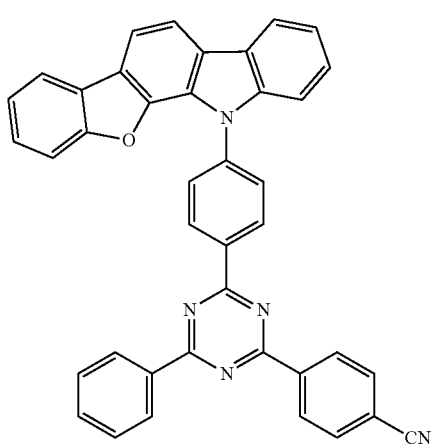
H2-348
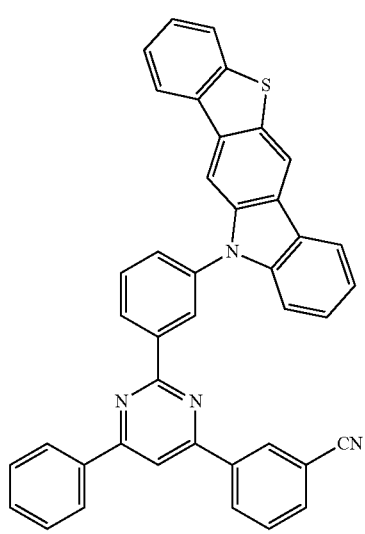
H2-349
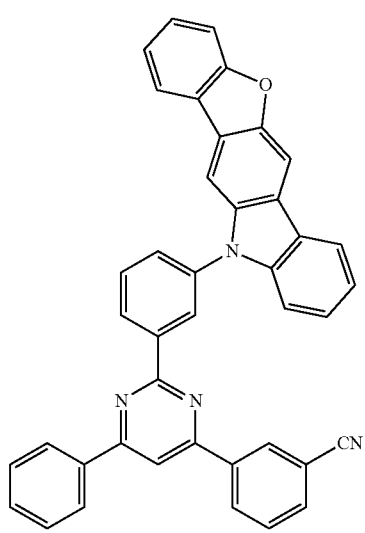
-continued
H2-350
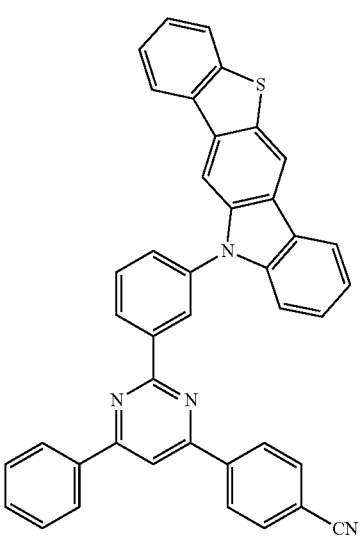
H2-351
H2-352
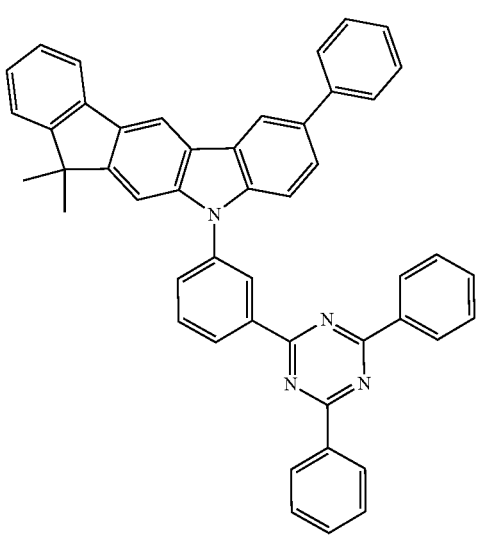

-continued
H2-353
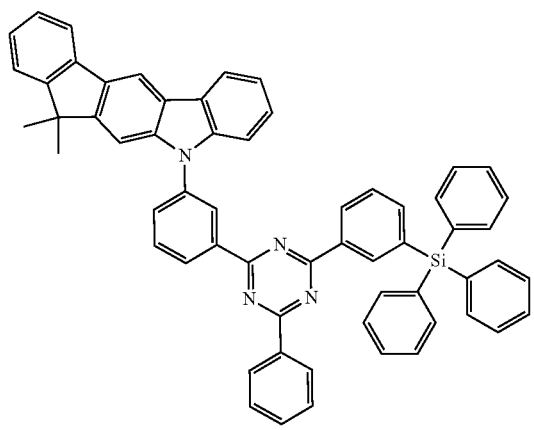
H2-354
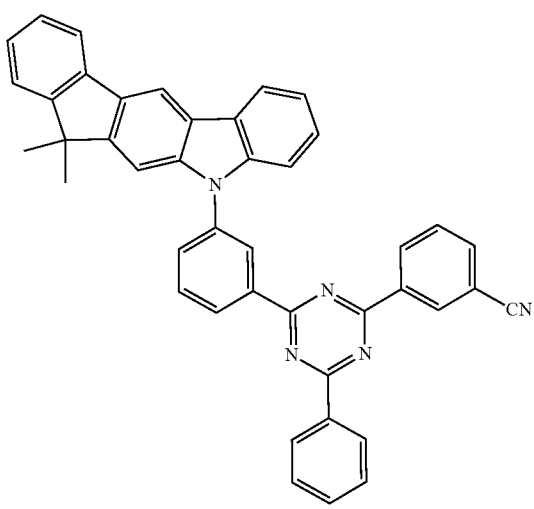
H2-355
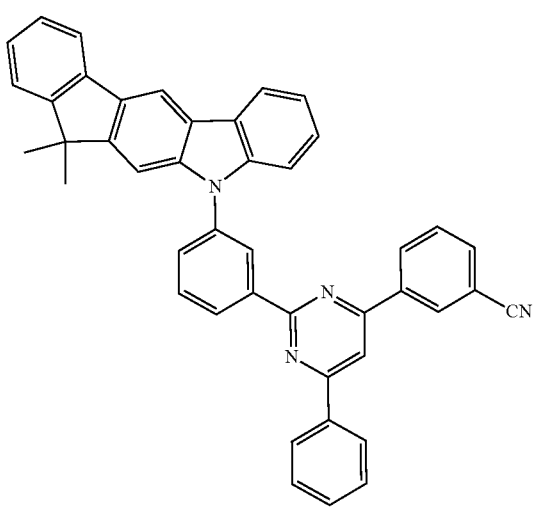
-continued
H2-356
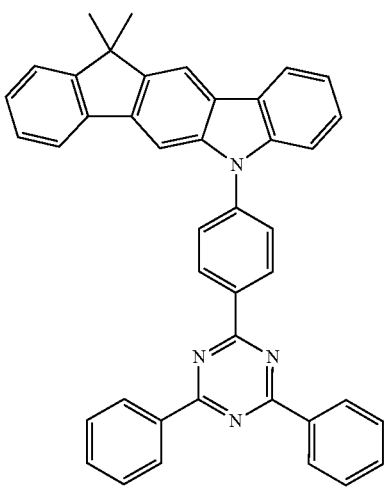
H2-357
H2-358
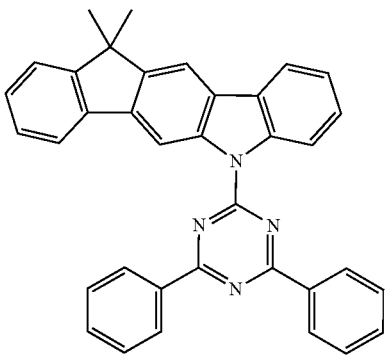

H2-359
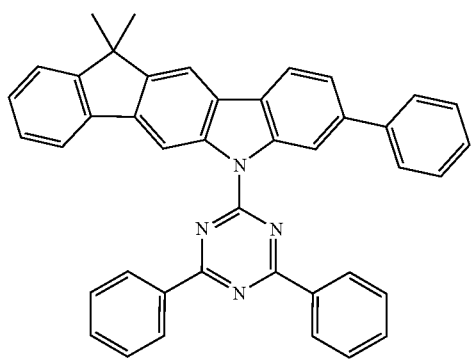
H2-360
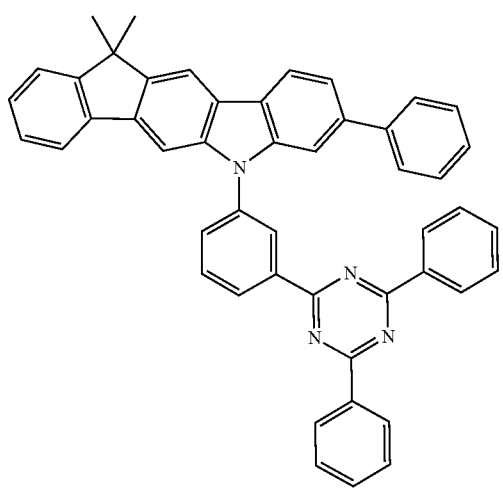
H2-361
H2-362
H2-363
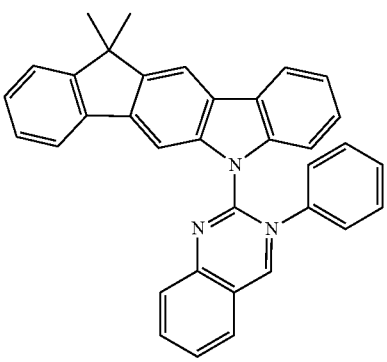
H2-364
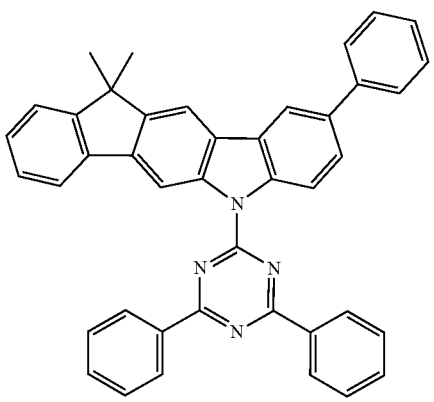
H2-365
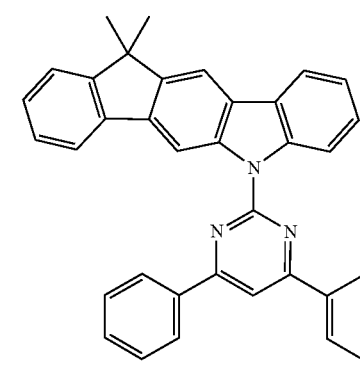
H2-366
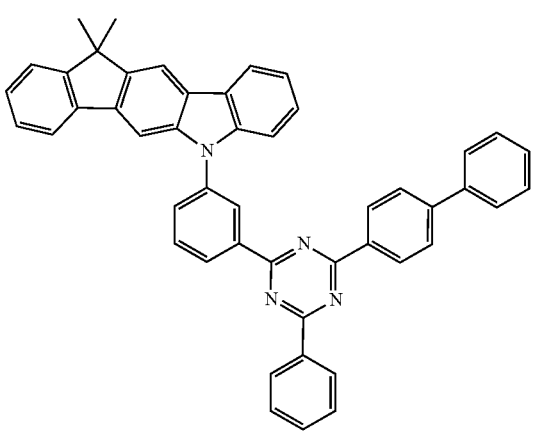

H2-367
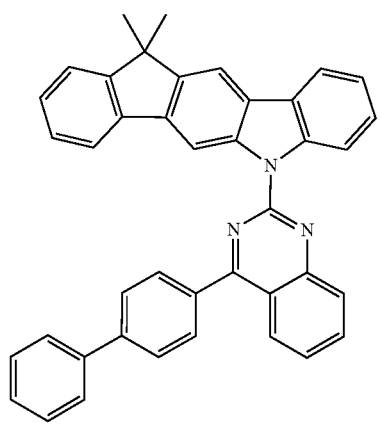
H2-370
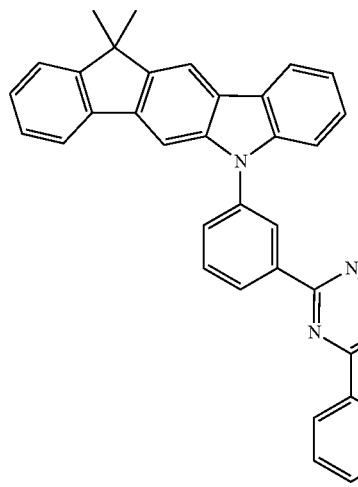
H2-368
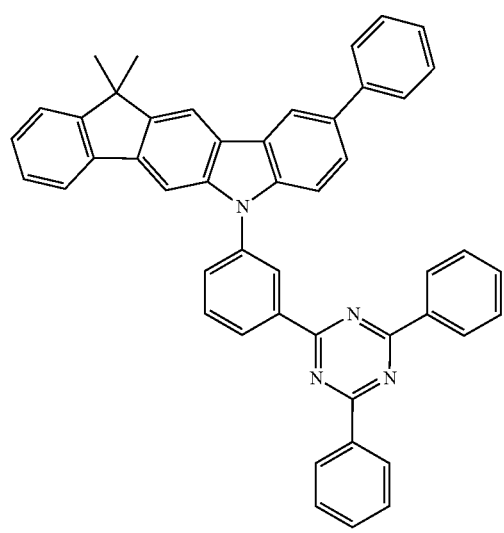
H2-371
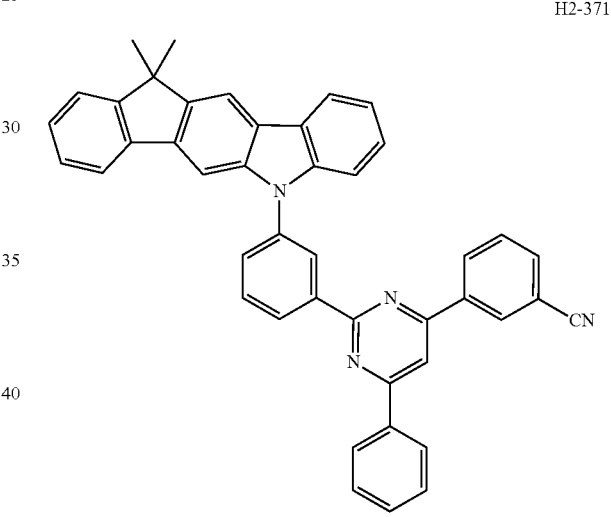
H2-369
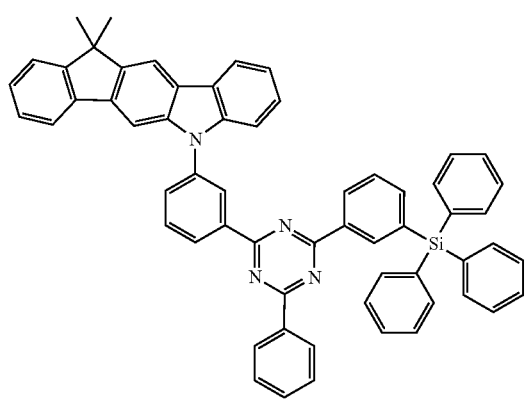
H2-372
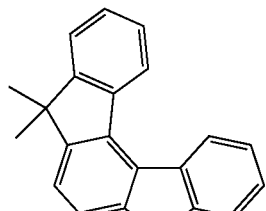
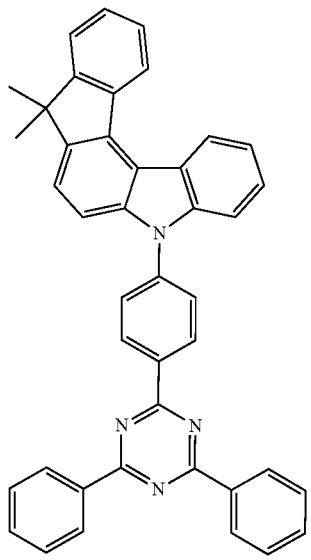

H2-373
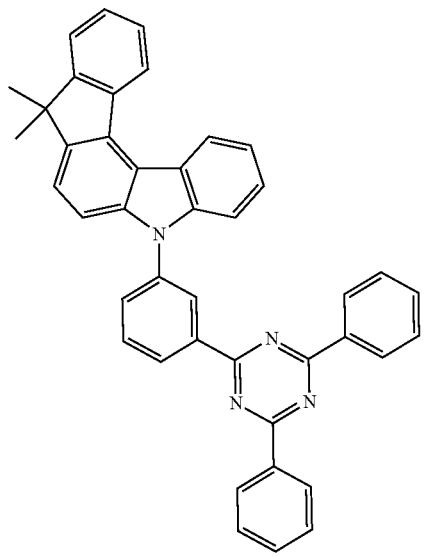
H2-374
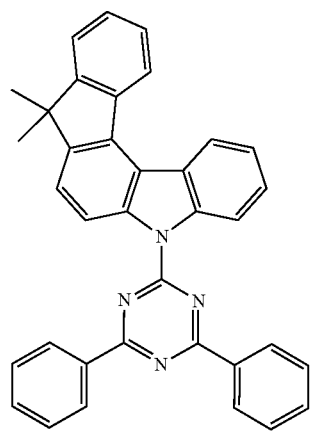
H2-375
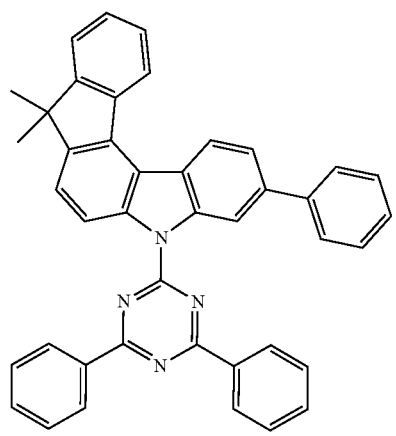
H2-376
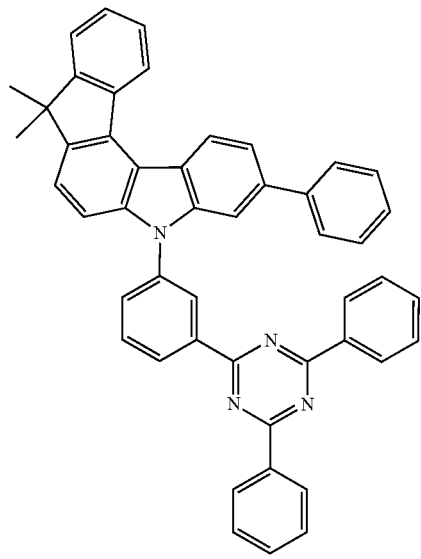
H2-377
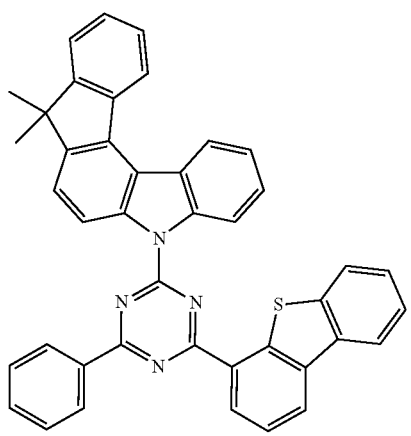
H2-378
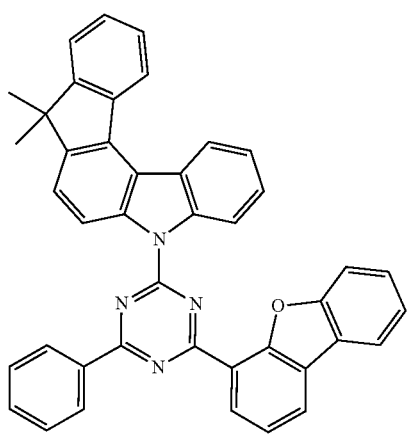

H2-379
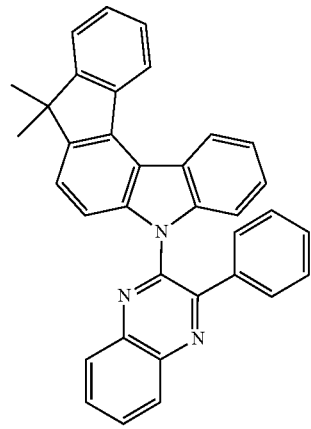
H2-382
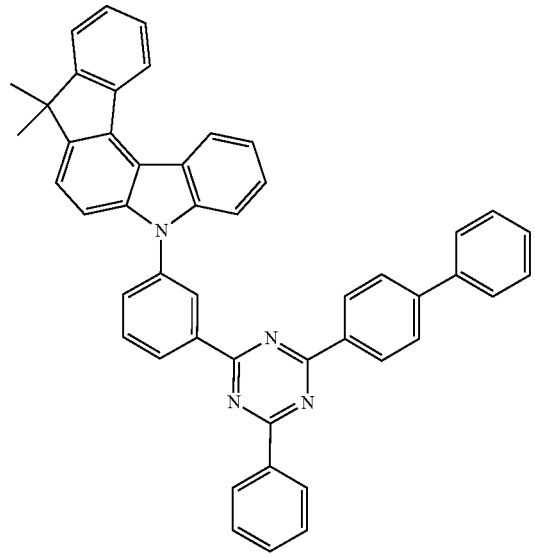
H2-380
H2-383
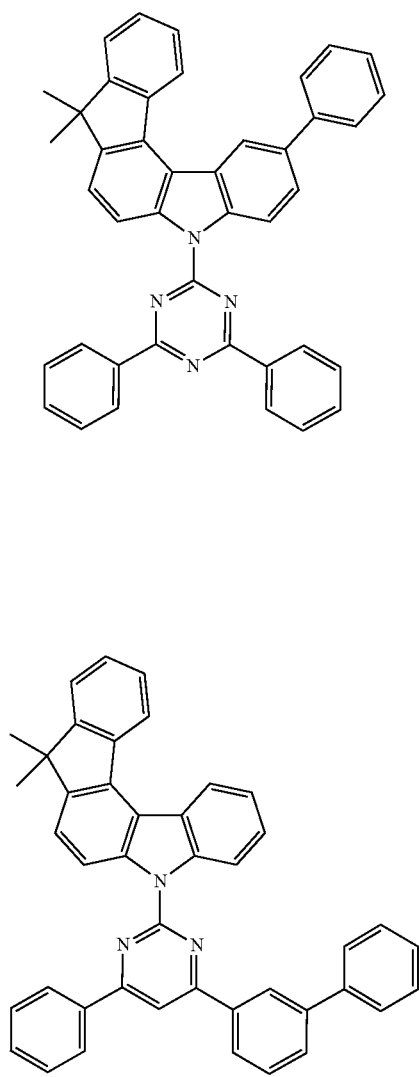
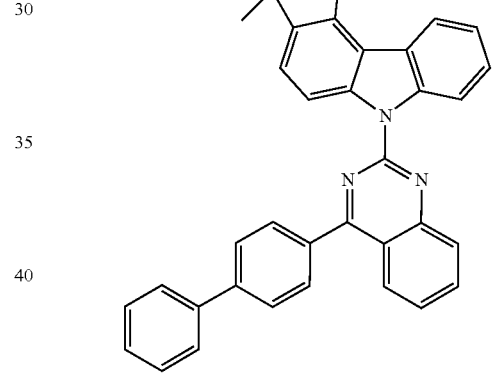
H2-384
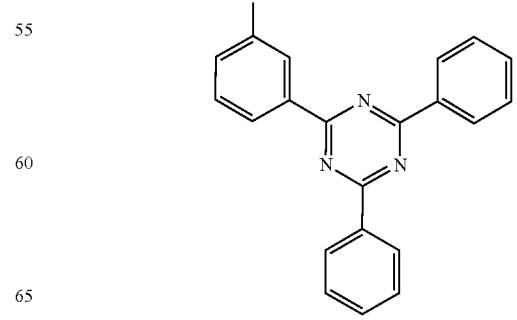
H2-381

H2-385
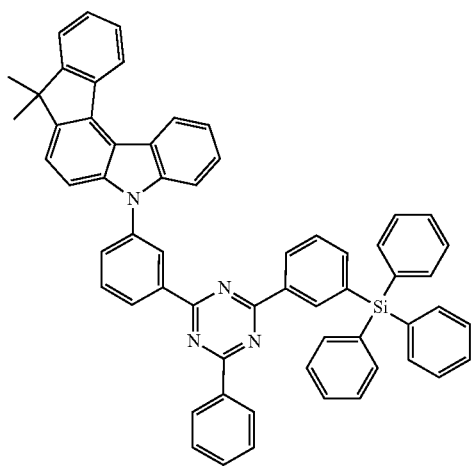
H2-388
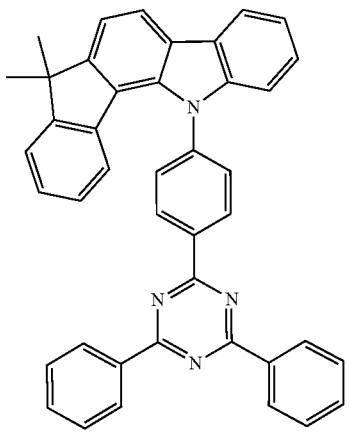
H2-386
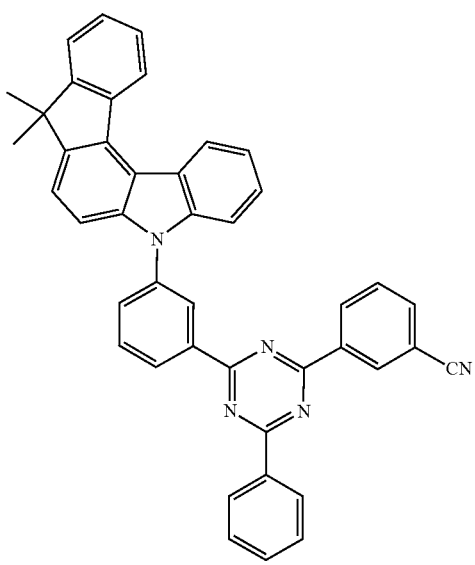
H2-389
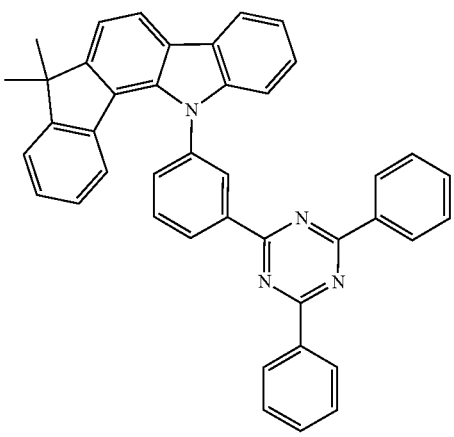
H2-387
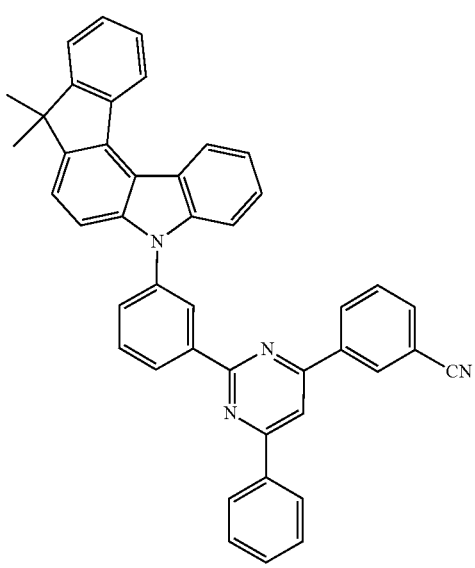
H2-390
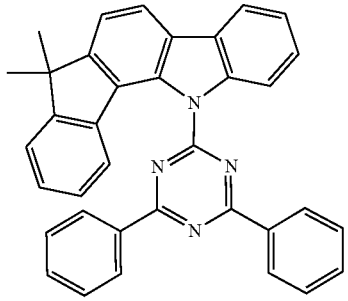
H2-391
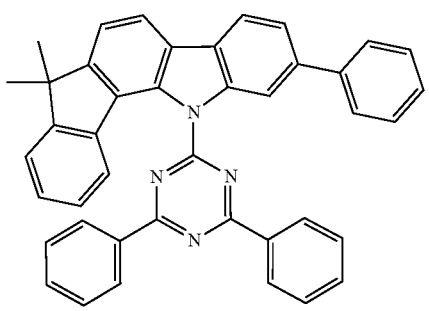

H2-392 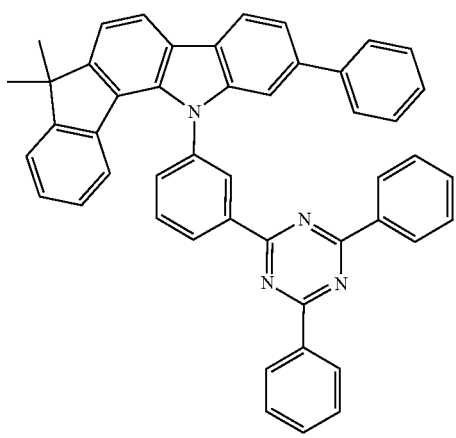
H2-396 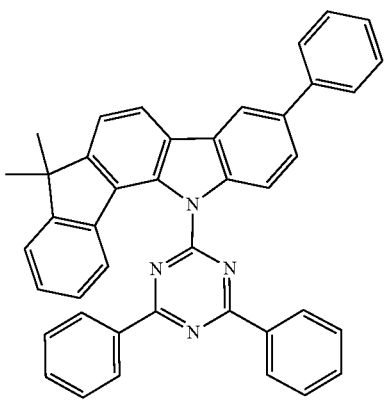
H2-393 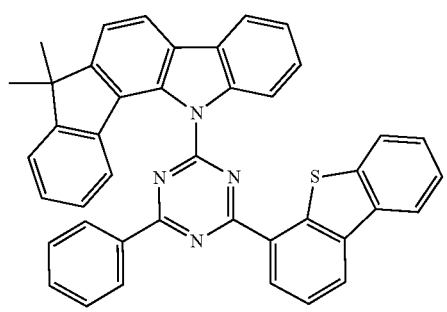
H2-397 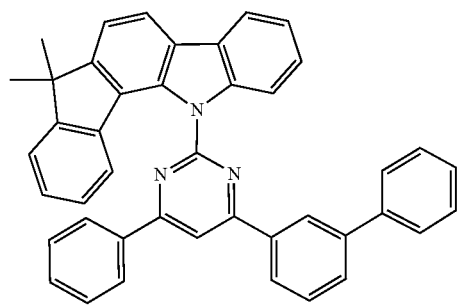
H2-394 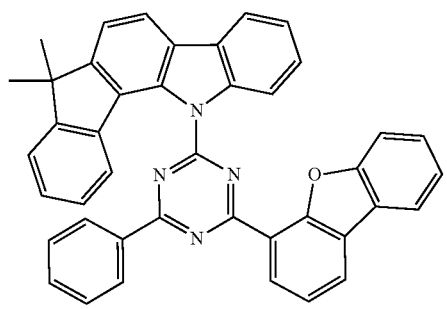
H2-398 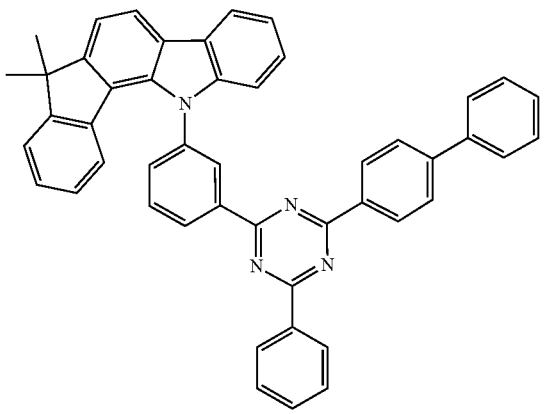
H2-395 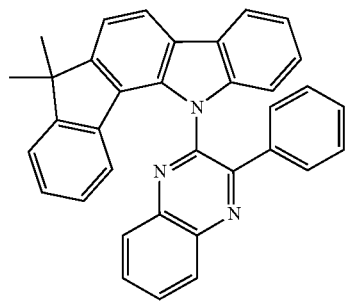
H2-399 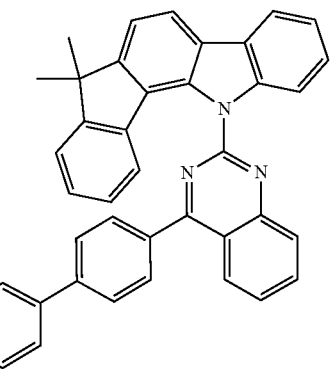

H2-400
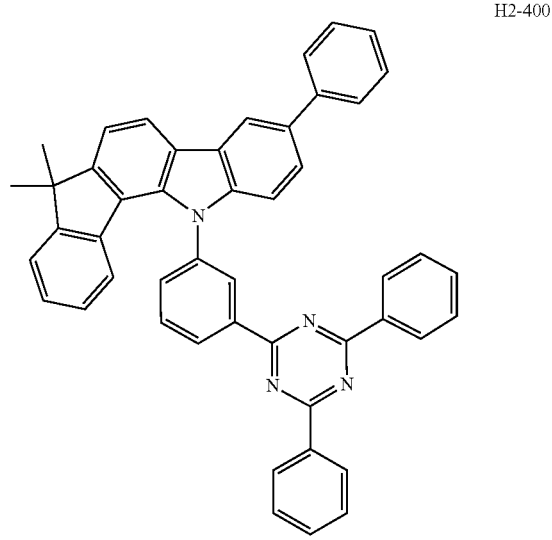
H2-401
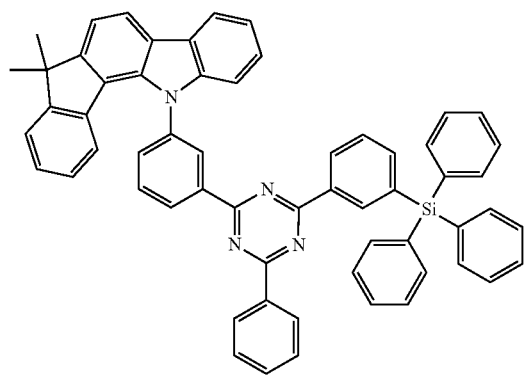
H2-402
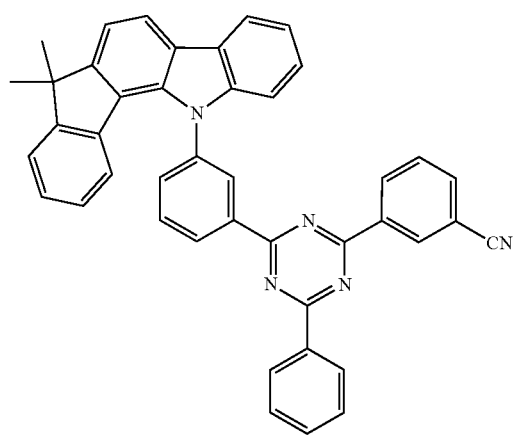
H2-403
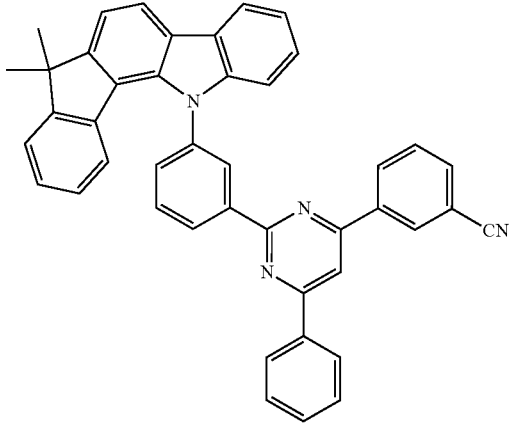
H2-404
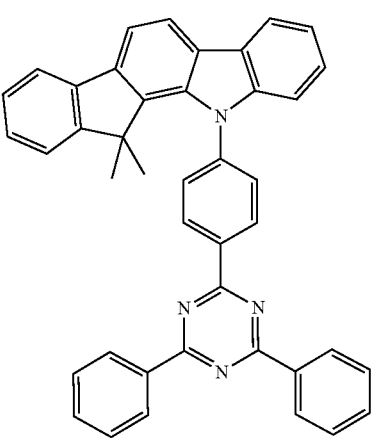
H2-405
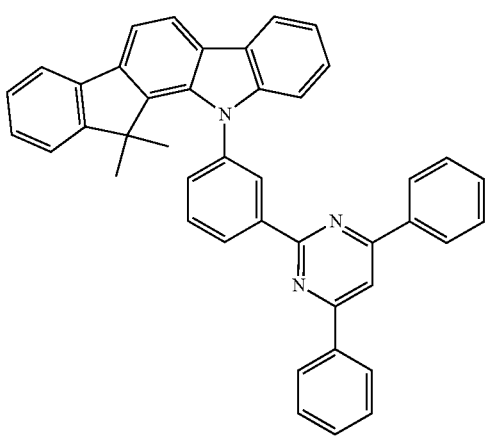
H2-406
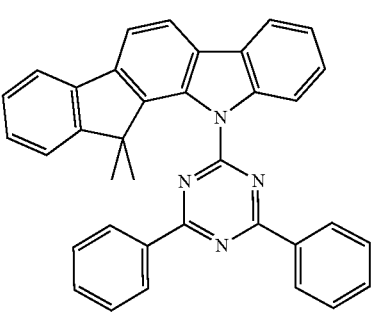

H2-407 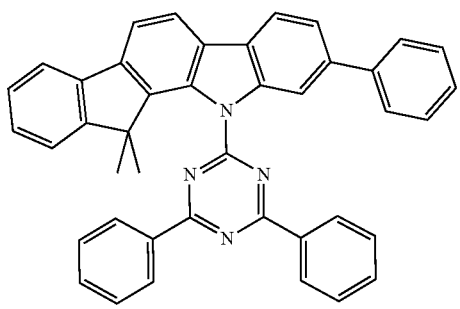
H2-408 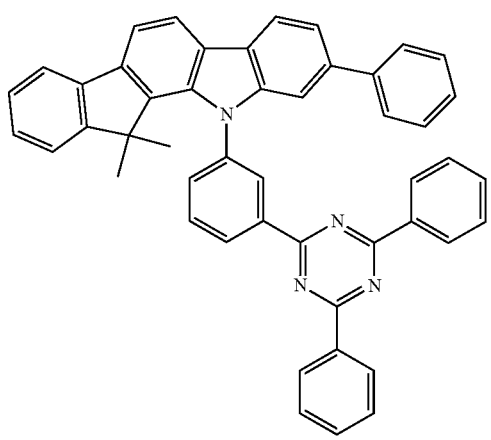
H2-409 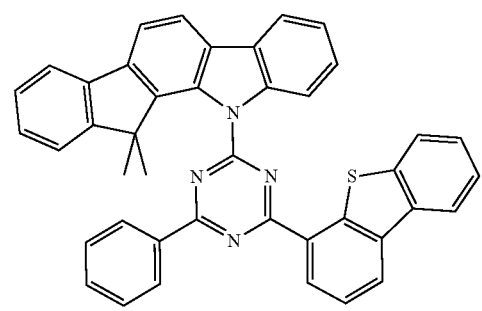
H2-410 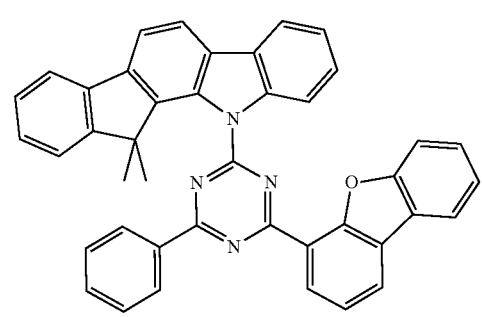
H2-411 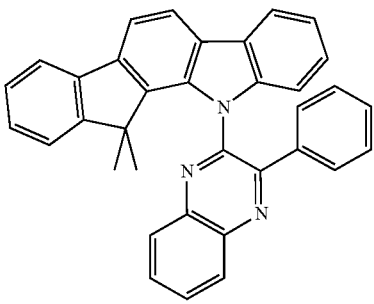
H2-412 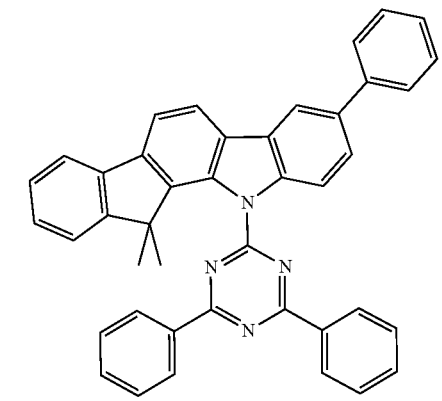
H2-413 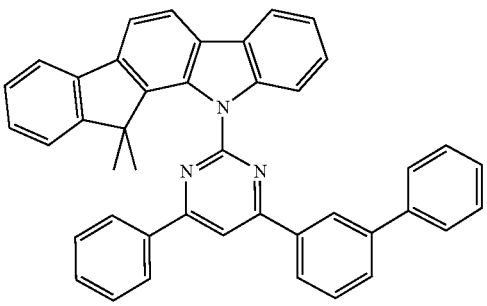
H2-414 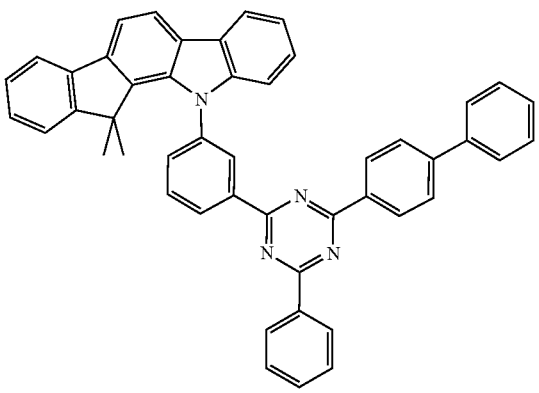

-continued
H2-415
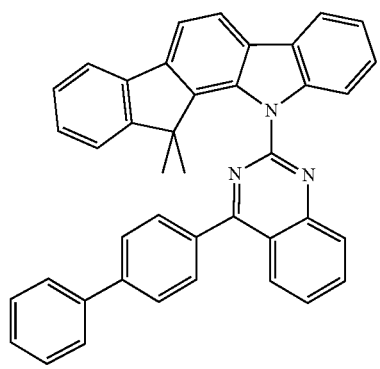
H2-416
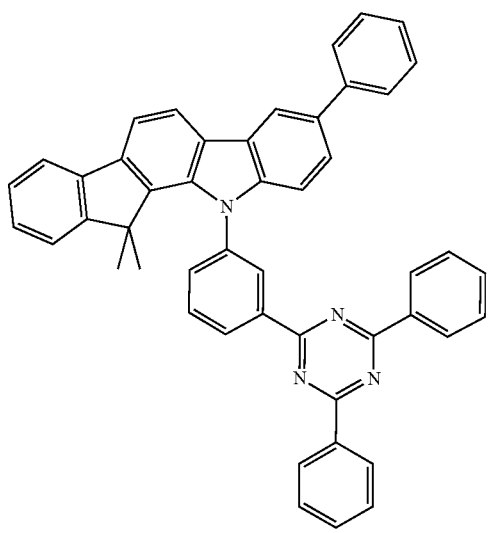
H2-417
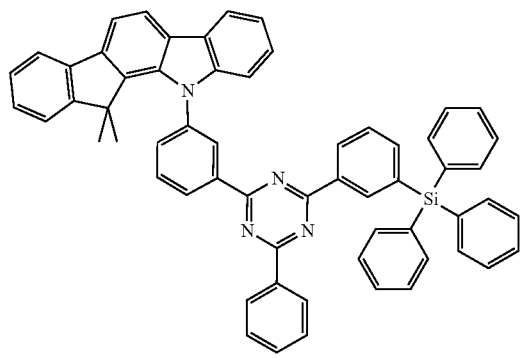
-continued
H2-418
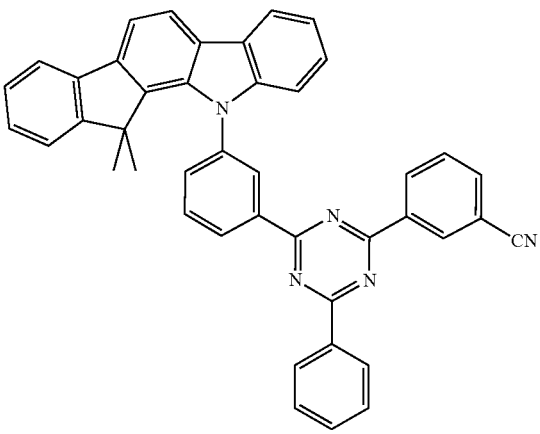
H2-419
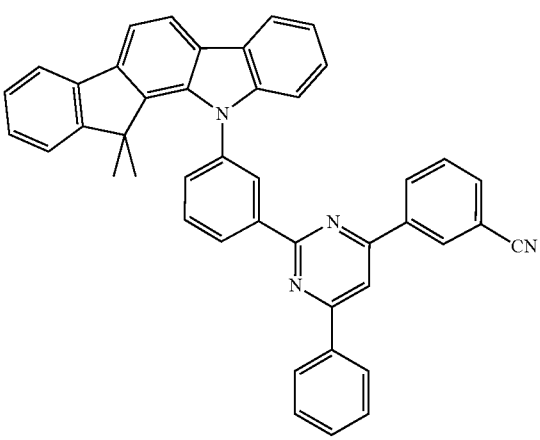
H2-420
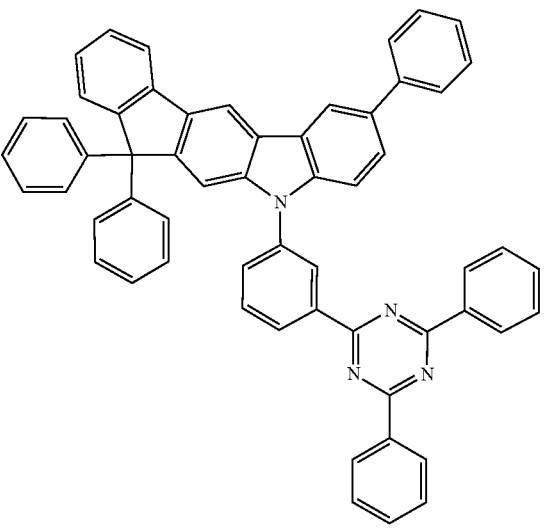

H2-421
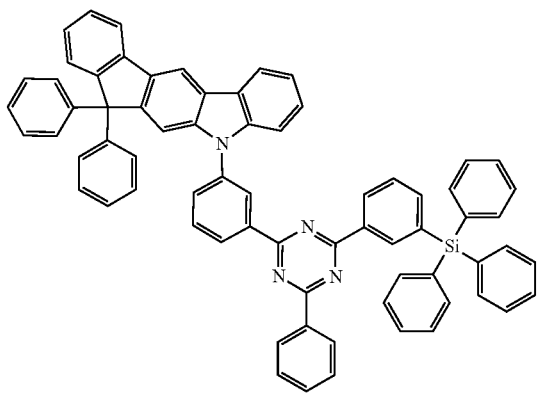
H2-422
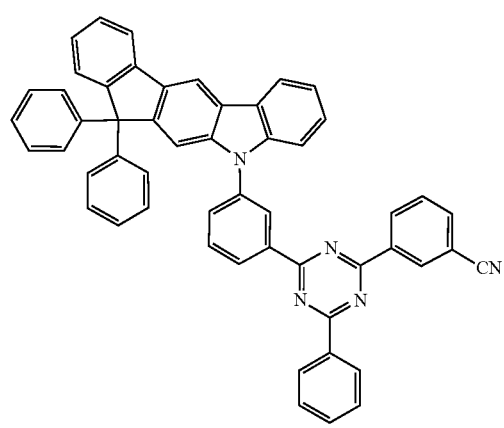
H2-423
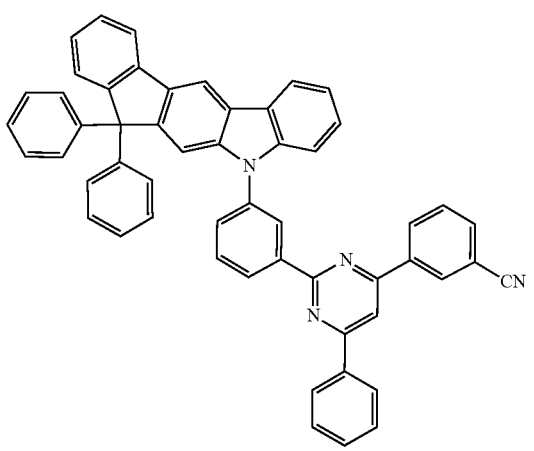
H2-424
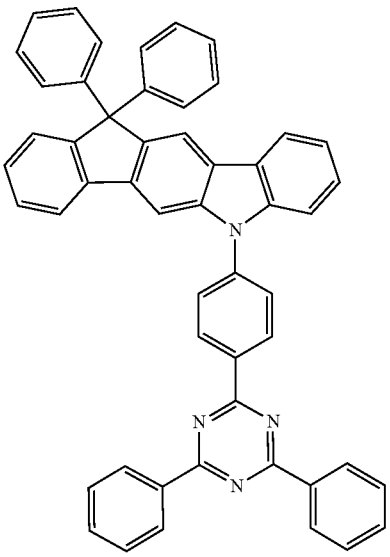
H2-425
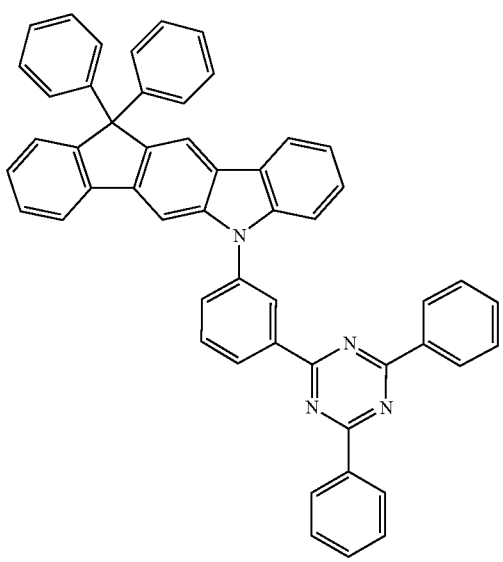
H2-426
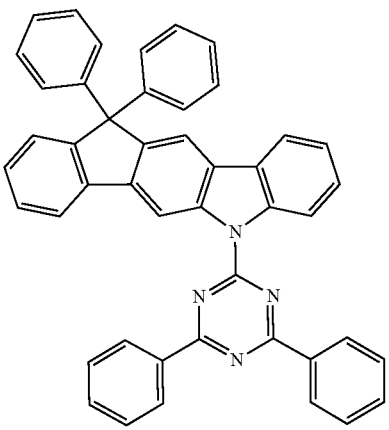

H2-427
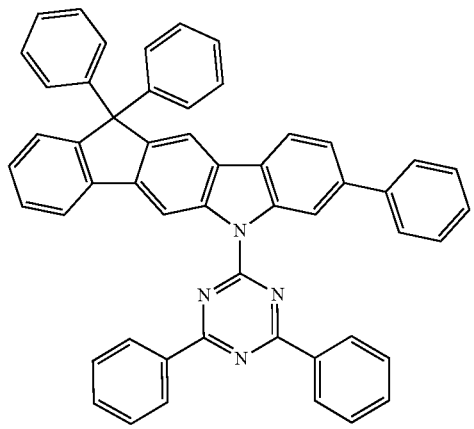
H2-428
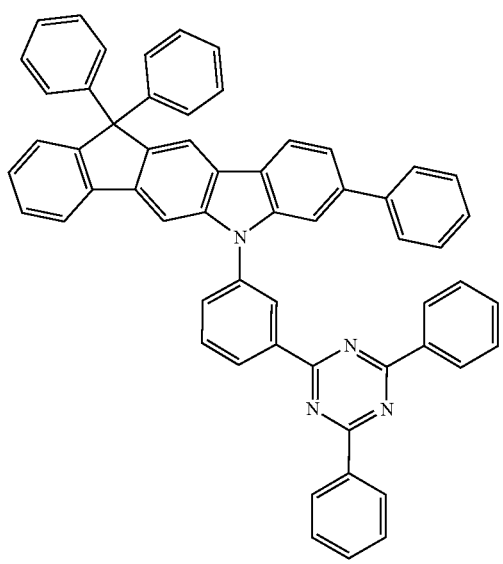
H2-429
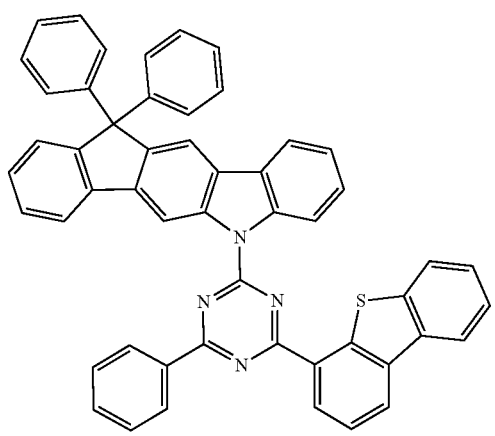
H2-430
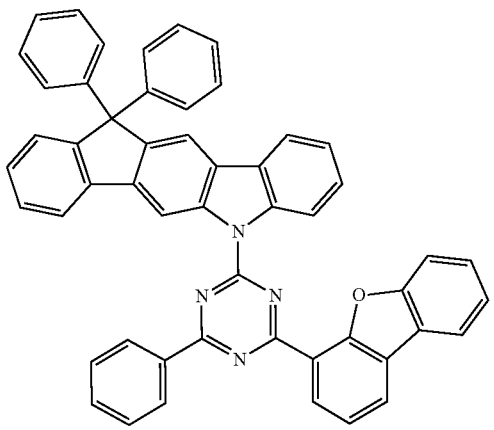
H2-431
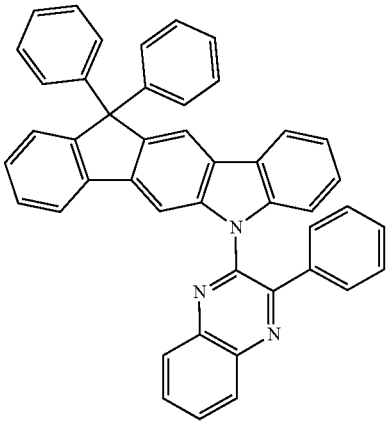
H2-432
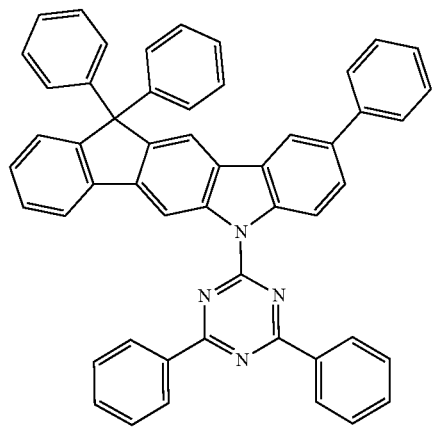

H2-433
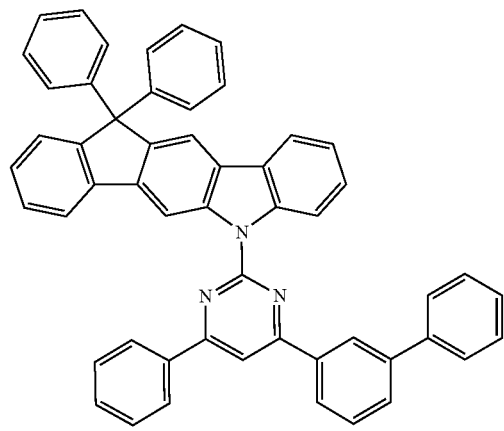
H2-434
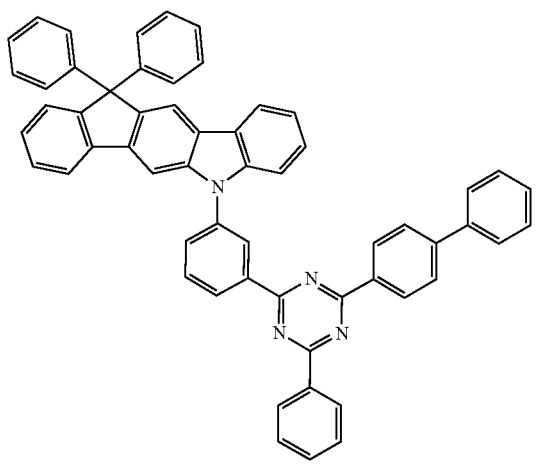
H2-435
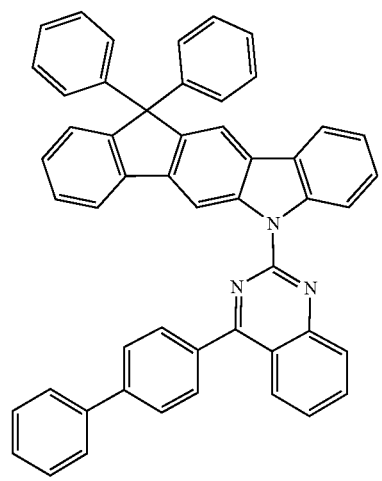
H2-436
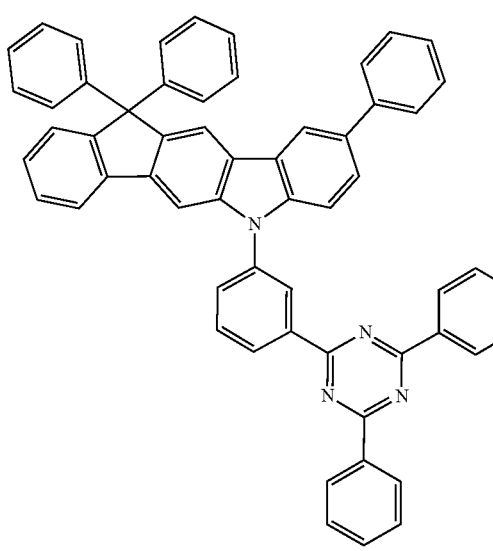
H2-437
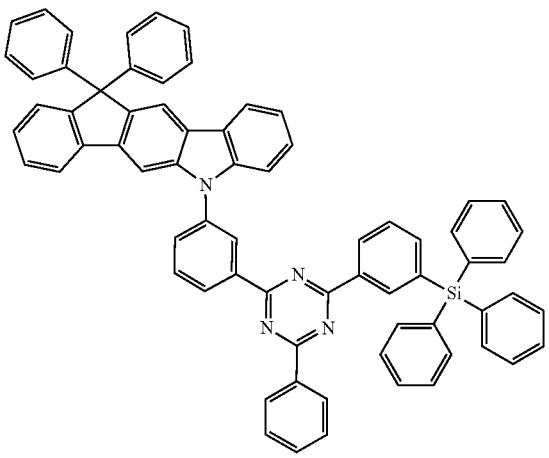
H2-438
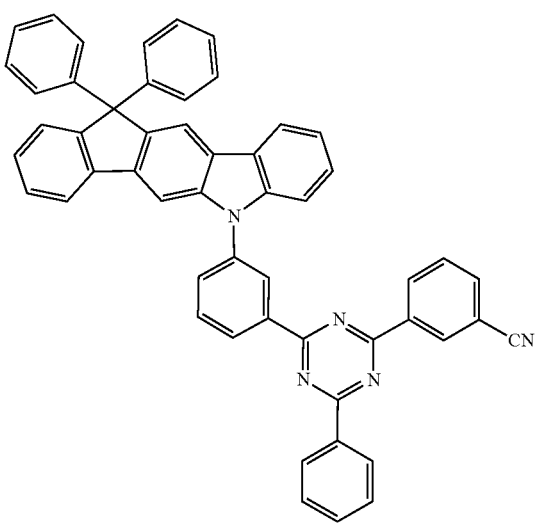

H2-439
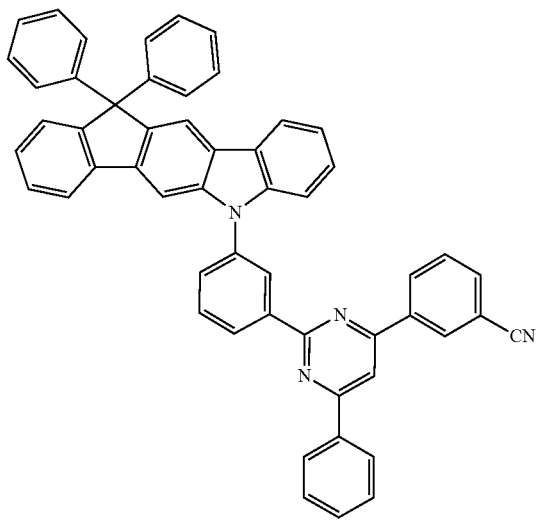
H2-440
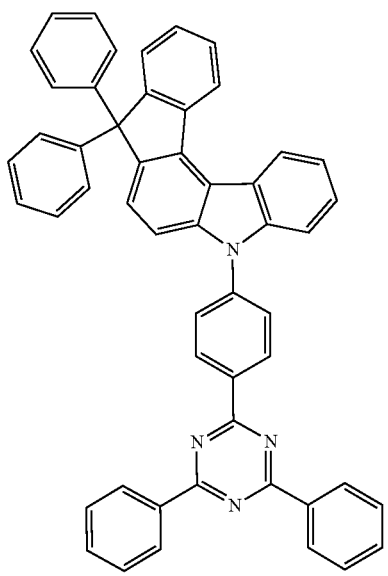
H2-441
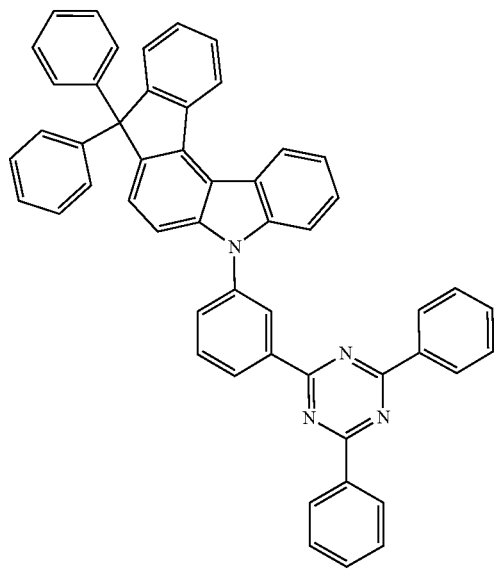
H2-442
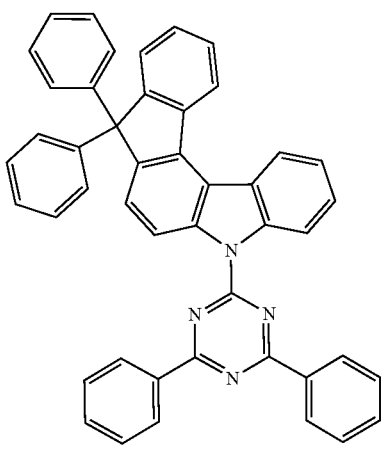
H2-443
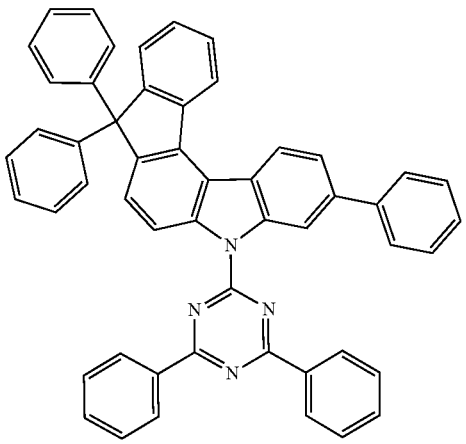

H2-444
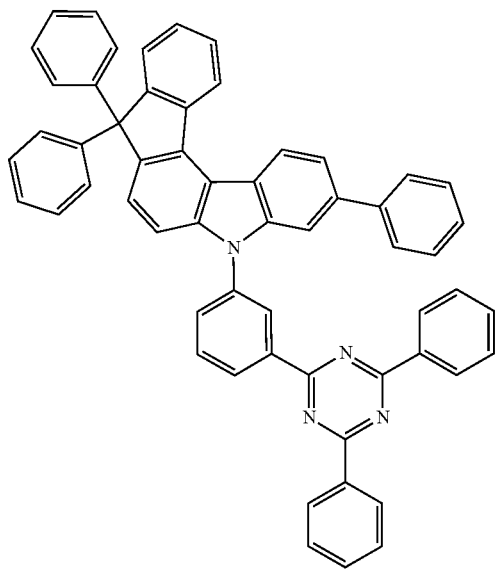
H2-445
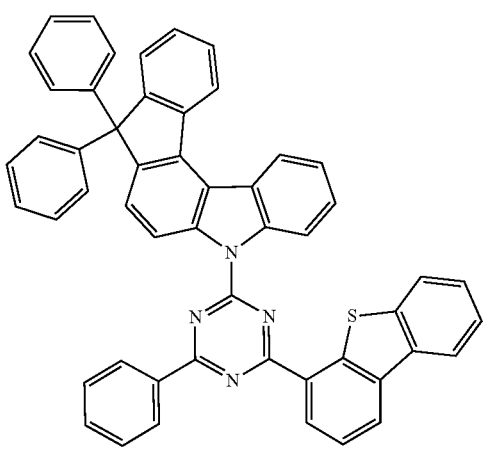
H2-446
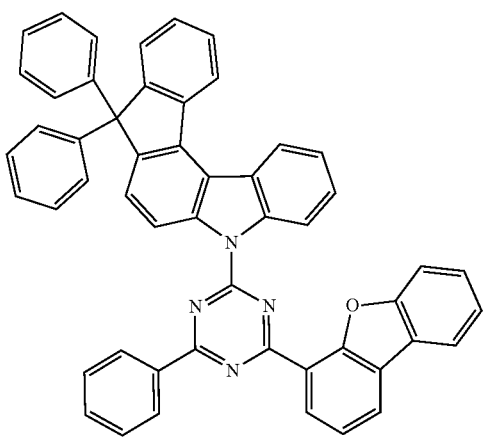
H2-447
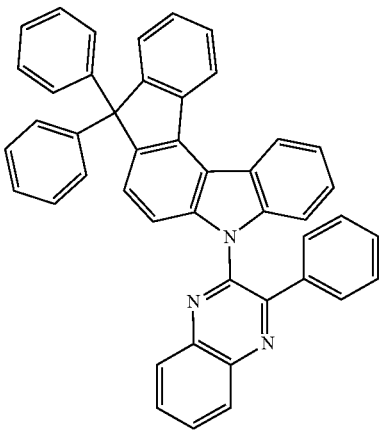
H2-448
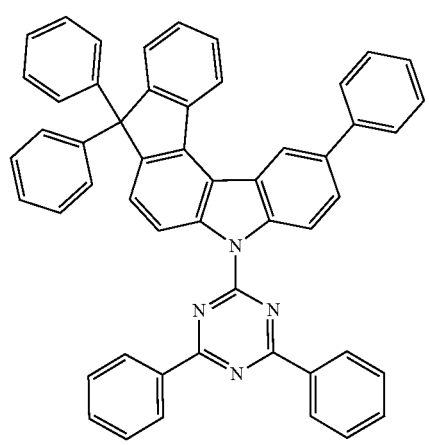
H2-449
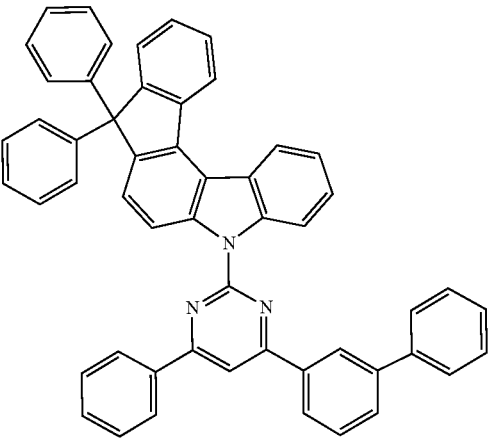

-continued
H2-450
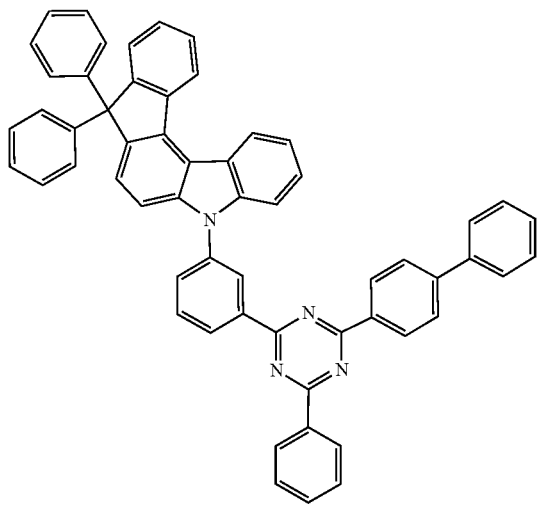
H2-451
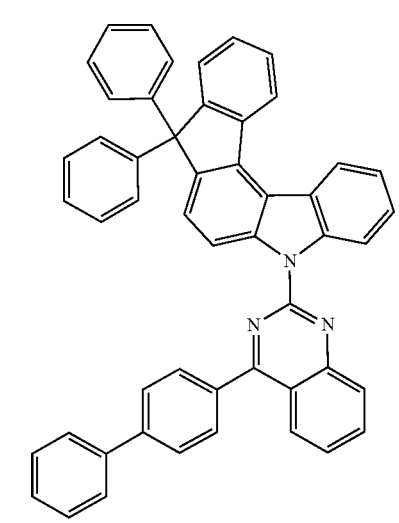
H2-452
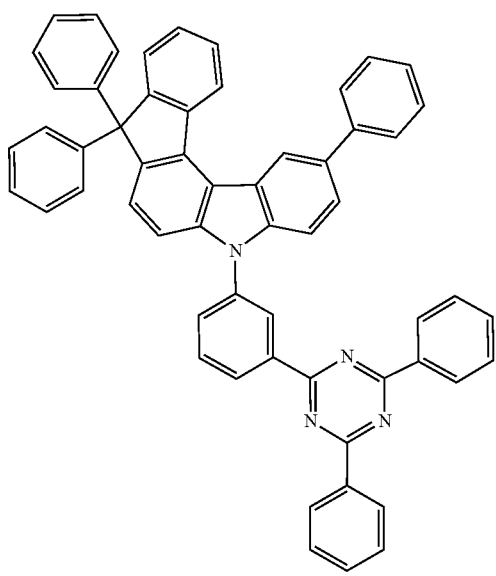
-continued
H2-453
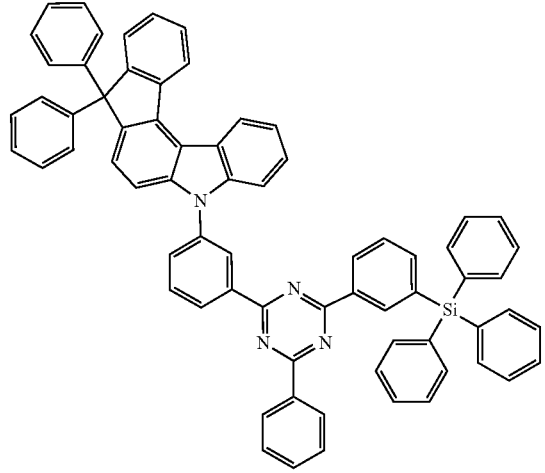
H2-454
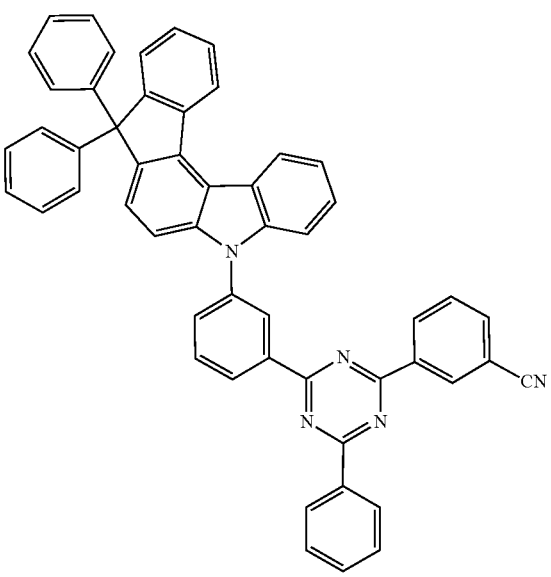
H2-455
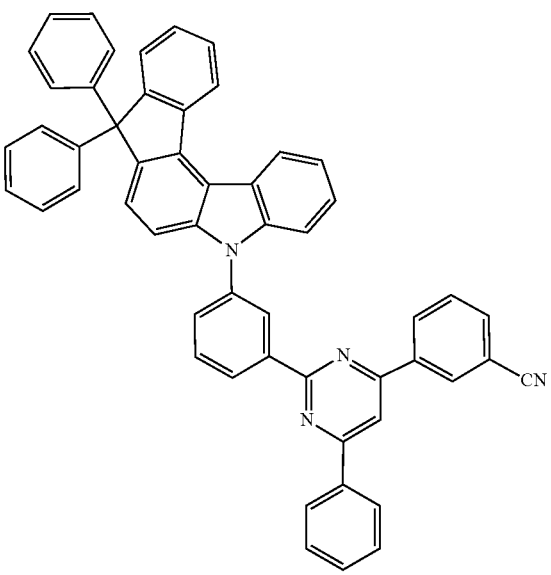

H2-456
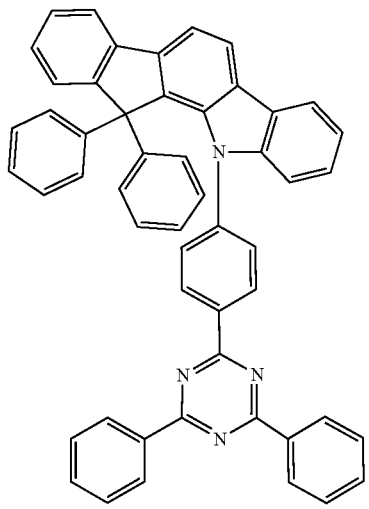
H2-457
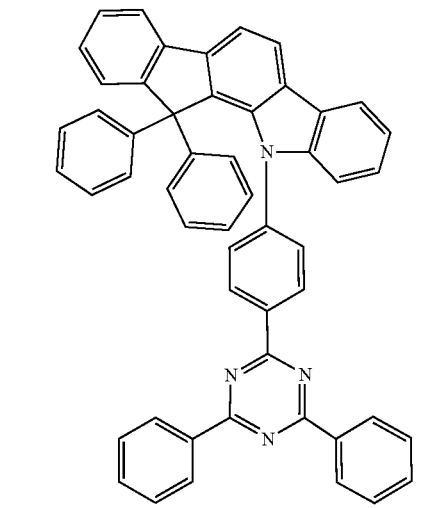
H2-458
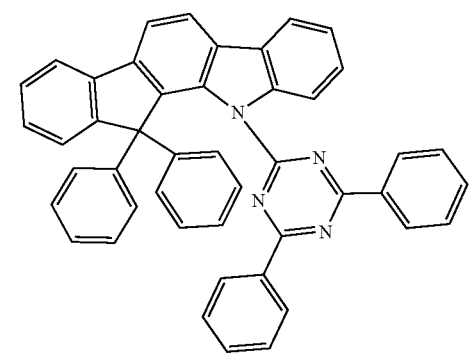
H2-459
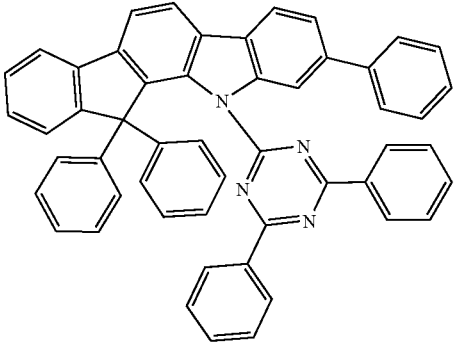
H2-460
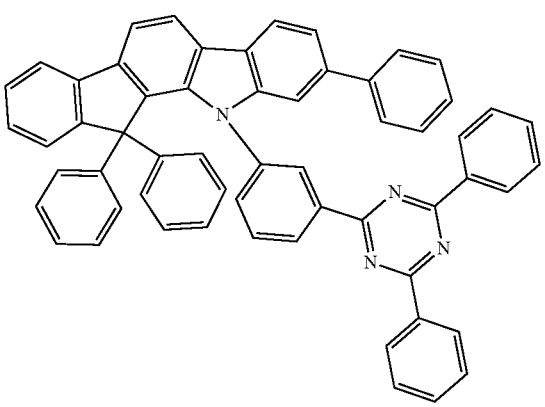
H2-461
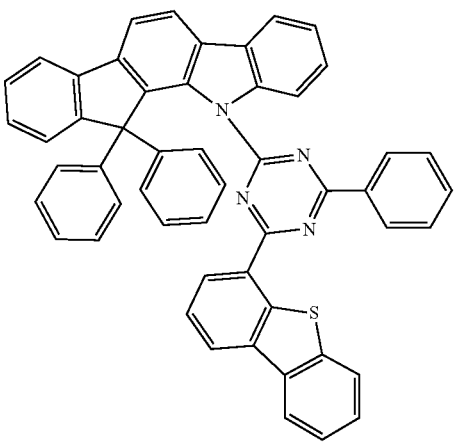
H2-462
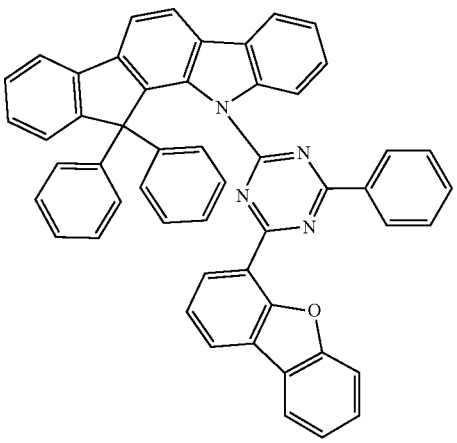

H2-463
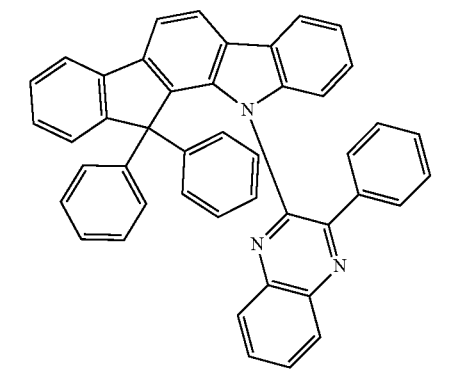
H2-464
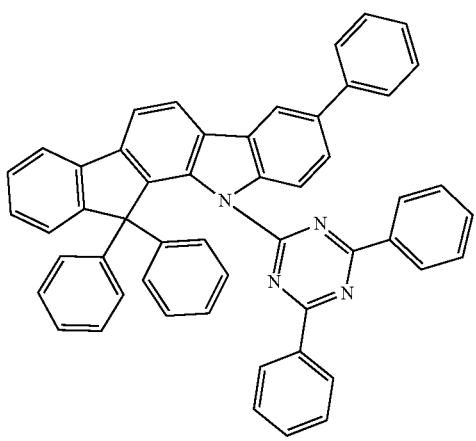
H2-465
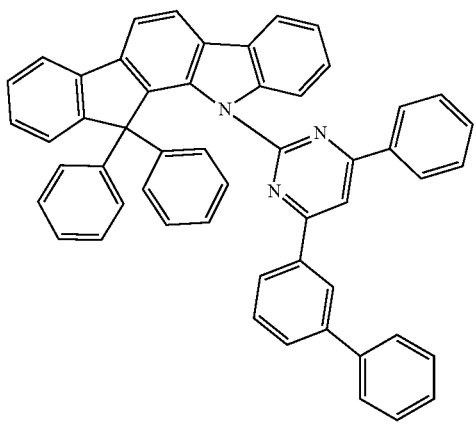
H2-466
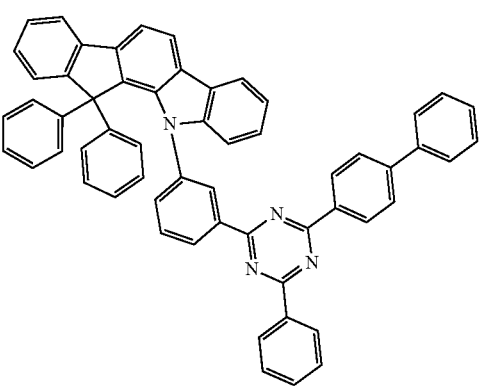
H2-467
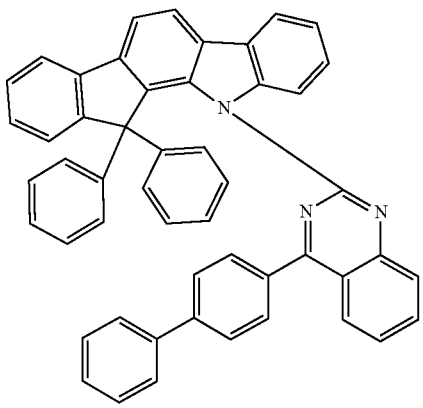
H2-468
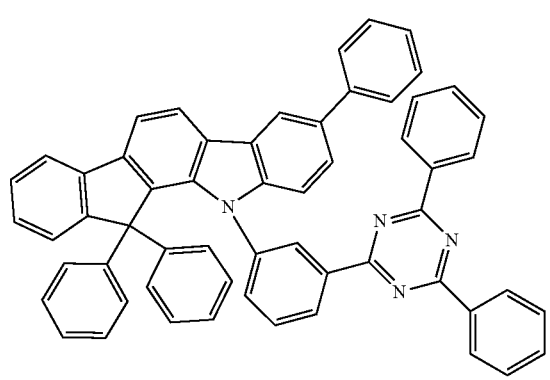
H2-469
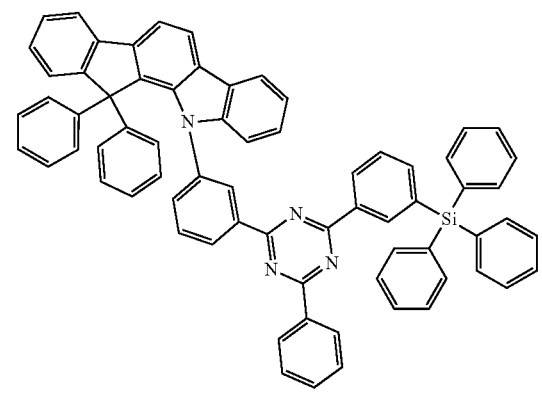
H2-470
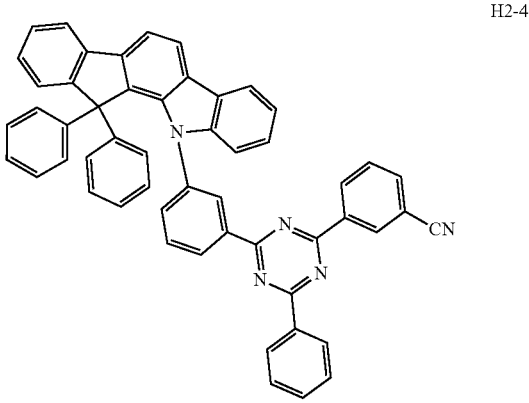

H2-471
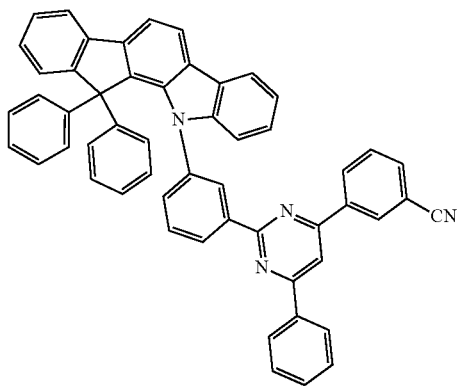
H2-472
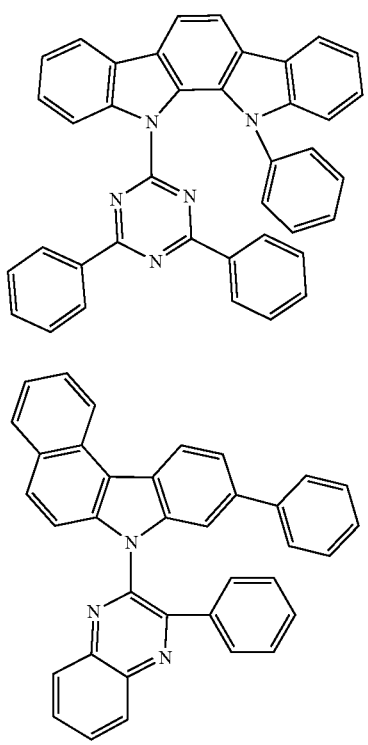
H2-473
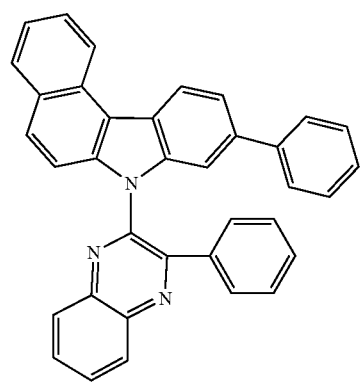
H2-474
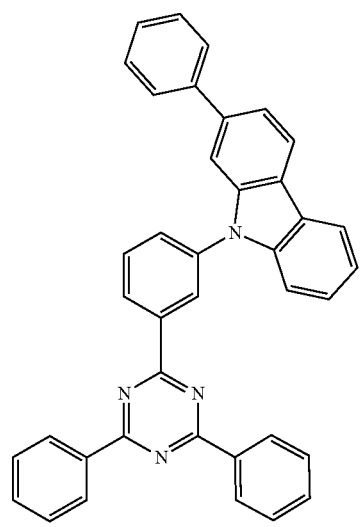
H2-475
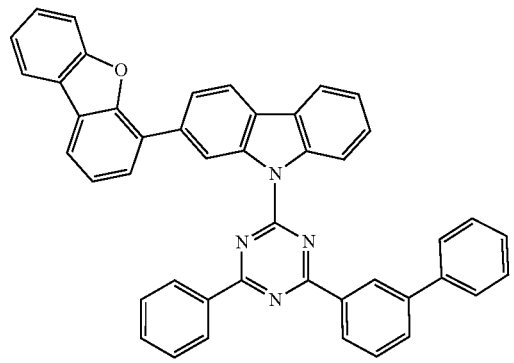
H2-476
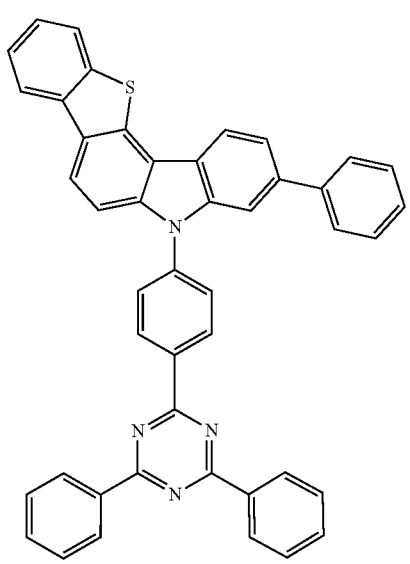
H2-477
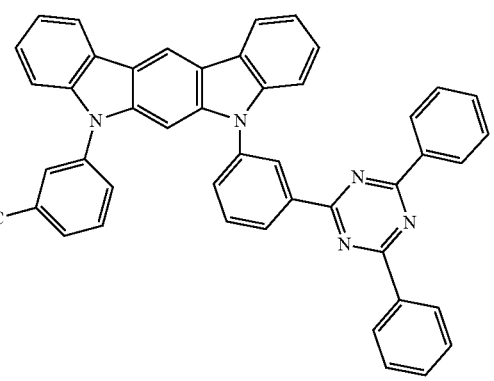

H2-478
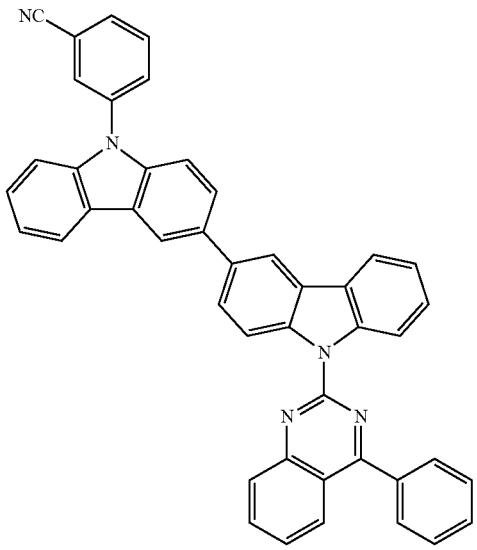
H2-479
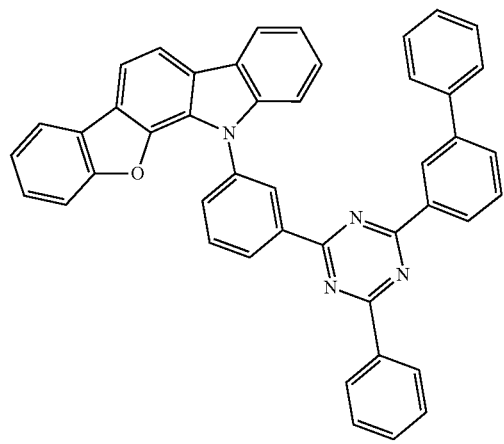
H2-480
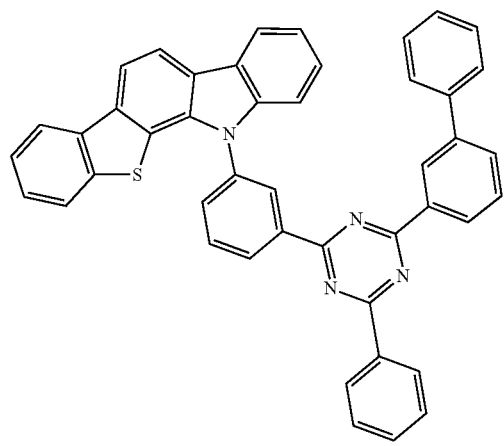
H2-481
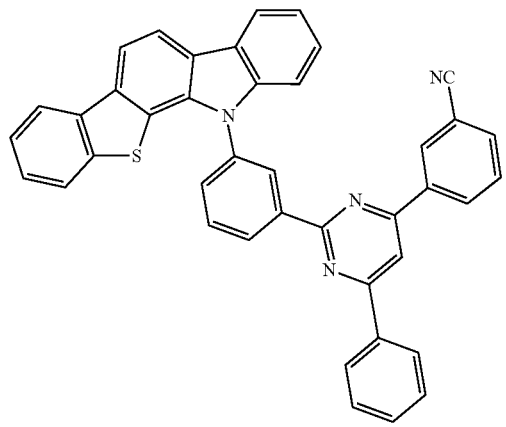
H2-482
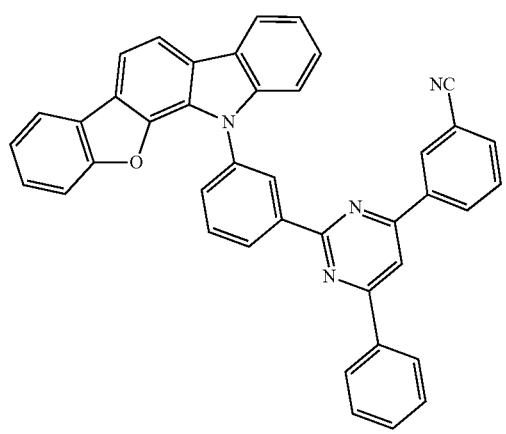
H2-483
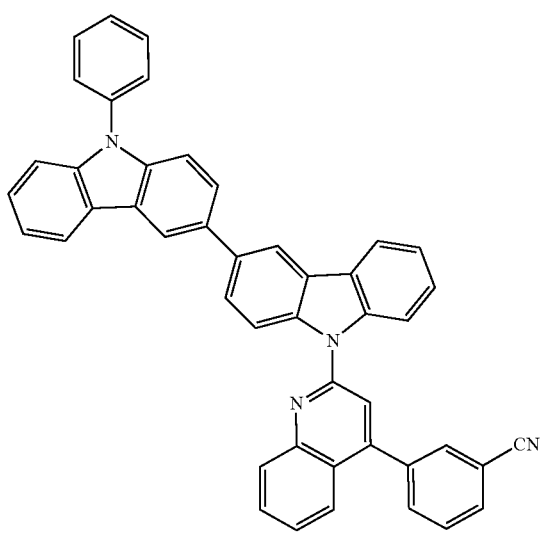

H2-484
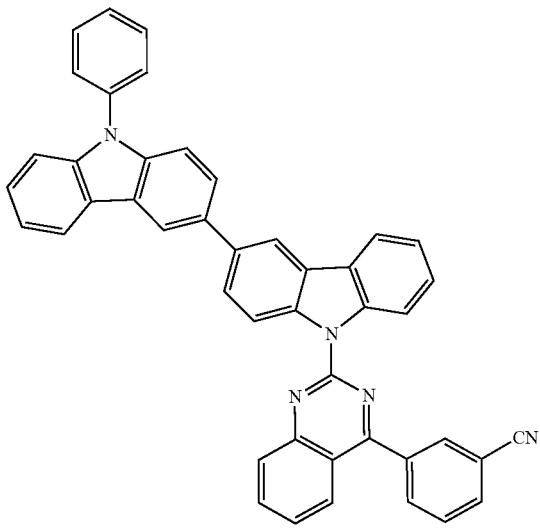
H2-485
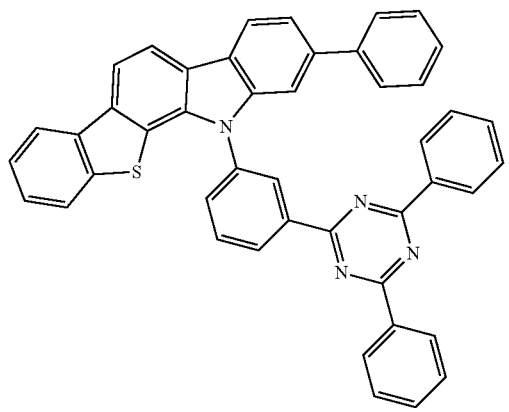
H2-486
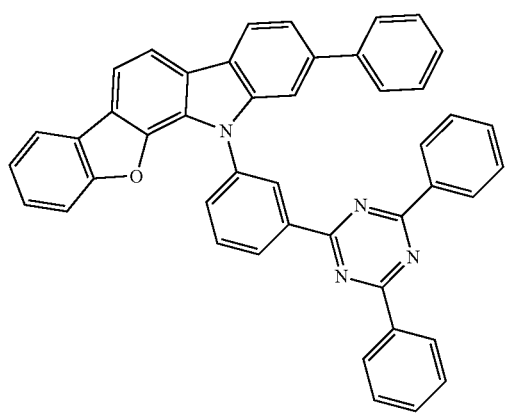
H2-487
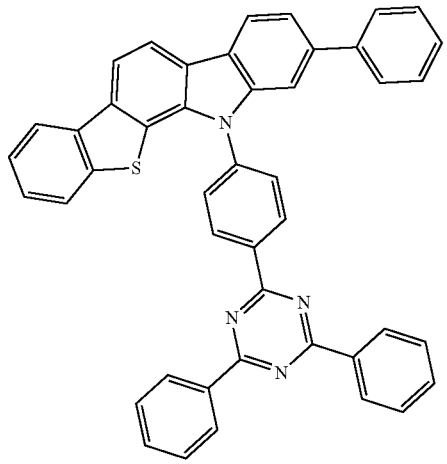
H2-488
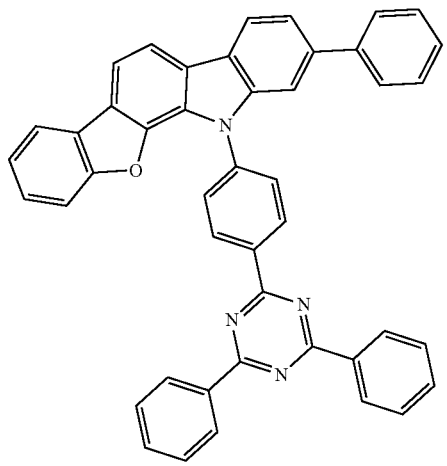
H2-489
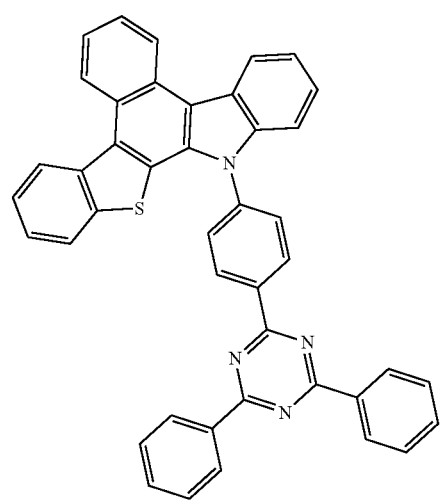

H2-490

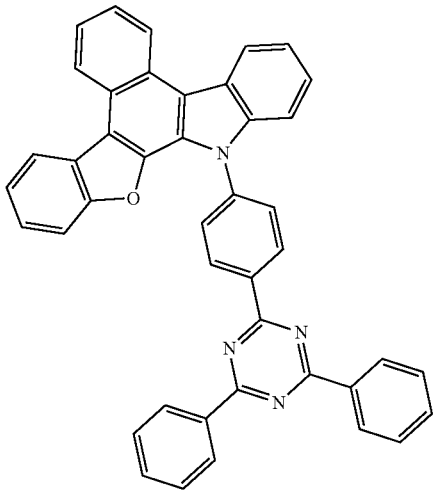

H2-491

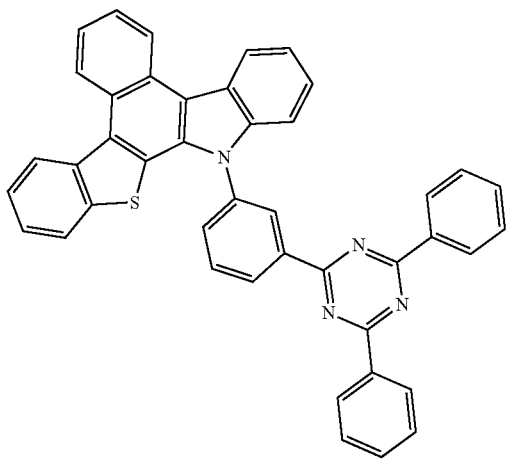

H2-492

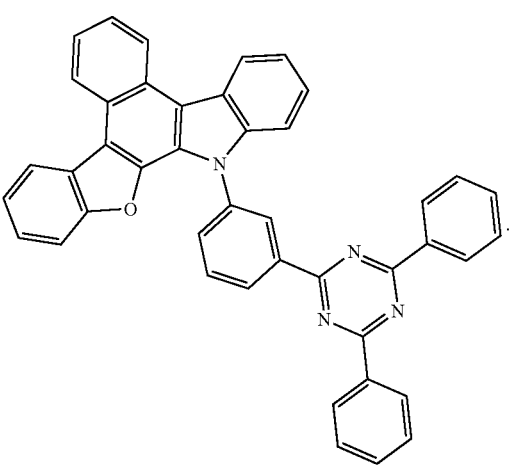

According to another embodiment of the present disclosure, a combination of the compound represented by formula 1 and the compound represented by formula 2, and an organic electroluminescent device comprising the combination are provided.

According to another embodiment of the present disclosure, a mixture or a composition for preparing an organic electroluminescent device is provided. The mixture or composition comprises the compound represented by formula 1. The mixture or composition may be for preparing a light-emitting layer of an organic electroluminescent device. The mixture or composition may comprise a host compound represented by formula 2, besides the compound of the present disclosure. In addition, the mixture or composition may comprise the compound represented by formula 1, which is combined with a host compound represented by formula 2. In addition, the mixture or composition may further comprise a conventional material which is included for preparing an organic electroluminescent device.

The organic electroluminescent device of the present disclosure comprises the compound represented by formula 1, at the same time, the organic electroluminescent device comprises at least one compound selected from the group consisting of arylamine-based compounds and styrylarylamine-based compounds.

In the organic electroluminescent device of the present disclosure, the organic layer may further comprise at least one metal selected from the group consisting of metals of Group 1, metals of Group 2, transition metals of the 4th period, transition metals of the 5th period, lanthanides and organic metals of the d-transition elements of the Periodic Table, or at least one complex compound, besides the compound represented by formula 1.

In addition, the organic electroluminescent device of the present disclosure may emit white light by further comprising at least one light-emitting layer, which comprises a blue electroluminescent compound, a red electroluminescent compound or a green electroluminescent compound known in the art, besides the light-emitting layer of the present disclosure. If necessary, it may further comprise a yellow light-emitting layer or an orange light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer, and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X(1 \le X \le 2)$, $AlO_X(1 \le X \le 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the compound according to the present disclosure, the preparation method thereof, and the luminescent properties of the device will be explained in detail with reference to the following representative compounds.

EXAMPLE 1: PREPARATION OF COMPOUND D-1

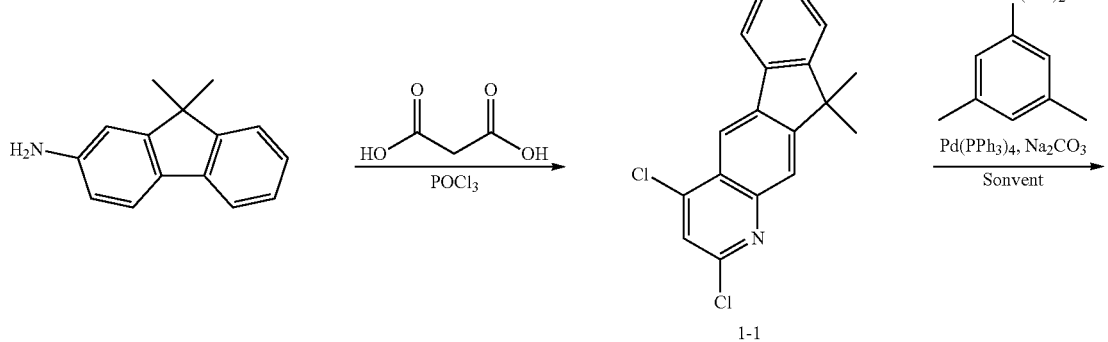

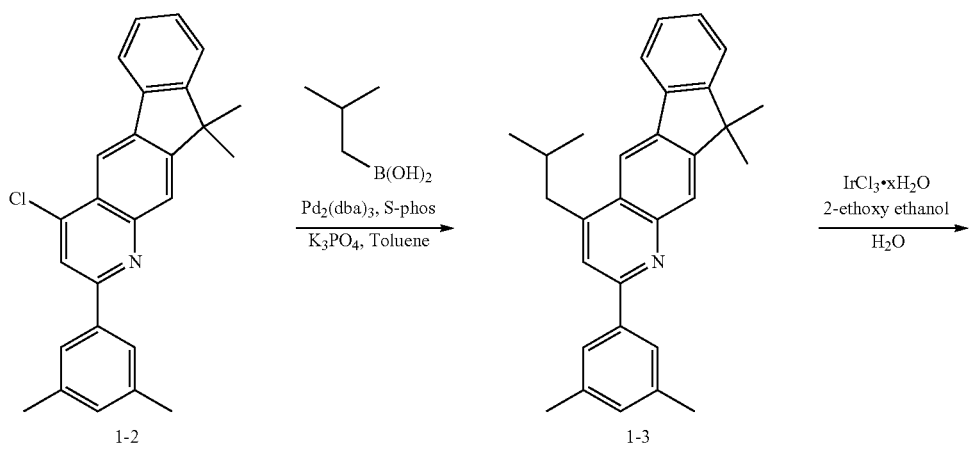

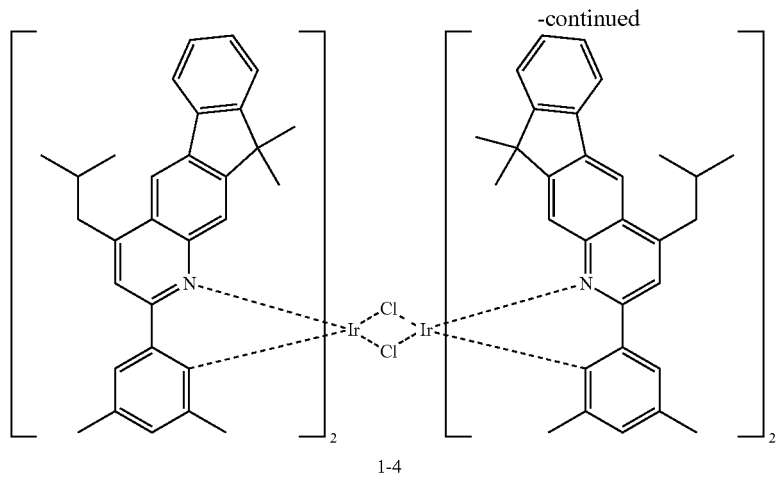

1-4

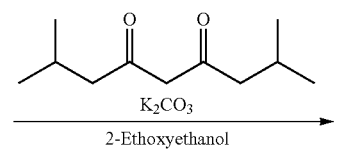

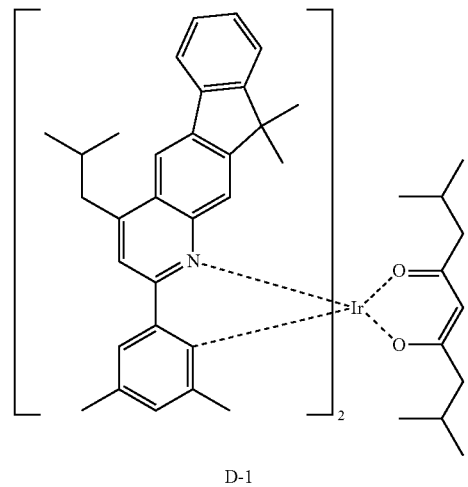

D-1

1) Preparation of Compound 1-1

After introducing malonic acid (38 g, 358 mmol) and POCl$_3$ (356 mL, 3822 mmol) into a reaction vessel, the mixture was stirred for 10 minutes at room temperature. After slowly adding 9,9-dimethyl-9H-fluorene-2-amine (50 g, 239 mmol) dropwise thereto, the mixture was stirred at 150° C. After slowly adding H$_2$O dropwise to the mixture, an extraction with methylene chloride (MC) was conducted. After removing the solvent, the resultant was purified by column chromatography to obtain compound 1-1 (33.5 g, 45%).

2) Preparation of Compound 1-2

After introducing compound 1-1 (16.5 g, 53 mmol), 3,5-dimethylphenylboronic acid (9.45 g, 63 mmol), Pd(PPh$_3$)$_4$ (1.82 g, 1.58 mmol), Na$_2$CO$_3$ (16.70 g, 157.53 mmol), toluene (214 mL), and H$_2$O (79 mL) into a reaction vessel, the mixture was under reflux at 120° C. The resultant was cooled to room temperature, extracted with ethyl acetate and H$_2$O, and then purified by column chromatography to obtain compound 1-2 (15.3 g, 76%).

3) Preparation of Compound 1-3

After introducing compound 1-2 (15.3 g, 39.85 mmol), isobutyl boronic acid (8.198 g, 79.71 mmol), 2-dicyclohexylphosphino-2',6'-dimethoxybiphenyl(S-Phos) (1.30 g, 2.81 mmol), K$_3$PO$_4$ (41.43 g, 172.28 mmol), tris(dibenzylideneacetone)dipalladium(0)(Pd$_2$(dba)$_3$) (1.46 g, 1.41 mmol), and toluene (266 mL) into the reaction vessel, the mixture was stirred for 12 hours. The resultant was cooled to room temperature, extracted with ethyl acetate and H$_2$O, and then purified by column chromatography to obtain compound 1-3 (15.1 g, 93%).

4) Preparation of Compound 1-4

After introducing compound 1-3 (15.1 g, 37.23 mmol), IrCl$_3$·xH$_2$O (5.05 g, 16.92 mmol), 2-ethoxy ethanol (130 mL), and H$_2$O (43.4 mL) into the reaction vessel, the mixture was under reflux for 24 hours at 130° C., and then the resultant was cooled to room temperature. After introducing H$_2$O, the mixture was stirred for 30 minutes, and then filtered to obtain compound 1-4 (7.9 g, 45%) as solid.

5) Preparation of Compound D-1

After introducing compound 1-4 (3.5 g, 1.69 mmol), 2,8-dimethylnonane-4,6-dione (3.11 g, 16.88 mmol), K$_2$CO$_3$ (2.34 g, 16.88 mmol), and 2-ethoxyethanol (21 mL) into the reaction vessel, the mixture was reacted overnight at room temperature and filtered. The obtained solid was purified by column chromatography to obtain compound D-1 (0.7 g, 18%).

| | Molecular Weight (MW) | MP (° C.) | UV (nm) | PL (nm) |
|---|---|---|---|---|
| D-1 | 1184.62 | 330 | 288 | 615 |

EXAMPLE 2: PREPARATION OF COMPOUND D-12
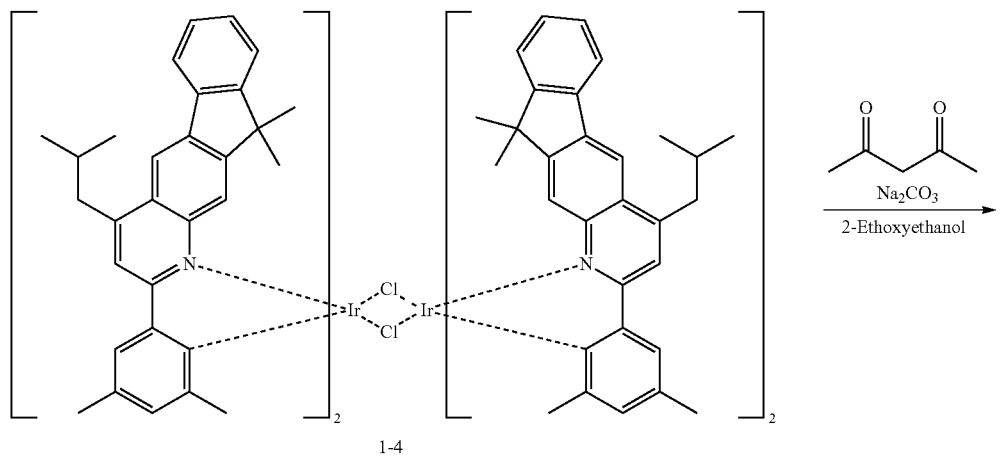
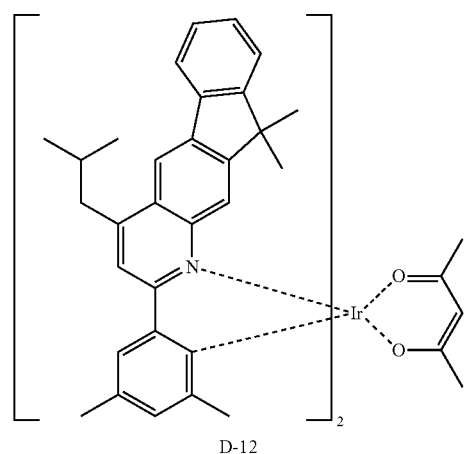
After introducing compound 1-4 (7.9 g, 3.81 mmol), acetylacetone (3.8 g, 38.10 mmol), Na$_2$CO$_3$ (4.04 g, 38.10 mmol), and 2-ethoxyethanol (48 mL), the mixture was reacted overnight and then filtered. The obtained solid was purified by column chromatography to obtain compound D-12 (3 g, 36%).
|  | MW | MP (° C.) | UV (nm) | PL (nm) |
|---|---|---|---|---|
| D-12 | 1100.46 | 372 | 276 | 617 |

EXAMPLE 3: PREPARATION OF COMPOUND D-61

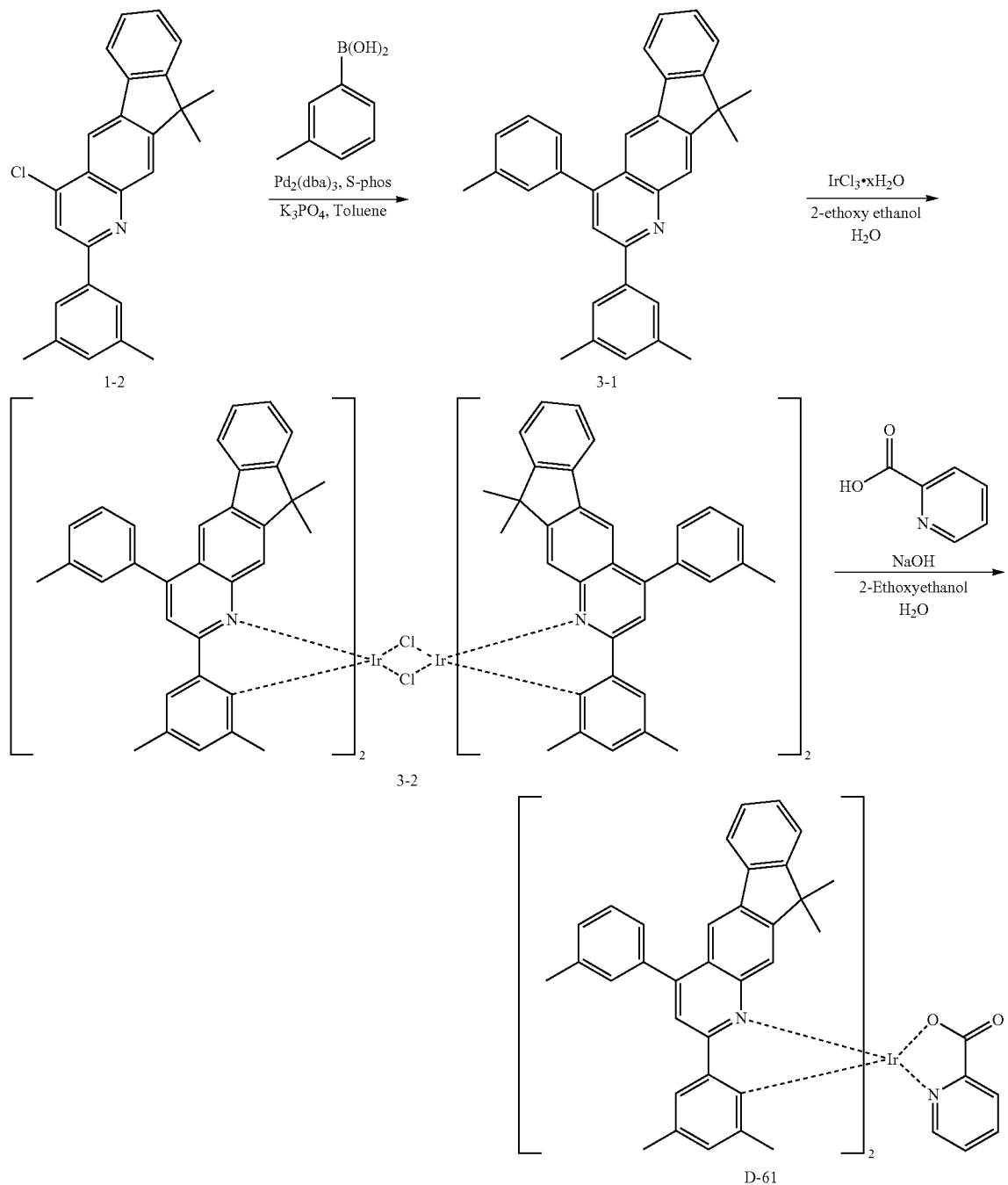

1) Preparation of Compound 3-1

After introducing compound 1-2 (67.2 g, 181.68 mmol), m-tolyl boronic acid (49.40 g, 363.35 mmol), tris(dibenzylideneacetone)dipalladium(0)(Pd$_2$(dba)$_3$) (6.65 g, 7.27 mmol), K$_3$PO$_4$ (188.97 g, 890.23 mmol), 2-dicyclohexylphosphino-2',6'-dimethoxybiphenyl(s-phos) (6.00 g, 14.53 mmol), and toluene (1200 mL) into a 2 L round-bottom flask, the mixture was stirred under reflux for 24 hours. After completion of the reaction, the reaction product was cooled to room temperature, then extracted with ethyl acetate and treated with MgSO$_4$. The reaction mixture was purified by column chromatography to obtain compound 3-1 (46 g, 58%).

2) Preparation of Compound 3-2

After introducing compound 3-1(46 g, 104.64 mmol), IrCl$_3$.xH$_2$O (14.22 g, 47.56 mmol), 2-ethoxyethanol (365 mL, 0.13 M), and H$_2$O (122 mL) into a 1 L round-bottom flask under nitrogen atmosphere, the mixture was stirred under reflux for 24 hours. The reaction mixture was cooled to room temperature. The solvent was removed therefrom as much as possible, and then after adding water (500 mL), the mixture was stirred for 30 minutes. The reaction mixture was rinsed with methanol and hexane and dried to obtain compound 3-2 (50.7 g, 97%).

3) Preparation of Compound D-61 After introducing compound 3-2 (10 g, 4.53 mmol), picolinic acid (1.11 g, 9.05 mmol), NaOH (0.36 g, 9.05 mmol), 2-ethoxyethanol (105 mL, 0.043 M) and H$_2$O (10 mL) into a 250 mL round-bottom flask under nitrogen atmosphere, the mixture was stirred at room temperature for 24 hours. After completion of the reaction, water (330 mL) was added. Thereafter, the mixture was stirred for 30 minutes and then filtered. The obtained resultant was purified by column chromatography to obtain compound D-61(0.8 g, 30%).

[DEVICE EXAMPLES 1-1 AND 1-2]
PREPARATION OF OLED COMPRISING A DOPANT OF THE PRESENT DISCLOSURE

OLED comprising the organic electroluminescent compound of the present disclosure was produced. A transparent electrode indium tin oxide (ITO) thin film (10 Ω/sq) on a glass substrate for an organic light-emitting diode (OLED) (Geomatec) was subjected to an ultrasonic washing with acetone, ethanol, and distilled water, sequentially, and then was stored in isopropanol. The ITO substrate was then mounted on a substrate holder of a vacuum vapor depositing apparatus. HI-1 was introduced into a cell of the vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. HI-2 was introduced into another cell of the vacuum vapor depositing apparatus, and was evaporated by applying an electric current to the cell, thereby forming a second hole injection layer having a thickness of 5 nm on the first hole injection layer. HT-1 was introduced into a cell of the vacuum vapor depositing apparatus, and was evaporated by applying an electric current to the cell, thereby forming a first hole transport layer having a thickness of 10 nm on the second hole injection layer. HT-2 was introduced into another cell of the vacuum vapor depositing apparatus, and was evaporated by applying an electric current to the cell, thereby forming a second hole transport layer having a thickness of 60 nm on the first hole transport layer. Then, the light-emitting layer on the hole injection layers and the hole transport layers was formed as follows. Compound H2-16 was introduced into one cell of the vacuum vapor depositing apparatus as a host, and a dopant material shown in Table 1 below was introduced into another cell. Thereafter, the host material was evaporated, and simultaneously, the dopant material was evaporated at different rates from the host material, so that the dopant was deposited in a doping amount of 3 wt % based on the total amount of the host and dopant to form a light-emitting layer having a thickness of 40 nm on the second hole transport layer. ET-1 and EI-1 were introduced into two cells of the vacuum vapor depositing apparatus, respectively, and evaporated at a 1:1 rate to form an electron transport layer having a thickness of 30 nm on the light-emitting layer. After depositing EI-1 as an electron injection layer having a thickness of 2 nm, an Al cathode having a thickness of 80 nm was then deposited by another vacuum vapor deposition apparatus on the electron injection layer to produce OLED.

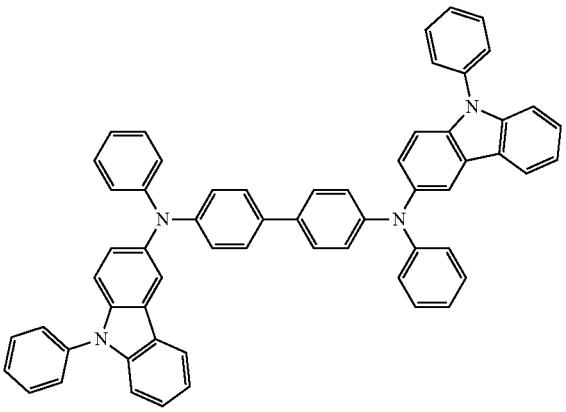

HI-1

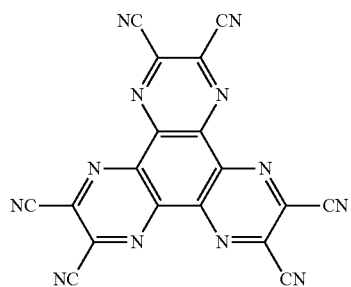

HI-2

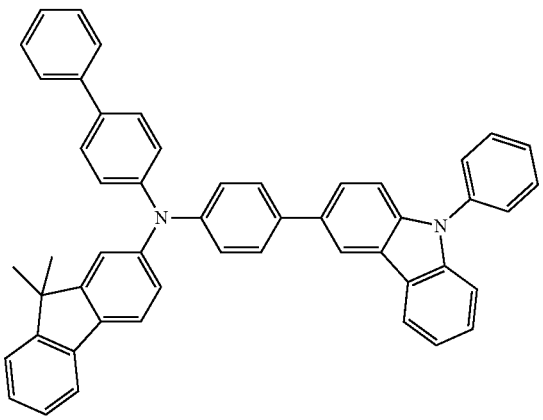

HT-1

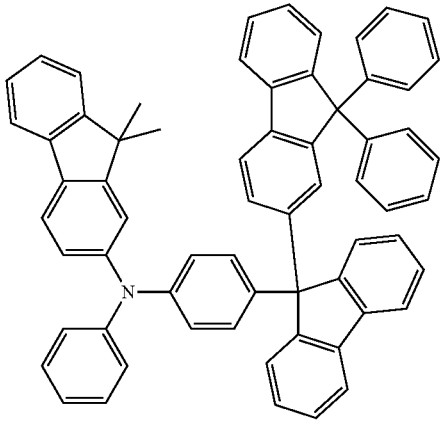

HT-2

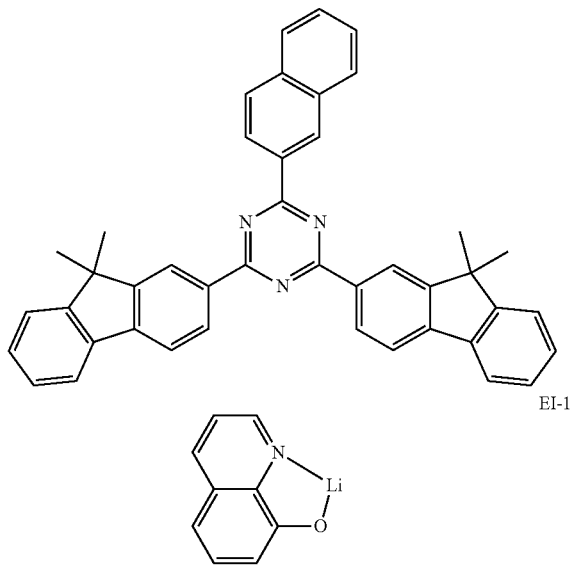

[COMPARATIVE EXAMPLE 1-1]
PREPARATION OF OLED COMPRISING A
CONVENTIONAL DOPANT

OLED was produced in the same manner as in Device Example 1-1, except that compound RD-1 below was used as a dopant for a light-emitting layer.

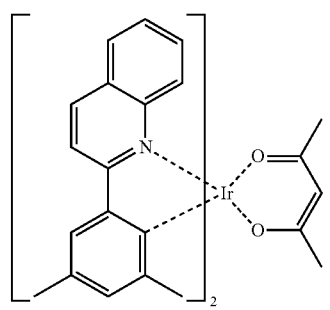

The evaluation result of the OLED prepared in Device Examples 1-1 and 1-2, and Comparative Example 1-1 above is shown in Table 1 below.

TABLE 1

| | Host | Dopant | Voltage (V) | Efficiency (cd/A) | Color Coordinate (x, y) | |
|---|---|---|---|---|---|---|
| Device Example 1-1 | H2-16 | D-12 | 4.2 | 32.7 | 668 | 331 |
| Device Example 1-2 | H2-16 | D-1 | 4.1 | 34.0 | 669 | 330 |
| Comparative Example 1-1 | H2-16 | RD-1 | 4.2 | 22.4 | 660 | 338 |

By using an organic electroluminescent compound of the present disclosure, it is possible to provide an organic electroluminescent device with excellent efficiency and color purity compared to the conventional electroluminescent compound.

This can be understood that an azabenzo[b]fluorene ligand of the Device Example attributes the organic electroluminescent device to have better efficiency compared to the quinoline ligand of the Comparative Example. Besides, the substituent (alkyl substituent in the Device Example above) is introduced on the outside of azabenzo[b]fluorene ligand according to the present disclosure, and it can be understood that the substituent applies a steric hindrance to the octahedral structure of the iridium complex, thereby reducing Triplet-Triplet Annihilation to maximize the characteristic which improves efficiency.

Upon comparing the azabenzo[b]fluorene ligand of the present disclosure with an azabenzo[a]fluorene ligand, according to the quantum mechanics simulation results, the bond distance between the azabenzo[b]fluorene ligand and the iridium metal is shorter than the one between the azabenzo[a]fluorene ligand and the iridium metal. It can be predicted that the shorter the bond distance, the stronger the spin orbital coupling by an iridium atom is applied to have better efficiency.

The invention claimed is:

1. An organic electroluminescent compound represented by the following formula 1:

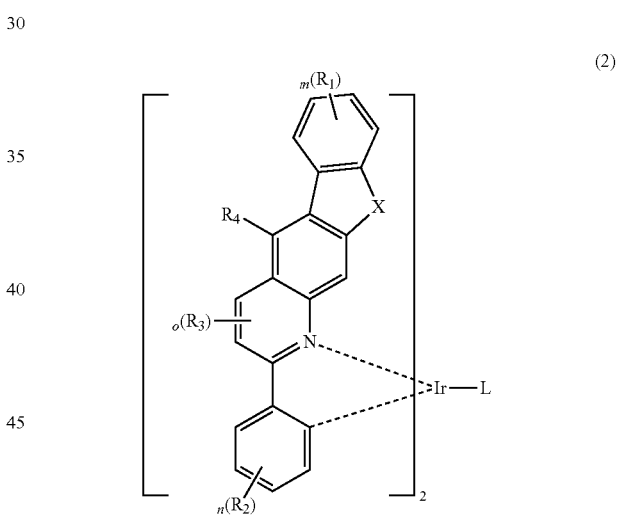

wherein

X represents $CR_{11}R_{12}$, O or S;

$R_1$ to $R_3$, each independently, represent hydrogen, deuterium, a substituted or unsubstituted (C1-C10)alkyl, or a substituted or unsubstituted (C6-C30)aryl;

$R_4$ represents hydrogen, or a substituted or unsubstituted (C1-C10)alkyl;

$R_{11}$ and $R_{12}$, each independently, represent a substituted or unsubstituted (C1-C10)alkyl, or a substituted or unsubstituted (C6-C30)aryl;

m and n, each independently, represent an integer of 0 to 4;

o represents an integer of 0 to 2;

where m, n or o is an integer of 2 or more, each of $R_1$, each of $R_2$, or each of $R_3$ may be the same or different;

L represents

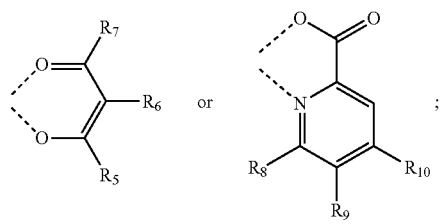

where L is

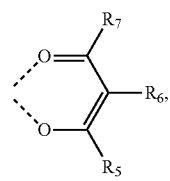

$R_5$ to $R_7$, each independently, represent hydrogen, deuterium, a substituted or unsubstituted (C1-C10)alkyl, or a substituted or unsubstituted (C6-C30)aryl;
where L is

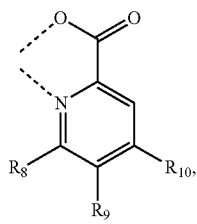

$R_8$ to $R_{10}$, each independently, represent hydrogen, deuterium, a substituted or unsubstituted (C1-C10)alkyl, or a substituted or unsubstituted (C6-C30)aryl; or may be linked to an adjacent substituent to form a substituted or unsubstituted 9- to 20-membered heteroaryl including the pyridine ring linked to $R_5$ to $R_{10}$; and the heteroaryl may comprise one or more hetero atoms selected from a nitrogen, an oxygen, and a sulfur in addition to the nitrogen atom of the pyridine ring.

2. The organic electroluminescent compound according to claim 1, wherein
$R_{11}$ and $R_{12}$ are each independently, a substituted or unsubstituted (C1-C5)alkyl, or a substituted or unsubstituted (C6-C20)aryl.

3. The organic electroluminescent compound according to claim 1, wherein
$R_1$ to $R_3$ are each independently hydrogen, a substituted or unsubstituted (C1-C5)alkyl, or a substituted or unsubstituted (C6-C20)aryl.

4. The organic electroluminescent compound according to claim 1, wherein
$R_{11}$ and $R_{12}$ are each independently, a (C1-C4)alkyl unsubstituted or substituted deuterium, or an unsubstituted (C6-C15)aryl;
$R_1$ to $R_3$ are each independently hydrogen, an unsubstituted (C1-C4)alkyl, or a (C6-C15)aryl unsubstituted or substituted with a (C1-C4)alkyl; and
$R_4$ is hydrogen.

5. The organic electroluminescent compound according to claim 1, wherein
$R_5$ to $R_7$ are each independently hydrogen, a substituted or unsubstituted (C1-C5)alkyl, or a substituted or unsubstituted (C6-C15)aryl.

6. The organic electroluminescent compound according to claim 1, wherein
$R_8$ to $R_{10}$ are each independently hydrogen, a substituted or unsubstituted (C1-C5)alkyl, or a substituted or unsubstituted (C6-C20)aryl; or at least two of $R_8$ to $R_{10}$ may be linked to each other as an adjacent substituent to form a 9- to 16-membered heteroaryl which includes the pyridine ring linked to $R_8$ to $R_{10}$ and is unsubstituted or substituted with a (C1-C15)alkyl, and the heteroaryl may comprise one or more hetero atoms selected from a nitrogen, an oxygen, and a sulfur in addition to a nitrogen atom of the pyridine ring.

7. The organic electroluminescent compound according to claim 1, wherein the compound represented by formula 1 is selected from the group consisting of:

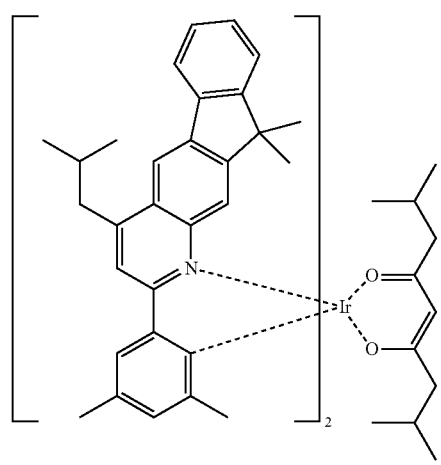

D-1

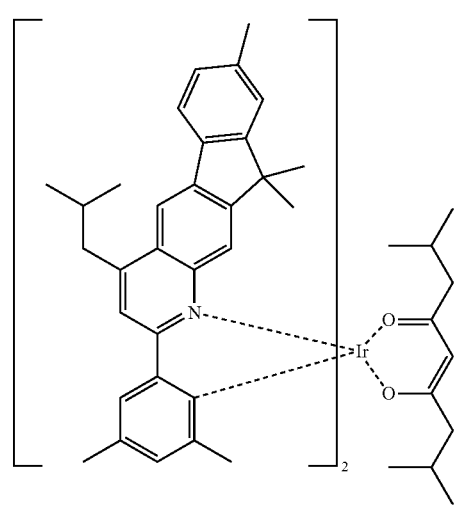

D-2

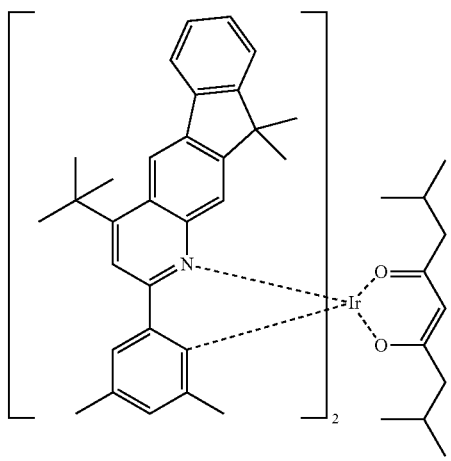
D-3
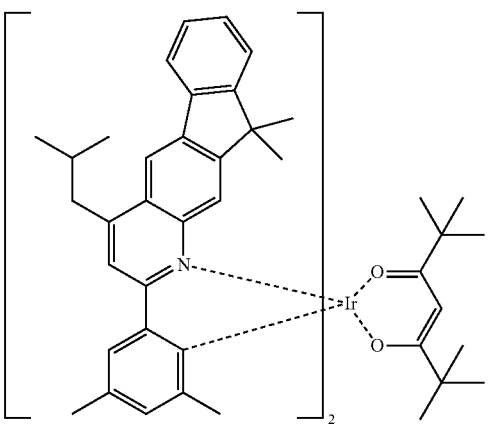
D-6
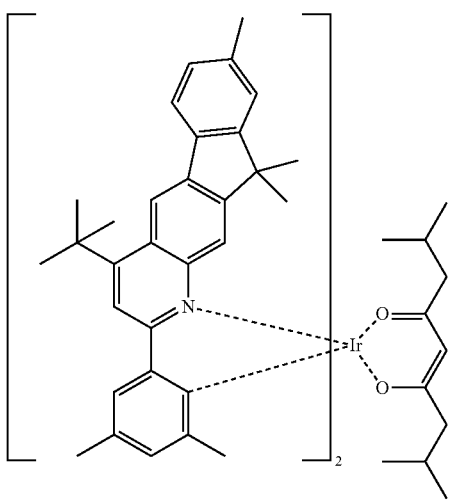
D-4
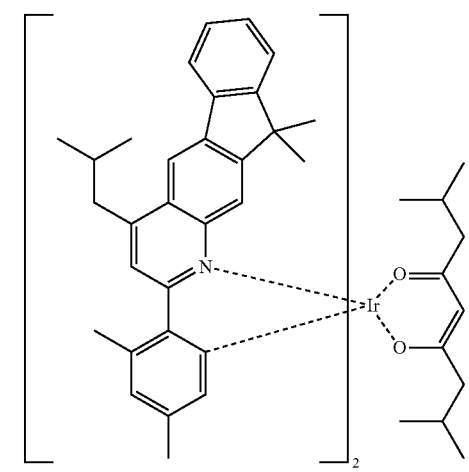
D-7
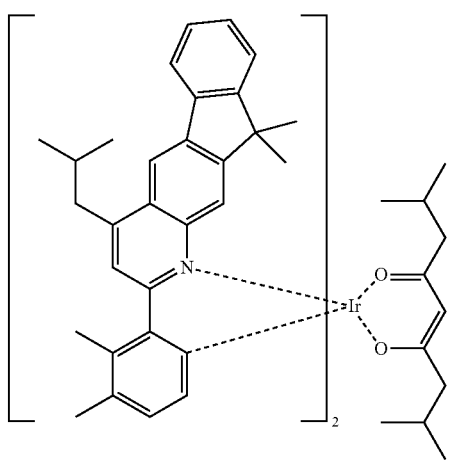
D-5
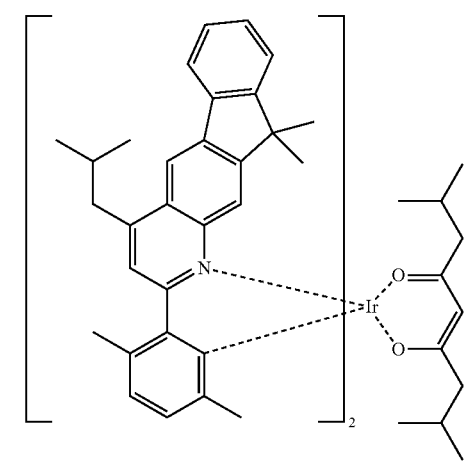
D-8

-continued
D-9
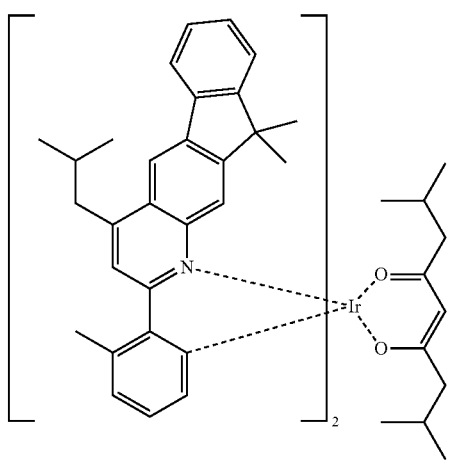
D-10
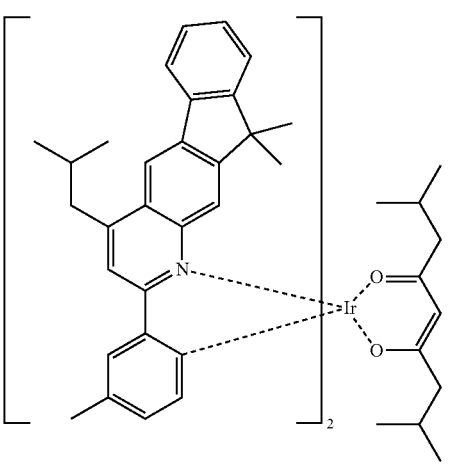
D-11
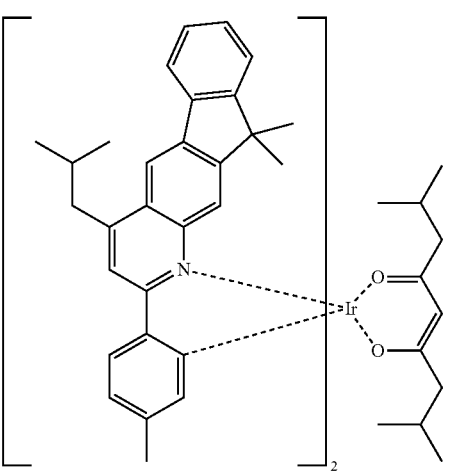
-continued
D-12
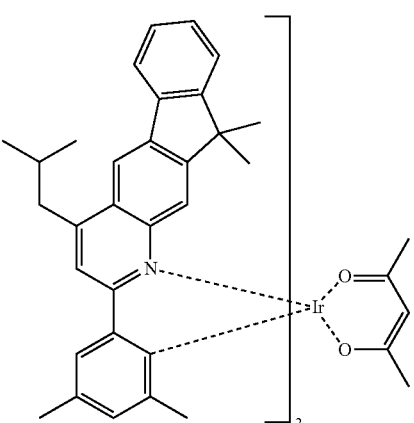
D-13
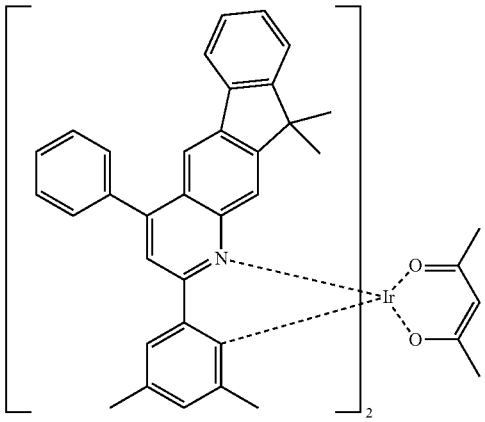
D-14
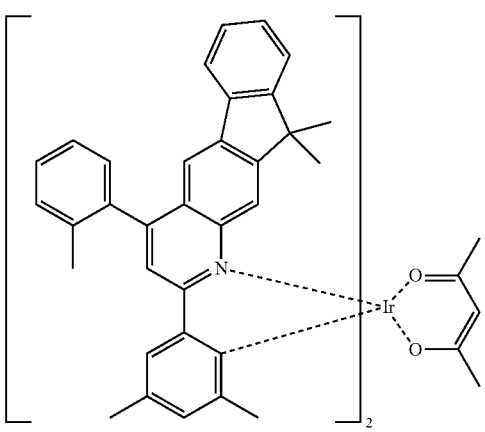

-continued
D-15
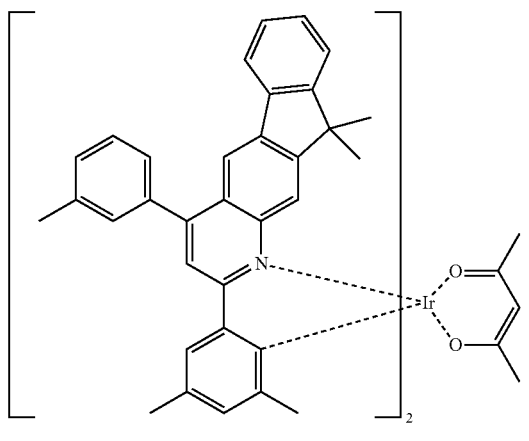
D-18
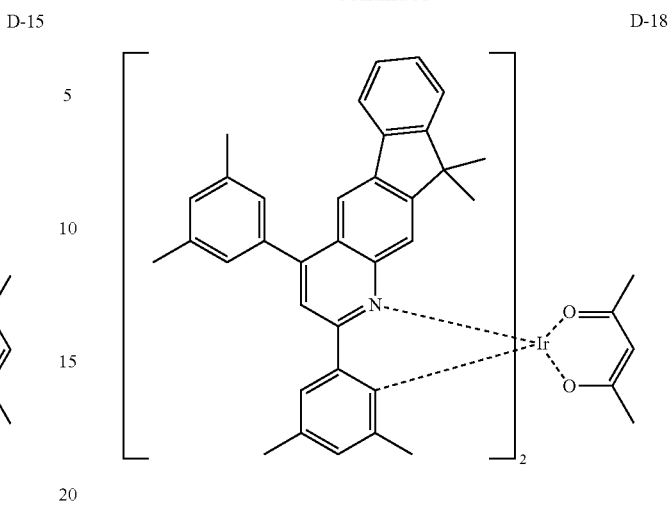
D-16
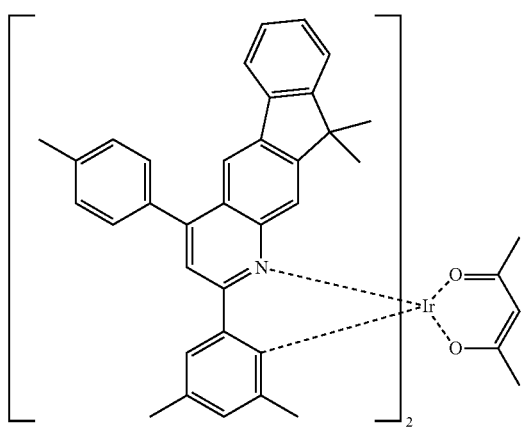
D-19
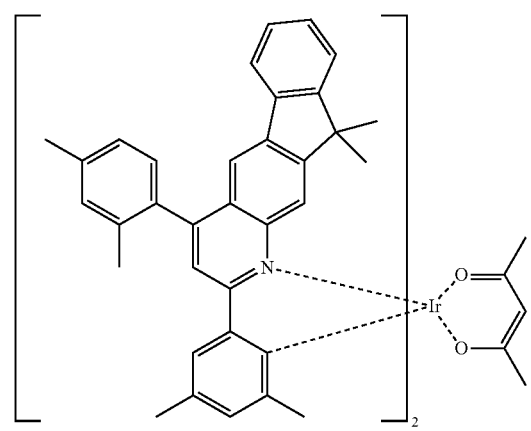
D-17
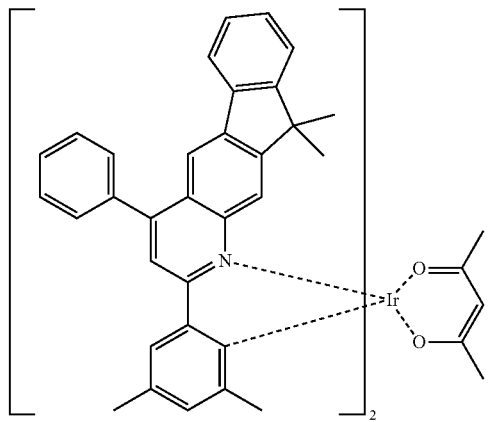
D-20
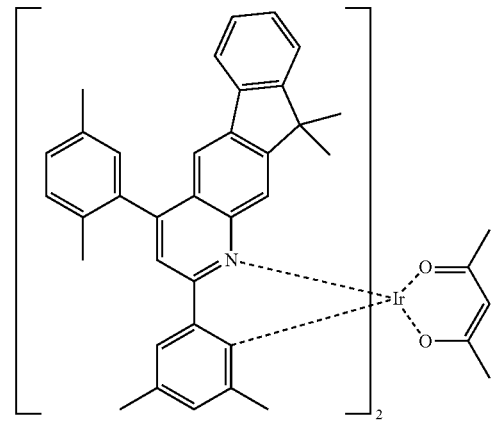

D-21
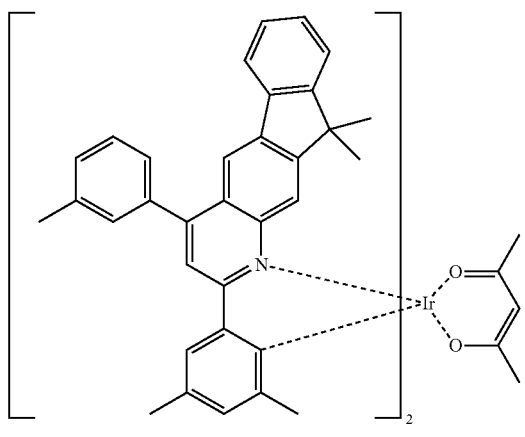
D-24
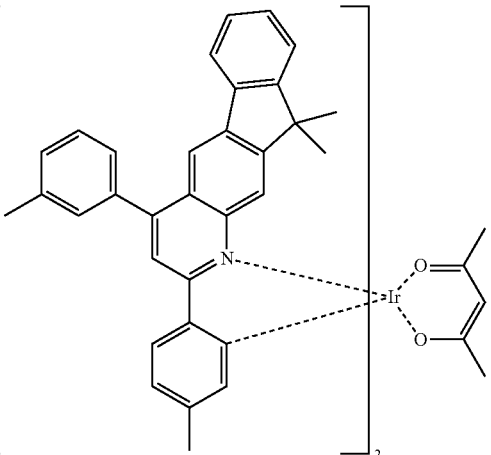
D-22
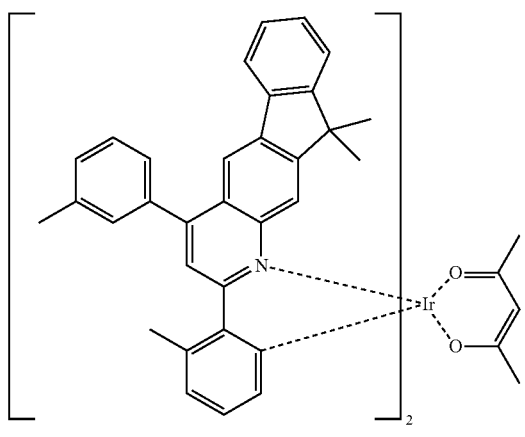
D-25
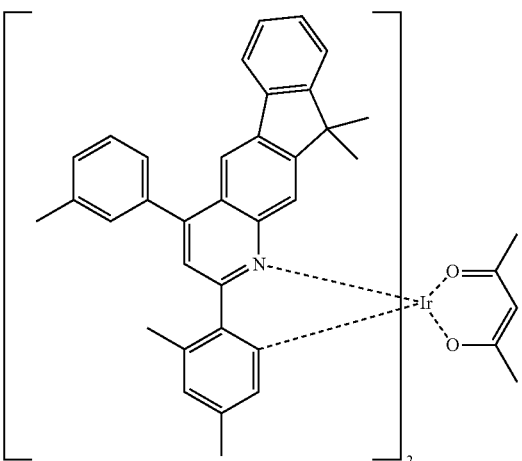
D-23
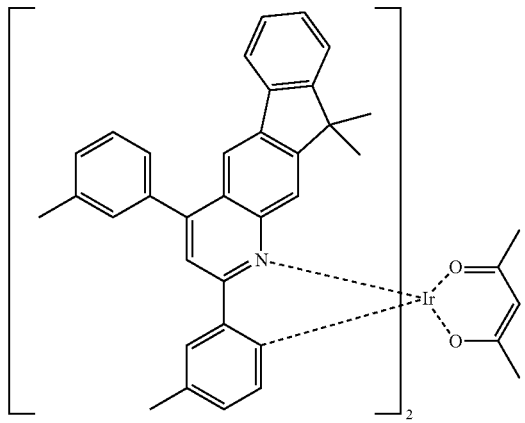
D-26
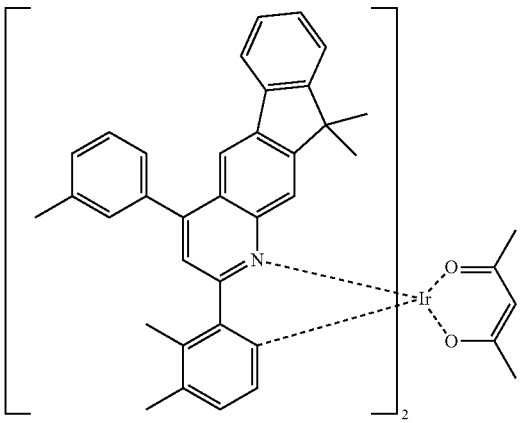

-continued
D-27
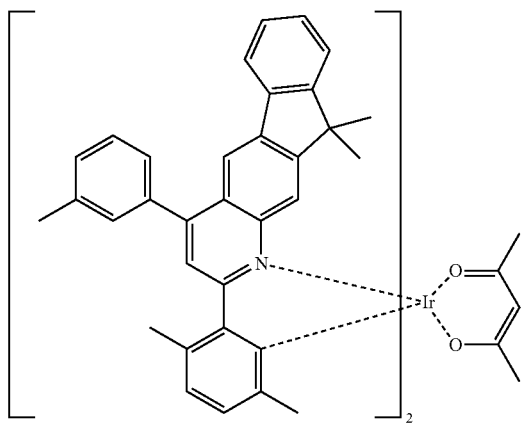
D-28
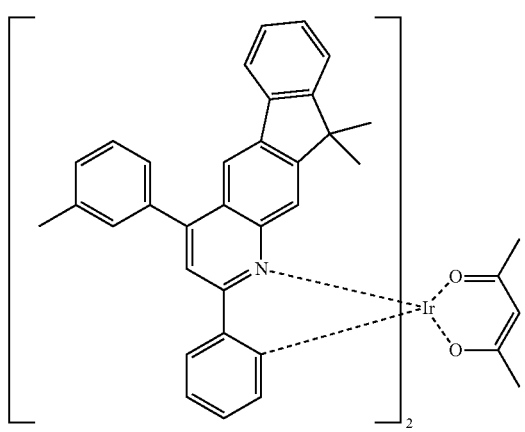
D-29
-continued
D-30
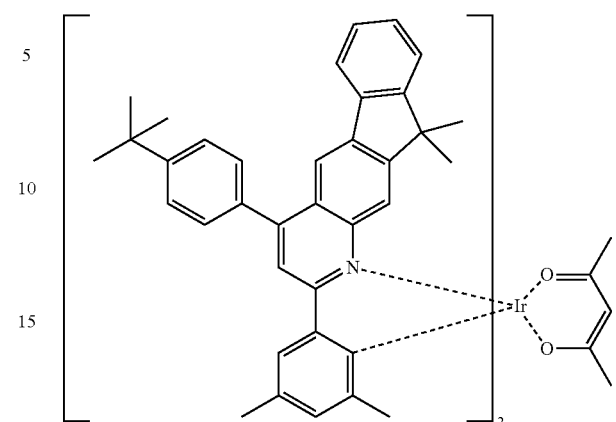
D-31
D-32
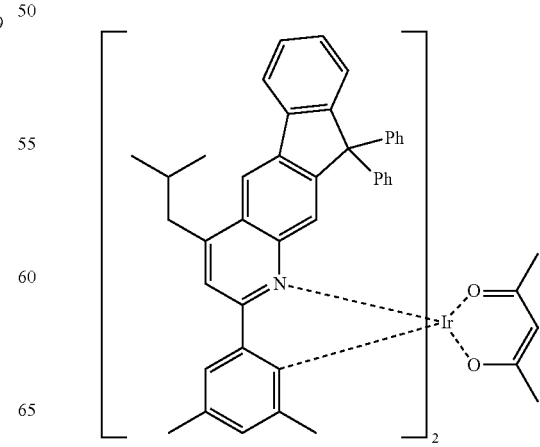

-continued
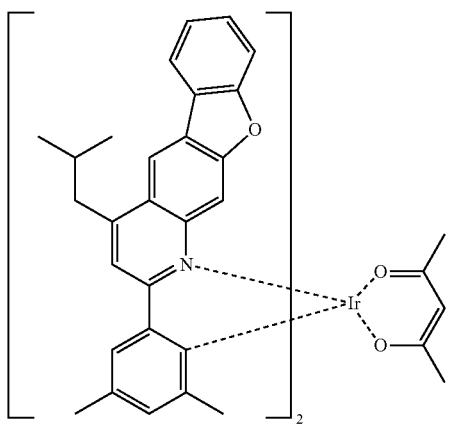
D-33
D-34
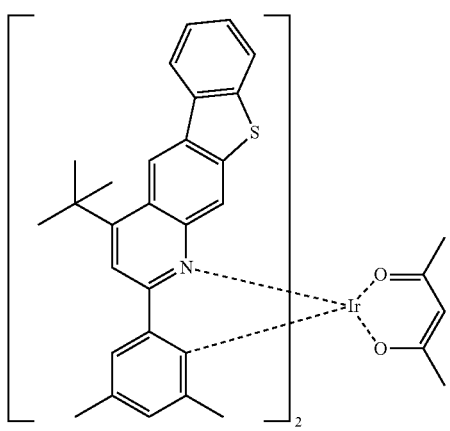
D-35
-continued
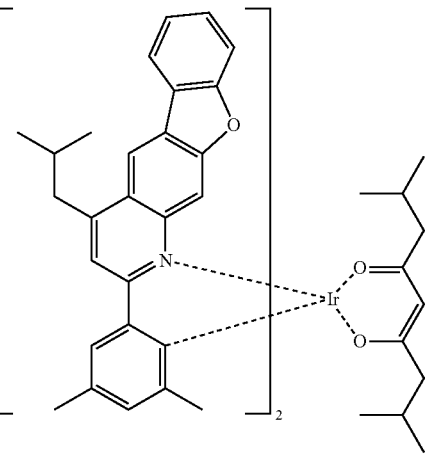
D-36
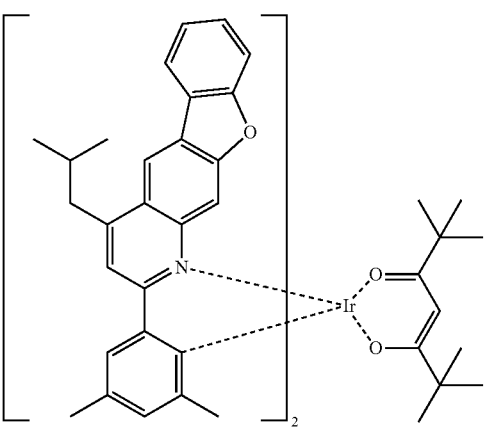
D-37
D-38

D-39
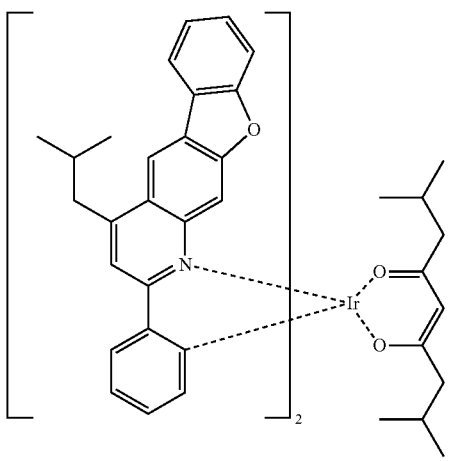
D-40
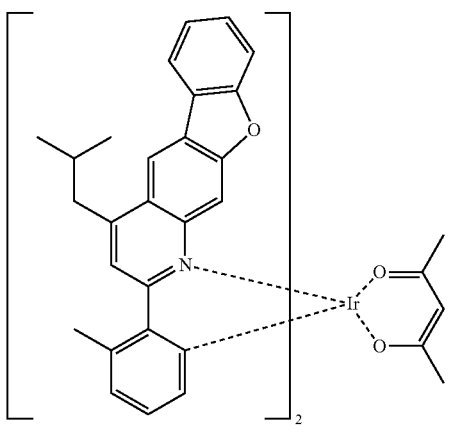
D-41
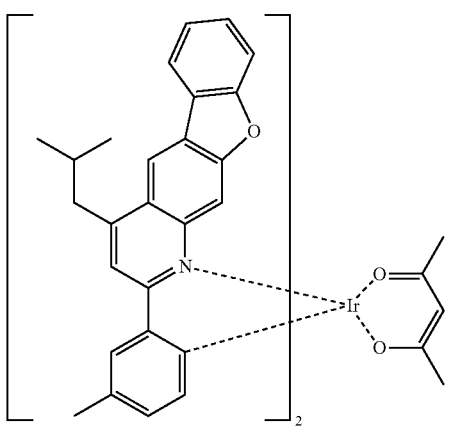
D-42
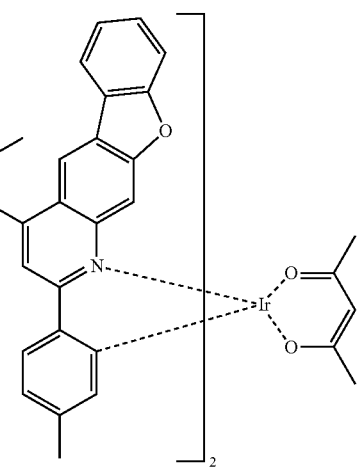
D-43
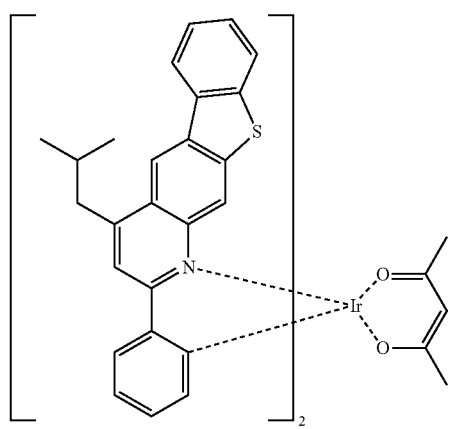
D-44
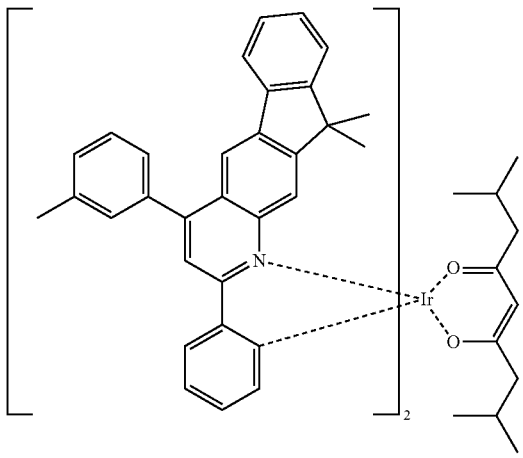

D-45
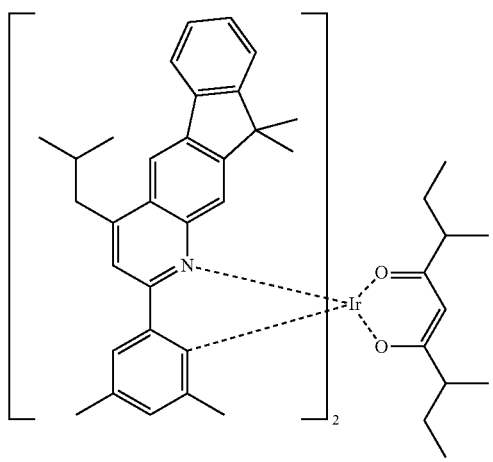
D-46
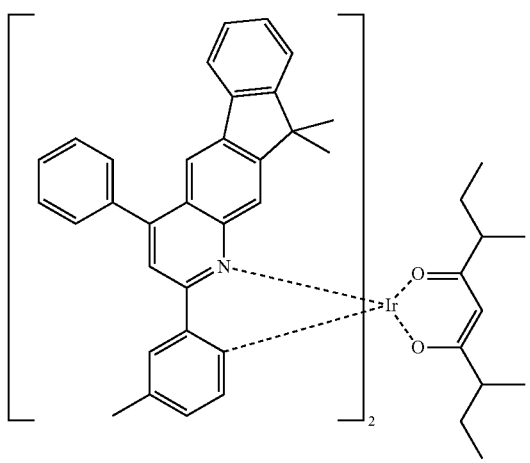
D-47
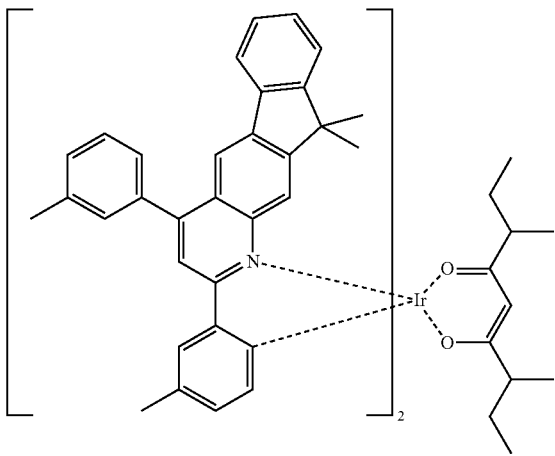
D-48
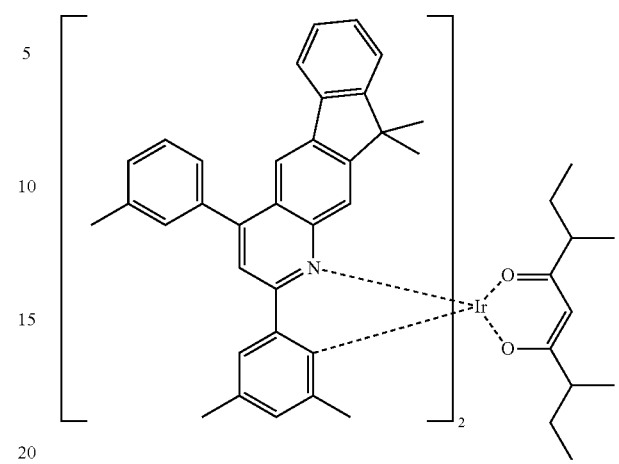
D-49
D-50
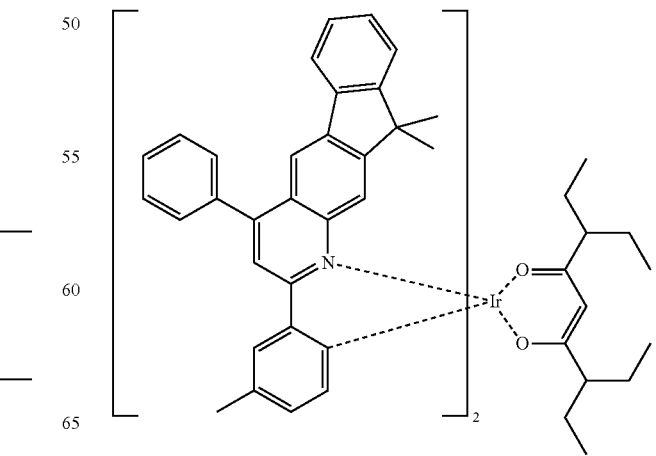

D-51
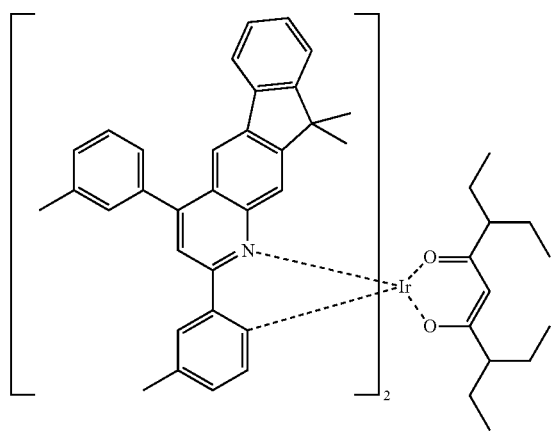
D-52
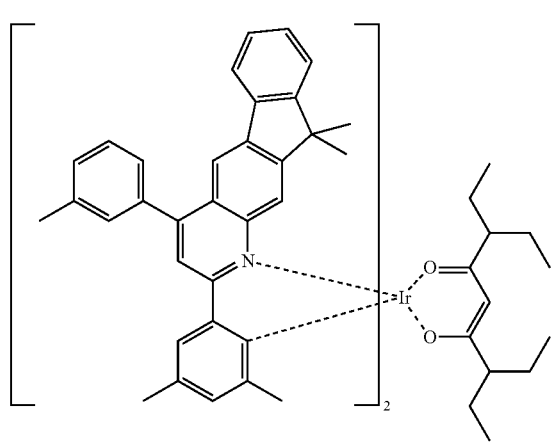
D-53
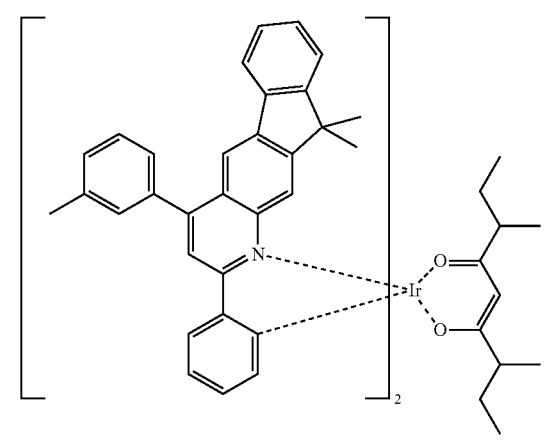
D-54
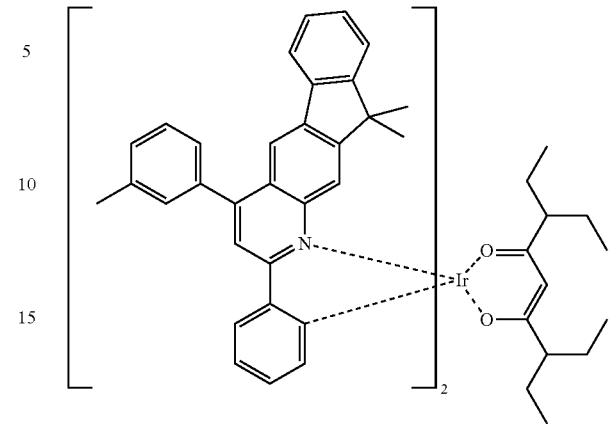
D-55
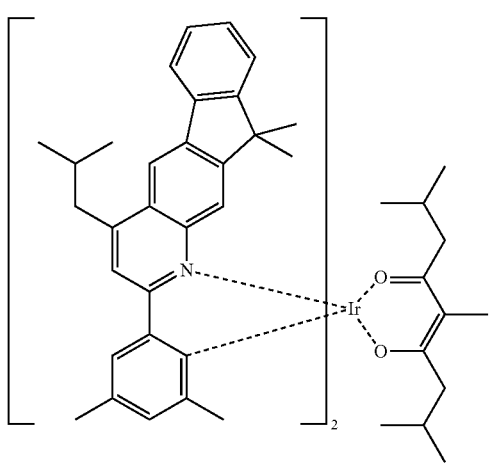
D-56
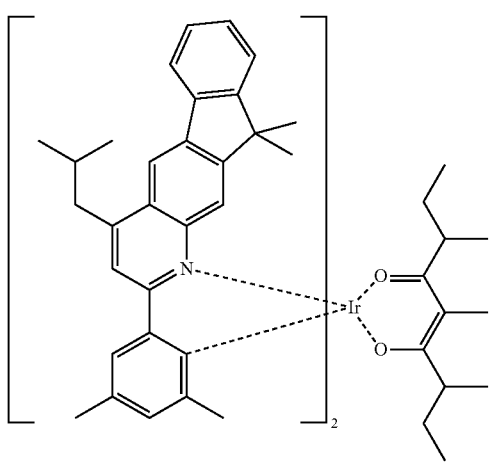

D-57
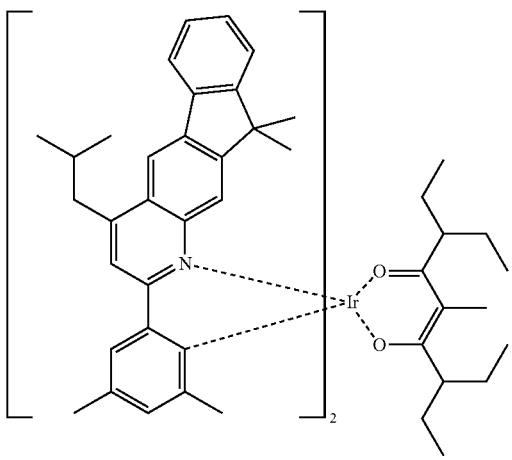
D-58
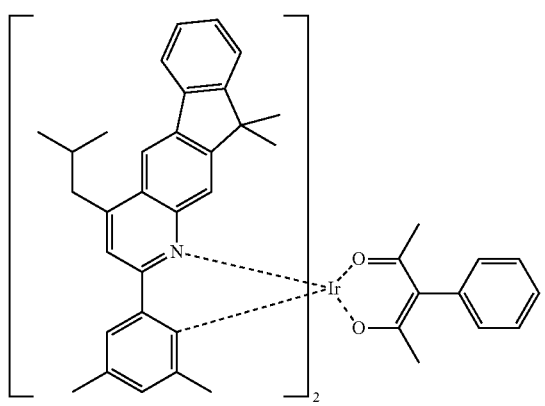
D-59
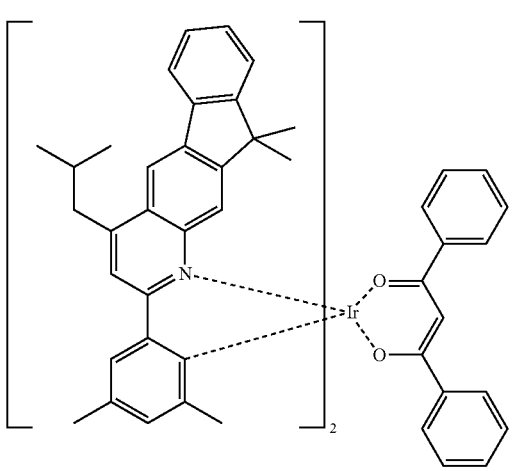
D-60
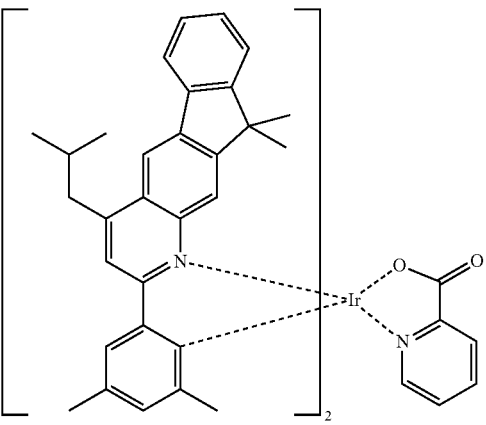
D-61
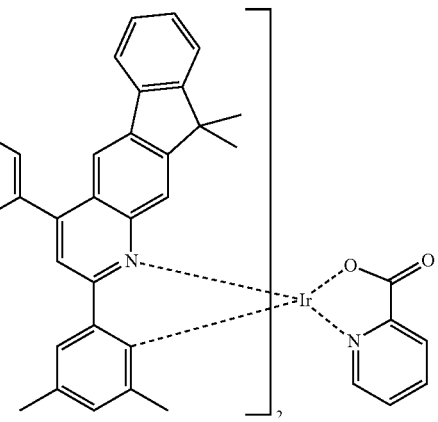
D-62
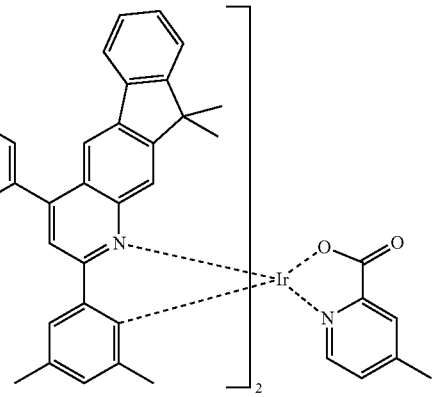

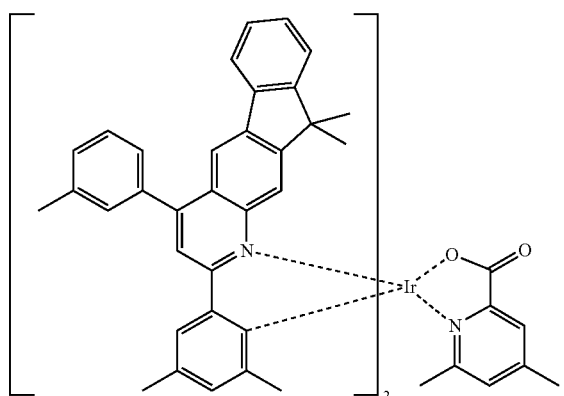
D-63
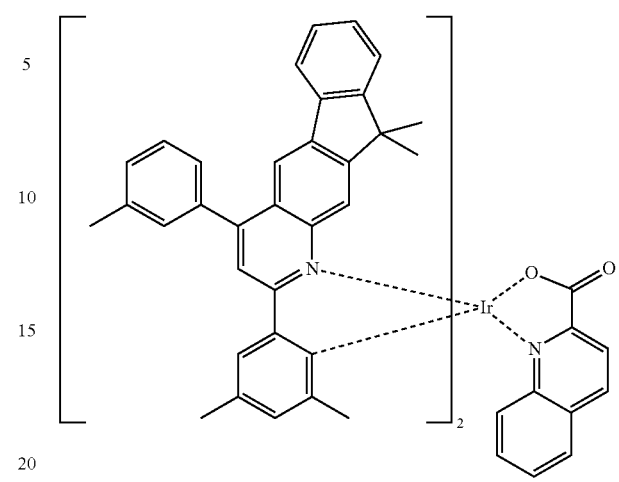
D-66
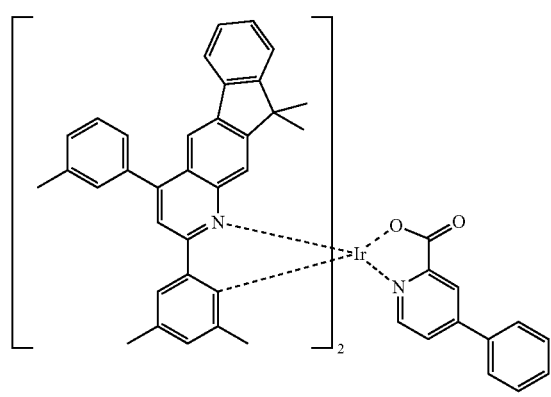
D-64
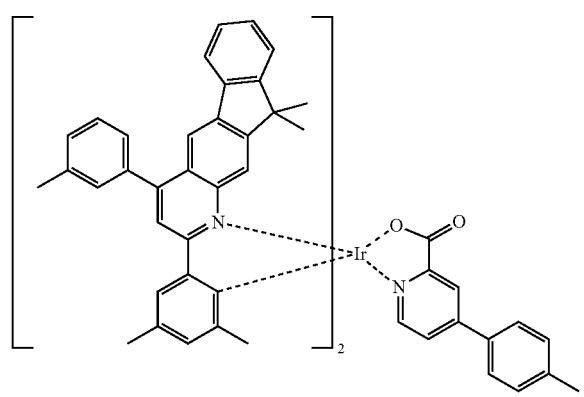
D-65
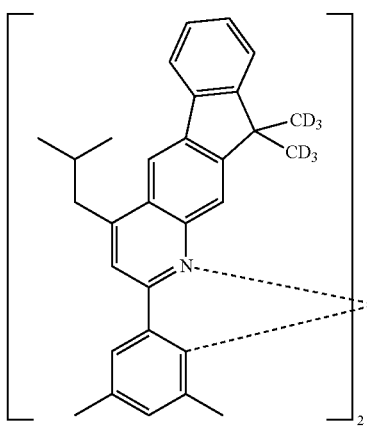
D-68

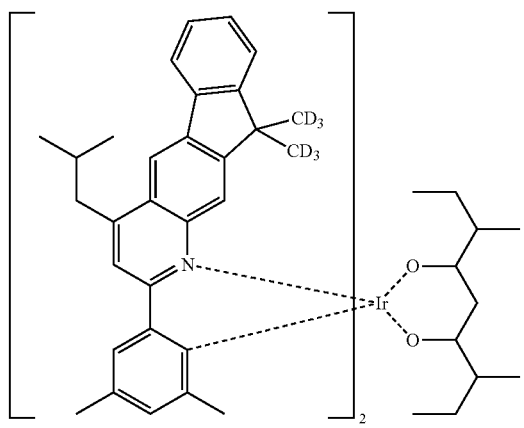
D-69
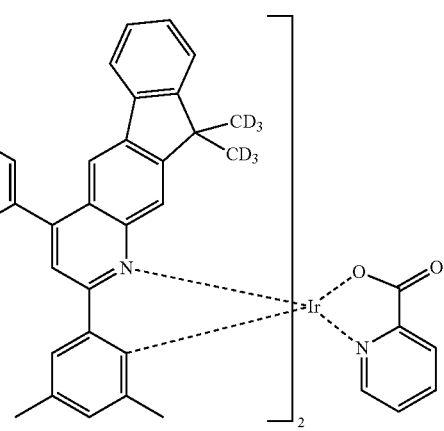
D-72
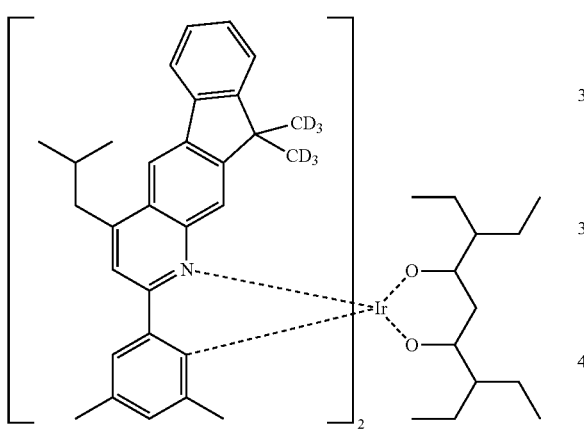
D-70
D-73
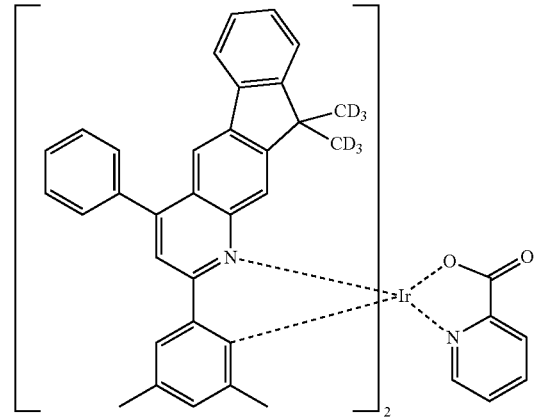
D-71
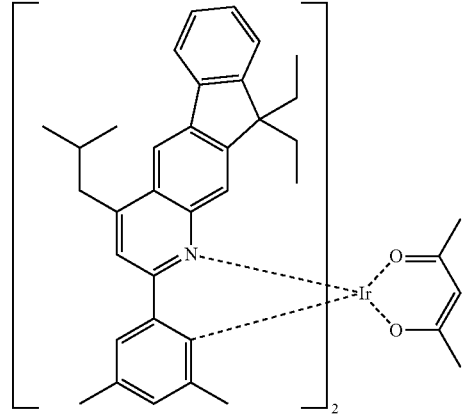
D-74

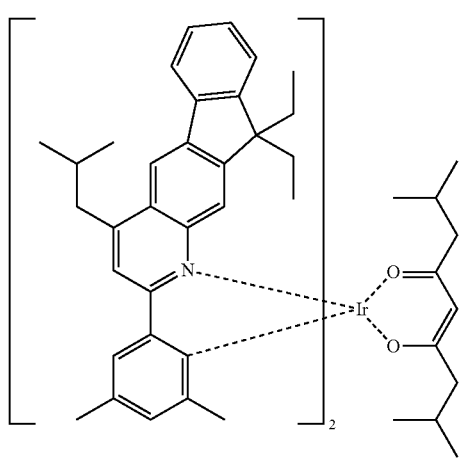
D-75
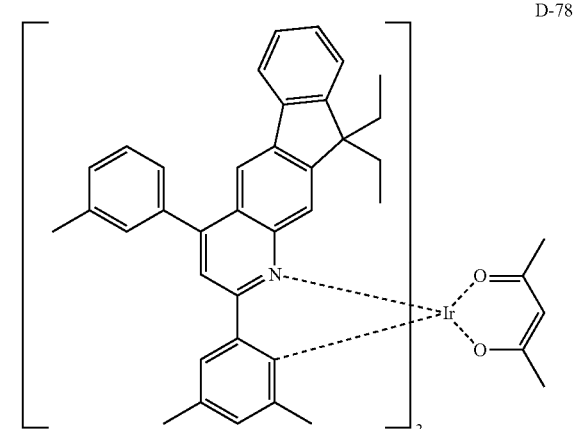
D-78
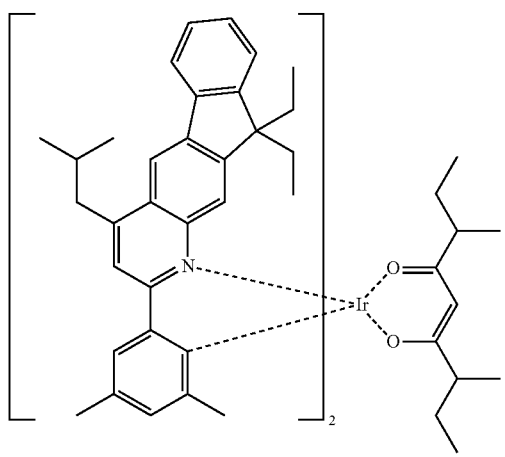
D-76
D-79
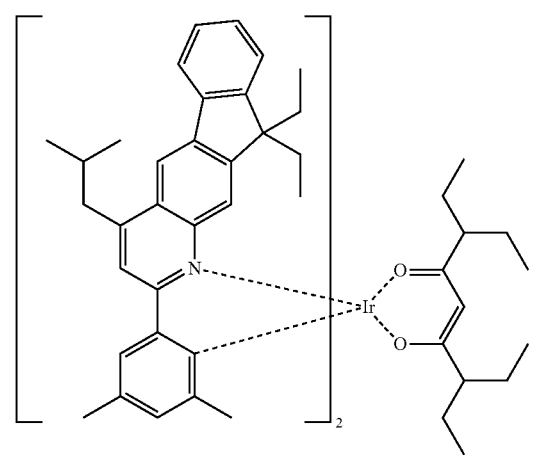
D-77
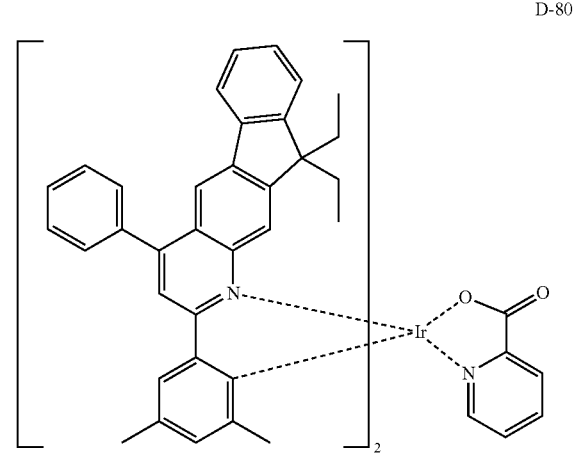
D-80

D-81
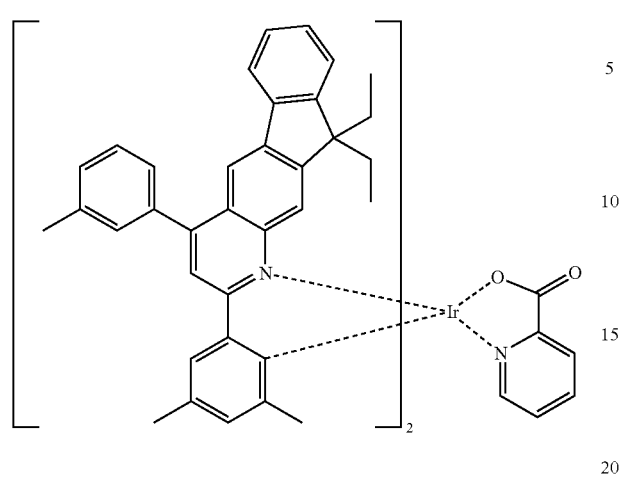
D-83
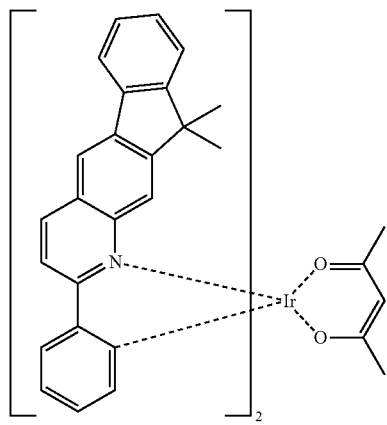
D-82
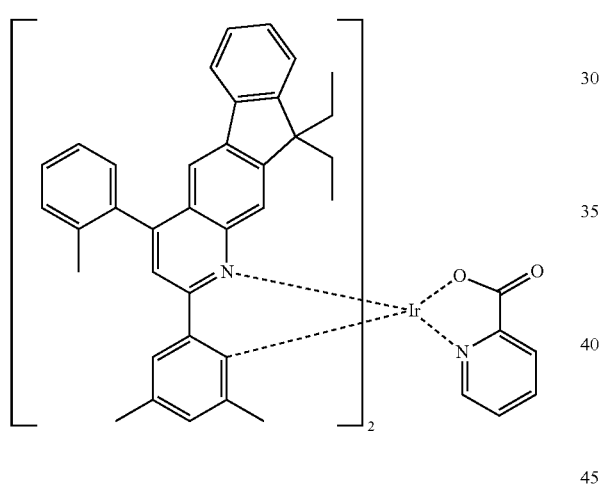
D-84
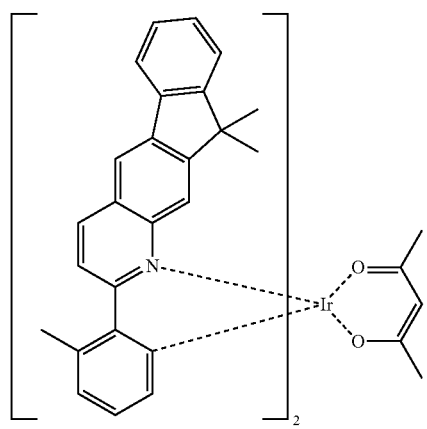
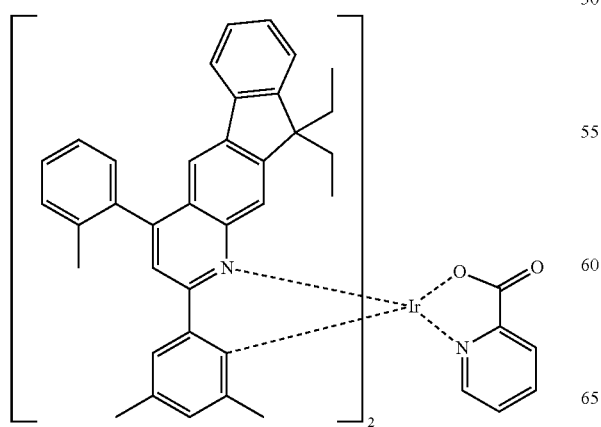
D-85
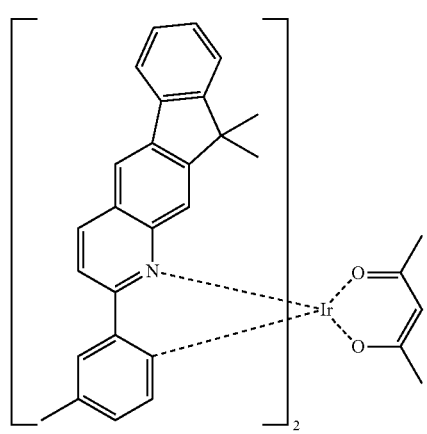

D-86 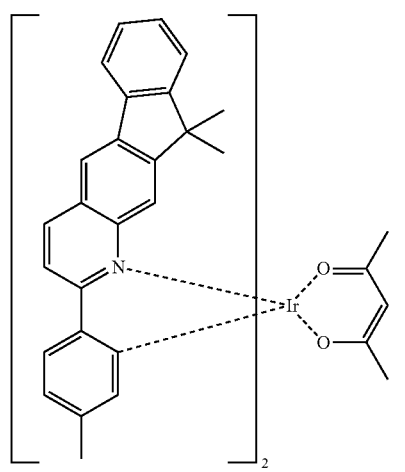
D-87 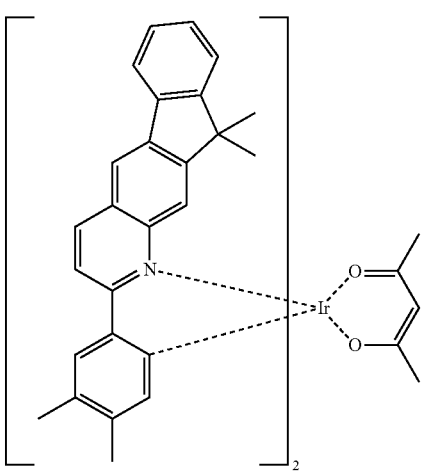
D-88 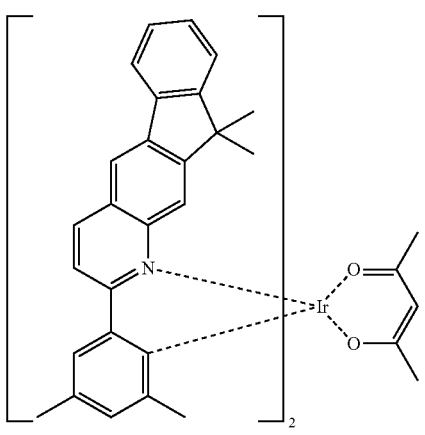
D-89 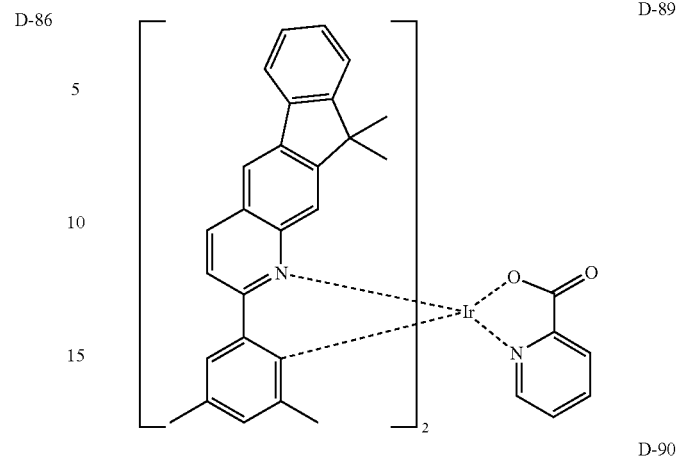
D-90 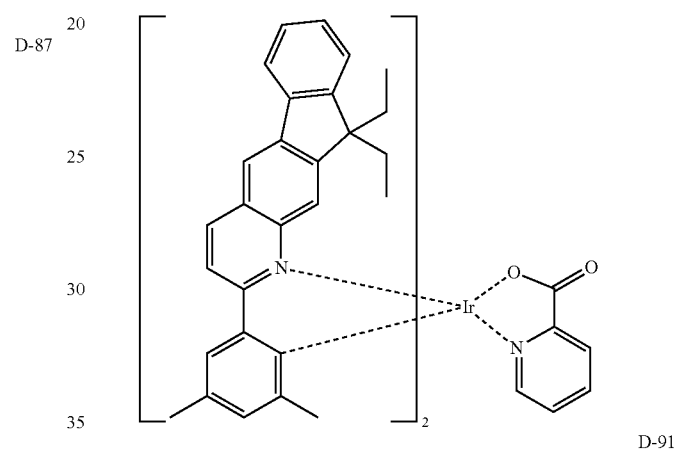
D-91 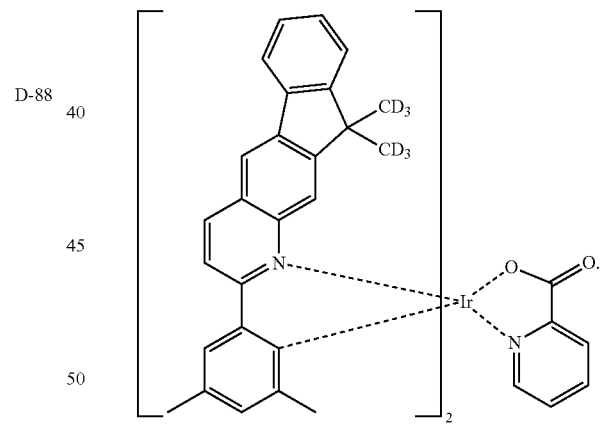
8. The organic electroluminescent device comprising the organic electroluminescent compound according to claim 1.
* * * * *